United States Patent
Babaoglu et al.

(10) Patent No.: US 9,464,096 B2
(45) Date of Patent: *Oct. 11, 2016

(54) THERAPEUTIC COMPOUNDS

(71) Applicant: Gilead Sciences, Inc., Foster City, CA (US)

(72) Inventors: Kerim Babaoglu, Lansdale, PA (US); Michael L. Mitchell, Castro Valley, CA (US); Ryan McFadden, Foster City, CA (US); Paul A. Roethle, Berkeley, CA (US); Lianhong Xu, Palo Alto, CA (US); Hong Yang, Fremont, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,771

(22) Filed: Feb. 26, 2015

(65) Prior Publication Data

US 2016/0024104 A1    Jan. 28, 2016

Related U.S. Application Data

(63) Continuation of application No. 14/112,473, filed as application No. PCT/US2012/034593 on Apr. 20, 2012, now Pat. No. 9,006,229.

(60) Provisional application No. 61/477,922, filed on Apr. 21, 2011.

(51) Int. Cl.

| | |
|---|---|
| *C07D 491/052* | (2006.01) |
| *A61K 31/4741* | (2006.01) |
| *A61K 45/06* | (2006.01) |
| *C07D 277/62* | (2006.01) |
| *C07D 277/64* | (2006.01) |
| *C07D 277/82* | (2006.01) |
| *C07D 417/04* | (2006.01) |
| *C07D 491/06* | (2006.01) |
| *A61K 31/428* | (2006.01) |

(52) U.S. Cl.
CPC ......... *C07D 491/052* (2013.01); *A61K 31/428* (2013.01); *A61K 31/4741* (2013.01); *A61K 45/06* (2013.01); *C07D 277/62* (2013.01); *C07D 277/64* (2013.01); *C07D 277/82* (2013.01); *C07D 417/04* (2013.01); *C07D 491/06* (2013.01)

(58) Field of Classification Search
None
See application file for complete search history.

(56) References Cited

U.S. PATENT DOCUMENTS

| | | |
|---|---|---|
| 3,895,028 A | 7/1975 | Wada et al. |
| 3,900,486 A | 8/1975 | Suzuki et al. |
| 4,816,570 A | 3/1989 | Farquhar |
| 4,968,788 A | 11/1990 | Farquhar |
| 5,434,188 A | 7/1995 | Boschelli et al. |
| 5,663,159 A | 9/1997 | Starrett, Jr. et al. |
| 5,733,906 A | 3/1998 | Jungheim et al. |
| 5,738,985 A | 4/1998 | Miles et al. |
| 5,792,756 A | 8/1998 | Starrett, Jr. et al. |
| 5,798,365 A | 8/1998 | Kirsch et al. |
| 7,514,233 B2 | 4/2009 | Debyser et al. |
| 8,008,470 B2 | 8/2011 | Debyser et al. |
| 2005/0165052 A1 | 7/2005 | Fakhfakh et al. |
| 2005/0239819 A1 | 10/2005 | Satoh et al. |
| 2005/0261336 A1 | 11/2005 | Mousnier et al. |
| 2006/0035926 A1 | 2/2006 | Lee et al. |
| 2006/0094755 A1 | 5/2006 | Rajagopalan et al. |
| 2006/0275748 A1 | 12/2006 | Debyser et al. |
| 2009/0197862 A1 | 8/2009 | Steinig et al. |
| 2010/0311735 A1 | 12/2010 | Tsantrizos et al. |
| 2011/0223131 A1 | 9/2011 | Jin et al. |
| 2012/0329780 A1 | 12/2012 | Thormann et al. |
| 2012/0329785 A1 | 12/2012 | Thormann et al. |
| 2013/0203727 A1 | 8/2013 | Babaoglu et al. |
| 2013/0210801 A1 | 8/2013 | Babaoglu et al. |
| 2013/0231331 A1 | 9/2013 | Pendri et al. |
| 2013/0281433 A1 | 10/2013 | Babaoglu et al. |
| 2013/0281434 A1 | 10/2013 | Babaoglu et al. |
| 2014/0031338 A1 | 1/2014 | Chasset et al. |
| 2014/0120087 A1 | 5/2014 | Schulze et al. |

OTHER PUBLICATIONS

Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.

Balakrishnan, M. et al. (Sep. 9, 2013). "Non-catalytic site HIV-1 integrase inhibitors disrupt core maturation and induce a reverse transcription block in target cells," *PloS One* 8(9):e74163, 12 Total Pages.

Balakrishnan, M. et al. (Sep. 9, 2013). "Non-catalytic site HIV-1 integrase inhibitors disrupt core maturation and induce a reverse transcription block in target cell," *PloS One* 8(9):e74163, 12 Total Pages.

Batholomeeusen, K. et al. (Apr. 24, 2009; e-pub. Feb. 25, 2009). "Lens epithelium-derived growth factor/p75 interacts with the transposase-derivved DDE domain of PogZ," *J. Biol. Chem,* 284(17):11467-11477.

(Continued)

*Primary Examiner* — Timothy R Rozof

(57) ABSTRACT

The invention provides compounds of formula I:

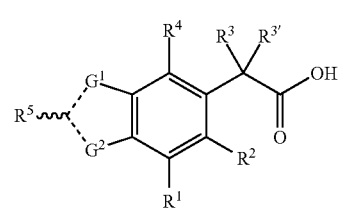

or a salt thereof as described herein. The invention also provides pharmaceutical compositions comprising a compound of formula I, processes for preparing compounds of formula I, intermediates useful for preparing compounds of formula I and therapeutic methods for treating the proliferation of the HIV virus, treating AIDS or delaying the onset of AIDS or ARC symptoms in a mammal using compounds of formula I.

6 Claims, No Drawings

(56) References Cited

OTHER PUBLICATIONS

Benzaria, S. et al. (Dec. 6, 1996). "Synthesis, In Vitro Anlviral Evaluation, and Stability Studies of Bis(S-Acyl-2-Thioethyl) Ester Derivatives of 9-[2-(Phosphonomethoxy)Ethyl]adenine(PMEA) as Potential PMEA Prodrugs with Improved Oral Bioavailability," J. Med. Chem. 39(25):4958-4965.

Bolivian Opposition submitted to the Bolivian Patent Office for Bolivian Patent Application No. SP-0194-2011, filed on Jul. 1, 2011, two pages.

Bolivian Opposition submited to the Bolivian Patent Office for Bolivian Patent Application No. SP-0195-2011, filed on Jul. 1, 2011, two pages.

Bundgaard, H. (1991). "Design and Application of Prodrugs," Chapter 5 in a Textbook of Drug Design and Development, Krogsgaard-Larsen, P. et al. eds., Harwood Academic Publishers, Chur, Switzerland, pp. 113-191.

Busschots, K. et al. (Feb. 2, 2007; e-pub. Nov. 3, 2006). "Identification of the LEDGF/p75 binding site in HIV-1 integrase," J. Mol. Biol. 365(5):1480-1492.

Busschots, K. et al. (Jan. 2009; e-pub. Oct. 16, 2008). "In search of small molecules blocking interactions between HIV proteins and intracellular cofactors," Mol. Biosyst. 5(1):21-31.

Chakraborty, A. et al. (Mar. 1, 2013; e-pub. Dec. 25, 2012). "Biochemical interactions between HIV-1 integrase and reverse transcriptase," FEBS Letters 587(5):425-429.

Cherepanov, P. et al. (Jun. 2005; e-pub. May 15, 2005). "Solution structure of the HIV-1 integrase-binding domain in LEDGF/p75," Nat. Struct. Mol. Biol. 12(6):526-532.

Cherepanov, P. et al. (Nov. 29, 2005; e-pub. Oct. 31, 2005). "Structural basis for the recognition between HIV-1 integrase and transcriptional coactivator p75," PNAS 102(48):17308-17313.

Christ, F. et al. (Aug. 2012; e-pub. Jun. 4, 2012). "Small-molecule inhibitors of the LEDGF/p75 binding site of integrase block HIV replication and modulate integrase multimerization," Antimocrob. Agents Chemother. 56(8):4365-4374.

Christ, F. et al. (Jun. 2012; e-pub. May 16, 2010). "Rational design of small-molecule inhibitors of the LEDGF/p75-integrase interaction and HIV replication," Nat. Chem. Biol., 25 total pages.

Costa Rican Office Action mailed on Aug. 23, 2013 for Costa Rican Patent Application No. 20130045, filed on Jul. 1, 2011, three pages.

Costa Rican Opposition submitted to the Costa Rican Patent Office for Costa Rican Patent Application No. 20130043, filed on Jul. 1, 2011, three pages.

De Lombaert, S. et al. (Feb. 18, 1994). "N-Phosphonmethyl Dipeptides and Their Phosphonate Prodrugs, A New Generation of Neutral Endopeptidase (NEP, EC 3.4.24.11) Inhibitors," J. Med. Chem. 37(4):498-511.

De Luca, L. et al. (Jul. 2011). "Inhibition of the interaction between HIV-1 integrase and its cofactor LEDGF/p75: a promising approach in anti-retroviral therapy," Mini Rev. Med. Chem. 11(8):714-727.

Desimmie, B.A. et al. (May 30, 2013). "LEDGINs inhibit late stage HIV-1 replication by modulating integrase multimerization in the virons," Retrovirology 10:57, 16 Total Pages.

Engleman, A. et al. (Mar. 28, 2008). "The lentiviral integrase binding protein LEDGF/p75 and HIV-1 replication," PloS Pathog. 4(3):e1000046, 9 Total Pages.

European Communication mailed on Feb. 8, 2013 for European Patent Application No. 11738878.5 filed on Jul. 1, 2011, two pages.

European Communication mailed on Mar. 12, 2014 for European Patent Application No. 11738878.5 filed on Jul. 1, 2011, eight pages.

European Communication mailed on Oct. 15, 2013 for European Patent Application No. 11738878.5 filed on Jul. 1, 2011, four pages.

Graham, R.L.J. et al. (2011). "Proteomic Analysis of LEDGF/p75 interactions with Nuclear Proteins," ASMS Poster, 1 page.

Hauser, F.M. et al. (1978). "Singlet Oxygen and Epoxidation from the Dehydration of Hydrogen Peroxide," J. Org. Chem. 43(1):180.

Hayouka, Z. et al. (2010). "Cyclic Peptide Inhibitors of HIV-1 Integrase Derived from the LEDGF/p75 Protein," Bioorganic & Medicinal Chemistry 18:8388-8395.

Hombrouck, A. et al. (Mar. 2007). "Virus Evolution Reveals an Exclusive Role for LEDGF/p75 in Chromosomal Tethering,"PloS 3(3):e47, 13 Total Pages.

Huang, X. et al. (2007). "A Novel Multicomponent Reaction of Arynes, β-Keto Sulfones, and Michael-Type Acceptors: A Direct Synthesis of Polysubstituted Naphthols and Naphthalenes," J. Org. Chem. 72:3965-3968.

Incorporation of a Masked Diketo Acid Pharmacophore, Tetrahedron Letters 42:8189-8192.

International Preliminary Report on Patentability mailed on Jan. 17, 2013, for PCT Patent Application No. PCT/US2011/042880 filed on Jul. 1, 2011, 7 pages.

International Search Report mailed on Aug. 5, 2013, for PCT Patent Application No. PCT/US2013/037483 filed on Apr. 19, 2013, three pages.

International Search Report mailed on Feb. 21, 2013, for PCT Patent Application No. PCT/US2013/020172 filed on Jan. 3, 2013, four pages.

International Search Report mailed on Jul. 2, 2012, for PCT Patent Application No. PCT/US2012/034593 filed on Apr. 20, 2013, five pages.

International Search Report mailed on Mar. 26, 2013, for PCT Patent Application No. PCT/US2013/020151 filed on Jan. 3, 2013, five pages.

International Search Report mailed on Sep. 1, 2011, for PCT Patent Application No. PCT/US2011/042880 filed on Jul. 1, 2011, four pages.

International Search Report mailed on Sep. 14, 2011, for PCT Patent Application No. PCT/US2011/042881 filed on Jul. 1, 2011, seven pages.

Johns, B.A. et al. (2013). "HIV Integrase Inhibitors," Chapter 6 in Successful Strategies for the Discovery of Antiviral Drugs, Desai, M.C. et al. eds., RSC Publishing, pp. 149-188.

Jurado, K.A. et al (2013). "Allosteric Integrase Inhibitor Potency is Determined through the Inhibition of HIV-1 Particle Maturation," PNAS 110(21):8690-8695.

Kessl, J.J. et al. (2011). "FRET Analysis Reveals Distinct Conformations of IN Tetramers in the Presence of Viral DNA or LEDGF/p75," Nuc. Acids Res., pp. 1-14.

Khamnei, S. et al. (Sep. 27, 1996). "Neighboring Group Catalysis in the Design of Nucleotide Prodrugs," J. Med. Chem. 39(20):4109-4115.

Kocienski, P.J. (May 1994). "Carbonyl Protecting Groups," Chapter 5 in Protecting Group, Thieme Publishing Group: New York, NY, pp. 155-184.

Kocienski, P.J. (May 1994). "Carbonyl Protecting Groups," Chapter 4 in Protecting Group, Thieme Publishing Group: New York, NY, pp. 118-154.

Kocienski, P.J. (May 1994). "Diol Protecting Groups," Chapter 3 in Protecting Group, Thieme Publishing Group: New York, NY, pp. 95-117.

Kocienski, P.J. (May 1994). "Hydroxyl Protecting Groups," Chapter 2 in Protecting Group, Thieme Publishing Group: New York, NY, pp. 21-94.

Kocienski, P.J. (May 1994). "Protecting Groups: An Overview," Chapter 1 in Protecting Group, Thieme Publishing Group: New York, NY, pp. 1-20.

Llano, M. et al. (Oct. 20, 2006; e-pub. Sep. 7, 2006). "An essential role for LEDGF/p75 in HIV integration," Science 314(5798):461-464.

Llano, M. et al. (Sep. 2004). "LEDGF/p75 determine cellular trafficking of diverse lentiviral but not murine oncoretroviral integrase proteins and is a component of functional lentiviral preintegration complexes," J. Virol. 78(17):9524-9537.

McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," Drug Metab. Dispos. 32(11):1247-1253.

Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," J. Med. Chem. 41(15):2846-2857.

(56) References Cited

OTHER PUBLICATIONS

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. II* 2345-2353.
Pakistani Office Action mailed on Nov. 10, 2012 for Pakistani Patent Application No. 4932011, filed on Jul. 1, 2011, two pages.
Pakistani Office Action mailed on Nov. 10, 2012 for Pakistani Patent Application No. 4942011, filed on Jul. 1, 2011, two pages.
Palella, F.J. et al. (Mar. 26, 1998). "Declining Morbidity and Morality Among Patients with Advanced Human Immunodeficiency Virus Infection," *N. Engl. J. Med.* 338(13):853-860.
Pauwels, R. et al. (Jun. 1987). "Sensitive and Rapid Assay on MT-4 Cells for Detection of Antiviral Compounds Against the AIDS Virus," *J. Virol. Methods* 16(3):171-185.
Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.
Philippines Office Action mailed on Mar. 14, 2014 for Philippine Patent Application No. 1/2013/500011, filed on Jul. 1, 2011, two pages.
Poeschla, E.M. et al. (2008). "Integrase, LEDGF/p75 and HIV Replication," *Cell. Mol. Life Sci.* 65:1403-1424.
Porto, S. et al. (2007). "Chiral Thiols: The Assignment of Their Absolute Configuration by 1HNMR," *Organic Letters* 9(24):5015-5018.
Puech, F. et al. (Oct. 1993). "Intracellular Delivery of Nucleoside Monophosphates Through a Reductase-Mediated Activation Process," *Antiviral Res.* 22(2-3):155-174.
Rain, J.C. et al. (2009). "Yeast-Two Hybrid Detection of Integrase-Host Factor Interactions," *Methods*, 7 Total Pages.
Rhodes, D.I. et al. (Oct. 17, 2011; e-pub. Aug. 17, 2011). "Crystal structures of novel allosteric peptide inhibitors of HIV integrase indentify new interactions at the LEDGF binding site," *Chembiochem.* 12(15):2311-2315.
Richman, D.D. (Apr. 19, 2001). "HIV Chemotherapy," *Nature* 410:995-1001.
Sagar, K.S. et al. (Aug. 1, 2004, e-pub. Jun. 19, 2004). "Preparation and Anti-HIV Activities of Retrojusticidin B Analogs and Azalignans," *Bioorg. Med. Chem.* 12(15):4045-4054.
Shun, M.C. et al. (Jul. 15, 2007). "LEDGF/p75 functions downstream from preintegration complex formation to effect gene-specific HIV-1 integration," *Genes Dev.* 21(14):1767-1778.
Suzuki, Y. et al. (Mar. 2007). "The road to chromatin—nuclear entry of retroviruses," *Nat. Rev. Microbiol.* 5(3):187-196.
Taiwanese Office Action mailed on Nov. 5, 2013 for Taiwanese Patent Application No. 100123357, filed on Jul. 1, 2011, nine pages.
Tsiang, M. et al. (Jun. 15, 2012; e-pub. Apr. 25, 2015). "New Class of HIV-1 integrase (IN) inhibitors with a dual mode of action," *J. Biol. Chem.* 287(25):21189-21203.
Vandekerckhove, L. et al. (Feb. 2006). "Transient and stable knockdown of the integrase cofactor LEDGF/p75 reveals its role in the replication cycle of human immunodeficiency virus," *J. Virol.* 80(4):1886-1896.
Walker, M.A. (2009). "New approaches for inhibiting HIV integrase: a journey beyond the active site," *Curr. Opin. Investig. Drugs* 10(2):129-136.
Wang, C.Y. et al. (Dec. 2004). "Pharmacokinetic and Metabolic Studies of Retrojusticidin B, A Potential Anti-Viral Lignan, in Rats," *Planta Medica* 70(12):1161-1165.
Willgerodt, C. et al. (1900). "Regarding Quino-?:p-?-Phenyl and Quino-?:p-? Methyl Quinoline-?-Hydroxy Acid," *Reports of the German Chemical Society* 33(3):2927-2935 (with full English Translation).
Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).
Written Opinion of the International Searching Authority mailed on Aug. 5, 2013, for PCT Patent Application No. PCT/US2013/037483 filed on Apr. 19, 2013, seven pages.
Written Opinion of the International Searching Authority mailed on Jul. 2, 2012, for PCT Patent Application No. PCT/US2012/034593 filed on Apr. 20, 2012, six pages.
Written Opinion of the International Searching Authority mailed on Sep. 1, 2011, for PCT Patent Application No. PCT/US2011/042880 filed on Jul. 1, 2011, six pages.
Written Opinion of the International Searching Authority mailed on Sep. 14, 2011, for PCT Patent Application No. PCT/US2011/042881 filed on Jul. 1, 2011, 12 pages.
Zouhiri, F. et al. (2001). HIV-1 Replication Inhibitors of the Styrylquinoline Class.

THERAPEUTIC COMPOUNDS

CROSS REFERENCE TO RELATED APPLICATION

This patent application claims the benefit of priority of U.S. application Ser. No. 61/477,922, filed Apr. 21, 2011, which application is hereby incorporated by reference.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the interaction of Lens Epithelial Derived Growth Factor (LEDGF/p75) and HIV-1 integrase.

SUMMARY OF THE INVENTION

The present invention provides compounds and methods for the treatment of an HIV infection. Accordingly, in one embodiment, the invention provides a compound of the invention which is a compound of formula I:

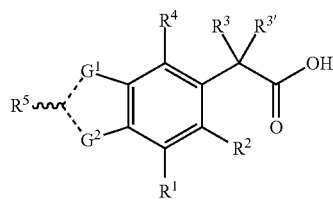

wherein:

$G^1$ is S, $G^2$ is N, the dashed bond connected to $G^1$ is a single bond, the dashed bond connected to $G^2$ is a double bond, and the wavy bond connected to $R^5$ is a single bond; or $G^1$ is N, $G^2$ is S, the dashed bond connected to $G^1$ is a double bond, the dashed bond connected to $G^2$ is a single bond, and the wavy bond connected to $R^5$ is a single bond; or $G^1$ is S, $G^2$ is $NR^6$, the dashed bond connected to $G^1$ is a single bond, the dashed bond connected to $G^2$ is a single bond, the wavy bond connected to $R^5$ is a double bond and $R^5$ is oxygen (e.g. "(wavy bond)-$R^5$" is "="));

$R^1$ is $R^{1a}$ or $R^{1b}$;
$R^2$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^5$ is $R^{5a}$ or $R^{5b}$;
$R^6$ is $R^{6a}$ or $R^{6b}$;

$R^{1a}$ is selected from:
a) halo;
b) $R^{11}$, $-C(=O)-R^{11}$, $-C(=O)-O-R^{11}$, $-O-R^{11}$, $-S-R^{11}$, $-S(O)-R^{11}$, $-SO_2-R^{11}$, $-(C_1-C_6)$alkyl-$R^{11}$, $-(C_1-C_6)$alkyl-C(O)-$R^{11}$, $-(C_1-C_6)$alkyl-C(=O)-O-$R^{11}$, $-(C_1-C_6)$alkyl-O-$R^{11}$, $-(C_1-C_6)$alkyl-S-$R^{11}$, $-(C_1-C_6)$alkyl-S(O)-$R^{11}$, and $-(C_1-C_6)$alkyl-SO_2-$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroacyl, wherein aryl, heterocycle or heteroaryl are each optionally substituted with one or more (e.g. 1, 2 or 3) $Z^{11}$ groups; and
c) $-N(R^9)R^{10}$, $-C(=O)-N(R^9)R^{10}$, $-O-C(=O)-N(R^9)R^{10}$, $-SO_2-N(R^9)R^{10}$, $-(C_1-C_6)$alkyl-N(R^9)R^{10}$, $-(C_1-C_6)$alkyl-C(=O)-N(R^9)R^{10}$, $-(C_1-C_6)$alkyl-O-C(=O)-N(R^9)R^{10}$ and $-(C_1-C_6)$alkyl-SO_2-N(R^9)R^{10}$, wherein each $R^9$ is independently selected from H, $(C_1-C_6)$alkyl and $(C_3-C_7)$cycloalkyl, and each $R^{10}$ is independently selected from $R^{11}$, $-(C_1-C_6)$alkyl-$R^{11}$, $-SO_2-R^{11}$, $-C(=O)-R^{11}$, $-C(=O)OR^{11}$ and $-C(=O)N(R^9)R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{1b}$ is selected from:
a) $-(C_1-C_6)$alkyl-O-$(C_1-C_6)$alkyl-$(C_3-C_7)$carbocycle, $-(C_1-C_6)$alkyl-S-$(C_1-C_6)$alkyl-$(C_3-C_7)$ carbocycle, $-(C_1-C_6)$alkyl-S(O)-$(C_1-C_6)$alkyl-$(C_3-C_6)$ carbocycle, $-(C_1-C_6)$alkyl-SO_2-$(C_1-C_6)$alkyl-$(C_3-C_7)$carbocycle, $-(C_1-C_6)$alkyl-SO_2-$(C_1-C_6)$alkyl $Z^{13}$, $-C(O)-(C_1-C_6)$alkyl-$Z^{13}$, $-O-(C_1-C_6)$alkyl-$Z^{13}$, $-S-(C_1-C_6)$alkyl-$Z^{13}$, $-S(O)-(C_1-C_6)$alkyl-$Z^{13}$, $-SO_2-(C_1-C_6)$alkyl-$Z^{13}$, $-(C_1-C_6)$alkyl-$Z^{14}$, $-(C_1-C_6)$alkyl-C(O)-(C_1-C_6)$alkyl-$Z^{13}$, $-(C_1-C_6)$alkyl-C(O)-O(C_1-C_6)$alkyl-$Z^{13}$, $-(C_1-C_6)$alkyl-O-$(C_1-C_6)$alkyl-$Z^{13}$, $-(C_1-C_6)$alkyl-S-$(C_1-C_6)$alkyl-$Z^{13}$, $-(C_2-C_6)$alkenyl-$(C_1-C_6)$haloalkyl, $-(C_2-C_6)$alkynyl-$(C_1-C_6)$haloalkyl, $-(C_3-C_7)$halocarbocycle, $-NR_aSO_2NR_cR_d$, $-NR_aSO_2O(C_3-C_7)$carbocycle, $-NR_aSO_2Oaryl$, $-(C_2-C_6)$alkenyl-$(C_3-C_7)$carbocycle, $-(C_2-C_6)$alkenyl-aryl, $-(C_2-C_6)$alkenyl-heteroaryl, $-(C_2-C_6)$alkenyl-heterocycle, $-(C_2-C_6)$alkynyl-$(C_3-C_7)$carbocycle, $-(C_2-C_6)$alkynyl-aryl, $-(C_2-C_6)$alkynyl-heteroaryl, $-(C_2-C_6)$alkynyl-heterocycle, $-(C_3-C_7)$carbocycle-$Z^1$ or $-(C_1-C_6)$haloalkyl-$Z^3$, wherein any $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl, either alone or as part of a group, is optionally substituted with one or more (e.g. 1, 2, 3, 4 or 5) $Z^1$ groups;
b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, or wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;
c) $(C_1-C_6)$alkyl, wherein $(C_1-C_6)$alkyl is substituted with one or more (e.g. 1, 2, 3, 4 or 5) $Z^2$ groups and optionally substituted with one or more (e.g. 1, 2, 3, 4 or 5) $Z^1$ groups;
d) $-X(C_1-C_6)$alkyl, $-X(C_1-C_6)$haloalkyl, $-X(C_2-C_6)$alkenyl, $-X(C_2-C_6)$alkynyl and $-X(C_3-C_7)$carbocycle, wherein $-X(C_1-C_6)$alkyl and $-X(C_1-C_6)$haloalkyl are each independently substituted with one or more $Z^3$ groups and optionally substituted with one or more $Z^1$ groups, and wherein $-X(C_2-C_6)$alkenyl, $-X(C_2-C_6)$alkynyl and $-X(C_3-C_7)$carbocycle, are each independently substituted with one or more (e.g. 1, 2, 3, 4 or 5) $Z^4$ groups and optionally substituted with one or more $Z^1$ groups;

e) aryl, heteroaryl, heterocycle, —Xaryl, —Xheteroaryl and —Xheterocycle; wherein aryl heteroaryl and heterocycle, either alone or as part of a group, are each independently substituted with one or more (e.g. 1, 2, 3, 4 or 5) $Z^5$ groups and optionally substituted with one or more $Z^1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more $Z^1$ groups;

g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$; wherein each $(C_1-C_6)$alkyl, as part of a group, is independently substituted with one or more (e.g. 1, 2, 3, 4 or 5) $Z^6$ groups and optionally substituted with one or more $Z^1$ groups; and h) nitro and cyano;

$R^{2a}$ is selected from:

a) halo;

b) $R^{11}$, $C(=O)$—$R^{11}$, —$C(=O)$—O—$R^{11}$, —O—$R^{11}$, —S—$R^{11}$, —S(O)—$R^{11}$, —$SO_2$—$R^{11}$, —$(C_1-C_6)$alkyl-$R^{11}$, —$(C_1-C_6)$alkyl-$C(=O)$—$R^{11}$, —$(C_1-C_6)$alkyl-$C(=O)$—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-$SO_2$—$R^{11}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl and heterocycle and heteroaryl, wherein aryl, heterocycle or heteroaryl are each optionally substituted with one or more (e.g. 1, 2 or 3) $Z^{11}$ groups; and c) —$N(R^9)R^{10}$, —$C(=O)$—$N(R^9)R^{10}$, —O—$C(=O)$—$N(R^9)R^{10}$, —$SO_2$—$N(R^9)R^{10}$, —$(C_1-C_6)$alkyl-$N(R^9)R^{10}$, —$(C_1-C_6)$alkyl-$C(=O)$—$N(R^9)R^{10}$, —$(C_1-C_6)$alkyl-O—$C(=O)$—$N(R^9)R^{10}$, and —$(C_1-C_6)$alkyl-$SO_2$—$N(R^9)R^{10}$, wherein each $R^9$ is independently selected from H, $(C_1-C_6)$alkyl and $(C_3-C_7)$cycloalkyl, wherein each $R^{10}$ is independently selected from $R^{11}$, —$(C_1-C_6)$alkyl-$R^{11}$, —$SO_2$—$R^{11}$, —$C(=O)$—$R^{11}$, —$C(=O)OR^{11}$ and —$C(=O)N(R^9)R^{10}$, wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{2b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C)$carbocycle, —$(C_1-C_6)$alkyl-S(O)—$(C_1-C_6)$alkyl-$(C_3-C_7)$carbocycle, —$(C_1-C_6)$alkyl-$SO_2$—$(C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_1-C_6)$alkyl-$SO_2$—$(C_1-C_6)$alkyl-$Z^{13}$, —C(O)—$(C_1-C_6)$alkyl-$Z^{13}$, —O—$(C_1-C_6)$alkyl-$Z^{13}$, —S—$(C_1-C_6)$alkyl-$Z^{13}$, —S(O)—$(C_1-C_6)$alkyl-$Z^{13}$, —$SO_2$—$(C_1-C_6)$alkyl-$Z^{13}$, —$(C_1-C_6)$alkyl-$Z^{14}$, —$(C_1-C_6)$alkyl-C(O)—$(C_1-C_6)$alkyl-$Z^{13}$, —$(C_1-C_6)$alkyl-C(O)—O$(C_1-C_6)$alkyl-$Z^{13}$, —$(C_1-C_6)$alkyl-O—$(C_1-C_6)$alkyl-$Z^{13}$, —$(C_1-C_6)$alkyl-S—$(C_1-C_6)$alkyl-$Z^{13}$, —$(C_3-C_7)$halocarbocycle, —$NR_aSO_2NR_cR_d$, —$NR_aSO_2O(C_3-C_7)$carbocycle, —$NR_aSO_2O$aryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or —$(C_1-C_6)$haloalkyl-$Z^3$, wherein any $(C_1-C_6)$alkyl, —$(C_1-C_6)$haloalkyl, $(C_3-C_7)$carbocycle, $(C_2-C_6)$alkenyl, $(C_2-C_6)$alkynyl, aryl or heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z_1$ groups, wherein two $Z_1$ groups together with the atom or atoms to which they are attached optionally form a $(C_3-C_7)$carbocycle or heterocycle wherein the $(C_3-C_6)$ carbocycle or heterocycle is optionally substituted with one or more (e.g. 1, 2, 3, 4 or 5) $Z_1$ groups;

c) $(C_1-C_6)$alkyl, wherein $(C_1-C_6)$alkyl is substituted with one or more $Z^2$ groups and optionally substituted with one or more (e.g. 1, 2, 3, 4 or 5) $Z_1$ groups;

d) —$X(C_1-C_6)$alkyl, —$X(C_1-C_6)$haloalkyl, —$X(C_2-C_6)$alkenyl, —$X(C_2-C_6)$alkynyl and —$X(C_3-C_7)$carbocycle, wherein —$X(C_1-C_6)$alkyl and $X(C_1-C_6)$haloalkyl are each independently substituted with one or more $Z^3$ groups and optionally substituted with one or more (e.g. 1, 2, 3, 4 or 5) $Z_1$ groups, and wherein —$X(C_2-C_6)$alkenyl, —$X(C_2-C_6)$alkynyl and —$X(C_3-C_7)$carbocycle are each independently substituted with one or more (e.g. 1, 2, 3, 4 or 5) $Z^4$ groups and optionally substituted with one or more $Z_1$ groups;

e) aryl, heteroaryl, heterocycle, —Xaryl, —Xheteroaryl and —Xheterocycle, wherein aryl heteroaryl and heterocycle, either alone or as part of a group, are each independently substituted with one or more (e.g. 1, 2, 3, 4 or 5) $Z^5$ groups and optionally substituted with one or more (e.g. 1, 2, 3, 4 or 5) $Z_1$ groups;

f) $(C_1-C_6)$haloalkyl, $(C_3-C_7)$carbocycle, $(C_2-C_6)$alkenyl, and $(C_2-C_6)$alkynyl, wherein $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups;

g) —$NR_eR_f$, —$C(O)NR_eR_f$, —$OC(O)NR_eR_f$, —$SO_2NR_eR_f$, —$(C_1-C_6)$alkyl-$NR_eR_f$, —$(C_1-C_6)$alkylC(O)—$NR_eR_f$, —$(C_1-C_6)$alkyl-O—C(O)—$NR_eR_f$ and —$(C_1-C_6)$alkyl-$SO_2NR_eR_f$, wherein each $(C_1-C_6)$alkyl, as part of a group, is independently substituted with one or more (e.g. 1, 2, 3, 4 or 5) $Z^6$ groups and optionally substituted with one or more (e.g. 1, 2, 3, 4 or 5) $Z^1$ groups; and h) nitro and cyano;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are optionally substituted with one or more $Z^1$ groups;

or $R^1$ and $R^2$ together with the atoms to which they are attached form a 5 or 6-membered carbocycle or a 4, 5, 6 or 7-membered heterocycle, wherein the 5 or 6-membered carbocycle or a 4, 5, 6 or 7-membered heterocycle are each independently substituted with one or more (e.g. 1, 2 or 3) $Z^7$ or $Z^8$ groups, or wherein when two $Z^7$ groups are on same atom the two $Z^7$ groups together with the atom to which they are attached optionally form a $(C_3-C_7)$carbocycle or 4, 5 or 6-membered heterocycle;

$R^{3a}$ is $(C_1-C_6)$alkyl, $(C_1-C_6)$haloalkyl, $(C_2-C_6)$alkenyl, $(C_2-C_6)$alkynyl, —$(C_1-C_6)$alkyl-$(C_3-C_7)$cycloalkyl, —$(C_1-C_6)$alkyl-aryl, —$(C_1-C_6)$alkyl-heterocycle, —$(C_1-C_6)$alkyl-heteroaryl, —$O(C_1-C_6)$alkyl, —$O(C_1-C_6)$haloalkyl, —$O(C_2-C_6)$alkenyl, —$O(C_2-C_6)$alkynyl, —$O(C_3-C_7)$cycloalkyl, —Oaryl, —$O(C_1-C_6)$alkyl-$(C_3-C_7)$cycloalkyl, —$O(C_1-C_6)$alkyl-aryl, —$O(C_1-C_6)$alkyl-heterocycle and —$O(C_1-C_6)$alkyl-heteroaryl, wherein any $(C_1-C_6)$alkyl, $(C_1-C_6)$haloalkyl, $(C_2-C_6)$alkenyl, $(C_2-C_6)$alkynyl, —$(C_1-C_6)$alkyl-$(C_3-C_7)$cycloalkyl, —$(C_1-C_6)$alkyl-aryl, —$(C_1-C_6)$alkyl-heterocycle, —$(C_1-C_6)$alkyl-heteroaryl, —$O(C_1-C_6)$alkyl, —$O(C_1-C_6)$haloalkyl, —$(C_2-C_6)$alkenyl, —$O(C_2-$ C$_6$)alkynyl, —O(C$_3$-C$_7$)cycloalkyl, —Oaryl, —O(C$_1$-C$_6$)alkyl-(C$_3$-C$_7$)cycloalkyl, —O(C$_1$-C$_6$)alkyl-aryl, —O(C$_1$-C$_6$)alkyl-heterocycle or —O(C$_1$-C$_6$)alkyl-heteroaryl of R$^{3a}$ is optionally substituted with one or more (e.g. 1, 2 or 3) groups selected from (C$_1$-C$_6$)alkyl, —O(C$_1$-C$_6$)alkyl, halo, oxo and —CN; and R$^{3a}$ is H;

R$^{3b}$ is —(C$_3$-C$_7$)carbocycle, aryl, heteroaryl, heterocycle, —(C$_1$-C$_6$)alkylOH, —(C$_1$-C$_6$)alkyl-O—(C$_1$-C$_6$)alkyl-Z$^{12}$, —(C$_1$-C$_6$)alkyl-O—(C$_2$-C$_6$)alkenyl-Z$^{12}$, —(C$_2$-C$_6$)alkyl-O—(C$_2$-C$_6$)alkynyl-Z$^{12}$, —(C$_1$-C$_6$)alkyl-S—(C$_1$-C$_6$)alkyl-Z$^{12}$, —(C$_1$-C$_6$)alkyl-S—(C$_2$-C$_6$)alkenyl-Z$^{12}$, —(C$_2$-C$_6$)alkyl-S—(C$_2$-C$_6$)alkynyl-Z$^{12}$, —(C$_1$-C$_6$)alkyl-S(O)—(C$_1$-C$_6$)alkyl-Z$^{12}$, —(C$_1$-C$_6$)alkyl-S(O)(C$_2$-C$_6$)alkenyl-Z$^{12}$, —(C$_2$-C$_6$)alkyl-S(O)—(C$_2$-C$_6$)alkynyl-Z$^{12}$, —(C$_1$-C$_6$)alkyl-SO$_2$—(C$_1$-C$_6$)alkyl-Z$^{12}$, —(C$_1$-C$_6$)alkyl-SO$_2$—(C$_2$-C$_6$)alkenyl-Z$^{12}$, —(C$_2$-C$_6$)alkyl-SO$_2$—(C$_2$-C$_6$)alkynyl-Z$^{12}$, —(C$_2$-C$_6$)alkyl-NR$_a$R$_b$, —(C$_2$-C$_6$)alkylOC(O)—NR$_c$R$_d$, —(C$_2$-C$_6$)alkyl-NR$_a$—C(O)—OR$_b$, —(C$_2$-C$_6$)alkyl-NR$_a$—C(O)—NR$_a$R$_b$, —(C$_1$-C$_6$)alkyl-SO$_2$(C$_1$-C$_6$)alkyl, —(C$_1$-C$_6$)alkyl-SO$_2$NR$_c$R$_d$, —(C$_1$-C$_6$)alkyl-NR$_a$SO$_2$NR$_c$R$_d$, —(C$_1$-C$_6$)alkyl-NR$_a$SO$_2$O(C$_3$-C$_7$)carbocycle, —(C$_1$-C$_6$)alkyl-NR$_a$SO$_2$Oaryl, —(C$_1$-C$_6$)alkyl-NR$_a$—SO$_2$—(C$_1$-C$_6$)alkyl, —(C$_1$-C$_6$)alkyl-NR$_a$—SO$_2$—(C$_1$-C$_6$)haloalkyl, —(C$_1$-C$_6$)alkyl-NR$_a$—SO$_2$—(C$_2$-C$_6$)alkenyl, —(C$_1$-C$_6$)alkyl-NR$_a$—SO$_2$—(C$_2$-C$_6$)alkynyl, —(C$_1$-C$_6$)alkyl-NR$_a$—SO$_2$—(C$_3$-C$_7$)carbocycle, (C$_1$-C$_6$)alkyl-NR$_a$—SO$_2$—(C$_3$-C$_7$)halocarbocycle, —(C$_1$-C$_6$)alkyl-NR$_a$—SO$_2$-alkyl, —(C$_1$-C$_6$)alkyl-NR$_a$—SO$_2$-heteroaryl, —(C$_1$-C$_6$)alkyl-NR$_a$—SO$_2$-heterocycle, —O(C$_1$-C$_6$)alkyl-NR$_a$R$_b$, —O(C$_1$-C$_6$)alkyl OC(O)—NR$_c$R$_d$, —O(C$_1$-C$_6$)alkyl-NR$_a$—C(O)—OR$_b$, —O(C$_1$-C$_6$)alkyl-NR$_a$—C(O)—NR$_a$R$_b$, —O(C$_1$-C$_6$)alkyl-NR$_a$—SO$_2$—(C$_1$-C$_6$)alkyl, —O(C$_1$-C$_6$)alkyl-NR$_a$—SO$_2$—(C$_1$-C$_6$)haloalkyl, —O(C$_1$-C$_6$)alkyl-NR$_a$—SO$_2$—(C$_2$-C$_6$)alkenyl, —O(C$_1$-C$_6$)alkyl-NR$_a$—SO$_2$—(C$_2$-C$_6$)alkynyl, —O(C$_1$-C$_6$)alkyl-NR$_a$—SO—(C$_3$-C$_7$)carbocycle, —O(C$_1$-C$_6$)alkyl-NR$_a$—SO$_2$—(C$_3$-C$_7$)halocarbocycle, —O(C$_1$-C$_6$)alkyl-NR$_a$—SO$_2$-aryl, —O(C$_1$-C$_6$)alkyl-NR$_a$—SO$_2$-heteroaryl, —O(C$_1$-C$_6$)alkyl-NR$_a$—SO$_2$-heterocycle, —O(C$_1$-C$_6$)alkyl-NR$_a$—SO$_2$—NR$_a$R$_b$, —O(C$_1$-C$_6$)alkyl-NR$_a$—SO$_2$—(C$_3$-C$_7$)carbocycle, —O(C$_1$-C$_6$)alkyl-NR$_a$—SO$_2$—(C$_3$-C$_7$)halocarbocycle, —O(C$_1$-C$_6$)alkyl-NR$_a$—SO$_2$-aryl, —O(C$_1$-C$_6$)alkyl-NR$_a$SO$_2$NR$_c$R$_d$, —O(C$_1$-C$_6$)alkyl-NR$_a$SO$_2$O(C$_3$-C$_7$)carbocycle, —O(C$_1$-C$_6$)alkyl-NR$_a$SO$_2$Oaryl, —Oheteroaryl, —Oheterocycle, —Sheteroaryl, —Sheterocycle, —S(O)heteroaryl, —S(O)heterocycle, —SO$_2$heteroaryl or —SO$_2$heterocycle, wherein any (C$_1$-C$_6$)alkyl, (C$_2$-C$_6$)alkenyl, (C$_2$-C$_6$)alkynyl, aryl, (C$_3$-C$_7$)carbocycle, heteroaryl or heterocycle of R$^{3b}$, either alone or as part of a group, is optionally substituted with one or more (e.g. 1, 2, 3, 4 or 5) Z$^1$ groups; and R$^{3b}$ is H, (C$_1$-C$_6$)alkyl or —O(C$_1$-C$_6$)alkyl; or R$^{3b}$ and R$^{3b'}$ together with the carbon to which they are attached form a heterocycle or (C$_3$-C$_7$)carbocycle, which heterocycle or (C$_3$-C$_7$)carbocycle of R$^{3b}$ and R$^{3b'}$ together with the carbon to which they are attached is optionally substituted with one or more (e.g. 1, 2, 3, 4 or 5) Z$_1$ groups;

R$^{4a}$ is selected from aryl, heterocycle and heteroaryl, wherein any aryl, heterocycle and heteroaryl of R$^{4a}$ is optionally substituted with one or more (e.g. 1, 2, 3, 4 or 5) groups each independently selected from halo, (C$_1$-C$_6$)alkyl, (C$_2$C)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, —NH$_2$, —NH(C$_1$—C)alkyl and —N((C$_1$-C$_6$)alkyl)$_2$, wherein (C$_1$-C$_6$)alkyl is optionally substituted with hydroxy, —O(C$_1$-C$_6$)alkyl, cyano or oxo;

R$^{4b}$ is selected from;

a) (C$_1$-C$_6$)alkyl, (C$_2$—C)alkenyl and (C$_2$-C$_6$)alkynyl, wherein (C$_1$-C$_6$)alkyl, (C$_2$-C$_6$)alkenyl or (C$_2$-C$_6$)alkynyl are each optionally substituted with one or more (e.g. 1, 2, 3, 4 or 5) Z$^1$ groups;

b) (C$_3$-C$_{14}$)carbocycle, wherein (C$_3$-C$_{14}$)carbocycle is optionally substituted with one or more (e.g. 1, 2, 3, 4 or 5) Z$^1$ groups, or wherein two Z$^1$ groups together with the atom or atoms to which they are attached optionally form a (C$_3$-C$_7$)carbocycle or heterocycle;

c) Spiro-heterocycle or bridged-heterocycle, wherein spiro-heterocycle or bridged-heterocycle is optionally substituted with one or more (e.g. 1, 2, 3, 4 or 5) Z$^1$ groups, or wherein two Z$^1$ groups together with the atom or atoms to which they are attached optionally form a (C$_3$-C$_7$)carbocycle or heterocycle; and d) aryl, heteroaryl, spiro-heterocycle, fused-heterocycle, or bridged-heterocycle, wherein aryl, heteroaryl, spiro-heterocycle, fused-heterocycle and bridged-heterocycle are each independently substituted with one or more Z$^7$ groups and optionally substituted with one or more (e.g. 1, 2, 3, 4 or 5) Z$^1$ groups; or R$^4$ and R$^3$ together with the atoms to which they are attached form a macroheterocycle or a macrocarbocycle, wherein any macroheterocycle or macrocarbocycle of R$^4$ and R$^3$ together with the atoms to which they are attached may be optionally substituted with one or more (e.g. 1, 2, 3, 4 or 5) Z$^1$ groups; and R$^{3b'}$ is H or (C$_1$-C$_6$)alkyl, —O(C$_1$-C$_6$)alkyl;

R$^{5a}$ is selected from:

a) halo;

b) R$^{11}$, —C(=O)—R$^{11}$, —C(=O)—O—R$^{11}$, —O—R$^{11}$, —S—R$^{11}$, —S(O)—R$^{11}$, —SO$_2$—R$^{11}$, —(C$_1$-C$_6$)alkyl-R$^{11}$, —(C$_1$-C$_6$)alkyl-C(=O)—R$^{11}$, —(C$_1$-C$_6$)alkyl-C(=O)—O—R$^{11}$, —(C$_1$-C$_6$)alkyl-O—R$^{11}$, —(C$_1$-C$_6$)alkyl-S—R$^{11}$, —(C$_1$-C$_6$)alkyl-S(O)—R$^{11}$ and —(C$_1$-C$_6$)alkyl-SO$_2$—R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, aryl, heterocycle and heteroaryl, wherein aryl, heterocycle and heteroaryl are each optionally substituted with one or more (e.g. 1, 2 or 3) Z$^{11}$ groups; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$, and —(C$_1$-C$_6$)alkyl-SO$_2$—N(R$^9$)R$^{10}$, wherein each R$^9$ is independently selected from H, (C$_1$-C$_6$)alkyl and (C$_3$-C$_7$)cycloalkyl, and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

R$^{5b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkylS(O)—(C$_1$-C$_6$)alkyl-(C$_3$-C$_6$)carbocycle, —(C$_1$-C$_6$)alkylSO$_2$(C$_1$-C$_6$)alkyl-(C$_3$—C)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or —(C$_1$-C$_6$)haloalkyl-Z$^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl, either alone or as part of a group is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle or bridged-bicyclic carbocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$)carbocycle or heterocycle wherein the ($C_3$-$C_7$)carbocycle or heterocycle is optionally substituted with one or more (e.g. 1, 2, 3, 4 or 5) $Z^1$ groups;

c) ($C_1$-$C_6$)alkyl, wherein ($C_1$-$C_6$)alkyl is substituted with one or more $Z^2$ groups and optionally substituted with one or more (e.g. 1, 2, 3, 4 or 5) $Z^1$ groups;

d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle, wherein —X($C_1$-$C_6$)alkyl and —X($C_1$-$C_6$)haloalkyl are each independently substituted with one or more $Z^3$ groups and optionally substituted with one or more $Z^1$ groups, and wherein —X($C_2$-$C_6$)alkenyl, —X($C_2$-$C_6$)alkynyl and —X($C_3$-$C_7$)carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein aryl, heteroaryl and heterocycle, either alone or as part of a group, are each independently substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl, and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups;

g) —$NR_eR_f$, —$C(O)NR_eR_f$, —$OC(O)NR_eR_f$, —$SO_2NR_eR_f$, —($C_1$-$C_6$)alkyl-$NR_eR_f$, —($C_1$-$C_6$)alkylC(O)—$NR_eR_f$, —($C_1$-$C_6$)alkyl-O—C(O)—$NR_eR_f$ and ($C_1$-$C_6$)alkyl-$SO_2NR_eR_f$, wherein each ($C_1$-$C_6$)alkyl is independently substituted with one or more (e.g. 1, 2, 3, 4 or 5) $Z^6$ groups and optionally substituted with one or more (e.g. 1, 2, 3, 4 or 5) $Z^1$ groups;

h) nitro and cyano;

i) aryl, heteroaryl and heterocycle, wherein aryl, heteroaryl and heterocycle are each independently substituted with one or more (e.g. 1, 2, 3, 4 or 5) $Z^5$ groups and optionally substituted with one or more (e.g. 1, 2, 3, 4 or 5) $Z^{15}$ groups;

and j) oxo;

$R^{6a}$ is selected from:

a) $R^{11}$, —C(=O)—$R^{11}$, —C(=O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, aryl, heterocycle and heteroaryl, wherein aryl, heterocycle and heteroaryl are each optionally substituted with one or more (e.g. 1, 2 or 3) $Z^{11}$ groups; and b) —C(=O)—N($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C(=O)—N($R^9$)$R^{10}$ and —($C_1$-$C_6$)alkyl-$SO_2$—N($R^9$)$R^{10}$, wherein each $R^9$ is independently selected from H, ($C_1$-$C_6$)alkyl and ($C_3$-$C_7$)cycloalkyl, and each $R^{10}$ is independently selected from $R^{11}$, —($C_1$-$C_6$)alkyl-$R^{11}$, —$SO_2$—$R^{11}$, —C(=O)—$R^{11}$, —C(=O)O$R^{11}$ and —C(=O)N($R^9$)$R^{11}$, wherein each $R^{11}$ is independently selected from H, ($C_1$-$C_6$)alkyl, ($C_2$-$C_6$)alkenyl, ($C_2$-$C_6$)alkynyl, ($C_1$-$C_6$)haloalkyl, ($C_3$-$C_7$)cycloalkyl, —($C_1$-$C_6$)alkylaryl, aryl, heterocycle and heteroaryl, wherein aryl, heterocycle and heteroaryl are each optionally substituted with one or more (e.g. 1, 2 or 3) $Z^{11}$ groups;

$R^{6b}$ is selected from:

a) —($C_1$-$C_6$)alkyl-$SO_2$—($C_1$-$C_6$)alkyl-$Z^{13}$, —C(O)—($C_1$-$C_6$)alkyl-$Z^{13}$, —O—($C_1$-$C_6$)alkyl-$Z^{13}$, —S—($C_1$-$C_6$)alkyl-$Z^{13}$, —S(O)—($C_1$-$C_6$)alkyl-$Z^{13}$, —$SO_2$—($C_1$-$C_6$))alkyl-$Z^{13}$, —($C_1$-$C_6$)alkyl-$Z^{14}$, —($C_1$-$C_6$)alkyl-C(O)—($C_1$-$C_6$)alkyl-$Z^{13}$, —($C_1$-$C_6$)alkyl-C(O)—O($C_1$-$C_6$)alkyl-$Z^{13}$, —($C_1$-$C_6$)alkyl-O—($C_1$-$C_6$)alkyl-$Z^{13}$, —($C_1$-$C_6$)alkyl-S—($C_1$-$C_6$)alkyl-$Z^{13}$, —($C_1$-$C_6$)alkyl-O—($C_1$-$C_6$)alkyl-($C_3$-$C_7$)carbocycle, —($C_1$-$C_6$)alkyl-S—($C_1$-$C_6$)alkyl-($C_3$-$C_7$)carbocycle, —($C_1$-$C_6$)alkyl-S(O)—($C_1$-$C_6$)alkyl-($C_3$-$C_7$)carbocycle, —($C_1$-$C_6$)alkyl-$SO_2$—($C_1$-$C_6$)alkyl-($C_3$-$C_7$)carbocycle, —($C_2$-$C_6$)alkenyl-($C_1$-$C_6$)haloalkyl, —($C_2$-$C_6$)alkynyl-($C_1$-$C_6$)haloalkyl, —($C_3$-$C_7$)halocarbocycle, —($C_2$-$C_6$)alkenyl-($C_3$-$C_7$)carbocycle, —($C_2$-$C_6$)alkenyl-aryl, —($C_2$-$C_6$)alkenyl-heteroaryl, —($C_2$-$C_6$)alkenyl-heterocycle, —($C_2$-$C_6$)alkynyl-($C_3$-$C_7$)carbocycle, —($C_2$-$C_6$)alkynyl-aryl, —($C_2$-$C_6$)alkynyl-heteroaryl, —($C_2$-$C_6$)alkynyl-heterocycle, —($C_3$-$C_7$)carbocycle-$Z^1$, —($C_1$-$C_6$)haloalkyl-$Z^3$, —$NR_aSO_2NR_cR_d$, —$NR_aSO_2O$($C_3$-$C_7$)carbocycle and —$NR_aSO_2O$aryl, wherein any ($C_1$-$C_6$)alkyl, ($C_1$-$C_6$)haloalkyl, ($C_3$-$C_7$)carbocycle, ($C_2$-$C_6$)alkenyl, ($C_2$-$C_6$)alkynyl, aryl, heterocycle and heteroaryl, either alone or as part of a group, is optionally substituted with one or more (e.g. 1, 2, 3, 4 or 5) $Z^1$ groups;

b) spiro-bicyclic carbocycle, fused-bicyclic carbocycle and bridged-bicyclic carbocycle, wherein any spiro-bicyclic carbocycle, fused-bicyclic carbocycle and bridged-bicyclic carbocycle is optionally substituted with one or more (e.g. 1, 2, 3, 4 or 5) $Z^1$ groups, or wherein two $Z^1$ groups together with the atom or atoms to which they are attached optionally form a ($C_3$-$C_7$)carbocycle or heterocycle wherein the ($C_3$-$C_7$)carbocycle or heterocycle is optionally substituted with one or more (e.g. 1, 2, 3, 4 or 5) $Z^1$ groups;

c) ($C_1$-$C_6$)alkyl, wherein ($C_1$-$C_6$)alkyl is substituted with one or more (e.g. 1, 2, 3, 4 or 5) $Z^2$ groups and optionally substituted with one or more (e.g. 1, 2, 3, 4 or 5) $Z^1$ groups;

d) —X($C_1$-$C_6$)alkyl, —X($C_1$-$C_6$)haloalkyl, —X($C_2$-$C_6$)alkenyl, —X($C_2$-$C_6$)alkynyl and —X($C_3$-$C_7$)carbocycle, wherein —X($C_1$-$C_6$)alkyl and —X($C_1$-$C_6$)haloalkyl, are each independently substituted with one or more (e.g. 1, 2, 3, 4 or 5) $Z^3$ groups and optionally substituted with one or more (e.g. 1, 2, 3, 4 or 5) $Z^1$ groups, and wherein —X($C_2$-$C_6$)alkenyl, —X($C_2$-$C_6$)alkynyl and —X($C_3$-$C_7$)carbocycle, are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle, wherein aryl, heteroaryl and heterocycle, either alone or as part of a group, are each independently substituted with one or more (e.g. 1, 2, 3, 4 or 5) $Z^5$ groups and optionally substituted with one or more (e.g. 1, 2, 3, 4 or 5) $Z^1$ groups;

f) ($C_1$-$C_6$)haloalkyl, ($C_3$-$C_7$)carbocycle, ($C_2$-$C_6$)alkenyl and ($C_2$-$C_6$)alkynyl, wherein ($C_1$-$C_6$)haloalkyl, ($C_3$-$C_7$)carbocycle, ($C_2$-$C_6$)alkenyl and ($C_2$-$C_6$)alkynyl are each independently substituted with one or more (e.g. 1, 2, 3, 4 or 5) $Z^6$ groups and optionally substituted with one or more (e.g. 1, 2, 3, 4 or 5) $Z^1$ groups; and g) —C(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$ wherein any (C$_1$-C$_6$) alkyl, as part of a group, is optionally substituted with one or more (e.g. 1, 2, 3, 4 or 5) Z$^1$ groups;

each X is independently selected from O, —C(O)—, —C(O)O—, —S—, —S(O)—, —SO$_2$—, —(C$_1$-C$_6$) alkylO—, —(C$_1$-C$_6$)alkylC(O)—, —(C$_1$-C$_6$)alkylC(O)O—, —(C$_1$-C$_6$)alkylS—, —(C$_1$-C$_6$)alkylS(O)— and —(C$_1$-C$_6$)alkylSO$_2$—;

each Z$^1$ is independently selected from halo, —NO$_2$, —OH, =NOR$_a$, —SH, —CN, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, (C$_3$-C$_7$)halocarbocycle, aryl, heteroaryl, heterocycle, —O(C$_1$-C$_6$)alkyl, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —Oheteroaryl, —Oheterocycle, —S(C$_1$-C$_6$)alkyl, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —Saryl, —Sheteroaryl, —Sheterocycle, —S(O)(C$_1$-C$_6$)alkyl, —S(O)(C$_2$-C$_6$)alkenyl, —S(O)C$_2$-C$_6$)alkynyl, —S(O)(C$_1$-C$_6$)haloalkyl, —S(O) (C$_3$-C$_7$)carbocycle, —S(O)(C$_3$-C$_7$)halocarbocycle, —SO$_2$(C$_1$-C$_6$)alkyl, —S(O)aryl, —S(O)carbocycle, —S(O)heteroaryl, —S(O)heterocycle, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$NR$_c$R$_d$, —NR$_a$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$^d$, wherein any (C$_1$-C$_6$) alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^1$, either alone or as part of a group, is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle or —S(O)$_2$NR$_c$R$_d$;

each Z$^2$ is independently selected from —NO$_2$, —CN, spiro-heterocycle, bridge-heterocycle, spiro-bicyclic carbocycle, bridged-bicyclic carbocycle, NR$_a$SO$_2$(C$_3$-C$_7$)carbocycle, —NR$_a$SO$_2$aryl, —NR$_a$SO$_2$heteroaryl, —NR$_a$SO$_2$R$_c$R$_d$, —NR$_a$SO$_2$O(C$_3$-C$_7$)carbocycle and —NR$_a$SO$_2$Oaryl;

each Z$^3$ is independently selected from —NO$_2$, —CN, —OH, oxo, =NOR$_a$, thioxo, aryl-heterocycle, heteroaryl, (C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O) (C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^4$ is independently selected from halogen, —(C$_1$-C$_6$)alkyl, (C$_3$-C$_7$)carbocycle, —(C$_1$-C$_6$)haloalkyl, —NO$_2$, —CN, —OH, oxo, =NOR$_a$ thioxo, -aryl, -heterocycle, -heteroaryl, —(C$_3$-C$_7$)halocarbocycle, —O(C$_1$-C$_6$)alkyl, —O(C$_3$-C$_7$)Carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroayl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_a$, —C(O)NR$_c$R$_d$, —SO$_2$NR$_c$R$_d$, —NR$_a$SO$_2$NR$_c$R$^d$, —NR$_a$SO$_2$O(C$_3$-C$_7$)carbocycle and —NR$_a$SO$_2$Oaryl;

each Z$^5$ is independently selected from —NO$_2$, —CN, —NR$_a$SO$_2$NR$_c$R$^d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$heteroaryl, —NR$_a$SO$_2$heteroaryl, —NR$_a$SO$_2$heterocycle, —NR$_a$C(O) alkyl, —NR$_a$C(O)alkenyl, —NR$_a$C(O)alkynyl, —NR$_a$C(O) (C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each Z$^6$ is independently selected from —NO$_2$, —CN, —NR$_a$R$_a$, NR$_a$C(O)R$_b$, —C(O)NR$_c$R$_d$, (C$_3$-C$_7$)halocarbocycle, aryl, heteroayl, heterocycle, —Oaryl, —Oheteroaryl, —Oheterocycle, —O(C$_3$-C$_7$)halocarbocycle, —O(C$_1$-C$_6$) alkyl, —(O(C$_3$-C$_7$)carbocycle, —O(C$_1$-C$_6$)haloalkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O) (C$_1$-C$_6$)alkyl, —S(O)(C$_3$-C$_7$)carbocycle, —S(O)(C$_1$-C$_6$)haloalkyl, —SO$_2$aryl, —SO$_2$heteroaryl, —SO$_2$heterocycle, —SO$_2$(C$_1$-C$_6$)alkyl, —SO$_2$(C$_1$-C$_6$)haloalkyl, —SO$_2$(C$_3$-C$_7$) carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$heteroaryl, —NR$_a$SO$_2$heteroaryl, —NR$_a$SO$_2$NR$_c$R$_d$, —NR$_a$SO$_2$(C$_3$-C$_7$)carbocycle and —NR$_a$SO$_2$Oaryl, wherein any aryl, of Z$^6$, either alone or as part of a group, is optionally substituted with one or more (e.g. 1, 2, 3, 4 or 5) halogen, —OH, —O(C$_1$-C$_6$)alkyl, —CN or —(C$_1$-C$_6$)alkyl;

each Z$^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl-Z$^{12}$, —(C$_2$-C$_6$)alknyl-OH, —(C$_1$-C$_6$)haloalkyl-Z$^{12}$, —(C$_1$-C$_6$)haloalkylOH, —(C$_3$-C$_7$)carbocycle-Z$^{12}$, —(C$_3$-C$_7$)carbocycleOH, —(C$_3$-C$_7$)halocarbocycle, —(C$_1$-C$_6$)alkyl NR$_c$R$_d$, —(C$_1$-C$_6$)alkylNR$_a$C(O)R$_a$, —(C$_1$-C$_6$)alkylNR$_a$SO$_2$R$_a$, aryl, heteroaryl, heterocycle, —O(C$_1$-C$_6$)alkyl-Z$^{12}$, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —O(C$_1$-C$_6$) alkyl NR$_c$R$_d$, —O(C$_1$-C$_6$)alkylNR$_a$C(O)R$_a$, —O(C$_1$-C$_6$) alkylNR$_a$SO$_2$R$_a$, —Oheteroaryl, —Oheterocycle, —S(C$_1$-C$_6$)alkyl-Z$^{12}$, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$) halocarbocycle, —S(C$_1$-C$_6$)alkylNR$_c$R$_d$, —S(C$_1$-C$_6$)alkyl-NR$_a$C(O)R$_a$, —S(C$_1$-C$_6$)alkylNR$_a$SO$_2$R$_a$, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$) haloalkyl, —S(O)(C$_3$-C$_7$)carbocycle, —S(O)(C$_3$-C$_7$) halocarbocycle, —SO$_2$(C$_1$-C$_6$)alkyl, —S(O)(C$_1$-C$_6$) alkylNR$_c$R$^d$, —S(O)(C$_1$-C$_6$)alkylNR$_a$C(O)R$_a$, —S(O)(C$_1$-C$_6$)alkylNR$_a$SO$_2$R$_a$, —S(O)aryl, —S(O)heteroaryl, —S(O) heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$(C$_1$-C$_6$)alkylN-R$_c$R$_d$, —SO$_2$(C$_1$-C$_6$)alkylNR$_a$C(O)R$_a$, —SO$_2$(C$_1$-C$_6$) alkylNR$_a$SO$_2$R$_a$, —SO$_2$NR$_c$R$_d$, —NR$_a$C(O)OR$_b$, —NR$_a$C (O)NR$_c$R$_d$, —NR$_a$SO$_2$R$_b$, —NR$_a$SO$_2$NR$_c$R$_d$, —NR$_a$SO$_2$O (C$_3$-C$_7$)carbocycle, —NR$_a$SO$_2$Oaryl, —OS(O)$_2$R$_a$, —C(O)

$NR_cR_d$, and —OC(O)$NR_cR_d$, wherein any ($C_1$-$C_6$)alkyl, ($C_2$-$C_6$)alkenyl, ($C_2$-$C_6$)alkynyl, ($C_3$-$C_7$)carbocycle, ($C_3$-$C_7$)halocarbocycle, aryl, heteroaryl or heterocycle of $Z^7$, either alone or as part of a group, is optionally substituted with one or more (e.g. 1, 2, 3, 4 or 5) halogen, —OH, —$OR_b$, —CN, —$NR_aC(O)_2R_b$, heteroaryl, heterocycle, —Oheteroaryl, —Oheterocycle, —NHheteroaryl, —NHheterocycle or —S(O)$_2NR_cR_d$.

each $Z^8$ is independently selected from —$NO_2$ or —CN;
each $Z^{10}$ is independently selected from
  i) halo, oxo, thioxo, ($C_2$-$C_6$)alkenyl, ($C_1$-$C_6$)haloalkyl, ($C_3$-$C_7$)cycloalkyl, ($C_3$-$C_7$)cycloalkyl-($C_1$-$C_6$)alkyl-, —OH, —O($C_1$-$C_6$)alkyl, —O($C_1$-$C_6$)haloalkyl, —SH, —S($C_1$-$C_6$)alkyl, —SO($C_1$-$C_6$)alkyl, —$SO_2$($C_1$-$C_6$)alkyl, —$NH_2$, —NH($C_1$-$C_6$)alkyl and —N(($C_1$-$C_6$)alkyl)$_2$;
  ii) ($C_1$-$C_6$)alkyl optionally substituted with —OH, —O—($C_1$-$C_6$)haloalkyl, or —O—($C_1$-$C_6$)alkyl; and
  iii) aryl, heterocycle and heteroaryl, which aryl, heterocycle and heteroaryl is optionally substituted with halo, ($C_1$-$C_6$)alkyl or COOH;

each $Z^{11}$ is independently selected from $Z^{10}$, —C(=O)—$NH_2$, —C(=O)—NH($C_1$-$C_4$)alkyl, —C(=O)—N(($C_1$-$C_4$)alkyl)$_2$, —C(=O)-aryl, —C(=O)-heterocycle and —C(=O)-heteroaryl;

each $Z^{12}$ is independently selected from —$NO_2$, =$NOR_a$, thioxo, aryl, heterocycle, heteroaryl, ($C_3$-$C_7$)halocarbocycle, ($C_3$-$C_7$)carbocycle, —O($C_3$-$C_7$)carbocycle, —O($C_3$-$C_7$)halocarbocycle, —Oaryl, —Oheterocycle, —Oheteroaryl, —S($C_1$-$C_6$)alkyl, —S($C_3$-$C_7$)carbocycle, —S($C_3$-$C_7$)halocarbocycle, —Saryl, —Sheterocycle, —Sheteroaryl, —S(O)($C_1$-$C_6$)alkyl, —S(O)($C_3$-$C_7$)carbocycle, —S(O)($C_3$-$C_7$)halocarbocycle, —S(O)aryl, —S(O)heterocycle, —S(O)heteroaryl, —$SO_2$($C_1$-$C_6$)alkyl, —$SO_2$($C_3$-$C_7$)carbocycle, —$SO_2$($C_3$-$C_7$)halocarbocycle, $SO_2$aryl, —$SO_2$heterocycle, —$SO_2$heteroayl, —$NR_aR_a$, —$NR_aC(O)R_b$, —C(O)$NR_cR_d$, —$SO_2NR_cR_d$, —$NR_aSO_2NR_cR_d$, —$NR_aSO_2O$($C_3$-$C_7$)carbocycle and —$NR_aSO_2$Oaryl;

each $Z^{13}$ is independently selected from —$NO_2$, —OH, =$NOR_a$, —SH, —CN, ($C_3$-$C_7$)halocarbocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —S(O)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR^d$, —$NR_aSO_2O$($C_3$-$C_7$)carbocycle, —$NR_aSO_2$Oaryl, —OS(O)$_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, ($C_3$-$C_7$)halocarbocycle, ($C_3$-$C_7$)carbocycle, ($C_3$-$C_7$)halocarbocycle, aryl, heteroayl or heterocycle of $Z^{13}$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —S(O)$_2NR_cR_d$;

each $Z^{14}$ is independently selected from —$NO_2$, =$NOR_a$, —CN, —($C_3$-$C_7$)halocarbocycle, —O($C_3$-$C_7$)halocarbocycle, —S($C_3$-$C_7$)halocarbocycle, —S(O)($C_3$-$C_7$)halocarbocycle, —$SO_2$($C_3$-$C_7$)halocarbocycle, —$NR_aSO_2NR_cR_d$, —$NR_aSO_2O$($C_3$-$C_7$)carbocycle, —$NR_aSO_2$Oaryl, —OS(O)$_2R_a$, wherein any —($C_3$-$C_7$)halocarbocycle of $Z^{14}$, either alone or as part of a group, is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —S(O)$_2NR_cR_d$;

each $Z^{15}$ is independently selected from aryl, heteroaryl, heterocycle, —Oaryl, —Oheteroaryl, —Oheterocycle, —O($C_1$-$C_6$)alkyl-aryl, —O($C_1$-$C_6$)alkyl-heteroaryl, —O($C_1$-$C_6$)alkyl-heterocycle, wherein aryl, heteroaryl and heterocycle are each independently substituted with one or more (e.g. 1, 2, 3, 4 or 5) $Z^{16}$ groups and optionally substituted with one or more (e.g. 1, 2, 3, 4 or 5) $Z^1$ groups, and wherein any —Oaryl, —Oheteroaryl, —Oheterocycle, —O($C_1$-$C_6$)alkyl-aryl, —O($C_1$-$C_6$)alkyl-heteroaryl or —O($C_1$-$C_6$)alkyl-heterocycle is optionally substituted with one or more (e.g. 1, 2, 3, 4 or 5) $Z^1$ groups;

each $Z^{16}$ is independently selected from —$NO_2$, —OH, =$NOR_a$, —SH, —CN, ($C_2$-$C_6$)alkenyl, ($C_2$-$C_6$)alkynyl, ($C_1$-$C_6$)haloalkyl, ($C_3$-$C_7$)carbocycle, ($C_3$-$C_7$)halocarbocycle, aryl, heteroaryl, heterocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$—C)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$—C)alkynyl, —S(O)($C_1$-$C_6$)haloalkyl, —S(O) ($C_3$-$C_7$)carbocycle, —S(O)($C_3$-$C_7$)halocarbocycle, —$SO_2$($C_1$-$C_6$)alkyl, —S(O)aryl, —S(O)carbocycle, —S(O)heteroaryl, —S(O)heterocycle, —$SO_2$($C_2$-$C_6$)alknyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_aC(O)OR_b$, —$NR_aC(O)NR_cR_d$, —$NR_aSO_2R_b$, —$NR_aSO_2NR_cR_d$, —$NR_aSO_2O$($C_3$-$C_7$)carbocycle, —$NR_aSO_2$Oaryl, —OS(O)$_2R_a$, —C(O)$R_a$, —C(O)$OR_b$, —C(O)$NR_cR_d$, and —OC(O)$NR_cR_d$, wherein any ($C_1$-$C_6$)alkyl, ($C_2$-$C_6$)alkenyl, ($C_2$-$C_6$)alkynyl, ($C_3$-$C_7$)halocarbocycle, ($C_3$-$C_7$)carbocycle, ($C_3$-$C_7$)halocarbocycle, aryl, heteroaryl or heterocycle of $Z^{16}$, either alone or as part of a group, is optionally substituted with one or more (e.g. 1, 2, 3, 4 or 5) halogen, ($C_1$-$C_6$)alkyl, —OH, —$OR_b$, —CN, —$NR_aC(O)_2R_b$, heteroaryl, heterocycle, —Oheteroaryl, —Oheterocycle, —NHheteroaryl, —NHheterocycle or —S(O)$_2NR_cR_d$;

each $R_a$ is independently H, ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$, either alone or as part of a group, is optionally substituted with one or more (e.g. 1, 2, 3, 4 or 5) halogen, OH or cyano;

each $R_b$ is independently ($C_1$-$C_6$)alkyl, ($C_2$-$C_6$)alkenyl, ($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-, wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_b$, either alone or as part of a group, is optionally substituted with one or more (e.g. 1, 2, 3, 4 or 5) halogen, OH and cyano;

$R_c$ and $R_d$ are each independently selected from H, ($C_1$-$C_6$)alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl or heteroaryl($C_1$-$C_6$)alkyl-, wherein any ($C_1$-$C_6$)alkyl, ($C_2$-$C_6$) alkenyl, ($C_2$-$C_6$)alkynyl, ($C_3$-$C_7$)carbocycle, heterocycle, aryl, or heteroaryl of $R_c$ or $R_d$, either alone or as part of a group, is optionally substituted with one or more (e.g. 1, 2, 3, 4 or 5) halogen, OH or cyano; or $R_c$ and $R_d$ together with the nitrogen to which they are attached form a heterocycle, wherein any heterocycle of $R_c$ and $R_d$ together with the nitrogen to which they are attached is optionally substituted with one or more (e.g. 1, 2, 3, 4 or 5) halogen, OH or cyano;

each $R_e$ is independently selected from —$OR_e$, ($C_1$-$C_6$) alkyl or ($C_3$-$C_7$)carbocycle, wherein ($C_1$-$C_6$)alkyl and ($C_3$-$C_7$)carbocycle are each independently substituted with one or more (e.g. 1, 2, 3, 4 or 5) $Z^6$ groups and optionally substituted with one or more (e.g. 1, 2, 3, 4 or 5) $Z^1$ groups; ($C_2$-$C_6$)haloalkyl, ($C_2$-$C_6$)alkenyl and ($C_1$-$C_6$)alkynyl, wherein any ($C_2$-$C_6$)haloalkyl, ($C_2$-$C_6$)alkenyl or ($C_2$-$C_6$) alkynyl is optionally substituted with one or more (e.g. 1, 2, 3, 4 or 5) $Z_1$ groups; and aryl, heterocycle and heteroaryl wherein aryl, heterocycle and heteroaryl are each independently substituted with one or more (e.g. 1, 2, 3, 4 or 5) $Z_5$ groups;

each $R_f$ is independently selected from —$R_g$, —$OR_g$, —($C_1$-$C_6$)alkyl-$Z^6$, —$SO_2R_g$, —$C(O)R_g$, $C(O)OR_g$ and —$C(O)NR_eR_g$; and each $R_g$ is independently selected from ($C_1$-$C_6$)alkyl, ($C_3$-$C_7$)carbocycle ($C_1$-$C_6$)haloalkyl, ($C_2$-$C_6$)alkenyl, ($C_2$-$C_6$)alkynyl, aryl, heterocycle and heteroaryl, wherein any ($C_1$-$C_6$)alkyl, ($C_3$-$C_7$)carbocycle —($C_1$-$C_6$)haloalkyl, ($C_2$-$C_6$)alkenyl, ($C_2$-$C_6$)alkynyl, aryl, heterocycle or heteroaryl of $R_g$ is optionally substituted with one or more (e.g. 1, 2, 3, 4 or 5) $Z_1$ groups;

or a salt thereof.

The invention also provides a pharmaceutical composition comprising a compound of formula I or a pharmaceutically acceptable salt thereof; and a pharmaceutically acceptable carrier.

The invention also provides a method for treating (e.g. preventing, mediating or inhibiting) the proliferation of the HIV virus, treating AIDS or delaying the onset of AIDS or ARC symptoms in a mammal (e.g. a human), comprising administering a compound of formula I, or a pharmaceutically acceptable salt thereof to the mammal.

The invention also provides a method of treating an HIV infection in a mammal (e.g. a human) comprising administering a compound of formula I, or a pharmaceutically acceptable salt thereof to the mammal.

The invention also provides a method for treating an HIV infection in a mammal (e.g. a human) comprising administering to the mammal in need thereof a therapeutically effective amount of a compound of formula I, or a pharmaceutically acceptable salt thereof in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV, and combinations thereof.

The invention also provides a compound of formula I, or a pharmaceutically acceptable salt thereof for use in medical therapy (e.g. for use in treating (e.g. preventing, mediating or inhibiting) the proliferation of the HIV virus or AIDS or delaying the onset of AIDS or ARC symptoms in a mammal (e.g. a human)).

The invention also provides a compound of formula I, or a pharmaceutically acceptable salt thereof for use in medical therapy (e.g. for use in treating (e.g. preventing, mediating or inhibiting) an HIV infection in a mammal (e.g. a human)).

The invention also provides a compound of formula I, or a pharmaceutically acceptable salt thereof for use in the manufacture of a medicament for treating (e.g. preventing, mediating or inhibiting) the proliferation of the HIV virus or AIDS or delaying the onset of AIDS or ARC symptoms in a mammal (e.g. a human).

The invention also provides a compound of formula I, or a pharmaceutically acceptable salt thereof for use in the prophylactic or therapeutic treatment (e.g. prevention, mediation or inhibiting) of the proliferation of the HIV virus or AIDS or for use in the therapeutic treatment of delaying the onset of AIDS or ARC symptoms.

The invention also provides a compound of formula I, or a pharmaceutically acceptable salt thereof for the manufacture of a medicament for treating an HIV infection in a mammal (e.g. a human).

The invention also provides a compound of formula I or a pharmaceutically acceptable salt thereof for use in the prophylactic or therapeutic treatment of an HIV infection in a mammal (e.g. a human).

The invention also provides processes and intermediates disclosed herein that are useful for preparing compounds of formula I or salts thereof.

DETAILED DESCRIPTION OF THE INVENTION

Definitions

Unless stated otherwise, the following terms and phrases as used herein are intended to have the following meanings.

When trade names are used herein, applicants intend to independently include the tradename product and the active pharmaceutical ingredient(s) of the tradename product.

"Alkyl" is hydrocarbon containing normal, secondary or tertiary atoms. For example, an alkyl group can have 1 to 20 carbon atoms (i.e, ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)$ $CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)$ $CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)$ $CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., $(C_1-C_{10})$ alkyl), or 1 to 6 carbon atoms (i.e., $(C_1-C_6)$alkyl) or 1-3 carbon atoms (i.e., $(C_1-C_3)$alkyl). Typical alkyl radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH(CH$_3$)—), 1,3-propyl (—CH$_2$CH$_2$CH$_2$—), 1,4-butyl (—CH$_2$CH$_2$CH$_2$CH$_2$—), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a $(C_1-C_6)$ haloalkyl is a $(C_1-C_6)$alkyl wherein one or more of the hydrogen atoms have been replaced by a halo substituent. Such a range includes one halo substituent on the alkyl group t to complete halogenation of the alkyl group.

The term "aryl" as used herein refers to a single aromatic ring or a bicyclic or multicyclic ring. For example, an aryl group can have 6 to 20 carbon atoms, 6 to 14 carbon atoms, or 6 to 12 carbon atoms. Aryl includes a phenyl radical or an ortho-fused bicyclic or multicyclic radical having about 9 to 14 atoms in which at least one ring is aromatic (e.g. an aryl fused to one or more aryl or carbocycle). Such bicyclic or multicyclic rings may be optionally substituted with one or more (e.g. 1, 2 or 3) oxo groups on any carbocycle portion of the bicyclic or multicyclic ring. It is to be understood that the point of attachment of a bicyclic or multicyclic radical, as defined above, can be at any position of the ring including an aryl or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1-C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2 or 3 rings) wherein a heteroaryl group, as defined above, can be fused with one or more heteroaryls (e.g. naphthyridinyl), carbocycles (e.g. 5,6,7,8-tetrahydroquinolyl) or aryls (e.g. indazolyl) to form a multiple condensed ring. Such multiple condensed rings may be optionally substituted with one or more (e.g. 1, 2 or 3) oxo groups on the carbocycle portions of the condensed ring. It is to be understood that the point of attachment of a heteroaryl multiple condensed ring, as defined above, can be at any position of the ring including a heteroaryl, aryl or a carbocycle portion of the ring. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring or a multiple condensed ring. The term includes single saturated or partially unsaturated ring (e.g. 3, 4, 5, 6 or 7-membered ring) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term also includes multiple condensed ring systems (e.g. ring systems comprising 2 or 3 rings) wherein a heterocycle group (as defined above) can be connected to two adjacent atoms (fused heterocycle) with one or more heterocycles (e.g. decahydronapthyridinyl), heteroaryls (e.g. 1,2,3,4-tetrahydronaphthyridinyl), carbocycles (e.g. decahydroquinolyl) or aryls. It is to be understood that the point of attachment of a heterocycle multiple condensed ring, as defined above, can be at any position of the ring including a heterocyle, heteroaryl, aryl or a carbocycle portion of the ring. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

The term "bridged-heterocycle" as used herein refers to a 4, 5, 6, 7 or 8-membered heterocycle as defined herein connected at two non-adjacent atoms of the 4, 5, 6, 7 or 8-membered heterocycle with one or more (e.g. 1 or 2) 3, 4, 5 or 6-membered heterocycles or $(C_3-C_7)$carbocycles as defined herein. Such bridged-heterocycles include bicyclic and tricyclic ring systems (e.g. 2-azabicyclo[2.2.1]heptane and 4-azatricyclo[4.3.1.$^{3,8}$]undecane).

The term "spiro-heterocycle" as used herein refers to a 3, 4, 5, 6, 7 or 8-membered heterocycle as defined herein connected to one or more (e.g. 1 or 2) single atoms of the 3, 4, 5, 6, 7 or 8-membered heterocycle with one or more (e.g. 1 or 2) 3, 4, 5, 6-membered heterocycles or a $(C_3-C_7)$ carbocycles as defined herein. Such spiro-heterocycles include bicyclic and tricyclic ring systems (e.g. 1,4-dioxaspiro[4.5]dec-7-enyl).

The term "macroheterocycle" as used herein refers to a saturated or partially unsaturated 8, 9, 10, 11 or 12-membered ring comprising about 5 to 11 carbon atoms and about 1 to 3 heteroatoms selected from the group consisting of oxygen, nitrogen and sulfur in the ring which may be optionally fused at two adjacent atoms of the macroheterocycle to one or more (e.g. 1, 2 or 3) aryls, carbocycles, heteroaryls or heterocycles. The macroheterocycle may be substituted with one or more (e.g. 1, 2 or 3) oxo groups and the sulfur and nitrogen atoms may also be present in their oxidized forms.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl($C_1-C_6$)alkyl). Heteroarylalkyl groups include, but are not limited to heteroaryl-CH$_2$—, heteroaryl-CH(CH$_3$)—, heteroaryl-CH$_2$CH$_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a saturated (i.e., cycloalkyl) or partially unsaturated (e.g., cycloalkenyl, cycloalkadienyl, etc.) ring having 3 to 7 carbon atoms as a monocycle or a mutlicyclic ring system. In one embodiment the carbocycle is a monocycle comprising 3-6 ring carbons (i.e. ($C_3$-$C_6$)carbocycle). Carbocycle includes multicyclic carbocycles having 7 to 12 carbon atoms as a bicycle, and up to about 20 carbon atoms as a polycycle provided that the largest single ring of a multicyclic carbocycle is 7 carbon atoms. The term "spirobicyclic carbocycle" refers to a carbocycle bicyclic ring system wherein the rings of the bicyclic ring system are connected to a single carbon atom (e.g. spiropentane, spiro[4,5]decane, spiro[4.5]decane, etc). The term "fused-bicyclic carbocycle" refers to a carbocycle bicyclic ring system wherein the rings of the bicyclic ring system are connected to two adjacent carbon atoms such as a bicyclo[4,5], [5,5], [5,6] or [6,6] system, or 9 or 10 ring atoms arranged as a bicycle [5,6] or [6,6] system (e.g. decahydronaphthalene, norsabinane, norcarane). The term "bridged-bicyclic carbocycle" refers to a carbocycle bicyclic ring system wherein the rings of the bicyclic ring system are connected to two non-adjacent carbon (e.g. norbornane, bicyclo[2.2.2]octane, etc). The "carbocycle" or "carbocyclyl" may be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

The term "halocarbocycle" as used herein refers to a carbocycle as defined herein, wherein one or more hydrogen atoms are each replaced by a halo substituent. For example, ($C_3$-$C_7$)halocarbocycle is a ($C_3$-$C_7$)carbocycle wherein one or more of the hydrogen atoms have been replaced by a halo substituent. Such a range includes one halo substituent on the carbocycle group to complete halogenation of the carbocycle group.

The term "macrocarbocycle" as used herein refers to a saturated or partially unsaturated 8, 9, 10, 11 or 12-membered ring comprising 8 to 12 carbon atoms which may be optionally fused at two adjacent atoms of the macrocarbocycle to one or more (e.g. 1, 2 or 3) aryls, carbocycles, heteroaryls or heterocycles. The macrocarbocycle may be substituted with one or more (e.g. 1, 2 or 3) oxo groups.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

It is to be understood that when a variable is substituted, for example, as described by the phrase "($C_1$-$C_6$)alkyl, either alone or as part of a group, is optionally substituted", the phrase means that the variable ($C_1$-$C_6$)alkyl can be substituted when it is alone and that it can also be substituted when the variable "($C_1$-$C_6$)alkyl" is part of a larger group such as for example an aryl($C_1$-$C_6$)alkyl or a —($C_1$-$C_6$)alkyl-$SO_2$—($C_1$-$C_6$)alkyl-($C_3$-$C_7$)carbocycle group. Similarly, when stated, other variables (e.g. ($C_1$-$C_6$)alkenyl, ($C_1$-$C_6$)alkynyl, aryl, heteroaryl, heterocycle, etc.) can also be substituted "either alone or as part of a group."

It is to be understood that certain variables of formula I that connect two chemical groups may be oriented in either direction. Thus, for the X group of formula I (e.g. O, —C(O)—, —C(O)O—, —S—, —S(O)—, —$SO_2$, —($C_1$-$C_6$)alkylO—, —($C_1$-$C_6$)alkylC(O)—, —($C_1$-$C_6$)alkylC(O)O—, —($C_1$-$C_6$)alkylS—, —($C_1$-$C_6$)alkylS(O)— and —($C_1$-$C_6$)alkyl$SO_2$—) certain values of X that are not symmetric can be oriented in either direction. For example, the —C(O)O—, can be oriented as either —C(O)O— or —OC(O)—, relative to the groups it connects.

It is to be understood that the nitrogen that is included in the core of the compound of formula I can be present in an oxidized form. For example, the thiazole nitrogen of either $G^1$ or $G^2$ of formula I can be an N-oxide. Accordingly, the invention includes a compound of formula I (as defined in the summary of the invention) or a salt or N-oxide thereof.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Certain compounds of the invention can exist as atropisomers. For example, it has been discovered that atropisomers exist for certain substituents at the $R^4$ position of formula I as marked by an asterisk in the formula below.

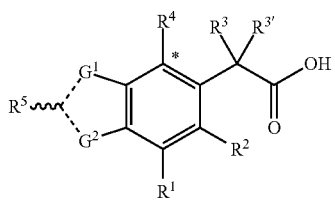

The chirality that results from the atropisomers at the asterisk position is a feature of certain compounds of the invention. Accordingly, the invention includes all atropisomers of compounds of the invention including mixtures of atropisomers and well as mixtures that are enriched in an atropisomer as well as single atropisomers, which mixtures or compounds possess the useful properties described herein.

In one embodiment, the compounds of the invention of formula I are greater than 50% a single atropisomer for the $R^4$ substituent at the asterisk position. In one embodiment, the compounds of the invention of formula I are at least 60% a single atropisomer for the $R^4$ substituent at the asterisk position. In another embodiment, the compounds of the invention of formula I are at least 70% a single atropisomer for the $R^4$ substituent at the asterisk position. In another embodiment, the compounds of the invention of formula I are at least 80% a single atropisomer for the $R^4$ substituent at the asterisk position. In another embodiment, the compounds of the invention of formula I are at least 90% a single atropisomer for the $R^4$ substituent at the asterisk position. In another embodiment, the compounds of the invention of formula I are at least 95% a single atropisomer for the $R^4$ substituent at the asterisk position. In one embodiment the stereochemistry for the $R^4$ substituent at the carbon marked with an asterisk as shown above for Formula I is the (R) stereochemistry. In another embodiment the stereochemistry for the $R^4$ substituent at the carbon marked with an asterisk as shown above for Formula I is the (S) stereochemistry.

For certain compounds of the invention the stereochemistry at the carbon bearing the $R^3$ substituent of formula I as marked by an asterisk in the formula below is another aspect of the invention.

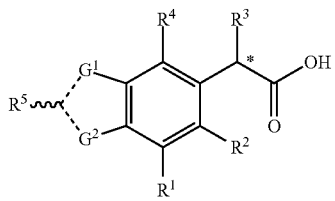

In one embodiment the stereochemistry at the carbon marked with an asterisk as shown above for Formula I is the (S) stereochemistry. In another embodiment the stereochemistry at the carbon marked with an asterisk as shown above for Formula I is the (R) stereochemistry.

In one embodiment, the compounds of the invention of formula I are greater than 50% a stereoisomer for the carbon at the asterisk position. In another embodiment, the compounds of the invention of formula I are at least 60% a single stereoisomer for the carbon at the asterisk position. In another embodiment, the compounds of the invention of formula I are at least 70% a single stereoisomer for the carbon at the asterisk position. In another embodiment, the compounds of the invention of formula I are at least 80% a single stereoisomer for the carbon at the asterisk position. In another embodiment, the compounds of the invention of formula I are at least 90% a single steroisomer for the carbon at the asterisk position. In another embodiment, the compounds of the invention of formula I are at least 95% a single stereoisomer for the carbon at the asterisk position The term "treatment" or "treating." to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*. Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*. Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a hydrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds of the invention will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific values listed below for radicals, substituents, and ranges in the embodiments of the invention are for illustration only; they do not exclude other defined values or other values within defined ranges for the radicals and substituents.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Compounds of Formula I.

A specific group of compounds of formula I are compounds of formula Ia:

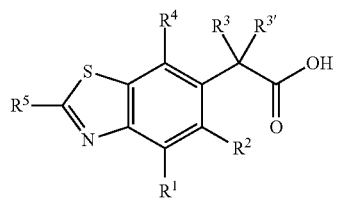

or a salt thereof.

Another specific group of compounds of formula I are compounds of formula Ib:

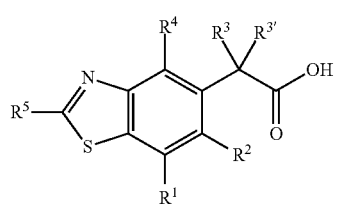

or a salt thereof.

Another specific group of compounds of formula I are compounds of formula Ic:

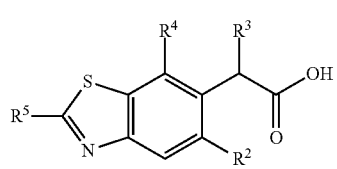

wherein R$^3$ is —O(C$_1$-C$_6$)alkyl or a salt thereof.

Another specific group of compounds of formula I are compounds of formula Ic':

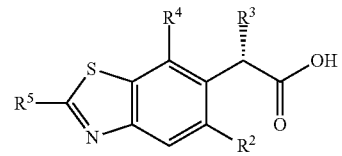

wherein R$^3$ is —O(C$_1$-C$_6$)alkyl or a salt thereof.

Another specific group of compounds of formula I are compounds of formula Id:

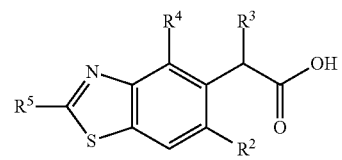

wherein R$^3$ is —O(C$_1$-C$_6$)alkyl, or a salt thereof.

Another specific group of compounds of formula I are compounds of formula Id':

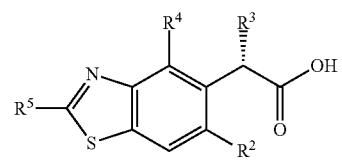

wherein R$^3$ is —O(C$_1$-C$_6$)alkyl, or a salt thereof.

Another specific group of compounds of formula I are compounds of formula Ie:

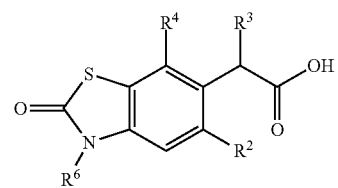

or a salt thereof.

Another specific group of compounds of formula I are compounds of formula Ie':

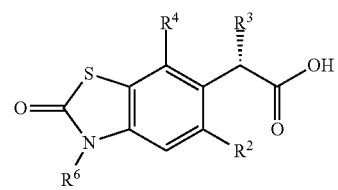

or a salt thereof.

Another specific group of compounds of formula I are compounds of formula If:

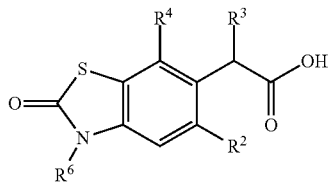

wherein $R^3$ is —O($C_1$-$C_6$)alkyl, or a salt thereof.

Another specific group of compounds of formula I are compounds of formula If':

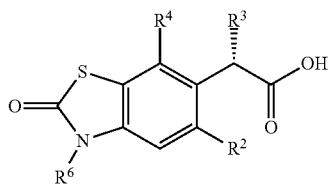

wherein R is —O($C_1$-$C_6$)alkyl, or a salt thereof.

Another specific group of compounds of formula I are compounds of formula Ig:

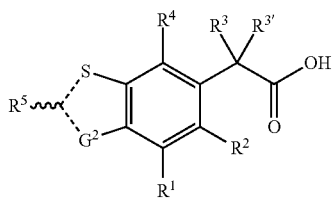

wherein:

$G^2$ is N, the dashed bond connected to $G^2$ is a double bond, and the wavy bond connected to $R^5$ is a single bond; or $G^2$ is $NR^6$, the dashed bond connected to $G^2$ is a single bond, the wavy bond connected to $R^5$ is a double bond and $R^5$ is oxygen (e.g. "(wavy bond)-$R^5$" is "=O").

Another specific group of compounds of formula I are compounds of formula Ig':

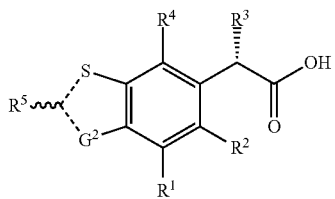

wherein:

$G^2$ is N, the dashed bond connected to $G^2$ is a double bond, and the wavy bond connected to $R^5$ is a single bond; or $G^2$ is $NR^6$, the dashed bond connected to $G^2$ is a single bond, the wavy bond connected to $R^5$ is a double bond and $R^5$ is oxygen (e.g. "(wavy bond)-$R^5$" is "=O").

Another specific group of compounds of formula I are compounds of formula Ih:

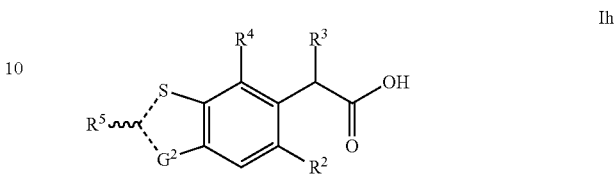

wherein:

$G^2$ is N, the dashed bond connected to $G^2$ is a double bond, and the wavy bond connected to $R^5$ is a single bond; or $G^2$ is $NR^6$, the dashed bond connected to G is a single bond, the wavy bond connected to $R^5$ is a double bond and $R^5$ is oxygen (e.g. "(wavy bond)-$R^5$" is "=O").

Another specific group of compounds of formula I are compounds of formula Ih':

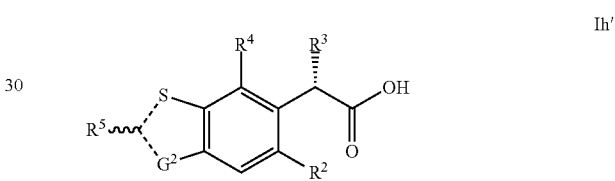

wherein:

$G^2$ is N, the dashed bond connected to $G^2$ is a double bond, and the wavy bond connected to $R^5$ is a single bond; or $G^2$ is $NR^6$, the dashed bond connected to $G^2$ is a single bond, the wavy bond connected to $R^5$ is a double bond and $R^5$ is oxygen (e.g. "(wavy bond)-$R^5$" is "=O").

Another specific group of compounds of formula I are compounds of formula Ii:

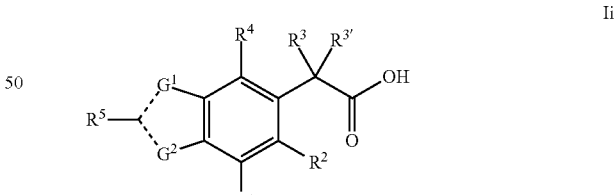

wherein:

$G^1$ is S; $G^2$ is N; the dashed bond connected to $G^1$ is a single bond and the dashed bond connected to $G^2$ is a double bond; or $G^1$ is N; $G^2$ is S; the dashed bond connected to $G^1$ is a double bond and the dashed bond connected to $G^2$ is a single bond;

or a salt thereof.

Another specific group of compounds of formula I are compounds of formula Ij:

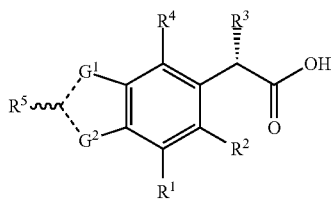

Ij

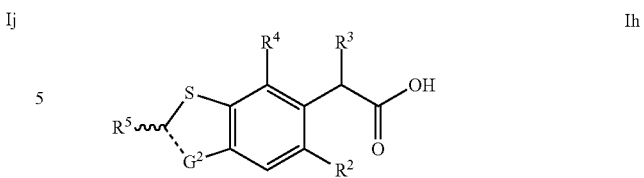

Ih or a salt thereof.

Specific embodiments of the invention (e.g. embodiments) and specific values listed below are embodiments and values for compounds of formula I including all of the compounds of sub-formulas of formula I (e.g. the compounds of formulas Ia, Ib, Ic, Ic', Id, Id', Ie, Ie', If, If', Ig, Ig', Ih, Ih' and Ia100-Ia145)

A specific group of compounds of formula I are compounds wherein at least one of $R^1$, $R^2$, $R^3$, $R^{3'}$, $R^4$ or $R^5$ is selected from $R^{1b}$, $R^{2b}$, $R^{3b}$, $R^{3b'}$, $R^{4b}$ or $R^{5b}$.

Another specific group of compounds of formula I are compounds wherein at least two of $R^1$, $R^2$, $R^3$, $R^{3'}$, $R^4$ or $R^5$ is selected from $R^{1b}$, $R^{2b}$, $R^{3b}$, $R^{3b'}$, $R^{4b}$ or $R^{5b}$.

Another specific group of compounds of formula I are compounds wherein at least three of $R^1$, $R^2$, $R^3$, $R^{3'}$, $R^4$ or $R^5$ is selected from $R^{1b}$, $R^{2b}$, $R^{3b}$, $R^{3b'}$, $R^{4b}$ or $R^{5b}$.

Another specific group of compounds of formula I are compounds wherein at least four of $R^1$, $R^2$, $R^3$, $R^{3'}$, $R^4$ or $R^5$ is selected from $R^{1b}$, $R^{2b}$, $R^{3b}$, $R^{3b'}$, $R^{4b}$ or $R^{5b}$.

Another specific group of compounds of formula I are compounds wherein at least five of $R^1$, $R^2$, $R^3$, $R^{3'}$ $R^4$ or $R^5$ is selected from $R^{1b}$, $R^{2b}$, $R^{3b}$, $R^{3b'}$, $R^{4b}$ or $R^5$.

Another specific group of compounds of formula I are compounds wherein at $R^1$, $R^2$, $R^3$, $R^{3'}$, $R^4$ and $R^5$ are $R^{1b}$, $R^{2b}$, $R^{3b}$, $R^{3b'}$, $R^{4b}$ and $R^{5b}$.

A specific value for $R^1$ is H.

Another specific value for $R^1$ is H or halo.

Another specific value for $R^1$ is H or F.

A specific value for $R^{3'}$ is H.

A specific value for $R^3$ is $R^{3b}$.

A specific value for $R^{3b}$ is —OC(CH$_3$)$_2$CH$_2$OH, —OC(CH$_3$)$_2$CH$_2$OH, —O(C$_1$-C$_6$)alkyl-O—C(O)—NH$_2$, —O(C$_1$-C$_6$)alkyl-O—C(O)—N(CH$_3$)$_2$ or —O(C$_1$-C$_6$)alkyl-O—C(O)—NH(phenyl).

Another specific value for $R^{3b}$ is —(C$_1$-C$_6$)alkylOH or —O(C$_1$-C$_6$)alkyl-O—C(O)—NR$_c$R$_d$.

Another specific value for $R^3$ is $R^{3a}$.

A specific value for $R^{3a}$ is (C$_1$-C$_6$)alkyl, (C$_2$-C$_6$)alkenyl or —O(C$_1$-C$_6$)alkyl wherein any (C$_1$-C$_6$)alkyl or (C$_2$-C$_6$)alkenyl of $R^{3a}$ is optionally substituted with one or more groups selected from —O(C$_1$-C$_6$)alkyl, halo, oxo and —CN.

Another specific value for $R^{3a}$ is —OC(CH$_3$).

A specific value for $R^{3'}$ is $R^{3b'}$.

Another specific value for $R^{3a}$ is —OC(CH$_3$)$_3$.

A specific value for $R^{3'}$ is $R^{3a'}$.

A specific value for $R^{3a'}$ is H.

A specific value for $R^3$ is (C$_1$-C$_6$)alkyl, (C$_2$-C$_6$)alkenyl or —O(C$_1$-C$_6$)alkyl, wherein any (C$_1$-C$_6$)alkyl or (C$_2$-C$_6$)alkenyl of $R^{3a}$ is optionally substituted with one or more groups selected from —O(C$_1$-C$_6$)alkyl, halo, oxo and —CN.

A specific value for $R^3$ is —OC(CH$_3$)$_3$.

A specific group of compounds of formula I are compounds wherein the compounds of formula I are compounds of formula Ih:

wherein:

$G^2$ is N, the dashed bond connected to $G^2$ is a double bond, and the wavy bond connected to $R^5$ is a single bond; or $G^2$ is NR$^6$, the dashed bond connected to $G^2$ is a single bond, the wavy bond connected to $R^5$ is a double bond and $R^5$ is oxygen.

A specific group of compounds of formula I are compounds wherein $R^{3b}$ and $R^{3b'}$ together with the carbon to which they are attached form a (C$_3$-C$_7$)carbocycle or heterocycle; wherein the (C$_3$-C$_7$)carbocycle or heterocycle is optionally substituted with one or more Z$^1$ groups.

Another specific group of compounds of formula I are compounds wherein $R^{3b}$ and $R^{3b'}$ together with the carbon to which they are attached form a (C$_3$-C$_7$)carbocycle or a 4, 5 or 6-membered heterocycle; wherein the (C$_3$-C$_6$)carbocycle or the 4, 5 or 6-membered heterocycle is optionally substituted with one or more Z$^1$ groups.

Another specific group of compounds of formula I are compounds wherein $R^{3b}$ and $R^{3b'}$ together with the carbon to which they are attached form a (C$_4$-C$_6$)carbocycle or a 5 or 6-membered heterocycle; wherein the (C$_4$-C$_6$)carbocycle or the 5 or 6-membered heterocycle is optionally substituted with one or more Z$^1$ groups.

Another specific group of compounds of formula I are compounds wherein $R^{3b}$ and $R^{3b'}$ together with the carbon to which they are attached form a 5 or 6-membered heterocycle; wherein the 5 or 6-membered heterocycle is optionally substituted with one or more Z$^1$ groups.

Another specific group of compounds of formula I are compounds wherein $R^{3b}$ and $R^{3b'}$ together with the carbon to which they are attached form a tetrahydropyran or tetrahydrofuran optionally substituted with one or more Z$^1$ groups.

Another specific group of compounds of formula I are compounds wherein $R^{3b}$ and $R^{3b'}$ together with the carbon to which they are attached form:

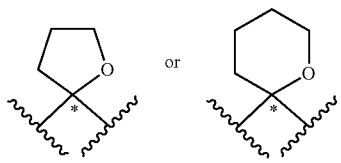 [SMILES: *C1(*)CCCO1 ; *C1(*)CCCCO1]

each of which is optionally substituted with one or more Z$^1$ groups; and wherein "*" denotes the point of attachment to the carbon of the compound of formula I.

A specific value for $R^4$ is $R^{4b}$.

A specific value for $R^{4b}$ is (C$_1$-C$_6$)alkyl, (C$_2$-C$_6$)alkenyl or (C$_2$-C$_6$)alkynyl; wherein (C$_1$-C$_6$)alkyl, (C$_2$-C$_6$)alkenyl or (C$_2$-C$_6$)alkynyl are each optionally substituted with one or more Z$^1$ groups.

Another specific value for $R^{4b}$ is:

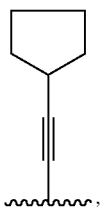

optionally substituted with one or more $Z^1$ groups.

Another specific value for $R^{4b}$ is $(C_3-C_7)$carbocycle; wherein $(C_3-C_7)$carbocycle is optionally substituted with one or more $Z^1$ groups; or wherein two $Z^1$ groups together with the atom or atoms to which they are attached optionally form a $(C_3-C_6)$carbocycle or 5-6-membered heterocycle.

Another specific value for $R^{4b}$ is:

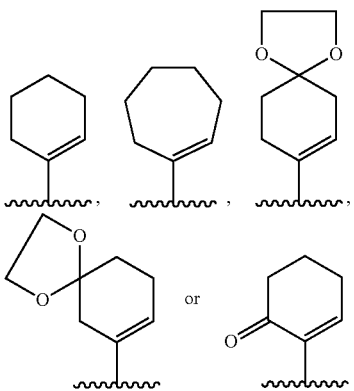

each of which is optionally substituted with one or more $Z^1$ groups.

Another specific value for $R^{4b}$ is aryl, heterocycle or heteroaryl; wherein aryl, heterocycle and heteroaryl are each independently substituted with one or more $Z^7$ groups and optionally substituted with one or more $Z^1$ groups.

Another specific value for $R^{4b}$ is:

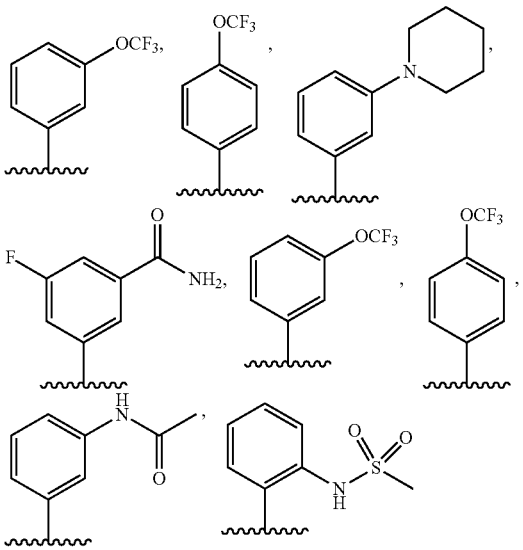

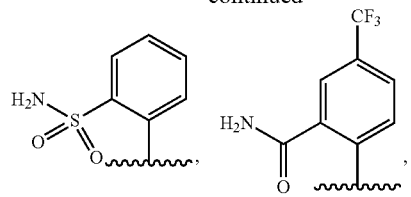

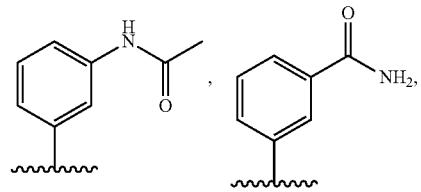

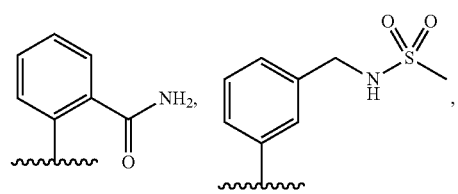

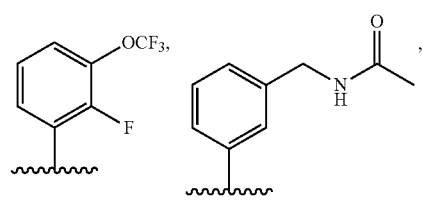

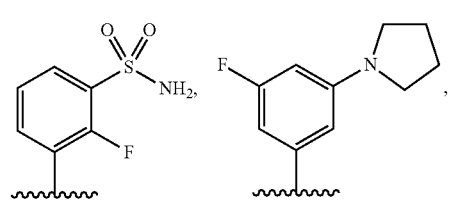

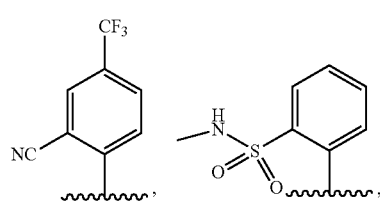

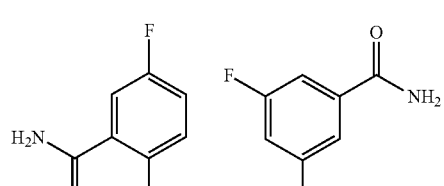

or

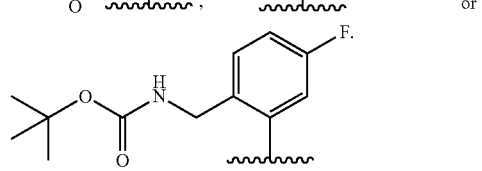

Another specific value for $R^4$ is $R^{4a}$.

A specific value for $R^{4a}$ is:

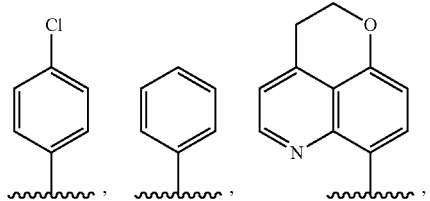
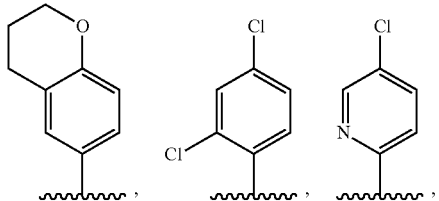
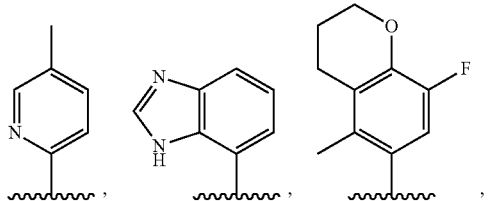
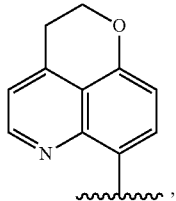
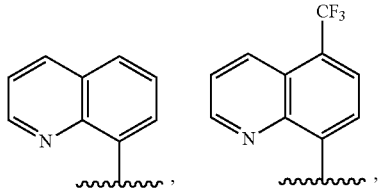
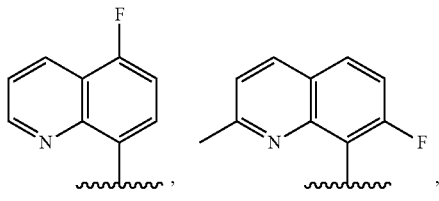
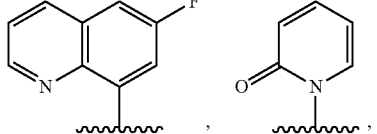
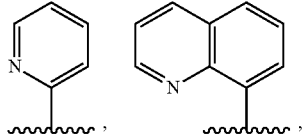
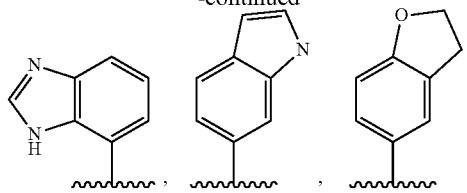

Another specific value for $R^{4a}$ is:

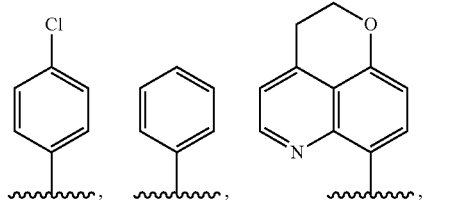
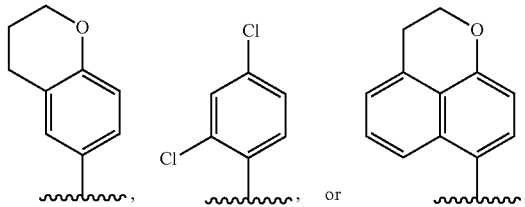

Another specific value for $R^{4a}$ is:

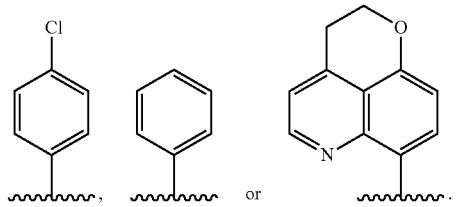

A specific value for $R^4$ is selected from:

a) aryl, heterocycle and heteroaryl, wherein any aryl, heterocycle and heteroaryl of $R^4$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —$(C_1-C_6)$alkyl-$(C_3-C_7)$cycloalkyl, —OH, —O$(C_1-C_6)$alkyl, —SH, —S$(C_1-C_6)$alkyl, —NH$_2$, —NH$(C_1-C_6)$alkyl and —N$((C_1-C_6)$alkyl$)_2$, wherein $(C_1-C_6)$alkyl is optionally substituted with hydroxy, —O$(C_1-C_6)$alkyl, cyano or oxo; and b) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g. 1, 2, 3, 4 or 5) $Z^1$ groups.

Another specific value for $R^4$ is selected from:

a) aryl, heterocycle and heteroaryl, wherein any aryl, heterocycle and heteroaryl of $R^4$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, —$(C_1-C_6)$alkyl-$(C_3-C_7)$cycloalkyl, —OH, —O$(C_1-C_6)$alkyl, —SH, —S$(C_1-C_6)$alkyl, —NH$_2$, —NH$(C_1-C_6)$alkyl and —N$((C_1-C_6)$alkyl$)_2$, wherein $(C_1-C_6)$alkyl is optionally substituted with hydroxy, —O$(C_1-C_6)$alkyl, cyano or oxo; and b) aryl and heteroaryl, wherein aryl and heteroaryl are each independently substituted with one or more $Z^7$ groups and optionally substituted with one or more (e.g. 1, 2, 3, 4 or 5) $Z_1$ groups.

Another specific value for $R^4$ is selected from aryl, heterocycle and heteroaryl, wherein any aryl, heterocycle and heteroaryl of $R^4$ is optionally substituted with one or more (e.g. 1, 2, 3, 4 or 5) groups each independently selected from halo, $(C_1-C_6)$alkyl, $(C_2-C_6)$alkenyl, $(C_1-C_6)$haloalkyl, $(C_3-C_7)$cycloalkyl, $-(C_1-C_6)$alkyl-$(C_3-C_7)$cycloalkyl, $-OH$, $-O(C_1-C_6)$alkyl, $-SH$, $-S(C_1-C_6)$alkyl, $-NH_2$, $-NH(C_1-C_6)$alkyl and $-N((C_1-C_6)$alkyl$)_2$, wherein $(C_1-C_6)$alkyl is optionally substituted with hydroxy, $-O(C_1-C_6)$alkyl, cyano or oxo.

Another specific value for $R^4$ is:

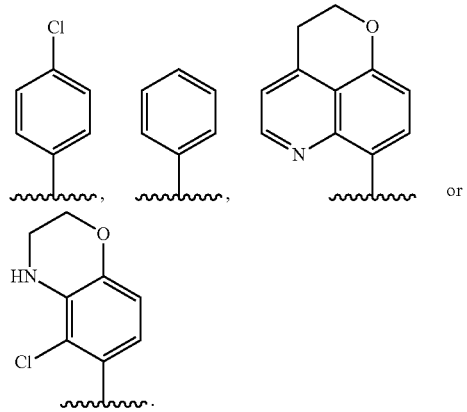

Another specific value for $R^4$ is:

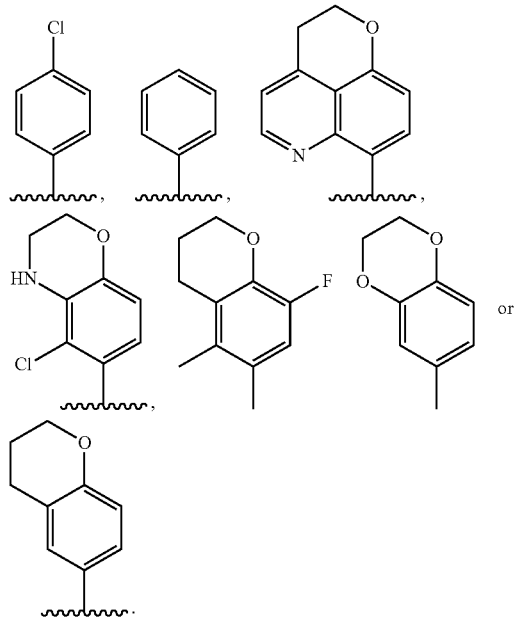

A specific group of compounds of formula I are compounds wherein $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more $Z^1$ groups; and $R^{3'}$ is H, $(C_1-C_6)$alkyl or $-O(C_1-C_6)$alkyl.

Another specific group of compounds of formula I are compounds wherein $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more $Z^1$ groups; and $R^{3'}$ is H.

Another specific group of compounds of formula I are compounds wherein $R^4$ and $R^3$ together with the atoms to which they are attached form the macroheterocycle or a macrocarbocycle which is further fused to a Z group;

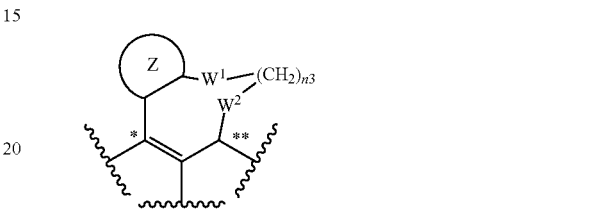

wherein:
Z is aryl, heteroaryl or $(C_3-C_6)$carbocycle;
n3 is 2, 3 or 4;
$W^1$ and $W^2$ are each independently O, NH or $CH_2$; and
wherein "*" denotes the $R^4$ point of attachment of the macroheterocycle or macrocarbocycle to the compound of formula I and "**" denotes the $R^3$ point of attachment of the macroheterocycle or macrocarbocycle to the compound of formula I; and wherein the macroheterocycle or a macrocarbocycle is optionally substituted with one or more $Z^1$ groups.

Another specific group of compounds of formula I are compounds wherein, $R^4$ and $R^3$ together with the atoms to which they are attached form the macroheterocycle:

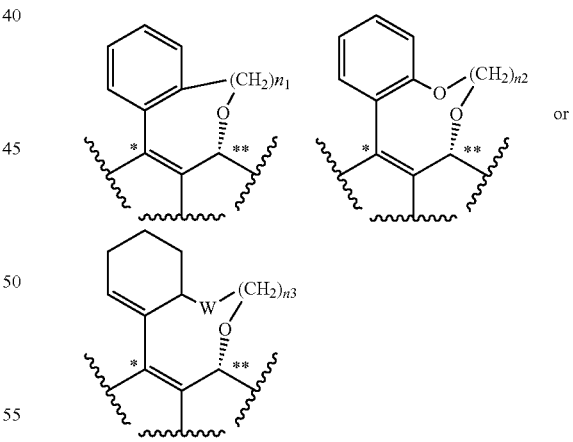

wherein:
n1 is 3 or 4; n2 is 2, 3 or 4; n3 is 2, 3 or 4; W is O, NH or $N(C_1-C_4)$alkyl; and wherein "*" denotes the $R^4$ point of attachment of the macroheterocycle to the compound of formula I and "**" denotes the $R^3$ point of attachment of the macroheterocycle to the compound of formula I; and wherein the macroheterocycle or a macrocarbocycle is optionally substituted with one or more $Z^1$ groups A specific value for $R^2$ is $R^{2b}$.
Another specific value $R^2$ is $R^{2a}$.

A specific value for $R^{2a}$ is H, halo or —CH$_3$.

Another specific value for $R^{2a}$ is Cl.

A specific value for $R^2$ is halo, H or (C$_1$-C$_6$)alkyl.

Another specific value for $R^2$ is halo, H or —CH$_3$.

Another specific value for $R^2$ is H or —CH$_3$.

Another specific value for $R^2$ is H or (C$_1$-C$_6$)alkyl.

Another specific value for $R^2$ is (C$_1$-C$_6$)alkyl.

Another specific value for $R^2$ is —CH$_3$.

Another specific value for $R^5$ is $R^{5a}$.

Another specific value for $R^{5a}$ is H, (C$_1$-C$_6$)alkyl, (C$_3$-C$_7$)carbocycle, —(C$_1$-C$_6$)alkyl-R$^{11}$, —C(=O)—R$^{11}$, —N(R$^9$)R$^{10}$, —C(=O)—N(R$^9$)R$^{10}$, heterocycle or heteroaryl, wherein heteroaryl is optionally substituted with one or more Z$^{11}$ groups.

Another specific value for $R^{5a}$ is H, (C$_1$-C$_6$)alkyl, (C$_3$-C$_7$)carbocycle, —C(=O)—R$^{11}$, —N(R$^9$)R$^{10}$, —C(=O)—N(R$^9$)R$^{10}$ or heterocycle.

Another specific value for $R^{5a}$ is H, (C$_1$-C$_6$)alkyl, (C$_3$-C$_7$)cycloalkyl or —(C$_1$-C$_6$)alkyl-R$^{11}$.

A specific value for $R^{11}$ is aryl.

Another specific value for $R^{11}$ is carbocycle or aryl.

Another specific value for $R^{11}$ is carbocycle.

Another specific value for $R^{5a}$ is —N(R$^9$)R$^{10}$.

A specific value for $R^9$ is H or (C$_1$-C$_6$)alkyl.

A specific value for $R^{10}$ is H or (C$_1$-C$_6$)alkyl.

Another specific value for $R^9$ is H, (C$_1$-C$_6$)alkyl or —C(=O)—R$^{11}$.

Another specific value for $R^{10}$ is H, (C$_1$-C$_6$)alkyl or —C(=O)—R$^{11}$.

A value for $Z^9$ is "each $Z^9$ is independently selected from —(C$_1$-C$_6$)alkyl, —O(C$_1$-C$_6$)alkyl".

A specific value for $R^{5a}$ is:

Another specific value for $R^{5a}$ is:

A specific value for $R^5$ is $R^{5b}$.

Another specific value for $R^{5b}$ is —(C$_2$-C$_6$)alkynyl-(C$_3$-C$_7$)carbocycle.

Another specific value for $R^{5b}$ is:

A specific value for $R^5$ is H, (C$_1$-C$_6$)alkyl, (C$_3$-C$_7$)carbocycle, —C(=O)—R$^{11}$, —N(R$^9$)R$^{10}$, —C(=O)—N(R$^9$)R$^{10}$, heterocycle or —(C$_2$-C$_6$)alkynyl-(C$_3$-C$_7$)carbocycle.

A specific value for $R^5$ is:

Another specific value for $R^5$ is:

-continued

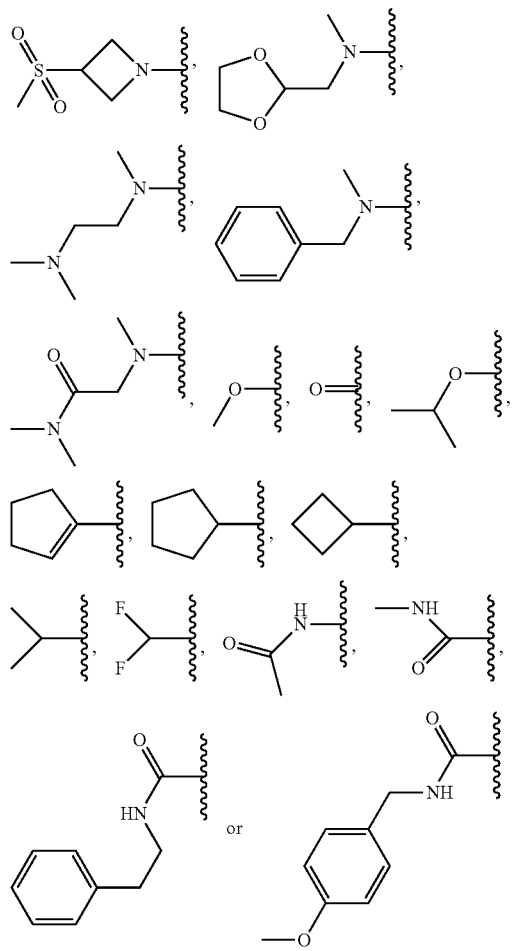

Another specific value for R⁵ is:

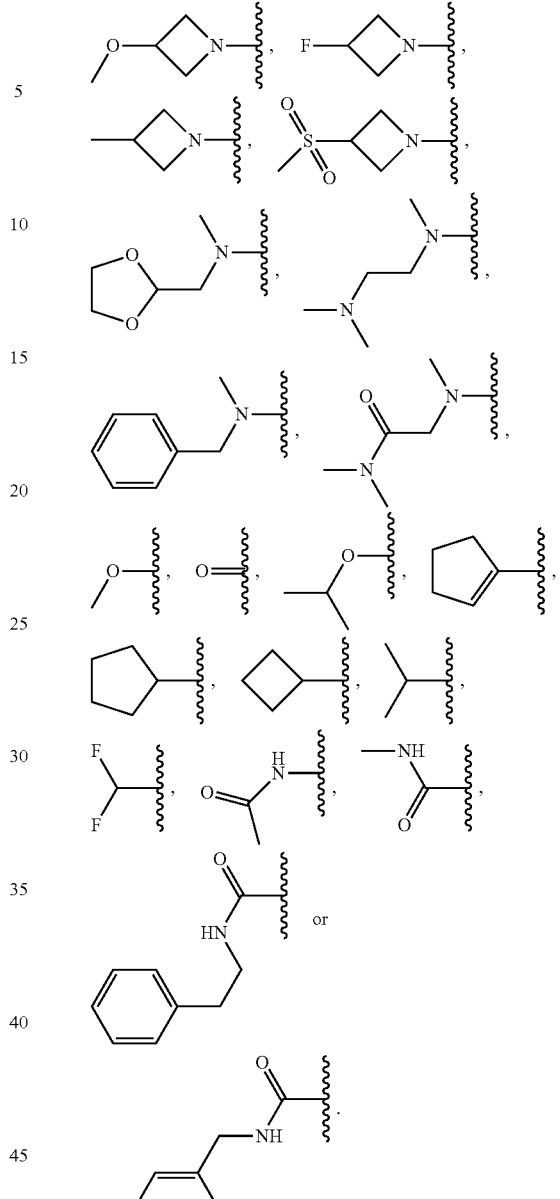

A specific value for R⁵ is selected from:
a) $R^{11}$, —C(=O)—$R^{11}$, —C(O)—O—$R^{11}$, —O—$R^{11}$, —S—$R^{11}$, —S(O)—$R^{11}$, —$SO_2$—$R^{11}$, —($C_1$-$C_6$)alkyl-$R^{11}$, —($C_1$-$C_6$)alkyl-C(=O)—$R^{11}$, —($C_1$-$C_6$)alkyl-C(=O)—O—$R^{11}$, —($C_1$-$C_6$)alkyl-O—$R^{11}$, —($C_1$-$C_6$)alkyl-S—$R^{11}$, —($C_1$-$C_6$)alkyl-S(O)—$R^{11}$ and —($C_1$-$C_6$)alkyl-$SO_2$—$R^{11}$, wherein each $R^{11}$ is independently selected from H, ($C_1$-$C_6$) alkyl, ($C_2$-$C_6$)alkenyl, ($C_2$-$C_6$)alkynyl, ($C_1$-$C_6$)haloalkyl, ($C_3$-$C_7$)carbocycle, aryl, heterocycle and heteroaryl, wherein aryl, heterocycle and heteroaryl are each optionally substituted with one or more (e.g. 1, 2 or 3) $Z^{11}$ groups;
b) —N($R^9$)$R^{10}$, —C(O)—N($R^9$)$R^{10}$, —O—C(=O)—N ($R^9$)$R^{10}$, —$SO_2$—N($R^9$)$R^{10}$, —($C_1$-$C_6$)alkyl-N($R^9$)$R^{10}$, —($C_1$-$C_6$)alkyl-C(=O)—N($R^9$)$R^{10}$, —($C_1$-$C_6$)alkyl-O—C (=O)—N($R^9$)$R^{10}$, and —($C_1$-$C_6$)alkyl-$SO_2$—N($R^9$)$R^{10}$; wherein each $R^9$ is independently selected from H, ($C_1$-$C_6$)

alkyl and (C$_3$-C$_7$)cycloalkyl; and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

c) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkylS(O)—(C$_1$-C$_6$)alkyl-(C$_3$-C$_6$)carbocycle, —(C$_1$-C$_6$)alkySO$_2$(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or —(C$_1$-C$_6$)haloalkyl-Z$^3$, wherein any (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl, either alone or as part of a group, is optionally substituted with one or more (e.g. 1, 2, 3, 4 or 5) Z$^1$ groups;

d) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$, wherein each (C$_1$-C$_6$)alkyl is independently substituted with one or more (e.g. 1, 2, 3, 4 or 5) Z$^6$ groups and optionally substituted with one or more (e.g. 1, 2, 3, 4 or 5) Z$^1$ groups; and e) oxo.

Another specific value for R$^5$ is selected from:

a) R$^{11}$, —C(=O)—R$^{11}$, —C(=O)—O—R$^{11}$ and —O—R$^{11}$; wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, aryl, heterocycle and heteroaryl, wherein any aryl, heterocycle or heteroaryl is each optionally substituted with one or more (e.g. 1, 2 or 3) Z$^{11}$ groups;

b) —N(R$^9$)R$^{10}$ and —C(=O)—N(R$^9$)R$^{10}$; wherein each R$^9$ is independently selected from H, (C$_1$-C$_6$)alkyl and (C$_3$-C$_7$)cycloalkyl; and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

c) —(C$_2$-C$_6$)alkynyl-(C$_3$-C$_7$)carbocycle, wherein —(C$_2$-C$_6$)alkynyl-(C$_3$-C$_7$)carbocycle is optionally substituted with one or more (e.g. 1, 2, 3, 4 or 5) Z$^1$ groups; and d) —NR$_e$R$_f$ and —C(O)NR$_e$R$_f$.

Another specific value for R$^5$ is selected from:

a) H, (C$_1$-C$_6$)alkyl, (C$_1$-C$_6$)haloalkyl, (C$_3$-C$_7$)carbocycle, heterocycle, —C(=O)—R$^{11}$, —C(=O)—O—R$^{11}$ and —O—R$^{11}$, wherein heterocycle is optionally substituted with one or more (e.g. 1, 2 or 3) Z$^{11}$ groups and wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)carbocycle, aryl, heterocycle and heteroaryl, wherein aryl, heterocycle and heteroaryl are each optionally substituted with one or more (e.g. 1, 2 or 3) Z$^{11}$ groups;

b) —N(R$^9$)R$^{10}$ and —C(=O)—N(R$^9$)R$^{10}$; wherein each R$^9$ is independently selected from H, (C$_1$-C$_6$)alkyl and (C$_3$-C$_7$)cycloalkyl; and each R$^{10}$ is independently selected from R$^{11}$, —(C$_1$-C$_6$)alkyl-R$^{11}$, —SO$_2$—R$^{11}$, —C(=O)—R$^{11}$, —C(=O)OR$^{11}$ and —C(=O)N(R$^9$)R$^{11}$, wherein each R$^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

c) —(C$_2$-C$_6$)alkynyl-(C$_3$-C$_7$)carbocycle, wherein —(C$_2$-C$_6$)alkynyl-(C$_3$-C$_7$)carbocycle is optionally substituted with one or more (e.g. 1, 2, 3, 4 or 5) Z$^1$ groups; and d) —NR$_e$R$_f$ and —C(O)NR$_e$R$_f$.

Another specific value for R$^5$ is selected from:

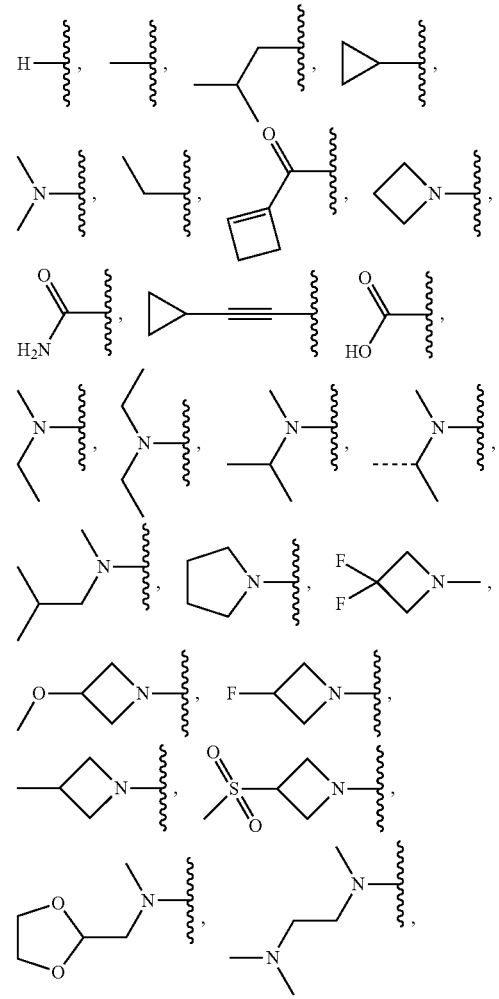

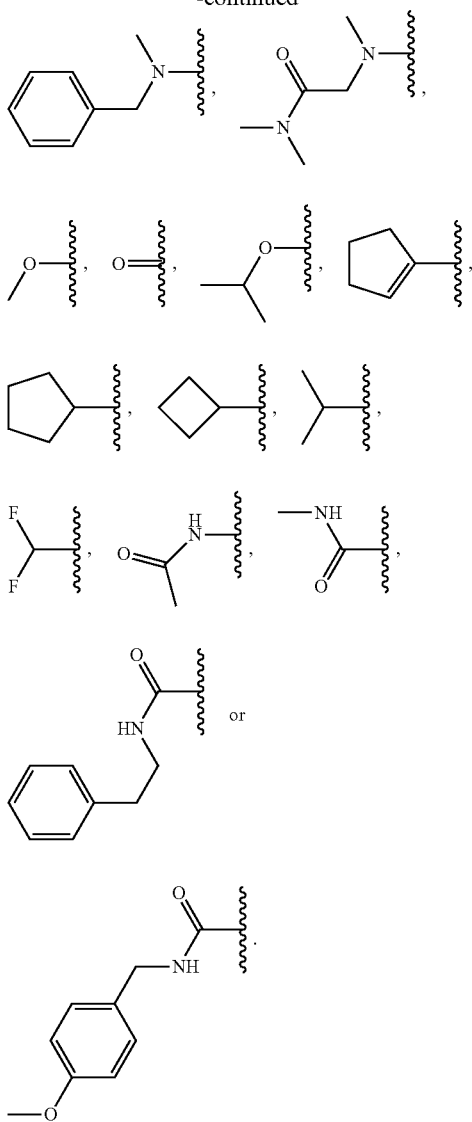

A specific group of compounds of formula I are compounds wherein $R^5$ is oxo and $R^6$ is selected from $R^{11}$ and —$(C_1$-$C_6)$alkyl-$R^{11}$, wherein each $R^{11}$ is independently selected from H, $(C_1$-$C_6)$alkyl, $(C_2$-$C_6)$alkenyl, $(C_2$-$C_6)$alkynyl, $(C_1$-$C_6)$haloalkyl, $(C_3$-$C_7)$cycloalkyl, aryl, heterocycle and heteroaryl, wherein aryl, heterocycle and heteroaryl are each optionally substituted with one or more (e.g. 1, 2 or 3) $Z^{11}$ groups.

Another specific group of compounds of formula I are compounds wherein $R^5$ is oxo and $R^6$ is selected from:

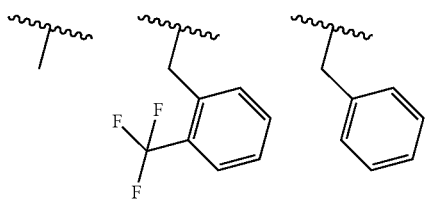

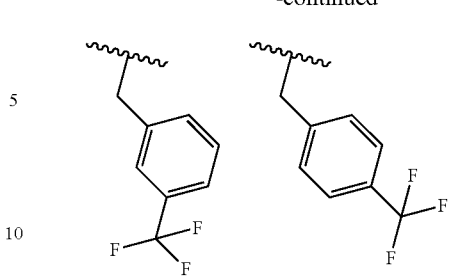

A specific group of compounds of formula I are compounds wherein $R^{4b}$ is selected from;
a) $(C_1$-$C_6)$alkyl, $(C_2$-$C_6)$alkenyl and $(C_2$-$C_6)$alkynyl, wherein any $(C_1$-$C_6)$alkyl, $(C_2$-$C_6)$alkenyl or $(C_2$-$C_6)$alkynyl is optionally substituted with one or more (e.g. 1, 2, 3, 4 or 5) $Z^1$ groups;
b) $(C_3$-$C_{14})$carbocycle, wherein $(C_3$-$C_{14})$carbocycle is optionally substituted with one or more (e.g. 1, 2, 3, 4 or 5) $Z^1$ groups;
c) Spiro-heterocycle or bridged-heterocycle, wherein spiro-heterocycle or bridged-heterocycle is optionally substituted with one or more (e.g. 1, 2, 3, 4 or 5) $Z^1$ groups; and
d) aryl, heterocycle and heteroaryl, wherein aryl, heterocycle and heteroaryl are each independently substituted with one or more $Z^7$ groups and optionally substituted with one or more (e.g. 1, 2, 3, 4 or 5) $Z^1$ groups.

Another specific group of compounds of formula I are compounds wherein $R^{4b}$ is selected from;
a) $(C_1$-$C_6)$alkyl, $(C_2$-$C_6)$alkenyl and $(C_2$-$C_6)$alkynyl, wherein any $(C_1$-$C_6)$alkyl, $(C_2$-$C_6)$alkenyl or $(C_2$-$C_6)$alkynyl is optionally substituted with one or more (e.g. 1, 2, 3, 4 or 5) $Z^1$ groups;
b) $(C_3$-$C_{14})$carbocycle, wherein $(C_3$-$C_{14})$carbocycle is optionally substituted with one or more (e.g. 1, 2, 3, 4 or 5) $Z^1$ groups; wherein two $Z^1$ groups together with the atom or atoms to which they are attached optionally form a $(C_3$-$C_7)$ carbocycle or heterocycle; and
c) aryl, heterocycle and heteroaryl, wherein aryl, heterocycle and heteroaryl are each independently substituted with one or more (e.g. 1, 2, 3, 4 or 5) $Z^7$ groups and optionally substituted with one or more (e.g. 1, 2, 3, 4 or 5) $Z^1$ groups.

Another specific group of compounds of formula I are compounds wherein $R^{4b}$ is selected from;
a) $(C_1$-$C_6)$alkyl, $(C_2$-$C_6)$alkenyl and $(C_2$-$C_6)$alkynyl, wherein any $(C_1$-$C_6)$alkyl, $(C_2$-$C_6)$alkenyl or $(C_2$-$C_6)$alkynyl is optionally substituted with one or more (e.g. 1, 2, 3, 4 or 5) $Z^1$ groups;
b) $(C_3$-$C_{14})$carbocycle, wherein $(C_3$-$C_{14})$carbocycle is optionally substituted with one or more (e.g. 1, 2, 3, 4 or 5) $Z^1$ groups; and
c) aryl, heterocycle and heteroaryl, wherein aryl, heterocycle and heteroaryl are each independently substituted with one or more (e.g. 1, 2, 3, 4 or 5) $Z^7$ groups and optionally substituted with one or more (e.g. 1, 2, 3, 4 or 5) $Z^1$ groups.

In another embodiment, the invention provides a compound of the invention which is a compound of formula I:

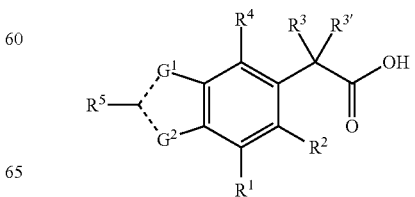

wherein:

$G^1$ is S; $G^2$ is N; the dashed bond connected to $G^1$ is a single bond and the dashed bond connected to $G^2$ is a double bond, or $G^1$ is N; $G^2$ is S; the dashed bond connected to $G^1$ is a double bond and the dashed bond connected to $G^2$ is a single bond;

$R^1$ is $R^{1a}$ or $R^{1b}$;
$R^1$ is $R^{2a}$ or $R^{2b}$;
$R^3$ is $R^{3a}$ or $R^{3b}$;
$R^{3'}$ is $R^{3a'}$ or $R^{3b'}$;
$R^4$ is $R^{4a}$ or $R^{4b}$;
$R^5$ is $R^{5a}$ or $R^{5b}$;

$R^{1a}$ is selected from:

a) halo;

b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl-$R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl, wherein aryl, heterocycle or heteroaryl are each optionally substituted with one or more (e.g. 1, 2 or 3) $Z^{11}$ groups; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$alkyl-O—C(=O)—N(R$^9$)R$^{10}$ and —(C$_1$-C$_6$)alkyl-SO$_2$—N(R$^9$)R$^{10}$; wherein each $R^9$ is independently selected from H, (C$_1$-C$_6$)alkyl and (C$_3$-C$_7$)cycloalkyl; and each $R^{10}$ is independently selected from $R^{11}$, —(C$_1$-C$_6$)alkyl-$R^{11}$, —SO$_2$—$R^{11}$, —C(=O)—$R^{11}$, —C(=O)OR$^{11}$ and —C(=O)N(R$^9$)R$^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl, heterocycle and heteroaryl;

$R^{1b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_6$)carbocycle, —(C$_1$-C$_6$)alkyl-SO$_2$—(C$_1$-C$_6$)alkyl-(C$_3$-C$_7$)carbocycle, —(C$_1$-C$_6$)alkyl-SO$_2$—(C$_1$-C$_6$)alkyl-Z$^{13}$, —C(O)—(C$_1$-C$_6$)alkyl-Z$^{13}$, —O—(C$_1$-C$_6$)alkyl-Z$^{13}$, —S—(C$_1$-C$_6$)alkyl-Z$^{13}$, —S(O)—(C$_1$-C$_6$)alkyl-Z$^{13}$, —SO$_2$(C$_1$-C$_6$)alkyl-Z$^{13}$, —(C$_1$-C$_6$)alkyl-Z$^{14}$, —(C$_1$-C$_6$)alkyl-C(O)—(C$_1$-C$_6$)alkyl-Z$^{13}$, —(C$_1$-C$_6$)alkyl-C(O)—O(C$_1$-C$_6$)alkyl-Z$^{13}$, —(C$_1$-C$_6$)alkyl-O—(C$_1$-C$_6$)alkyl-Z$^{13}$, —(C$_1$-C$_6$)alkyl-S—(C$_1$-C$_6$)alkyl-Z$^{13}$, —(C$_2$-C$_6$)alkenyl-(C$_1$-C$_6$)haloalkyl, —(C$_2$-C$_6$)alkynyl-(C$_1$-C$_6$)haloalkyl, —(C$_3$-C$_7$)halocarbocycle, —NR$_a$SO$_2$NR$_c$R$_d$, —NR$_a$SO$_2$O(C$_3$-C$_7$)carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or -halo(C$_1$-C$_6$)alkyl-Z$^3$; wherein (C$_1$-C$_6$)alkyl, (C$_1$-C$_6$)haloalkyl, (C$_3$-C$_7$)carbocycle, (C$_2$-C$_6$)alkenyl, (C$_2$-C$_6$)alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a carbocycle or heterocycle wherein the carbocycle or heterocycle is optionally substituted with one or more (e.g. 1, 2, 3, 4 or 5) $Z^1$ groups;

c) (C$_1$-C$_6$)alkyl; wherein (C$_1$-C$_6$)alkyl is substituted with one or more $Z^2$ groups and optionally substituted with one or more (e.g. 1, 2, 3, 4 or 5) $Z^1$ groups;

d) —X(C$_1$-C$_6$)alkyl, —X(C$_1$-C$_6$)haloalkyl, —X(C$_2$-C$_6$)alkenyl, —X(C$_2$-C$_6$)alkynyl and —X(C$_3$-C$_7$)carbocycle; wherein (C$_1$-C$_6$)alkyl and (C$_1$-C$_6$)haloalkyl are each substituted with one or more $Z^3$ groups and optionally substituted with one or more $Z^1$ groups; and wherein (C$_2$-C$_6$)alkenyl, (C$_2$-C$_6$)alkynyl and (C$_3$-C$_7$)carbocycle are each substituted with one or more (e.g. 1, 2, 3, 4 or 5) $Z^4$ groups and optionally substituted with one or more $Z^1$ groups;

e) aryl, heteroaryl, heterocycle, —Xaryl, —Xheteroaryl and —Xheterocycle; wherein aryl heteroaryl and heterocycle are each substituted with one or more (e.g. 1, 2, 3, 4 or 5) $Z^5$ groups and optionally substituted with one or more $Z^1$ groups;

f) (C$_1$-C$_6$)haloalkyl, (C$_3$-C$_7$)carbocycle, (C$_2$-C$_6$)alkenyl, and (C$_2$-C$_6$)alkynyl; wherein (C$_1$-C$_6$)haloalkyl, (C$_3$-C$_7$)carbocycle, (C$_2$-C$_6$)alkenyl and (C$_2$-C$_6$)alkynyl are each substituted with one or more (e.g. 1, 2, 3, 4 or 5) $Z^6$ groups and optionally substituted with one or more $Z^1$ groups;

g) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$, wherein each (C$_1$-C$_6$)alkyl is substituted with one or more (e.g. 1, 2, 3, 4 or 5) $Z^6$ groups and optionally substituted with one or more $Z^1$ groups: and h) nitro and cyano $R^{2a}$ is selected from:

a) halo;

b) $R^{11}$, C(=O)—$R^{11}$, —C(=O)—O—$R^{11}$, —O—$R^{11}$, —S—$R^{11}$, —S(O)—$R^{11}$, —SO$_2$—$R^{11}$, —(C$_1$-C$_6$)alkyl $R^{11}$, —(C$_1$-C$_6$)alkyl-C(=O)—$R^{11}$, —(C$_1$-C$_6$)alkyl-C(=O)—O—$R^{11}$, —(C$_1$-C$_6$)alkyl-O—$R^{11}$, —(C$_1$-C$_6$)alkyl-S—$R^{11}$, —(C$_1$-C$_6$)alkyl-S(O)—$R^{11}$ and —(C$_1$-C$_6$)alkyl-SO$_2$—$R^{11}$; wherein each $R^{11}$ is independently selected from H, (C$_1$-C$_6$)alkyl, (C$_2$-C$_6$)alkenyl, (C$_2$-C$_6$)alkynyl, (C$_1$-C$_6$)haloalkyl, (C$_3$-C$_7$)cycloalkyl, aryl and heterocycle and heteroaryl, wherein aryl, heterocycle or heteroaryl are each optionally substituted with one or more (e.g. 1, 2 or 3) $Z^{11}$ groups; and c) —N(R$^9$)R$^{10}$, —C(=O)—N(R$^9$)R$^{10}$, —O—C(=O)—N(R$^9$)R$^{10}$, —SO$_2$—N(R$^9$)R$^{10}$, —(C$_1$-C$_6$)alkyl-N(R$^9$)R$^{10}$, —(C$_1$-C$_6$)alkyl-C(=O)—N(R$^9$)R$^{10}$, —(C$_1$-C$_6$)alkyl-O—C(=O)—N(R$^9$)R$^{10}$, and —(C$_1$-C$_6$)alkyl-SO$_2$—N(R$^9$)R$^{10}$, wherein each $R^9$ is independently selected from H, (C$_1$-C$_6$)alkyl and (C$_3$-C$_7$)cycloalkyl;

each $R^{10}$ is independently selected from $R^{11}$, —(C$_1$-C$_6$)alkyl-$R^{11}$, —SO$_2$—$R^{11}$, —C(=O)$R^{11}$, —C(=O)OR$^{11}$ and —C(=O)N(R$^9$)R$^{11}$; wherein each $R^{11}$ is independently selected from H, (C$_1$-C$_6$)alkyl, (C$_2$-C$_6$)alkenyl, (C$_2$-C$_6$)alkynyl (C$_1$-C$_6$)haloalkyl, (C$_3$-C$_7$)cycloalkyl, aryl, heterocycle and heteroaryl;

$R^{2b}$ is selected from:

a) —(C$_1$-C$_6$)alkyl-O—(C$_1$-C$_6$)alkyl-(C$_3$-C$_7$)carbocycle, —(C$_1$-C$_6$)alkyl-S—(C$_1$-C$_6$)alkyl-(C$_3$-C$_7$)carbocycle, —(C$_1$-C$_6$)alkyl-S(O)—(C$_1$-C$_6$)alkyl-(C$_3$-C$_7$)carbocycle, —(C$_1$-C$_6$)alkyl-SO$_2$—(C$_1$-C$_6$)alkyl-(C$_3$-C$_7$)carbocycle, —(C$_2$-C$_6$)alkenyl-(C$_1$-C$_6$)haloalkyl, —(C$_2$-C$_6$)alkynyl-(C$_1$-C$_6$)haloalkyl, —(C$_1$-C$_6$)alkyl-SO$_2$—(C$_1$-C$_6$)alkyl-Z$^{13}$, —C(O)—(C$_1$-C$_6$)alkyl-Z$^{13}$, —O—(C$_1$-C$_6$)alkyl-Z$^{14}$, —(C$_1$-C$_6$)alkyl-C(O)—(C$_1$-C$_6$)alkyl-Z$^{13}$, —(C$_1$-C$_6$)alkylC(O)—O(C$_1$-C$_6$)alkyl-Z$^{13}$, —(C$_1$-C$_6$)alkyl-O—(C$_1$-C$_6$)alkyl-Z$^{13}$, —(C$_1$-C$_6$)alkyl-S—(C$_1$-C$_6$)alkyl-Z$^{13}$, —(C$_3$-C$_7$)halocarbocycle, —NR$_a$SO$_2$NR$_c$R$_d$, —NR$_a$SO$_2$O(C$_3$-C$_7$)

carbocycle, —NR$_a$SO$_2$Oaryl, —(C$_2$-C$_6$)alkenyl-(C$_3$-C$_7$)carbocycle, —(C$_2$-C$_6$)alkenyl-aryl, —(C$_2$-C$_6$)alkenyl-heteroaryl, —(C$_2$-C$_6$)alkenyl-heterocycle, —(C$_2$-C$_6$)alkynyl-(C$_3$-C$_7$)carbocycle, —(C$_2$-C$_6$)alkynyl-aryl, —(C$_2$-C$_6$)alkynyl-heteroaryl, —(C$_2$-C$_6$)alkynyl-heterocycle, —(C$_3$-C$_7$)carbocycle-Z$^1$ or -halo(C$_1$-C$_6$)alkyl-Z$^3$; wherein (C$_1$-C$_6$)alkyl, —(C$_1$-C$_6$)haloalkyl, (C$_3$-C$_7$)carbocycle, (C$_2$-C$_6$)alkenyl, (C$_2$-C$_6$)alkynyl, aryl or heteroaryl are each optionally substituted with one or more (e.g. 1, 2, 3, 4 or 5) Z$^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) Z$^1$ groups; wherein two Z$^1$ groups together with the atom or atoms to which they are attached optionally form a (C$_3$-C$_7$)carbocycle or heterocycle wherein the (C$_3$-C$_6$)carbocycle or heterocycle is optionally substituted with one or more (e.g. 1, 2, 3, 4 or 5) Z$^1$ groups;

c) (C$_1$-C$_6$)alkyl; wherein (C$_1$-C$_6$)alkyl is substituted with one or more Z$^2$ groups and optionally substituted with one or more (e.g. 1, 2, 3, 4 or 5) Z$^1$ groups;

d) —X(C$_1$-C$_6$)alkyl, X(C$_1$-C$_6$)haloalkyl, X(C$_2$-C$_6$)alkenyl, —X(C$_2$-C$_6$)alkynyl and —X(C$_3$-C$_7$)carbocycle; wherein (C$_1$-C$_6$)alkyl and (C$_1$-C$_6$)haloalkyl are each substituted with one or more Z$^3$ groups and optionally substituted with one or more (e.g. 1, 2, 3, 4 or 5) Z$^1$ groups; and wherein (C$_2$-C$_6$)alkenyl, (C$_2$-C$_6$)alkynyl and (C$_3$-C$_7$)carbocycle are each substituted with one or more (e.g. 1, 2, 3, 4 or 5) Z$^4$ groups and optionally substituted with one or more Z$^1$ groups;

e) aryl, heteroaryl, heterocycle, —Xaryl, —Xheteroaryl and —Xheterocycle; wherein aryl heteroaryl and heterocycle are each substituted with one or more (e.g. 1, 2, 3, 4 or 5) Z$^5$ groups and optionally substituted with one or more (e.g. 1, 2, 3, 4 or 5) Z$^1$ groups;

f) (C$_1$-C$_6$)haloalkyl, (C$_3$-C$_7$)carbocycle, (C$_2$-C$_6$)alkenyl, and (C$_2$-C$_6$)alkynyl; wherein (C$_1$-C$_6$)haloalkyl, (C$_3$-C$_7$)carbocycle, (C$_2$-C$_6$)alkenyl and (C$_2$-C$_6$)alkynyl are each substituted with one or more (e.g. 1, 2, 3, 4 or 5) Z$^6$ groups and optionally substituted with one or more (e.g. 1, 2, 3, 4 or 5) Z$^1$ groups;

g) —NR$_e$R$_f$, —C(O)NR$_e$R$_f$, —OC(O)NR$_e$R$_f$, —SO$_2$NR$_e$R$_f$, —(C$_1$-C$_6$)alkyl-NR$_e$R$_f$, —(C$_1$-C$_6$)alkylC(O)—NR$_e$R$_f$, —(C$_1$-C$_6$)alkyl-O—C(O)—NR$_e$R$_f$ and —(C$_1$-C$_6$)alkyl-SO$_2$NR$_e$R$_f$, wherein each (C$_1$-C$_6$)alkyl is substituted with one or more (e.g. 1, 2, 3, 4 or 5) Z$^6$ groups and optionally substituted with one or more (e.g. 1, 2, 3, 4 or 5) Z$^1$ groups; and h) nitro and cyano;

R$^{3a}$ is (C$_1$-C$_6$)alkyl, (C$_1$-C$_6$)haloalkyl, (C$_2$-C$_6$)alkenyl, (C$_2$-C$_6$)alkynyl, —(C$_1$-C$_6$)alkyl-(C$_3$-C$_7$)cycloalkyl, —(C$_1$-C$_6$)alkyl-aryl, —(C$_1$-C$_6$)alkyl-heterocycle, —(C$_1$-C$_6$)alkyl-heteroaryl, —O(C$_1$-C$_6$)alkyl, —O(C$_1$-C$_6$)haloalkyl, —O(C$_2$-C$_6$)alkenyl, —O(C$_2$-C$_6$)alkynyl, —O(C$_3$-C$_7$)cycloalkyl, —Oaryl, —O(C$_1$-C$_6$)alkyl-(C$_3$-C$_7$)cycloalkyl, —O(C$_1$-C$_6$)alkyl-aryl, —O(C$_1$-C$_6$)alkyl-heterocycle and —O(C$_1$-C$_6$)alkyl-heteroaryl; wherein any (C$_1$-C$_6$)alkyl, (C$_1$-C$_6$)haloalkyl, (C$_2$-C$_6$)alkenyl, (C$_2$-C$_6$)alkynyl, —(C$_1$-C$_6$)alkyl-(C$_3$-C$_7$)cycloalkyl, —(C$_1$-C$_6$)alkyl-aryl, —(C$_1$-C$_6$)alkyl-heterocycle, —(C$_1$-C$_6$)alkyl-heteroaryl, —O(C$_1$-C$_6$)alkyl, —O(C$_1$-C$_6$)haloalkyl, —O(C$_2$-C$_6$)alkenyl, —O(C$_2$-C$_6$)alkynyl, —O(C$_3$-C$_7$)cycloalkyl, —Oaryl, —O(C$_1$-C$_6$)alkyl-(C$_3$-C$_7$)cycloalkyl, —O(C$_1$-C$_6$)alkyl-aryl, —O(C$_1$-C$_6$)alkyl-heterocycle or —O(C$_1$-C$_6$)alkyl-heteroaryl of R$^{3a}$ is optionally substituted with one or more (e.g. 1, 2 or 3) groups selected from (C$_1$-C$_6$)alkyl, —O(C$_1$-C$_6$)alkyl, halo, oxo and —CN; and R$^{3a'}$ is H;

R$^{3b}$ is —(C$_3$-C$_7$)carbocycle, aryl, heteroaryl, heterocycle, —(C$_1$-C$_6$)alkylOH, —(C$_1$-C$_6$)alkyl-O—(C$_1$-C$_6$)alkyl-Z$^{12}$, —(C$_1$-C$_6$)alkyl-O(C$_2$-C$_6$)alkenyl-Z$^{12}$, —(C$_2$-C$_6$)alkyl-O—(C$_2$-C$_6$)alkynyl-Z$^{12}$, —(C$_1$-C$_6$)alkyl-S—(C$_1$-C$_6$)alkyl-Z$^{12}$, —(C$_1$-C$_6$)alkyl-S—(C$_2$-C$_6$)alkenyl-Z$^{12}$, —(C$_2$-C$_6$)alkyl-S—(C$_2$-C$_6$)alkynyl-Z$^{12}$, —(C$_1$-C$_6$)alkyl-S(O)—(C$_1$-C$_6$)alkyl-Z$^{12}$, —(C$_1$-C$_6$)alkyl-S(O)—(C$_2$-C$_6$)alkenyl-Z$^{12}$, —(C$_2$-C$_6$)alkyl-S(O)—(C$_2$-C$_6$)alkynyl-Z$^{12}$, —(C$_1$-C$_6$)alkyl-SO$_2$—(C$_1$-C$_6$)alkyl-Z$^{12}$, —(C$_1$-C$_6$)alkyl-SO$_2$—(C$_2$-C$_6$)alkenyl-Z$^{12}$, —(C$_2$-C$_6$)alkyl-SO$_2$—(C$_2$-C$_6$)alkynyl-Z$^{12}$, —(C$_2$-C$_6$)alkyl-NR$_a$R$_b$, —(C$_2$-C$_6$)alkyl OC(O)—NR$_c$R$_d$, —(C$_2$-C$_6$)alkyl-NR$_a$—C(O)—OR$_b$, —(C$_2$-C$_6$)alkyl-NR$_a$—C(O)—NR$_a$R$_b$, —(C$_1$-C$_6$)alkyl-SO$_2$(C$_1$-C$_6$)alkyl, —(C$_1$-C$_6$)alkyl-SO$_2$NR$_c$R$_d$, —(C$_1$-C$_6$)alkyl-NR$_a$SO$_2$NR$_a$R$_d$, —(C$_1$-C$_6$)alkyl-NR$_a$SO$_2$O(C$_3$-C$_7$)carbocycle, —(C$_1$-C$_6$)alkyl-NR$_a$SO$_2$Oaryl, —(C$_1$-C$_6$)alkyl-NR$_a$—SO$_2$—(C$_1$-C$_6$)alkyl, —(C$_1$-C$_6$alkyl-NR$_a$—SO$_2$-halo(C$_1$-C$_6$)alkyl, —(C$_1$-C$_6$)alkyl-NR$_a$—SO$_2$—(C$_2$-C$_6$)alkenyl, —(C$_1$-C$_6$)alkyl-NR$_a$—SO$_2$—(C$_2$-C$_6$)alkynyl, —(C$_1$-C$_6$)alkyl-NR$_a$—SO$_2$—(C$_3$-C$_7$)carbocycle, —(C$_1$-C$_6$)alkyl-NR$_a$—SO$_2$-halo(C$_3$-C$_7$)carbocycle, —(C$_1$-C$_6$)alkyl NR$_a$—SO$_2$-aryl, —(C$_1$-C$_6$)alkyl-NR$_a$—SO$_2$-heteroaryl, —(C$_1$-C$_6$)alkyl-NR$_a$—SO$_2$-heterocycle, —O(C$_1$-C$_6$)alkyl-NR$_a$R$_b$, —O(C$_1$-C$_6$)alkylOC(O)—NR$_c$R$_d$, —O(C$_1$-C$_6$)alkyl-NR$_a$—C(O)—OR$_b$, —O(C$_1$-C$_6$)alkyl-NR$_a$C(O)—NR$_a$R$_b$, —O(C$_1$-C$_6$)alkyl-NR$_a$—SO$_2$—(C$_1$-C$_6$)alkyl, —O(C$_1$-C$_6$)alkyl-NR$_a$—SO$_2$-halo(C$_1$-C$_6$)alkyl, —O(C$_1$-C$_6$)alkyl-NR$_a$—SO$_2$—(C$_2$-C$_6$)alkenyl, —O(C$_1$-C$_6$)alkyl-NR$_a$—SO$_2$—(C$_2$-C$_6$)alkynyl, —O(C$_1$-C$_6$)alkyl-NR$_a$—SO$_2$—(C$_3$-C$_7$)carbocycle, —O(C$_1$-C$_6$)alkyl-NR$_a$—SO$_2$-halo(C$_3$-C$_7$)carbocycle, —O(C$_1$-C$_6$)alkyl-NR$_a$—SO$_2$-aryl, —O(C$_1$-C$_6$)alkyl-NR$_a$—SO$_2$-heteroaryl, —O(C$_1$-C$_6$)alkyl-NR$_a$—SO$_2$-heterocycle, —O(C$_1$-C$_6$)alkyl-NR$_a$—SO$_2$—NR$_a$R$_b$, —O(C$_1$-C$_6$)alkyl-NR$_a$—SO$_2$—(C$_3$-C$_7$)carbocycle, —O(C$_1$-C$_6$)alkyl-NR$_a$—SO$_2$-halo(C$_3$-C$_7$)carbocycle, —O(C$_1$-C$_6$)alkyl-NR$_a$—SO$_2$-aryl, —O(C$_1$-C$_6$)alkyl-NR$_a$SO$_2$NR$_c$R$^d$, —O(C$_1$-C$_6$)alkyl-NR$_a$SO$_2$O(C$_3$-C$_7$)carbocycle, —O(C$_1$-C$_6$)alkyl-NR$_a$SO$_2$Oaryl, —Oheteroaryl, —Oheterocycle, —Sheteroaryl, —Sheterocycle, —S(O)heteroaryl, —S(O)heterocycle, —SO$_2$heteroaryl or —SO$_2$heterocycle; wherein any (C$_1$-C$_6$)alkyl, aryl(C$_3$-C$_7$)carbocycle, heteroaryl or heterocycle of R$^{3b}$ is optionally substituted with one or more (e.g. 1, 2, 3, 4 or 5) Z$^1$ groups; and R$^{3b'}$ is H, (C$_1$-C$_6$)alkyl or —O(C$_1$-C$_6$)alkyl; or R$^{3b}$ and R$^{3b'}$ together with the carbon to which they are attached form a heterocycle or (C$_3$-C$_7$)carbocycle which heterocycle or (C$_3$-C$_7$)carbocycle of R$^{3b}$ and R$^{3b'}$ together with the carbon to which they are attached is optionally substituted with one or more (e.g. 1, 2, 3, 4 or 5) Z$^1$ groups;

R$^{4a}$ is selected from aryl, heterocycle and heteroaryl, wherein any aryl, heterocycle and heteroaryl of R$^{4a}$ is optionally substituted with one or more (e.g. 1, 2, 3, 4 or 5) groups each independently selected from halo, (C$_1$-C$_6$)alkyl, (C$_2$-C$_6$)alkenyl, (C$_1$-C$_6$)haloalkyl, (C$_3$-C$_7$)cycloalkyl, —(C$_1$-C$_6$)alkyl-(C$_3$-C$_7$)cycloalkyl, —OH, —O(C$_1$-C$_6$)alkyl, —SH, —S(C$_1$-C$_6$)alkyl, —NH$_2$, —NH(C$_1$-C$_6$)alkyl and —N((C$_1$-C$_6$)alkyl)$_2$; wherein (C$_1$-C$_6$)alkyl is optionally substituted with hydroxy, —O(C$_1$-C$_6$)alkyl, cyano or oxo;

R$^{4b}$ is selected from;

a) (C$_1$-C$_6$)alkyl, (C$_2$-C$_6$)alkenyl and (C$_2$-C$_6$)alkynyl; wherein (C$_1$-C$_6$)alkyl, (C$_2$-C$_6$)alkenyl or (C$_2$-C$_6$)alkynyl are each optionally substituted with one or more (e.g. 1, 2, 3, 4 or 5) Z$^1$ groups;

b) $(C_3-C_{14})$carbocycle; wherein $(C_3-C_{14})$carbocycle is optionally substituted with one or more (e.g. 1, 2, 3, 4 or 5) $Z^1$ groups; wherein two $Z^1$ groups together with the atom or atoms to which they are attached optionally form a $(C_3-C_7)$ carbocycle or heterocycle;

c) Spiro-heterocycle or bridged-heterocycle; wherein spiro-heterocycle or bridged-heterocycle is optionally substituted with one or more (e.g. 1, 2, 3, 4 or 5) $Z^1$ groups; or wherein two $Z^1$ groups together with the atom or atoms to which they are attached optionally form a $(C_3-C_7)$carbocycle or heterocycle; and d) aryl, heteroaryl, spiro-, fused-, or bridged-heterocycle; wherein aryl, heteroaryl, or spiro-, fused-, or bridged-heterocycle are each independently substituted with one or more $Z^7$ groups and optionally substituted with one or more (e.g. 1, 2, 3, 4 or 5) $Z^1$ groups; or $R^4$ and $R^3$ together with the atoms to which they are attached form a macroheterocycle or a macrocarbocycle wherein any macroheterocycle or macrocarbocycle of $R^4$ and $R^3$ together with the atoms to which they are attached may be optionally substituted with one or more (e.g. 1, 2, 3, 4 or 5) $Z^1$ groups; and $R^{3b'}$ is H or $(C_1-C_6)$alkyl, —O$(C_1-C_6)$alkyl.

$R^{5a}$ is selected from:

a) halo;

b) $R^{11}$, —C(=O)—$R^{11}$, —C(=O)—O—$R^{11}$, —O—$R^{11}$, —S—$R^{11}$, —S(O)—$R^{11}$, —SO$_2$—$R^{11}$, —$(C_1-C_6)$alkyl-$R^{11}$, —$(C_1-C_6)$alkyl-C(=O)—$R^{11}$, —$(C_1-C_6)$alkyl-C(=O)—O—$R^{11}$, —$(C_1-C_6)$alkyl-O—$R^{11}$, —$(C_1-C_6)$alkyl-S—$R^{11}$, —$(C_1-C_6)$alkyl-S(O)—$R^{11}$ and —$(C_1-C_6)$alkyl-SO$_2$—$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$carbocycle, aryl, heterocycle and heteroaryl, wherein aryl, heterocycle and heteroaryl are each optionally substituted with one or more (e.g. 1, 2 or 3) $Z^{11}$ groups; and c) —N($R^9$)$R^{10}$, —C(=O)—N($R^9$)$R^{10}$, —O—C(=O)—N($R^9$)$R^{10}$, —SO$_2$—N($R^9$)$R^{10}$, —$(C_1-C_6)$alkyl-N($R^9$)$R^{10}$, —$(C_1-C_6)$alkyl-C(=O)—N($R^9$)$R^{10}$, —$(C_1-C_6)$alkyl-O—C(=O)—N($R^9$)$R^{10}$, and —$(C_1-C_6)$alkyl-SO$_2$—N($R^9$)$R^{10}$; wherein each $R^9$ is independently selected from H, $(C_1-C_6)$alkyl and $(C_3-C_7)$cycloalkyl; and each $R^{10}$ is independently selected from $R^{11}$, —$(C_1-C_6)$alkyl-$R^{11}$, —SO$_2$—$R^{11}$, —C(=O)—$R^{11}$, —C(=O)O$R^{11}$ and —C(=O)N($R^9$)$R^{11}$; wherein each $R^{11}$ is independently selected from H, $(C_1-C_6)$alkyl, $(C_2-C_6)$alkenyl, $(C_2-C_6)$alkynyl, $(C_1-C_6)$haloalkyl, $(C_3-C_7)$cycloalkyl, aryl, heterocycle and heteroaryl;

$R^{5b}$ is selected from:

a) —$(C_1-C_6)$alkyl-O—$(C_1-C_6)$alkyl-$(C_3-C_7)$carbocycle, —$(C_1-C_6)$alkyl-S—$(C_1-C_6)$alkyl-$(C_3-C_7)$carbocycle, —$(C_1-C_6)$alkylS(O)—$(C_1-C_6)$alkyl-$(C_3-C_7)$carbocycle, —$(C_1-C_6)$alkylSO$_2$($C_1-C_6)$alkyl-$(C_3-C_7)$carbocycle, —$(C_2-C_6)$alkenyl-$(C_1-C_6)$haloalkyl, —$(C_2-C_6)$alkynyl-$(C_1-C_6)$haloalkyl, —$(C_3-C_7)$halocarbocycle, —NR$_a$SO$_2$NR$_c$R$_d$, —NR$_a$SO$_2$O$(C_3-C_7)$carbocycle, —NR$_a$SO$_2$Oaryl, —$(C_2-C_6)$alkenyl-$(C_3-C_7)$carbocycle, —$(C_2-C_6)$alkenyl-aryl, —$(C_2-C_6)$alkenyl-heteroaryl, —$(C_2-C_6)$alkenyl-heterocycle, —$(C_2-C_6)$alkynyl-$(C_3-C_7)$carbocycle, —$(C_2-C_6)$alkynyl-aryl, —$(C_2-C_6)$alkynyl-heteroaryl, —$(C_2-C_6)$alkynyl-heterocycle, —$(C_3-C_7)$carbocycle-$Z^1$ or -halo$(C_1-C_6)$alkyl-$Z^3$; wherein $(C_1-C_6)$alkyl, $(C_1-C_6)$haloalkyl, $(C_3-C_7)$carbocycle, $(C_2-C_6)$alkenyl, $(C_2-C_6)$alkynyl, aryl or heteroaryl are each optionally substituted with one or more (e.g. 1, 2, 3, 4 or 5) $Z^1$ groups;

b) spiro-bicyclic carbocycle, fused-bicyclic carbocycle and bridged-bicyclic carbocycle; wherein spiro-bicyclic carbocycle, fused-bicyclic carbocycle or bridged-bicyclic carbocycle are optionally substituted with one or more (e.g. 1, 2, 3, 4 or 5) $Z^1$ groups; wherein two $Z^1$ groups together with the atom or atoms to which they are attached optionally form a $(C_3-C_7)$carbocycle or heterocycle wherein the $(C_3-C_7)$ carbocycle or heterocycle is optionally substituted with one or more (e.g. 1, 2, 3, 4 or 5) $Z^1$ groups;

c) $(C_1-C_6)$alkyl; wherein $(C_1-C_6)$alkyl is substituted with one or more $Z^2$ groups and optionally substituted with one or more (e.g. 1, 2, 3, 4 or 5) $Z^1$ groups;

d) —X$(C_1-C_6)$alkyl, —X$(C_1-C_6)$haloalkyl, —X$(C_2-C_6)$alkenyl, —X$(C_2-C_6)$alkynyl and —X$(C_3-C_7)$carbocycle; wherein $(C_1-C_6)$alkyl or $(C_1-C_6)$haloalkyl are each substituted with one or more $Z^3$ groups and optionally substituted with one or more $Z^1$ groups; and wherein $(C_2-C_6)$alkenyl, $(C_2-C_6)$alkynyl and $(C_3-C_7)$carbocycle are each independently substituted with one or more (e.g. 1, 2, 3, 4 or 5) $Z^4$ groups and optionally substituted with one or more (e.g. 1, 2, 3, 4 or 5) $Z^1$ groups;

e) aryl, heteroaryl, heterocycle, —Xaryl, —Xheteroaryl and —Xheterocycle; wherein aryl heteroaryl are heterocycle are each independently substituted with one or more (e.g. 1, 2, 3, 4 or 5) $Z^5$ groups and optionally substituted with one or more (e.g. 1, 2, 3, 4 or 5) $Z^1$ groups;

f) $(C_1-C_6)$haloalkyl, $(C_3-C_7)$carbocycle, $(C_2-C_6)$alkenyl, and $(C_2-C_6)$alkynyl; where $(C_1-C_6)$haloalkyl, $(C_3-C_7)$carbocycle, $(C_2-C_6)$alkenyl and $(C_2-C_6)$alkynyl are each independently substituted with one or more (e.g. 1, 2, 3, 4 or 5) $Z^6$ groups and optionally substituted with one or more (e.g. 1, 2, 3, 4 or 5) $Z^1$ groups;

g) —NR$_e$R$_f$, —C(O)NR$_e$R$_f$, —OC(O)NR$_e$R$_f$, —SO$_2$NR$_e$R$_f$, —$(C_1-C_6)$alkyl-NR$_e$R$_f$, —$(C_1-C_6)$alkylC(O)—NR$_e$R$_f$, —$(C_1-C_6)$alkyl-O—C(O)—NR$_e$R$_f$ and —$(C_1-C_6)$alkyl-SO$_2$NR$_e$R$_f$; wherein each $(C_1-C_6)$alkyl is independently substituted with one or more (e.g. 1, 2, 3, 4 or 5) $Z^6$ groups and optionally substituted with one or more (e.g. 1, 2, 3, 4 or 5) $Z^1$ groups; and h) nitro and cyano;

or $R^1$ and $R^2$ together with the atoms to which they are attached form a 5 or 6-membered carbocycle or a 4, 5, 6 or 7-membered heterocycle; wherein the 5 or 6-membered carbocycle or a 4, 5, 6 or 7-membered heterocycle are each independently substituted with one or more (e.g. 1, 2 or 3) $Z^7$ or $Z^8$ groups; wherein when two $Z^7$ groups are on same atom the two $Z^7$ groups together with the atom to which they are attached optionally form a $(C_3-C_7)$carbocycle or 4, 5 or 6-membered heterocycle;

X is independently selected from O, —C(O)—, —C(O)O—, —S—, —S(O)—, —SO$_2$—, —$(C_1-C_6)$alkylO—, —$(C_1-C_6)$alkylC(O)—, —$(C_1-C_6)$alkylC(O)O—, —$(C_1-C_6)$alkylS—, —$(C_1-C_6)$alkylS(O)—, —$(C_1-C_6)$alkylSO$_2$—;

each $Z^1$ is independently selected from halo, —NO$_2$, —OH, =NOR$_a$, —SH, —CN, —$(C_1-C_6)$alkyl, —$(C_2-C_6)$alkenyl, —$(C_2-C_6)$alkynyl, —$(C_1-C_6)$haloalkyl, $(C_3-C_7)$carbocycle, —$(C_3-C_7)$halocarbocycle, -aryl, -heteroaryl, -heterocycle, —O$(C_1-C_6)$alkyl, —O$(C_2-C_6)$alkenyl, —O$(C_2-C_6)$alkynyl, —O$(C_1-C_6)$haloalkyl, —O$(C_3-C_7)$carbocycle, —O$(C_3-C_7)$halocarbocycle, —Oaryl, —Oheteroaryl, —Oheterocycle, —S$(C_1-C_6)$alkyl, —S$(C_2-C_6)$alkenyl, —S$(C_2-C_6)$alkynyl, —S$(C_1-C_6)$haloalkyl, —S$(C_3-C_7)$carbocycle, —S$(C_3-C_7)$halocarbocycle, —Saryl, —Sheteroaryl, —Sheterocycle, —S(O)$(C_1-C_6)$alkyl, —S(O)$(C_2-C_6)$alkenyl, —S(O)$(C_2-C_6)$alkynyl, —S(O)$(C_1-C_6)$haloalkyl, —S(O) $(C_3-C_7)$carbocycle, —S(O)$(C_3-C_7)$halocarbocycle, —SO$_2$$(C_1-C_6)$alkyl, —S(O)aryl, —S(O) carbocycle, —S(O)heteroaryl, —S(O)heterocycle, —SO$_2$$(C_2-C_6)$alkenyl, —SO$_2$$(C_2-C_6)$alkynyl, —SO$_2$$(C_1-C_6)$haloalkyl, —SO$_2$$(C_3-C_7)$carbocycle, —SO$_2$$(C_3-C_7)$halocarbocycle, —SO$_2$aryl, —SO$_2$heteroaryl, —SO$_2$heterocycle, —SO$_2$NR$_c$R$_d$, —NR$_c$R$_d$, —NR$_a$C(O)R$_a$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O(C$_3$-C$_7$)carbocycle, —NR$_a$SO$_2$Oaryl, —OS(O)$_2$R$_a$, —C(O)R$_a$, —C(O)OR$_b$, —C(O)NR$_c$R$_d$, and —OC(O)NR$_c$R$_d$, wherein any (C$_1$-C$_6$) alkyl, (C$_2$-C$_6$)alkenyl, (C$_2$-C$_6$)alkynyl, —(C$_3$-C$_7$)halocarbocycle, (C$_3$-C$_7$)carbocycle, (C$_3$-C$_7$)halocarbocycle, aryl, heteroaryl or heterocycle of Z$^1$ is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHhetemoaryl, —NHheterocycle, or —S(O)$_2$NR$_c$R$_d$;

each Z$^2$ is independently selected from —NO$_2$, —CN, spiro-heterocycle, bridge-heterocycle, spiro-bicyclic carbocycle, bridged-bicyclic carbocycle, NR$_a$SO$_2$(C$_3$-C$_7$)carbocycle, —NR$_a$SO$_2$aryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl;

each Z$^3$ is independently selected from —NO$_2$, —CN, —OH, oxo, =NOR$_a$, thioxo, aryl, heterocycle, -heteroaryl, —(C$_3$-C$_7$)halocarbocycle, —O(C$_1$-C$_6$)alkyl, —O(C$_3$-C$_7$)carbocycle, —Ohalo(C$_3$-C$_7$)carbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O) (C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^4$ is independently selected from halogen, —(C$_1$-C$_6$)alkyl, (C$_3$-C$_7$)carbocycle, -halo(C$_1$-C$_6$)alkyl, —NO$_2$, —CN, —OH, oxo, =NOR$_a$ thioxo, -aryl, -heterocycle, -heteroaryl, —(C$_3$-C$_7$)halocarbocycle, —O(C$_1$-C$_6$)alkyl, —O(C$_3$-C$_7$)carbocycle, —O(C$_3$-C$_7$)halocarbocycle, —Oaryl, —Oheterocycle, —Oheteroaryl, —S(C$_1$-C$_6$)alkyl, —S(C$_3$-C$_7$)carbocycle, —S(C$_3$-C$_7$)halocarbocycle, —Saryl, —Sheterocycle, —Sheteroaryl, —S(O)(C$_1$-C$_6$)alkyl, —S(O)(C$_3$-C$_7$)carbocycle, —S(O)(C$_3$-C$_7$)halocarbocycle, —S(O)aryl, —S(O)heterocycle, —S(O)heteroaryl, —SO$_2$(C$_1$-C$_6$)alkyl, —SO$_2$(C$_3$-C$_7$)carbocycle, —SO$_2$(C$_3$-C$_7$)halocarbocycle, SO$_2$aryl, —SO$_2$heterocycle, —SO$_2$heteroaryl, —NR$_a$R$_b$, —NR$_a$C(O)R$_b$, —C(O)NR$_c$R$_d$, —SO$_2$NR$_c$R$_d$, —NR$_a$SO$_2$NR$_c$R$_d$, —NR$_a$SO$_2$O(C$_3$-C$_7$)carbocycle and —NR$_a$SO$_2$Oaryl;

each Z$^5$ is independently selected from —NO$_2$, —CN, —NR$_a$SO$_2$NR$_c$R$_d$, —NR$_a$SO$_2$O(C$_3$-C$_7$)carbocycle, —NR$_a$SO$_2$Oaryl, —NR$_a$SO$_2$(C$_1$-C$_6$)alkyl, —NR$_a$SO$_2$(C$_2$-C$_6$)alkenyl, —NR$_a$SO$_2$(C$_2$-C$_6$)alkynyl, —NR$_a$SO$_2$(C$_3$-C$_7$)carbocycle, —NR$_a$SO$_2$(C$_3$-C$_7$)halocarbocycle, —NR$_a$SO$_2$aryl, —NR$_a$SO$_2$heteroaryl, —NR$_a$SO$_2$heterocycle, —NR$_a$SO$_2$heterocycle, —NR$_a$C(O)alkyl, —NR$_a$C(O)alkenyl, —NR$_a$C(O)alkynyl, —NR$_a$C(O)(C$_3$-C$_7$)carbocycle, —NR$_a$C(O)(C$_3$-C$_7$)halocarbocycle, —NR$_a$C(O)aryl, —NR$_a$C(O)heteroaryl, —NR$_a$C(O)heterocycle, —NR$_a$C(O)NR$_c$R$_d$ and —NR$_a$C(O)OR$_b$;

each Z$^6$ is independently selected from —NO$_2$, —CN, —NR$_a$R$_a$, NR$_a$C(O)R$_b$, —C(O)NR$_c$R$_d$, —(C$_3$-C$_7$)halocarbocycle, -aryl, -heteroaryl, -heterocycle, —Oaryl, —Oheteroaryl, —Oheterocycle, —O(C$_3$-C$_7$)halocarbocycle, —O(C$_1$-C$_6$)alkyl, —O(C$_3$-C$_7$)carbocycle, —Ohalo(C$_1$-C$_6$)alkyl, —Saryl, —Sheteroaryl, —Sheterocycle, —S(C$_3$-C$_7$)halocarbocycle, —S(C$_1$-C$_6$)alkyl, —S(C$_3$-C$_7$)carbocycle, —S(C$_1$-C$_6$)haloalkyl, —S(O)aryl, —S(O)heteroaryl, —S(O)heterocycle, —S(O)(C$_3$-C$_7$)halocarbocycle, —S(O)(C$_1$-C$_6$)alkyl, —S(O)(C$_3$-C$_7$)carbocycle, —S(O)halo(C$_1$-C$_6$)alkyl, —SO$_2$aryl, —SO$_2$heteroaryl, —SO$_2$heterocycle, —SO$_2$(C$_1$-C$_6$)alkyl, —SO$_2$halo(C$_1$-C$_6$)alkyl, —SO$_2$(C$_3$-C$_7$)carbocycle, —SO$_2$(C$_3$-C$_7$)halocarbocycle, —SO$_2$NR$_c$R$_d$, —NR$_a$SO$_2$(C$_3$-C$_7$)halocarbocycle, —NR$_a$SO$_2$aryl, —NR$_a$SO$_2$heteroaryl, —NR$_a$SO$_2$heteroaryl, —NR$_a$SO$_2$NR$_c$R$_d$, —NR$_a$SO$_2$O(C$_3$-C$_7$)carbocycle and —NR$_a$SO$_2$Oaryl.

each Z$^7$ is independently selected from —NO$_2$, =NOR$_a$, —CN, —(C$_1$-C$_6$)alkyl-Z$^{12}$, —(C$_2$-C$_6$)alkenyl-Z$^{12}$, —(C$_2$-C$_6$)alkenylOH, —(C$_2$-C$_6$)alkynyl Z$^{12}$, —(C$_2$-C$_6$)alkynyl-OH, —(C$_1$-C$_6$)haloalkyl-Z$^{12}$, —(C$_1$-C$_6$)haloalkylOH, —(C$_3$-C$_7$)carbocycle-Z$^{12}$, —(C$_3$-C$_7$)carbocycleOH, —(C$_3$-C$_7$)halocarbocycle, —(C$_1$-C$_6$)alkylNR$_c$R$_d$, —(C$_1$-C$_6$)alkyl-NR$_a$C(O)R$_a$, —(C$_1$-C$_6$)alkylNR$_a$SO$_2$R$_a$, aryl, -heteroaryl, -heterocycle, —O(C$_1$-C$_6$)alkyl-Z$^{12}$, —O(C$_2$-C$_6$)alkenyl, —O(C$_2$-C$_6$)alkynyl, —O(C$_1$-C$_6$)haloalkyl, —O(C$_3$-C$_7$)carbocycle, —O(C$_3$-C$_7$)halocarbocycle, —Oaryl, —O(C$_1$-C$_6$)alkylNR$_c$R$^d$, —O(C$_1$-C$_6$)alkylNR$_a$C(O)R$_a$, —O(C$_1$-C$_6$)alkylNR$_a$SO$_2$R$_a$, —Oheteroaryl, —Oheterocycle, —S(C$_1$-C$_6$)alkyl-Z$^{12}$, —S(C$_2$-C$_6$)alkenyl, —S(C$_2$-C$_6$)alkynyl, —S(C$_1$-C$_6$)haloalkyl, —S(C$_3$-C$_7$)carbocycle, —S(C$_3$-C$_7$)halocarbocycle, —S(C$_1$-C$_6$)alkylNR$_c$R$_d$, —S(C$_1$-C$_6$)alkyl-NR$_a$C(O)R$_a$, —S(C$_1$-C$_6$)alkylNR$_a$SO$_2$R$_a$, —Saryl, —Sheteroaryl, —Sheterocycle, —S(O)(C$_1$-C$_6$)alkyl, —S(O)(C$_2$-C$_6$)alkenyl, —S(O)(C$_2$-C$_6$)alkynyl, —S(O)(C$_1$-C$_6$)haloalkyl, —S(O)(C$_3$-C$_7$)carbocycle, —S(O)(C$_3$-C$_7$)halocarbocycle, —SO$_2$(C$_1$-C$_6$)alkyl, —S(O)(C$_1$-C$_6$)alkylNR$_c$R$_d$, —S(O)(C$_1$-C$_6$)alkylNR$_a$C(O)R$_a$, —S(O)(C$_1$-C$_6$)alkylNR$_a$SO$_2$R$_a$, —S(O)aryl, —S(O)heteroayl, —S(O)heterocycle, —SO$_2$(C$_1$-C$_6$)alkyl, —SO$_2$(C$_2$-C$_6$)alkenyl, —SO$_2$(C$_2$-C$_6$)alkynyl, —SO$_2$(C$_1$-C$_6$)haloalkyl, —SO$_2$(C$_3$-C$_7$)carbocycle, —SO$_2$(C$_3$-C$_7$)halocarbocycle, —SO$_2$aryl, —SO$_2$heteroaryl, —SO$_2$heterocycle, —SO$_2$(C$_1$-C$_6$)alkylNR$_c$R$_d$, —SO$_2$(C$_1$-C$_6$)alkylNR$_a$C(O)R$_a$, —SO$_2$(C$_1$-C$_6$)alkylNR$_a$SO$_2$R$_a$, —SO$_2$NR$_c$R$_d$, —NR$_a$C(O)OR$_b$, —NR$_a$C(O)NR$_c$R$_d$, —NR$_a$SO$_2$R$_b$, —NR$_a$SO$_2$NR$_c$R$_d$, —NR$_a$SO$_2$O (C$_3$-C$_7$)carbocycle, —NR$_a$SO$_2$Oaryl, —OS(O)$_2$R$_a$, —C(O)NR$_c$R$_d$, and —OC(O)NR$_c$R$_d$, wherein any (C$_1$-C$_6$)alkyl, (C$_2$-C$_6$)alkenyl, (C$_2$-C$_6$)alkynyl, (C$_3$-C$_7$)carbocycle, (C$_3$-C$_7$)halocarbocycle, aryl, heteroayl or heterocycle of Z$^7$ is optionally substituted with one or more (e.g. 1, 2, 3, 4 or 5) halogen, —OH, —OR$_b$, —CN, —NR$_a$C(O)$_2$R$_b$, -heteroaryl, -heterocycle, —Oheteroaryl, —Oheterocycle, —NHheteroaryl, —NHheterocycle, or —S(O)$_2$NR$_c$R$_d$.

each Z$^8$ is independently selected from —NO$_2$ or —CN;

each Z$^9$ is independently selected from —(C$_1$-C$_6$)alkyl, —O(C$_1$-C$_6$)alkyl;

each Z$^{10}$ is independently selected from
i) halo, oxo, thioxo, (C$_2$-C$_6$)alkenyl, (C$_1$-C$_6$)haloalkyl, (C$_3$-C$_7$)cycloalkyl, (C$_3$-C$_7$)cycloalkyl-(C$_1$-C$_6$)alkyl-, —OH, —O(C$_1$-C$_6$)alkyl, —O(C$_1$-C$_6$)haloalkyl, —SH, —S(C$_1$-C$_6$)alkyl, —SO(C$_1$-C$_6$)alkyl, —SO$_2$(C$_1$-C$_6$)alkyl, —NH$_2$, —NH(C$_1$-C$_6$)alkyl and —N((C$_1$-C$_6$)alkyl)$_2$;
ii) (C$_1$-C$_6$)alkyl optionally substituted with —OH, —O—(C$_1$-C$_6$)haloalkyl, or —O—(C$_1$-C$_6$)alkyl; and
iii) aryl, heterocycle and heteroaryl, which aryl, heterocycle and heteroaryl is optionally substituted with halo, (C$_1$-C$_6$)alkyl or COOH;

each Z$^{11}$ is independently selected from Z$^{10}$, —C(=O)—NH$_2$, —C(=O)—NH(C$_1$-C$_4$)alkyl, —C(=O)—N((C$_1$-C$_4$)alkyl)$_2$, —C(=O)-aryl, —C(=O)-heterocycle and —C(=O)-heteroaryl;

each $Z^{12}$ is independently selected from —$NO_2$, =$NOR_a$, thioxo, -aryl, -heterocycle, -heteroaryl, —($C_3$-$C_7$)halocarbocycle, —($C_3$-$C_7$)carbocycle, —$O$($C_3$-$C_7$)carbocycle, —Ohalo($C_3$-$C_7$)carbocycle, —Oaryl, —Oheterocycle, —Oheteroaryl, —S($C_1$-$C_6$)alkyl, —S($C_3$-$C_7$)carbocycle, —Shalo($C_3$-$C_7$)carbocycle, —Saryl, —Sheterocycle, —Sheteroaryl, —S(O)($C_1$-$C_6$)alkyl, —S(O)($C_3$-$C_7$)carbocycle, —S(O)halo($C_3$-$C_7$)carbocycle, —S(O)aryl, —S(O)heterocycle, —S(O)heteroaryl, —$SO_2$($C_1$-$C_6$)alkyl, —$SO_2$($C_3$-$C_7$)carbocycle, —$SO_2$($C_3$-$C_7$)halocarbocycle, $SO_2$aryl, —$SO_2$heterocycle, —$SO_2$heteroaryl, —$NR_aR_a$, —$NR_aC(O)R_b$, —$C(O)NR_cR_d$, —$SO_2NR_cR_d$, —$NR_aSO_2NR_cR_d$, —$N_aSO_2O$($C_3$-$C_7$)carbocycle and —$NR_aSO_2$Oaryl;

each $Z^{13}$ is independently selected from —$NO_2$, —OH, =$NOR_a$, —SH, —CN, —($C_3$-$C_7$)halocarbocycle, —O($C_1$-$C_6$)alkyl, —O($C_2$-$C_6$)alkenyl, —O($C_2$-$C_6$)alkynyl, —O($C_1$-$C_6$)haloalkyl, —O($C_3$-$C_7$)carbocycle, —O($C_3$-$C_7$)halocarbocycle, —Oaryl, —Oheteroaryl, —Oheterocycle, —S($C_1$-$C_6$)alkyl, —S($C_2$-$C_6$)alkenyl, —S($C_2$-$C_6$)alkynyl, —S($C_1$-$C_6$)haloalkyl, —S($C_3$-$C_7$)carbocycle, —S($C_3$-$C_7$)halocarbocycle, —Saryl, —Sheteroaryl, —Sheterocycle, —S(O)($C_1$-$C_6$)alkyl, —S(O)($C_2$-$C_6$)alkenyl, —S(O)($C_2$-$C_6$)alkynyl, —S(O)($C_1$-$C_6$)haloalkyl, —S(O)($C_3$-$C_7$)carbocycle, —S(O)($C_3$-$C_7$)halocarbocycle, —S(O)aryl, —S(O)heteroaryl, —S(O)heterocycle, —$SO_2$($C_1$-$C_6$)alkyl, —$SO_2$($C_2$-$C_6$)alkenyl, —$SO_2$($C_2$-$C_6$)alkynyl, —$SO_2$($C_1$-$C_6$)haloalkyl, —$SO_2$($C_3$-$C_7$)carbocycle, —$SO_2$($C_3$-$C_7$)halocarbocycle, —$SO_2$aryl, —$SO_2$heteroaryl, —$SO_2$heterocycle, —$SO_2NR_cR_d$, —$NR_cR_d$, —$NR_aC(O)R_a$, —$NR_1C(O)OR_b$, —$NR_aC(O)NR_cR_d$, —$NR_aSO_2R_b$, —$NR_aSO_2NR_cR_d$, —$NR_aSO_2O$($C_3$-$C_7$)carbocycle, —$NR_a SO_2$Oaryl, —$S(O)_2R_a$, —$C(O)R_a$, —$C(O)OR_b$, —$C(O)NR_cR_d$, and —$OC(O)NR_cR_d$; wherein any ($C_1$-$C_6$)alkyl, ($C_2$-$C_6$)alkenyl, ($C_2$-$C_6$)alkynyl, —($C_3$-$C_7$)halocarbocycle, ($C_3$-$C_7$)carbocycle, ($C_3$-$C_7$)halocarbocycle, aryl, heteroaryl or heterocycle of $Z^{13}$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $Z^{14}$ is independently selected from —$NO_2$, =$NOR_a$, —CN, —($C_3$-$C_7$)halocarbocycle, —O($C_3$-$C_7$)halocarbocycle, —S($C_3$-$C_7$)halocarbocycle, —S(O)($C_3$-$C_7$)halocarbocycle, —$SO_2$($C_3$-$C_7$)halocarbocycle, —$NR_aSO_2NR_cR_d$, —$NR_aSO_2O$($C_3$-$C_7$)carbocycle, —$NR_aSO_2$Oaryl, —OS(O)$_2$ $R_a$; wherein any —($C_3$-$C_7$)halocarbocycle of $Z^4$ is optionally substituted with one or more (e.g. 1, 2, 3, 4 or 5) halogen, —OH, —$OR_b$, —CN, —$NR_aC(O)_2R_b$, -heteroaryl, -heterocycle, —Oheteroaryl, —Oheterocycle, —NHheteroaryl, —NHheterocycle, or —$S(O)_2NR_cR_d$;

each $R_a$ is independently H, ($C_1$-$C_6$)alkyl, —($C_2$-$C_6$)alkenyl, —($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-; wherein any ($C_1$-$C_6$)alkyl, ($C_2$-$C_6$)alkenyl, ($C_2$-$C_6$)alkynyl, ($C_3$-$C_7$)carbocycle, heterocycle, aryl, or heteroaryl of $R_a$ is optionally substituted by halogen, OH and cyano;

each $R_b$ is independently —($C_1$-$C_6$)alkyl, —($C_2$-$C_6$)alkenyl, —($C_2$-$C_6$)alkynyl, ($C_3$-$C_7$)carbocycle, heterocycle, aryl, aryl($C_1$-$C_6$)alkyl-, heteroaryl or heteroaryl($C_1$-$C_6$)alkyl-; wherein any ($C_1$-$C_6$)alkyl, —($C_2$-$C_6$)alkenyl, —($C_2$-$C_6$)alkynyl, ($C_3$-$C_7$)carbocycle, heterocycle, aryl, or heteroaryl of $R_b$ is optionally substituted by halogen, OH and cyano;

$R_c$ and $R_d$ are each independently selected from H, ($C_1$-$C_6$)alkyl, ($C_2$-$C_6$)alkenyl, ($C_2$-$C_6$)alkynyl, ($C_3$-$C_7$)carbocycle, aryl, aryl($C_1$-$C_6$)alkyl-, heterocycle, heteroaryl or heteroaryl($C_1$-$C_6$)alkyl- wherein any ($C_1$-$C_6$)alkyl, —($C_2$—C)alkenyl, —($C_2$-$C_6$)alkynyl, ($C_3$-$C_7$)carbocycle, heterocycle, aryl or heteroaryl of $R_c$ or $R_d$ is optionally substituted by halogen, OH and cyano; or $R_c$ and $R_d$ together with the nitrogen to which they are attached form a heterocycle; wherein any heterocycle of $R_c$ and $R_d$ together with the nitrogen to which they are attached is optionally substituted by halogen, OH or cyano;

each $R_e$ is independently selected from —$OR_a$, ($C_1$-$C_6$) alkyl or ($C_3$-$C_7$)carbocycle wherein ($C_1$-$C_6$)alkyl or ($C_3$-$C_7$) carbocycle is substituted by one or more Z and optionally substituted with one or more $Z_1$; —($C_2$-$C_6$)haloalkyl, —($C_2$-$C_6$)alkenyl, or —($C_2$-$C_6$)alkynyl wherein any haloalkyl, alkenyl or alkynyl is optionally substituted with one or more $Z_1$; aryl, heterocycle or heteroaryl wherein aryl, heterocycle or heteroaryl is substituted by one or more $Z_5$;

each $R_f$ is independently selected from —$R_g$, —$OR_a$, —($C_1$-$C_6$)alkyl-$Z^6$, —$SO_2R_g$, —$C(O)R_g$, $C(O)OR_g$, or —$C(O)NR_eR_g$; and each $R_g$ is independently selected from ($C_1$-$C_6$)alkyl, ($C_3$-$C_7$)carbocycle ($C_1$-$C_6$)haloalkyl, ($C_2$-$C_6$)alkenyl, ($C_2$-$C_6$)alkynyl, aryl, heterocycle or heteroaryl wherein any ($C_1$-$C_6$)alkyl, ($C_3$-$C_7$)carbocycle —($C_1$-$C_6$)haloalkyl, ($C_2$-$C_6$)alkenyl, ($C_2$-$C_6$)alkynyl, aryl, heterocycle or heteroaryl of $R_g$ is optionally substituted with one or more $Z_1$ groups;

or a salt thereof.

In one embodiment, the compounds of formula I are selected from:

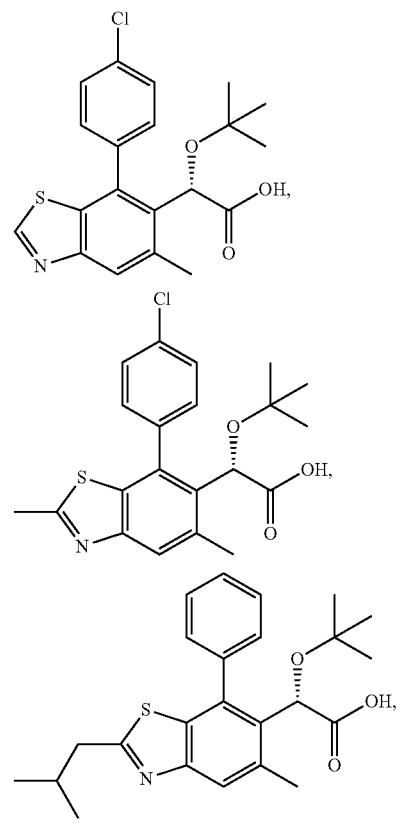

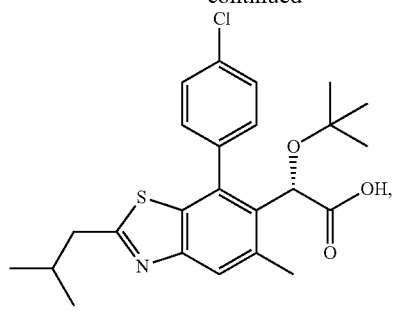
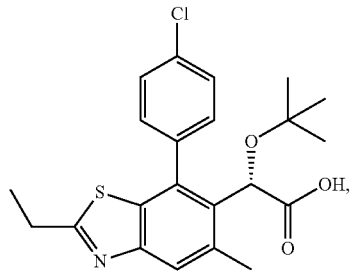
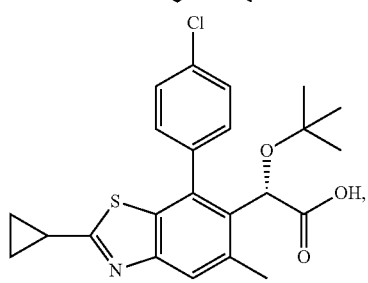
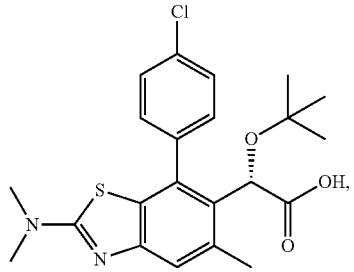
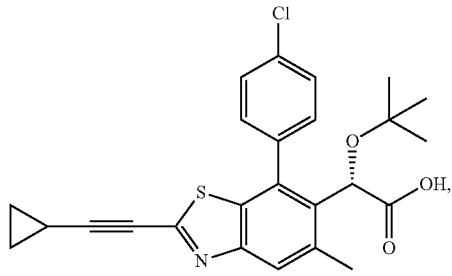
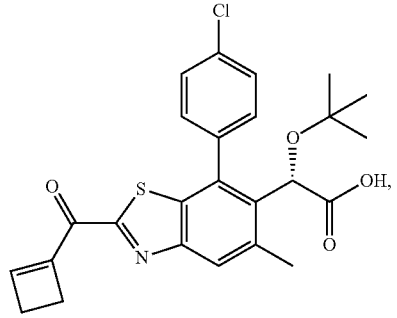
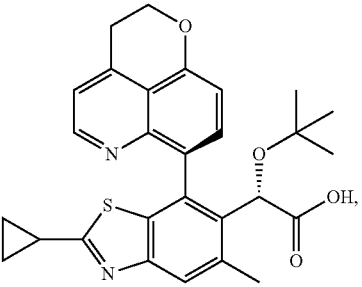
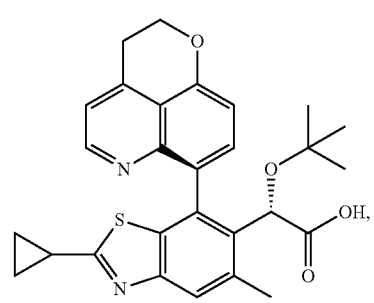
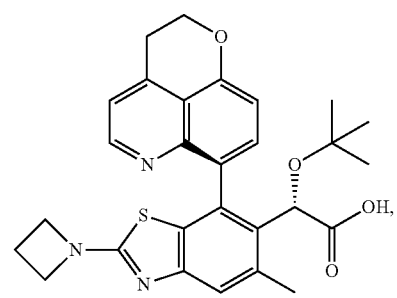
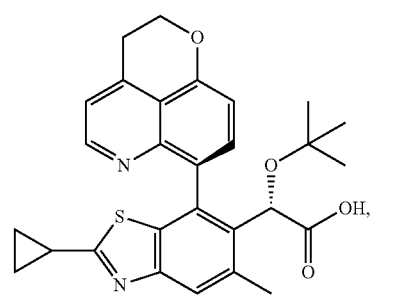
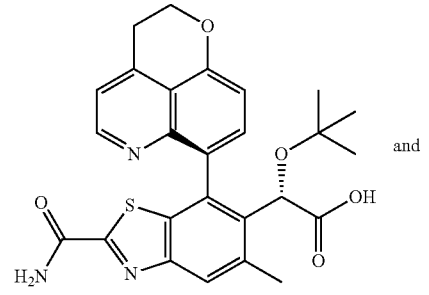 and -continued
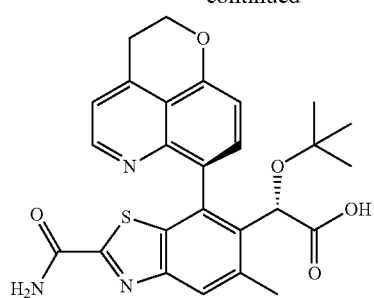
and salts thereof
In one embodiment, the compounds of formula I are selected from:
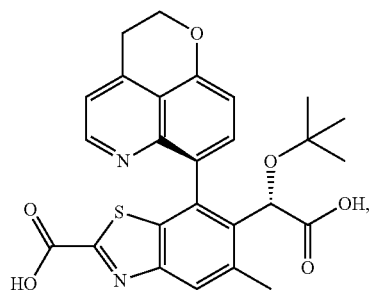
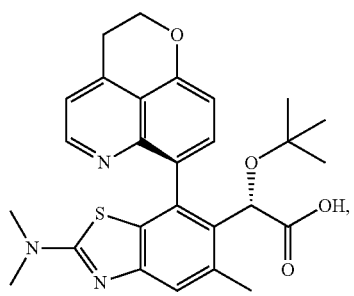
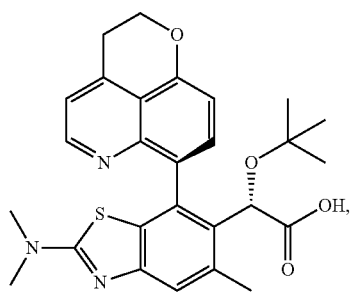
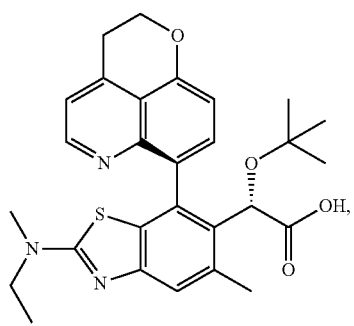
-continued
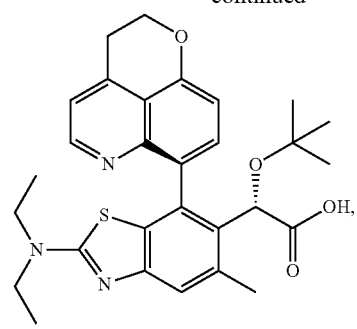
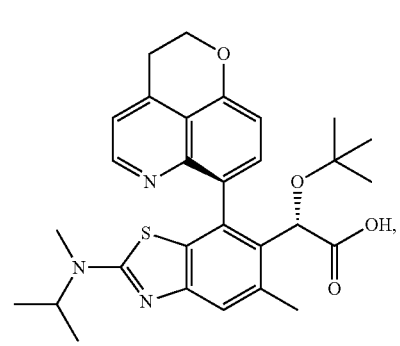
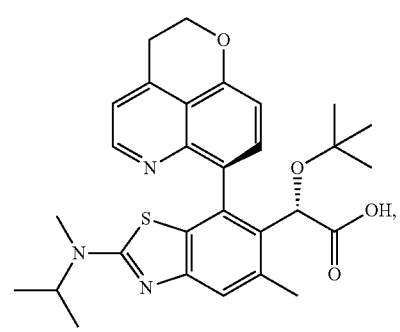
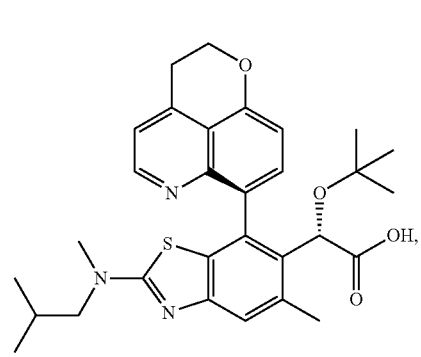
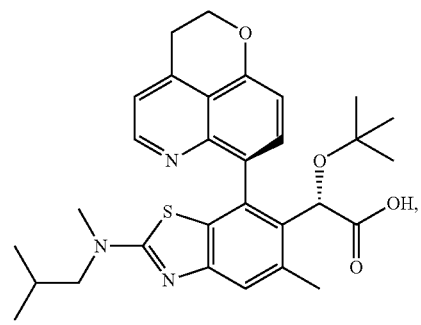

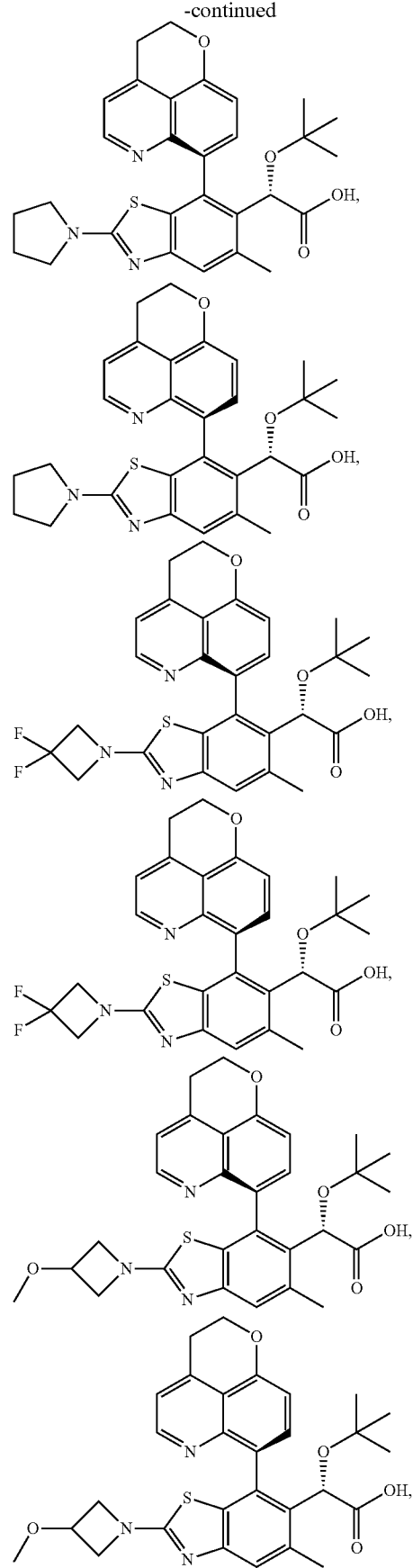
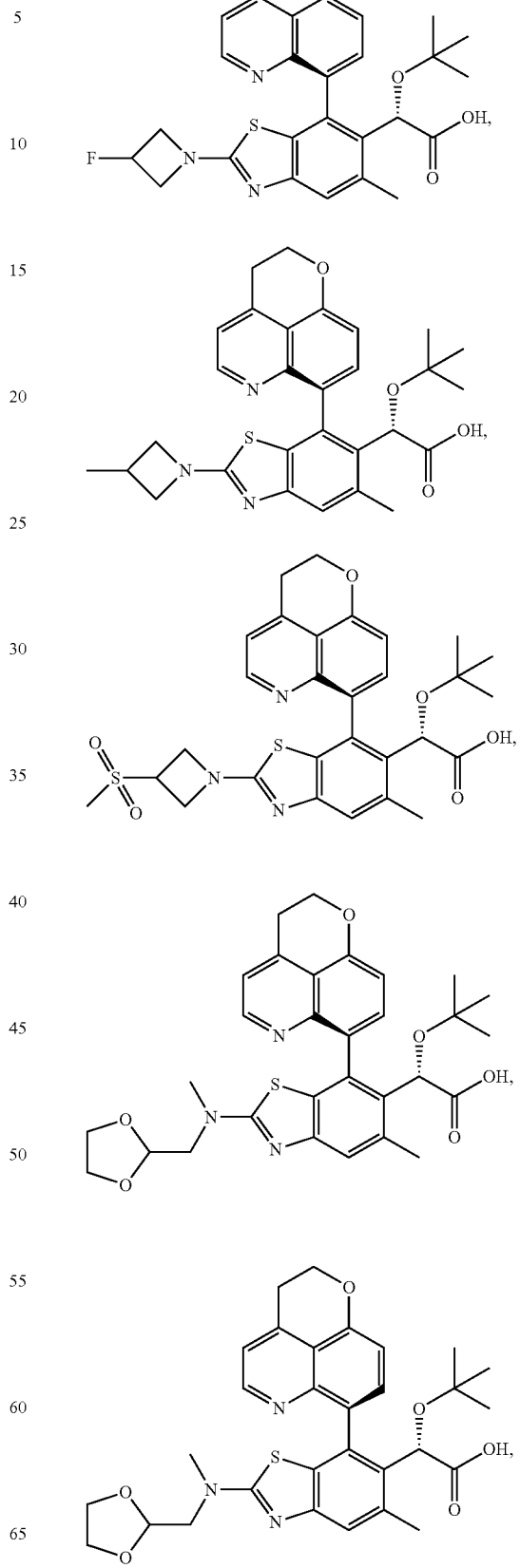

59
-continued
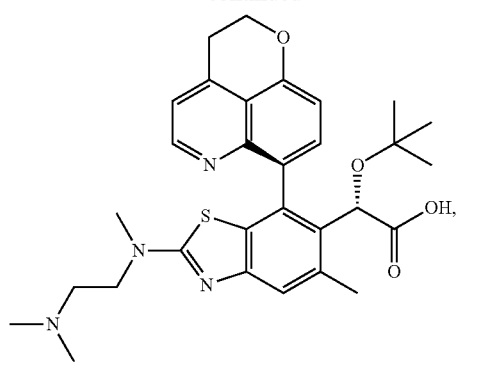
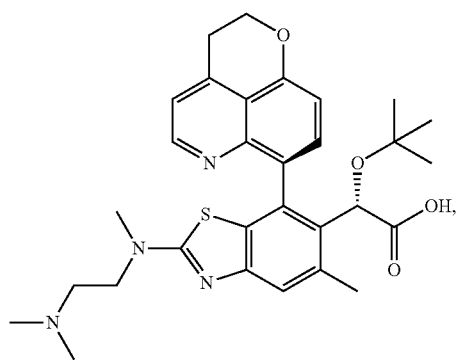
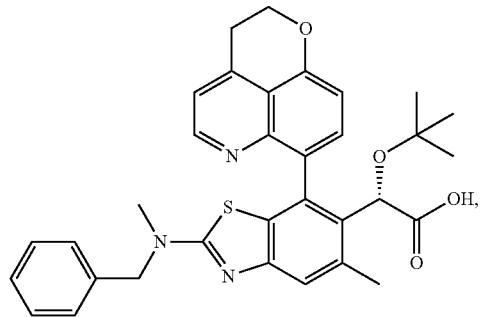
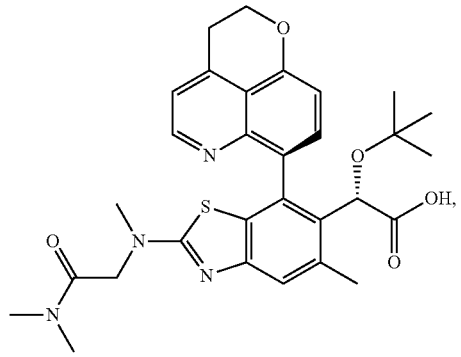
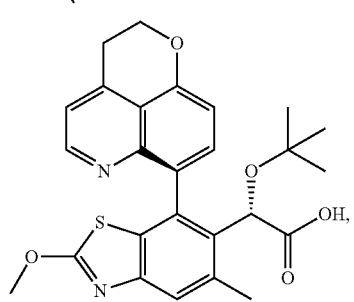
60
-continued
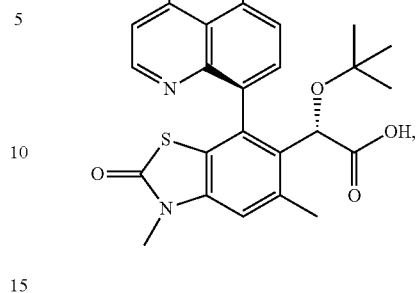
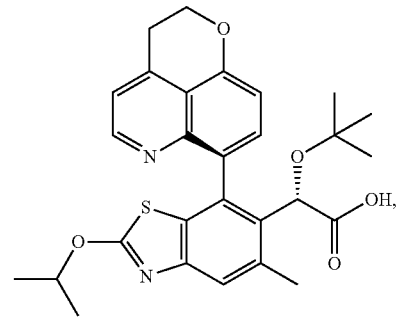
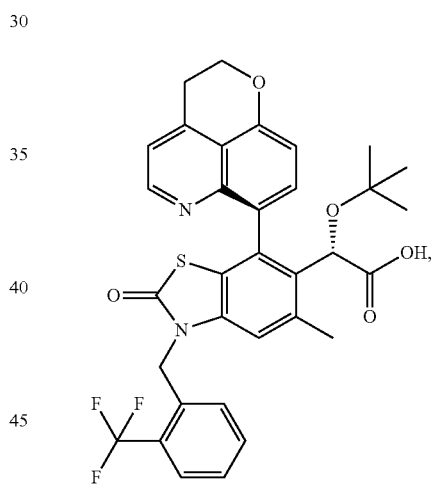
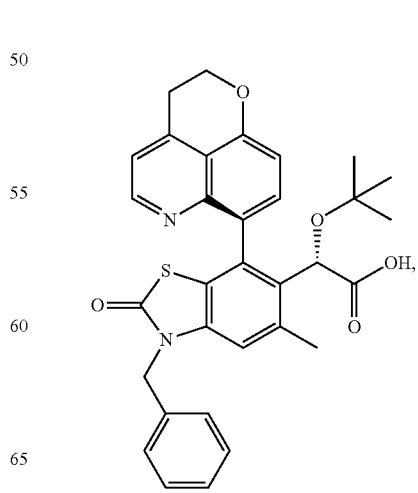

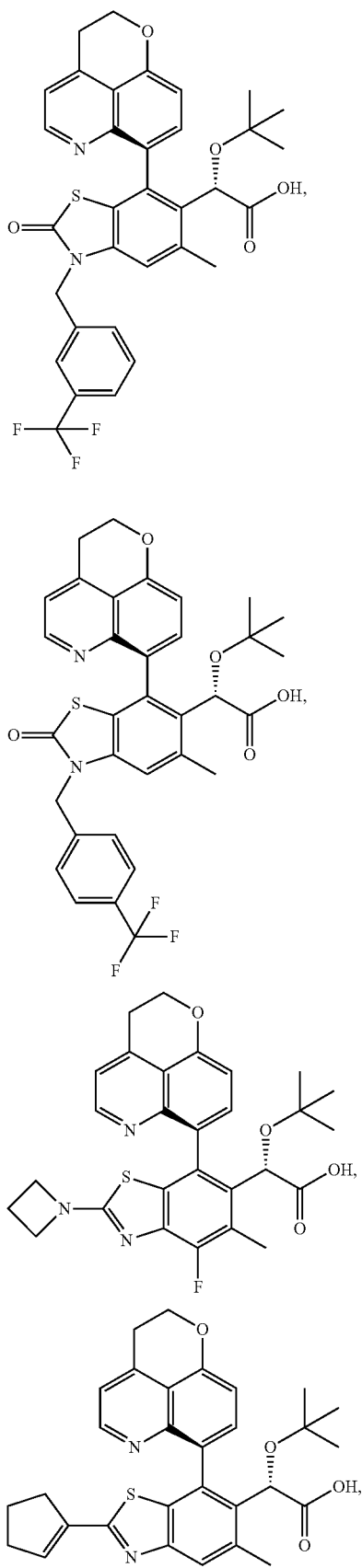
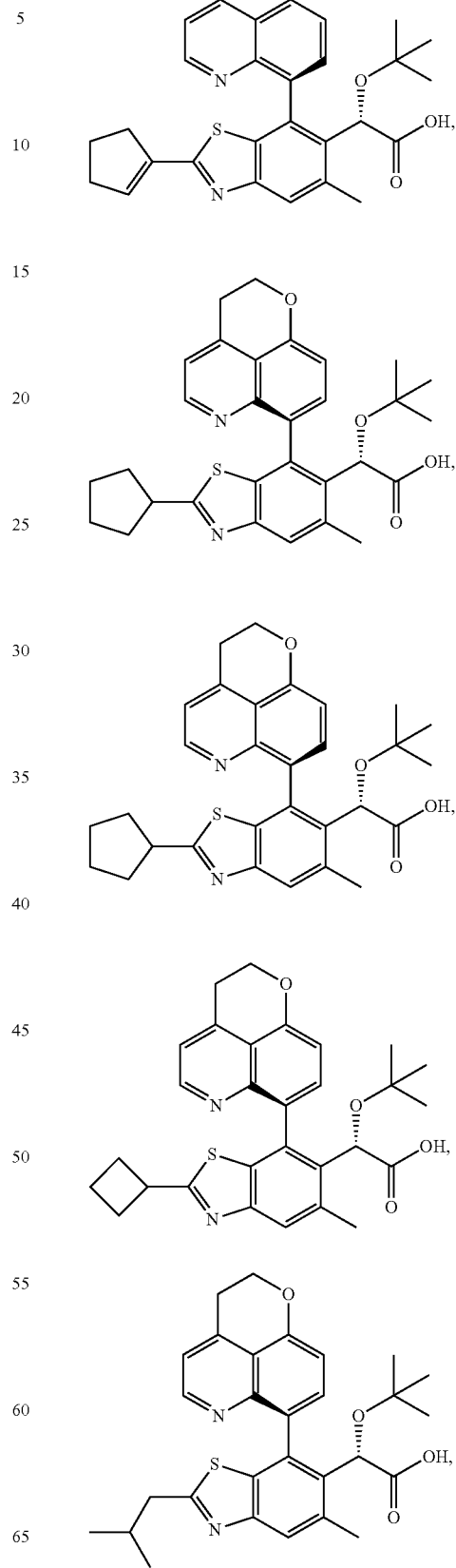

-continued
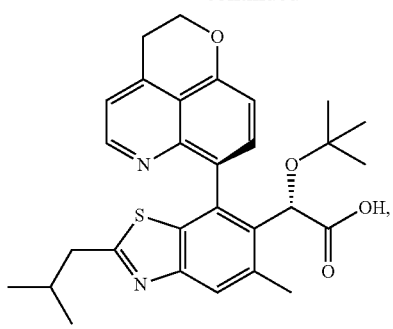
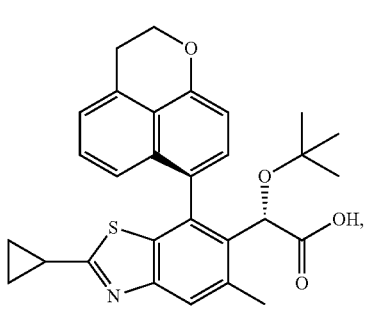
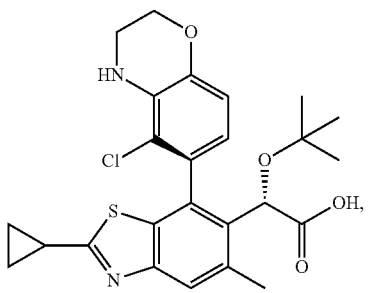
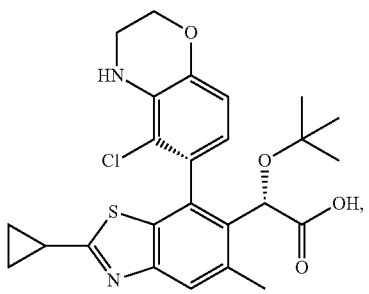
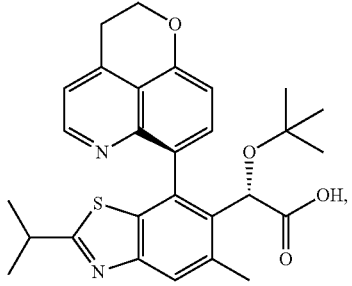
-continued
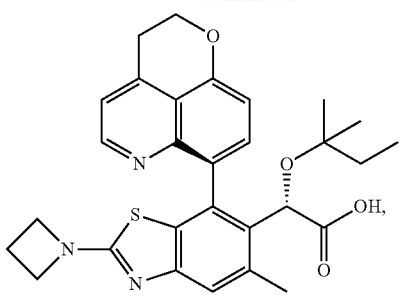
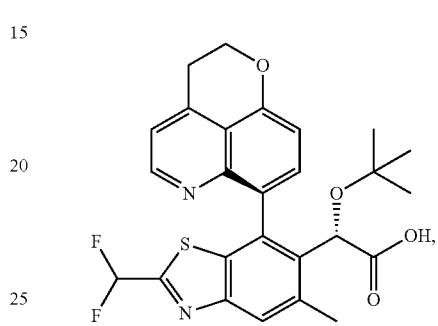
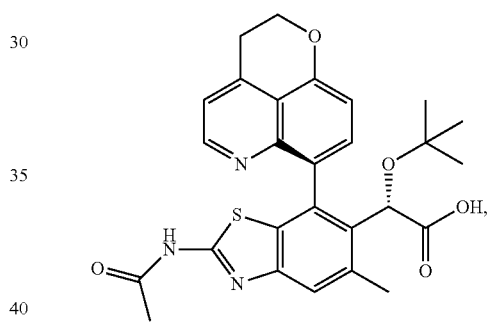
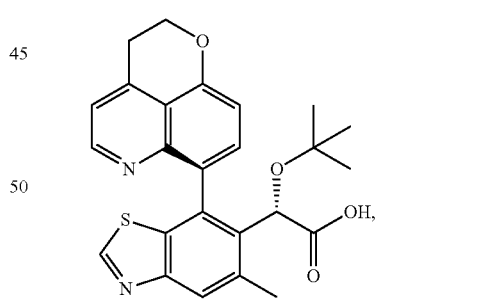
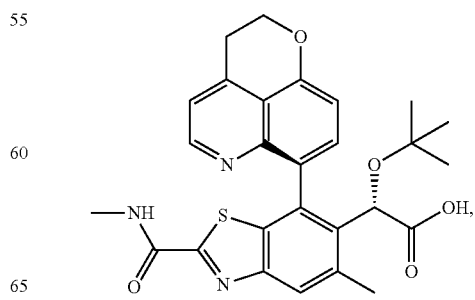

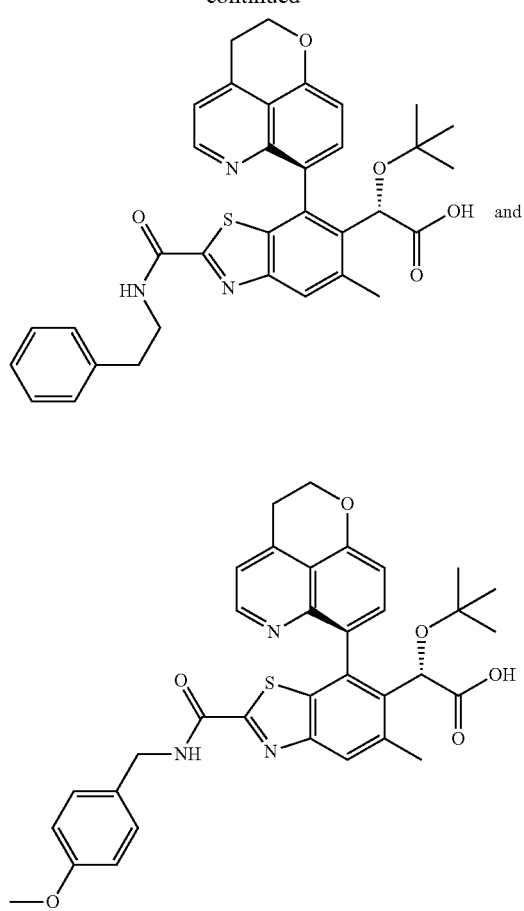
and salts thereof.
In one embodiment, the compounds of formula I are selected from:
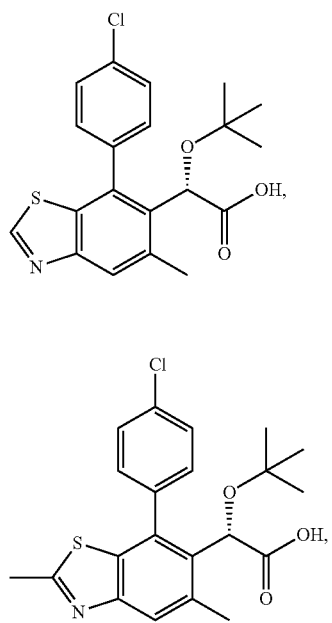
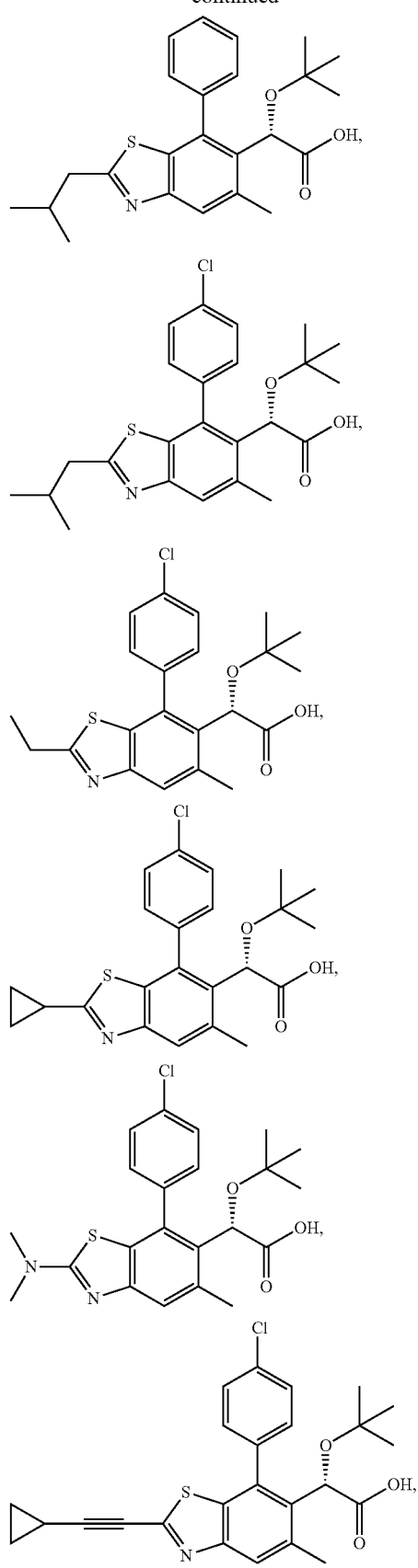

-continued
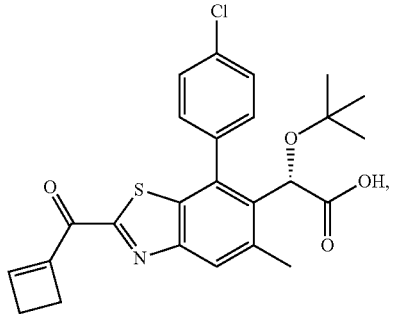
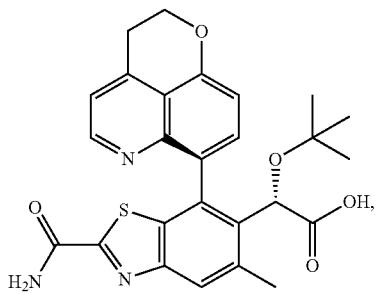
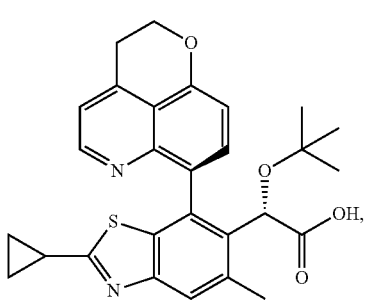
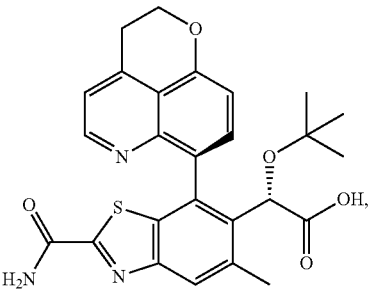
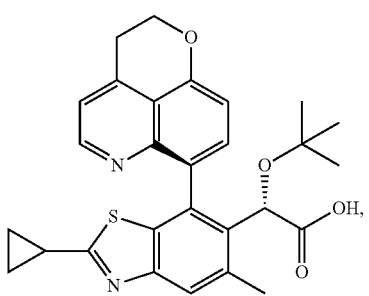
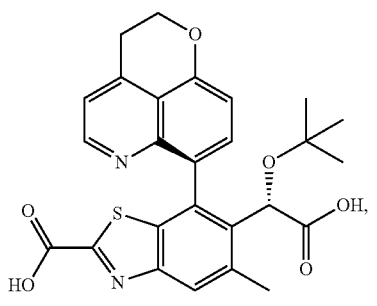
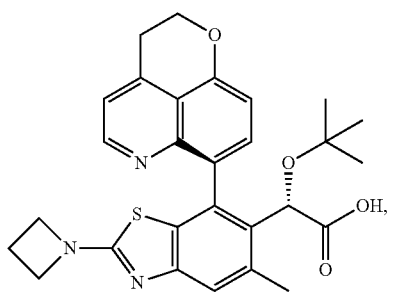
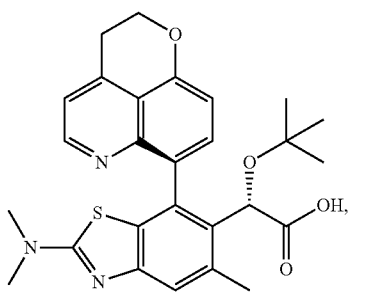
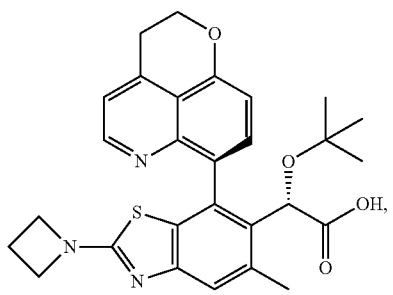
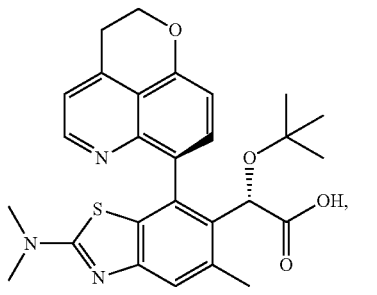

69
-continued
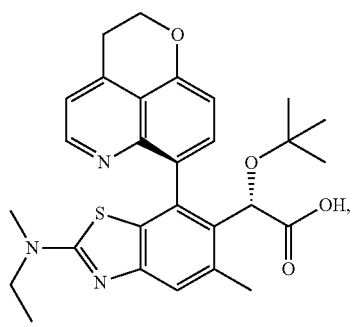
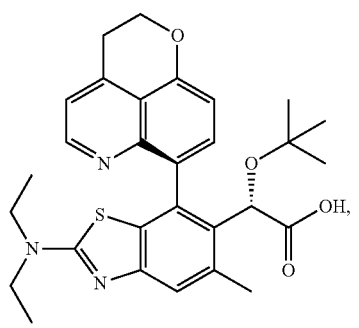
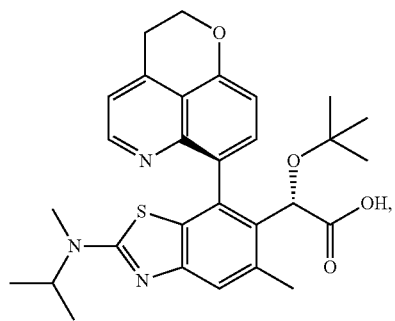
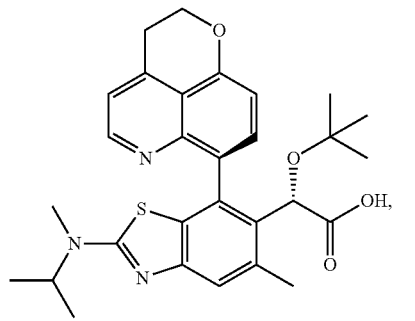
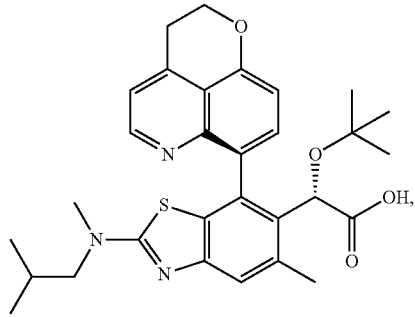
70
-continued
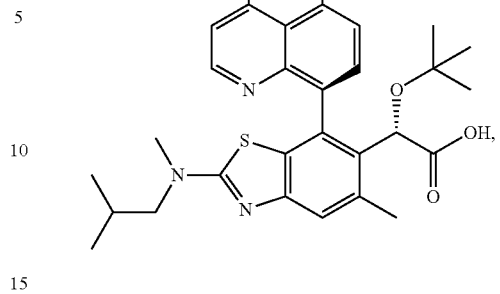
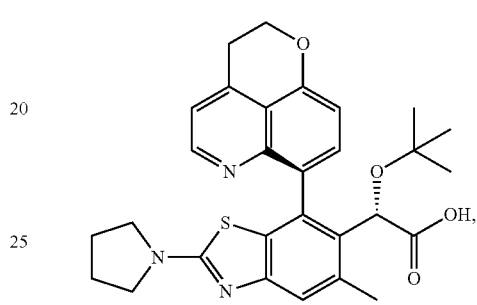
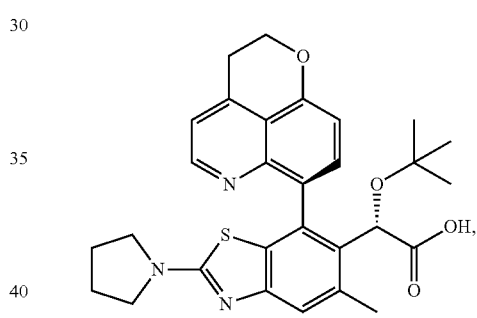
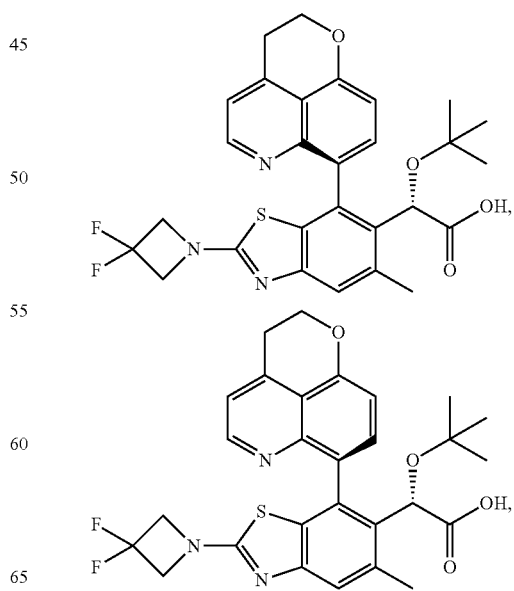

| 71 -continued | 72 -continued |
|---|---|
| 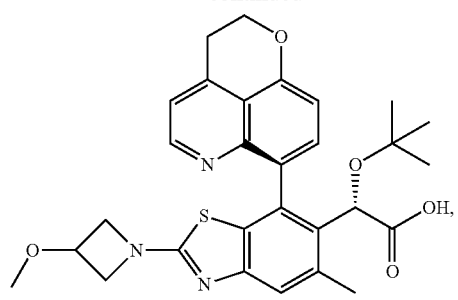 | 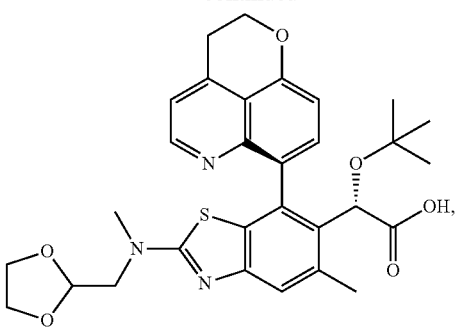 |
| 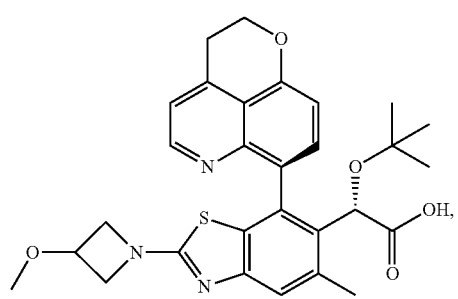 | 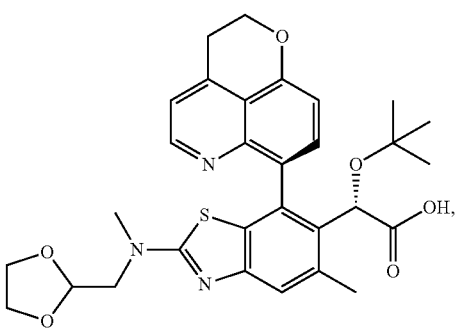 |
| 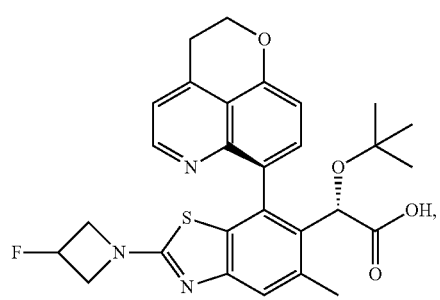 | 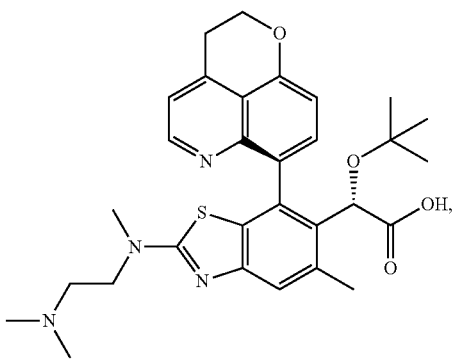 |
| 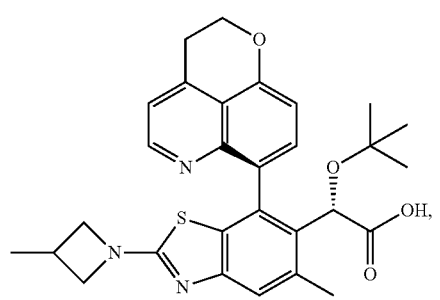 | 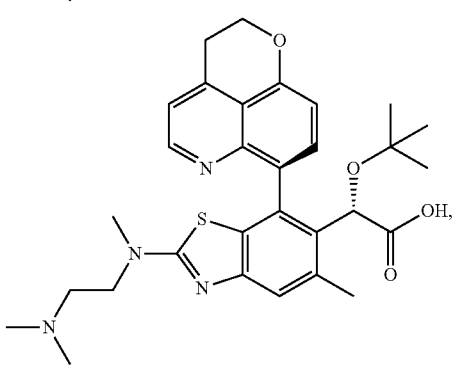 |
| 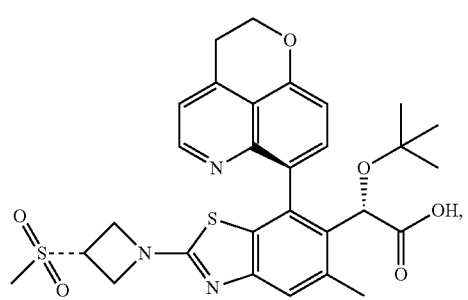 | 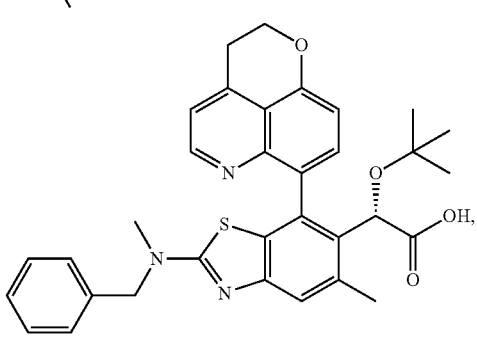 |

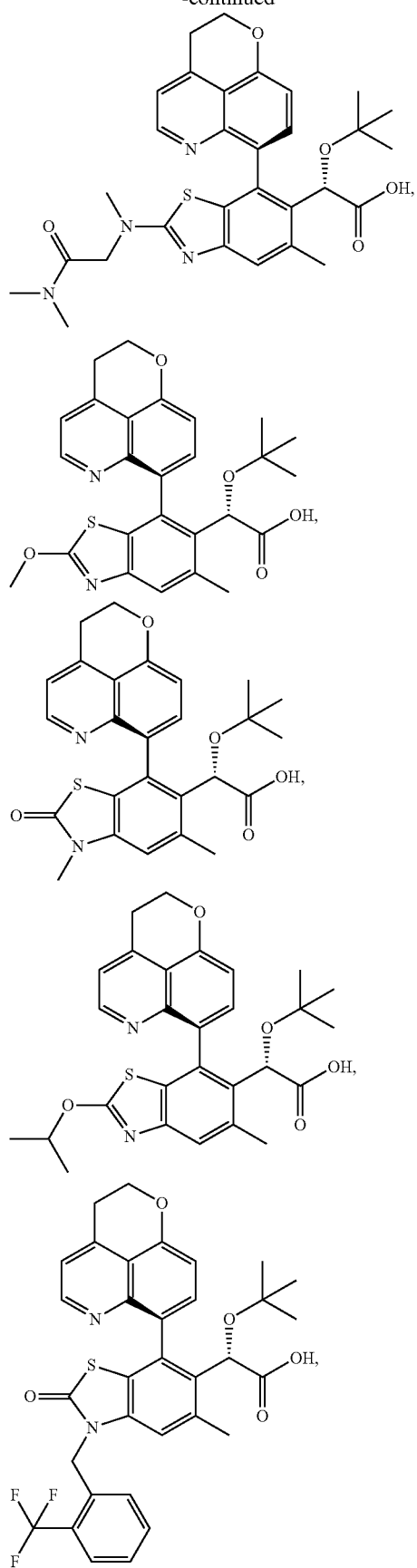
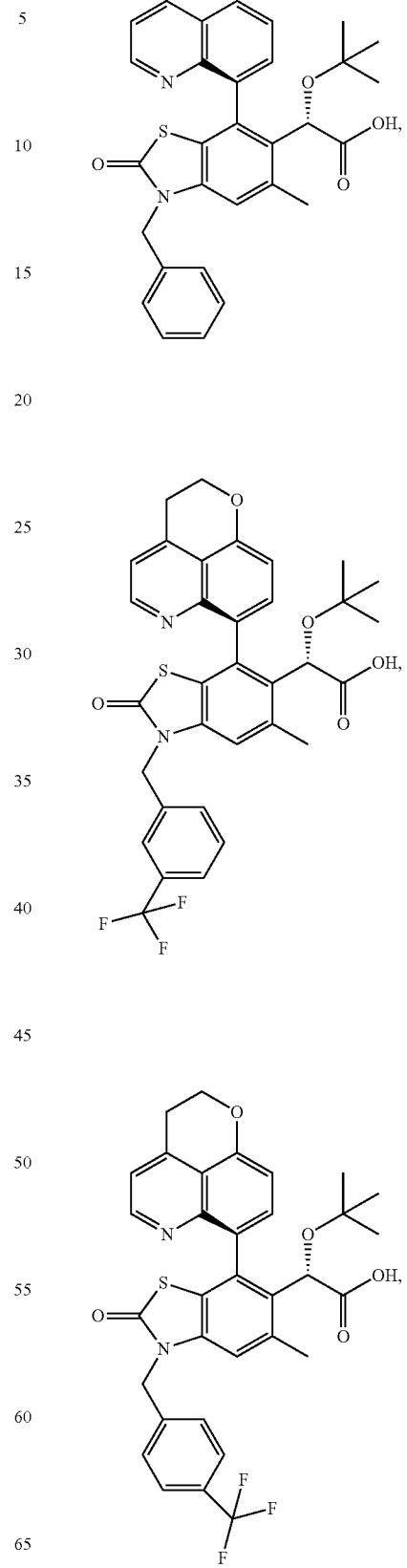

75
-continued
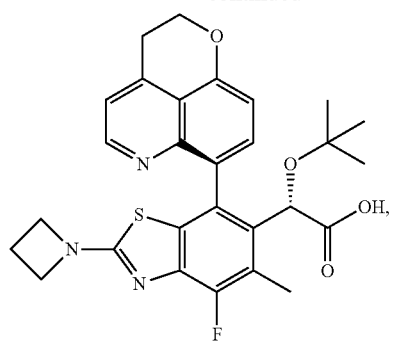
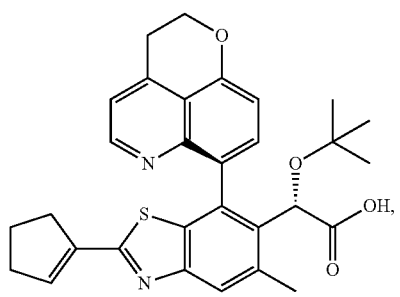
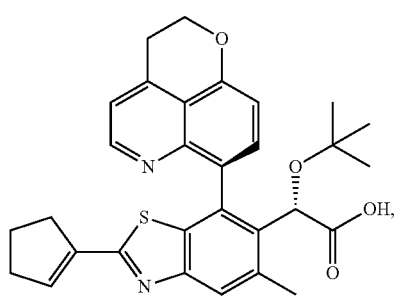
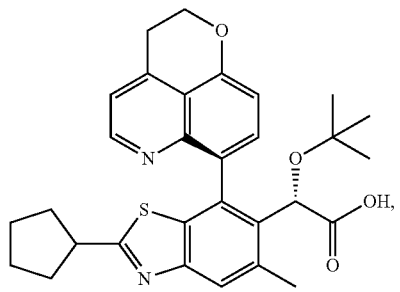
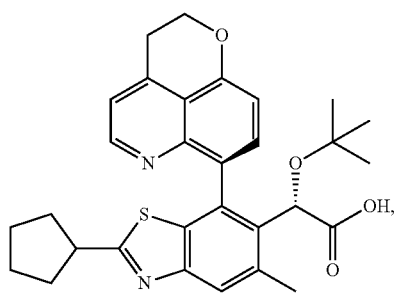
76
-continued
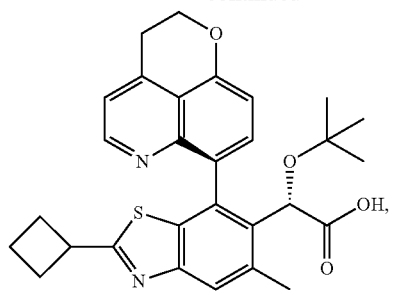
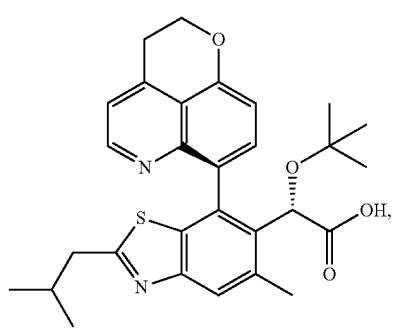
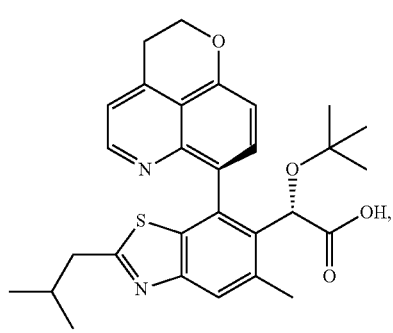
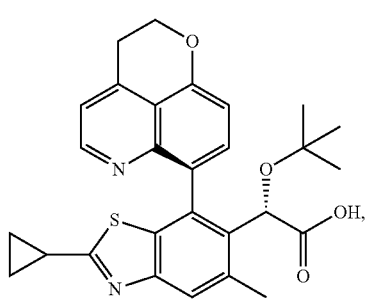
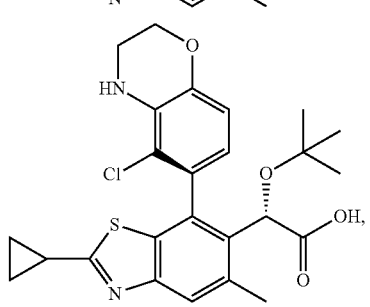

77
-continued
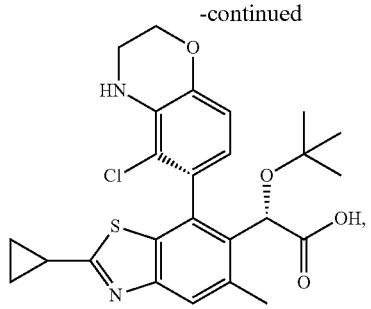
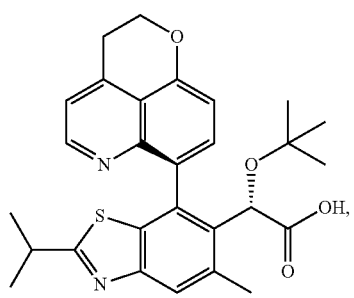
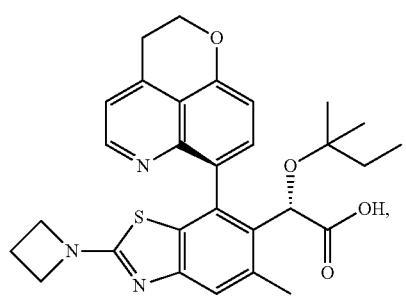
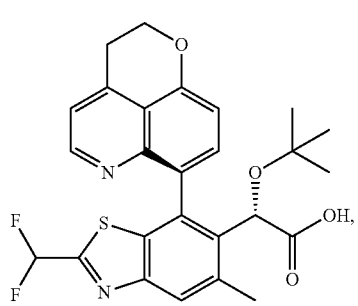
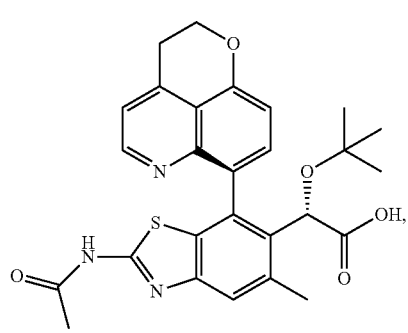
78
-continued
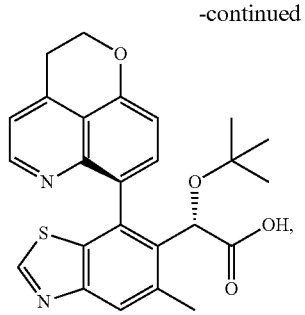
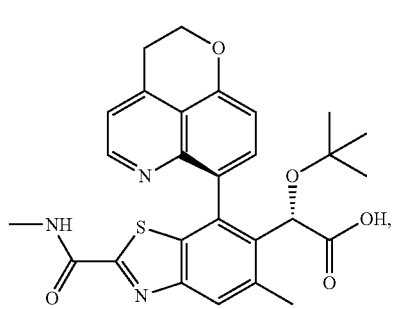
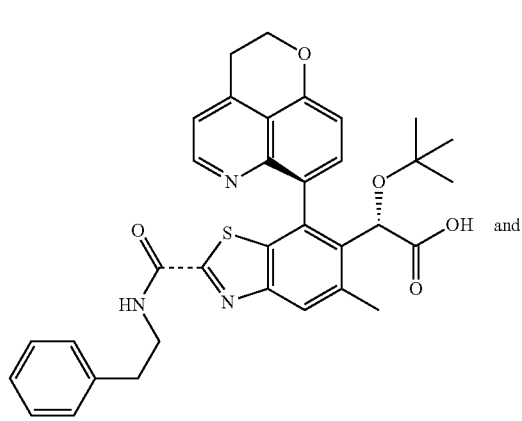 and
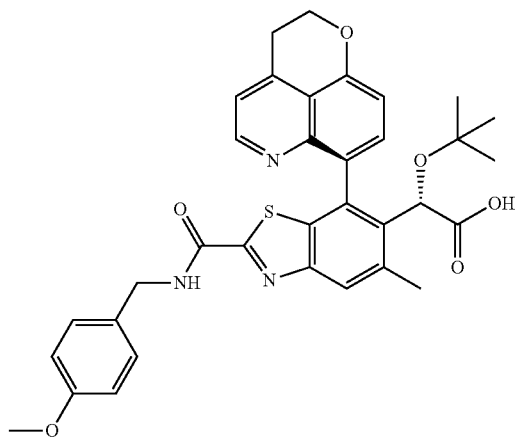
and salts thereof.
In another embodiment, the compounds of formula I are selected from:

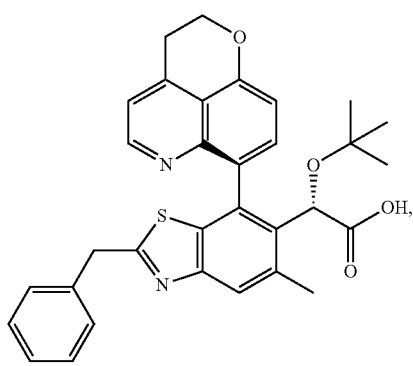
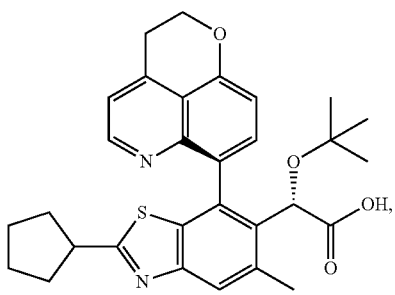
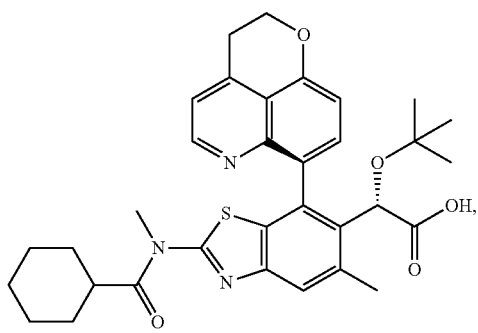
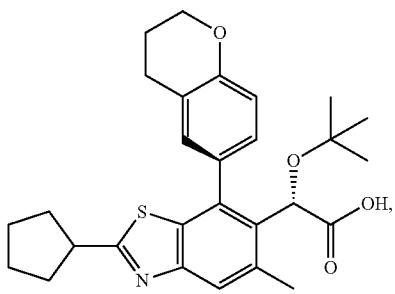
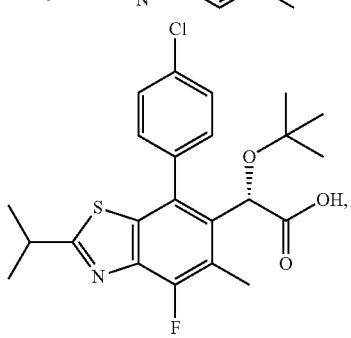
-continued
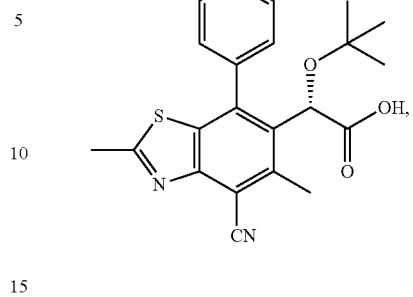
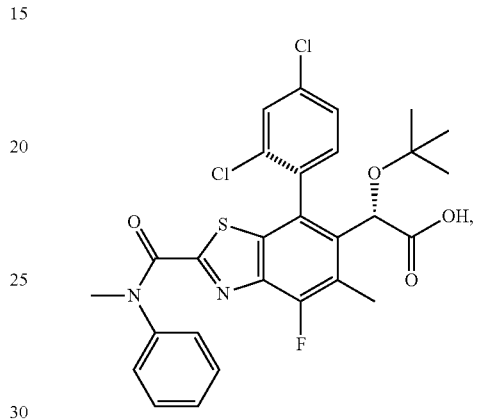
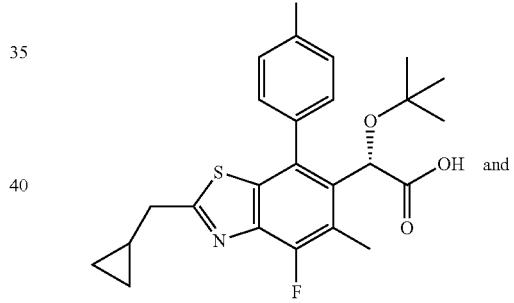
and
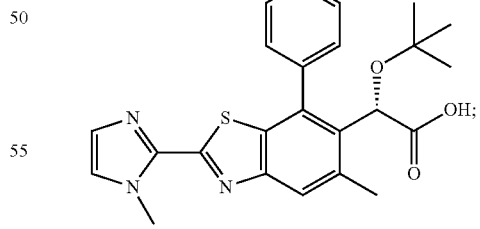
and salts thereof.
General Synthetic Procedure
Schemes 1, 2, 3, 4, 5, 6 and 7 are provided as further embodiments of the invention and illustrate general methods which were used to prepare compounds of formula I and which can be used to prepare additional compounds of formula I.

Scheme 1
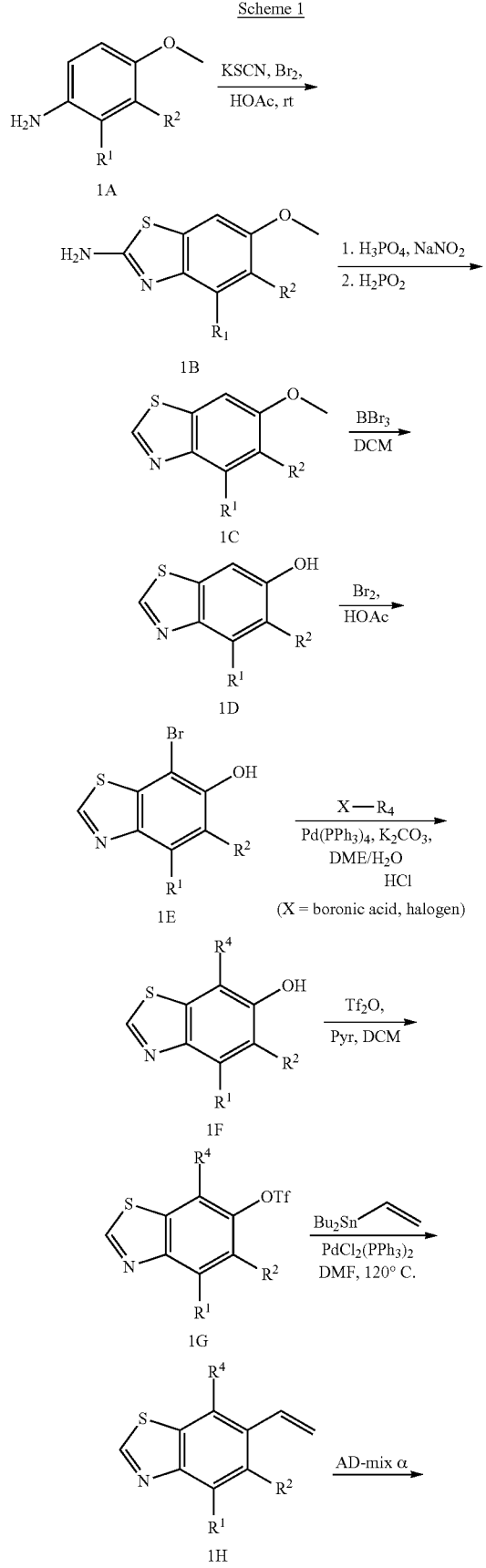
-continued
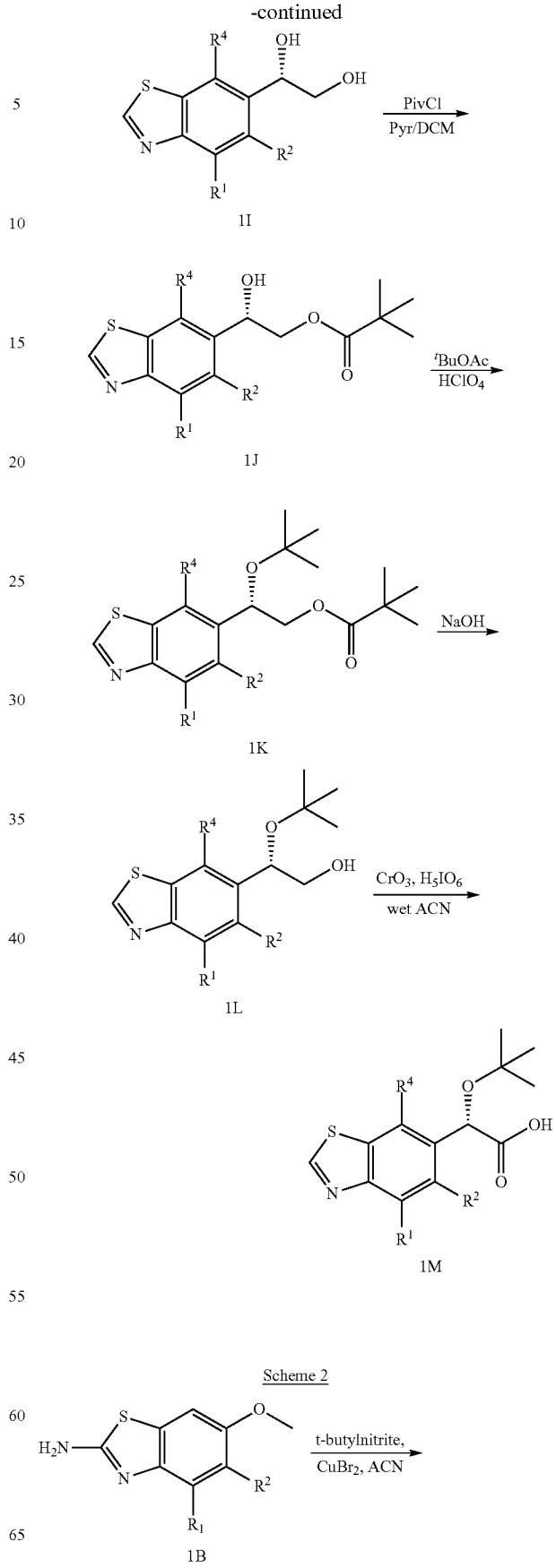
Scheme 2

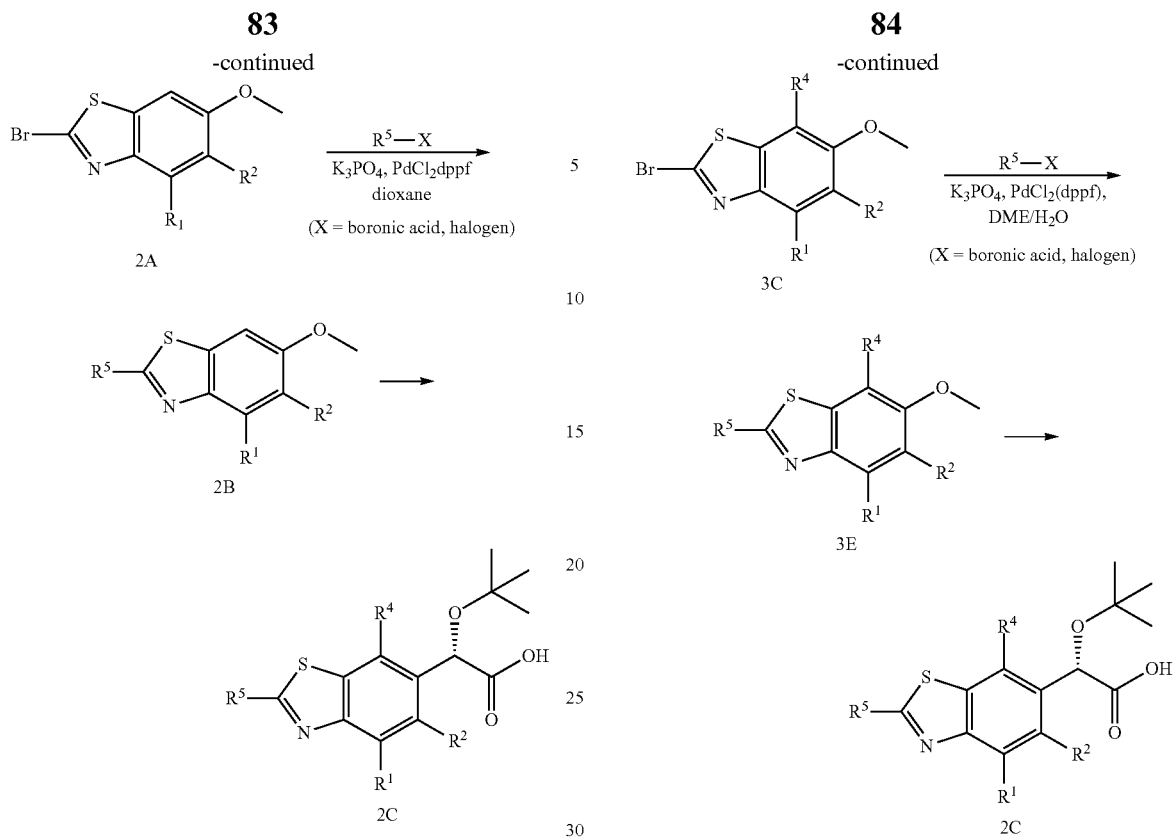
The benzothiazole intermediate 2B can be converted to the final compound 2C by the methods used to convert 1C to 1M as outlined in Scheme 1.
The benzothiazole intermediate 3E can be converted to the final compound 2C by the methods used to convert 1C to 1D and 1F to 1M as outlined in Scheme 1,
Scheme 3
Scheme 4
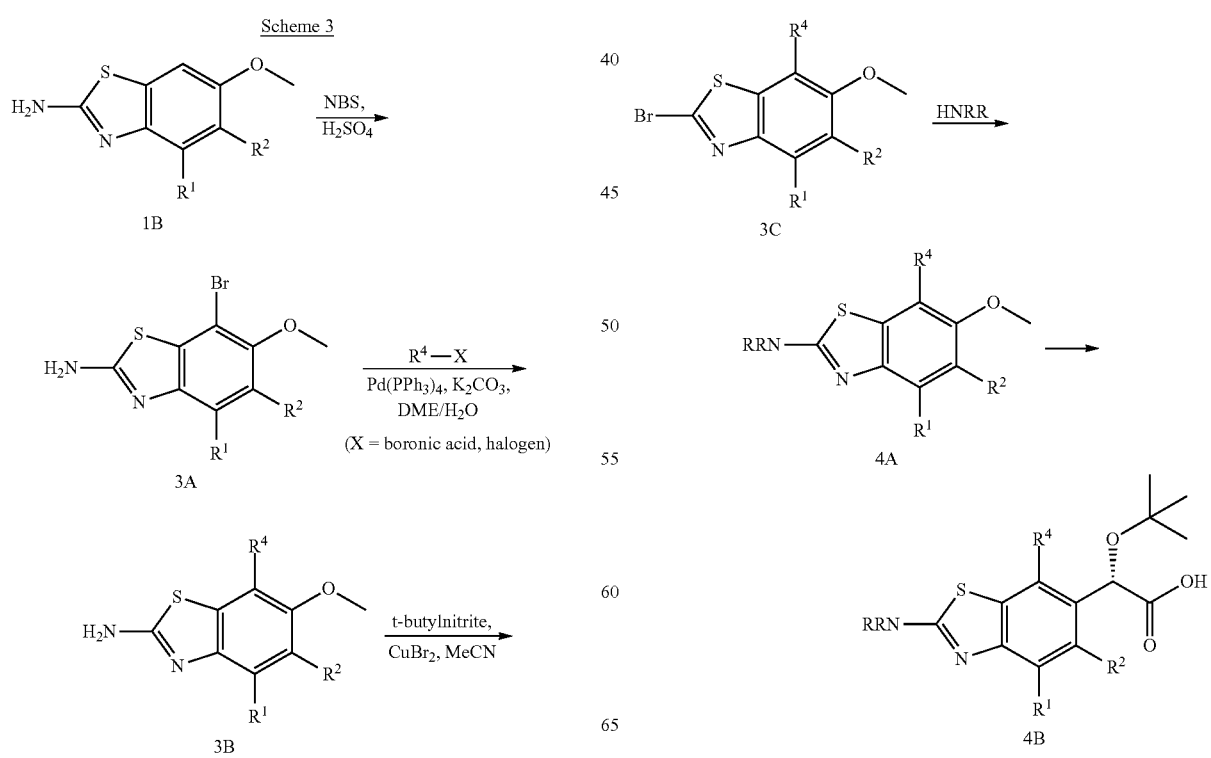

The benzothiazole intermediate 4A can be converted to the final compound 4B by the methods used to convert 1C to 1D and 1F to 1M as outlined in Scheme 1 wherein HNRR represents an $HNR^9R^{10}$, $HNR_eR_f$ or a heterocycle (when R and R taken together with the nitrogen to which they are attached form a ring).
Scheme 5
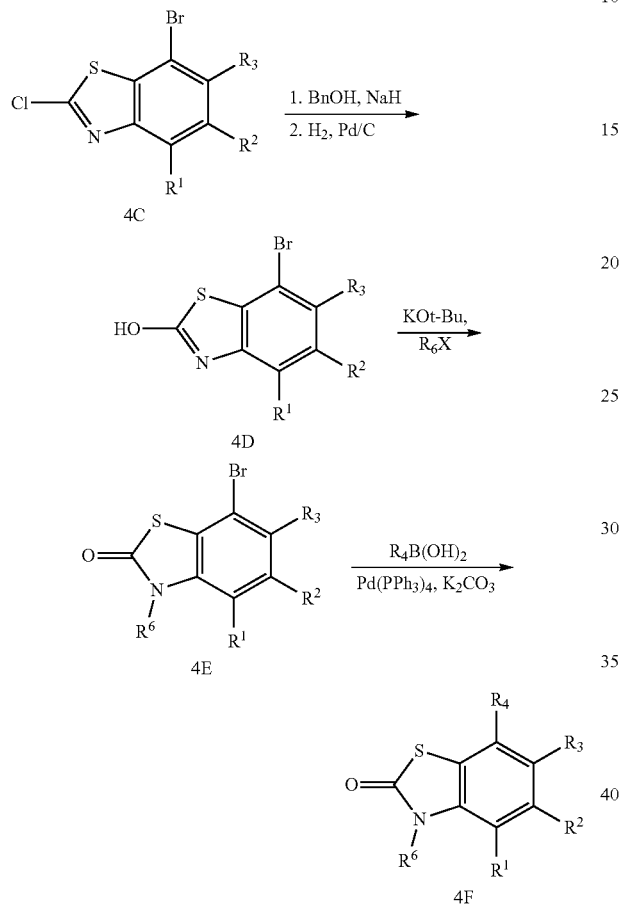
Scheme 6
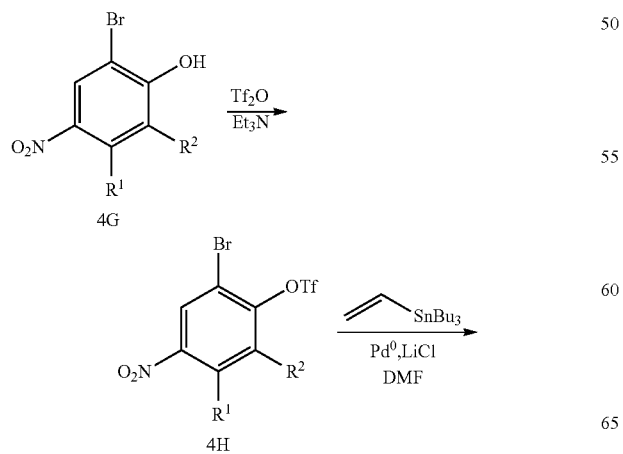
-continued
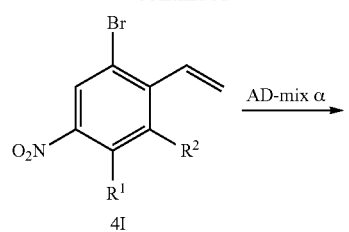
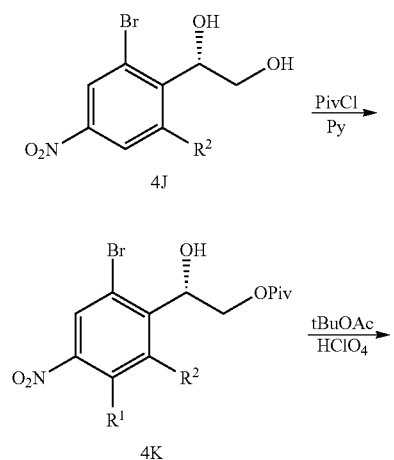
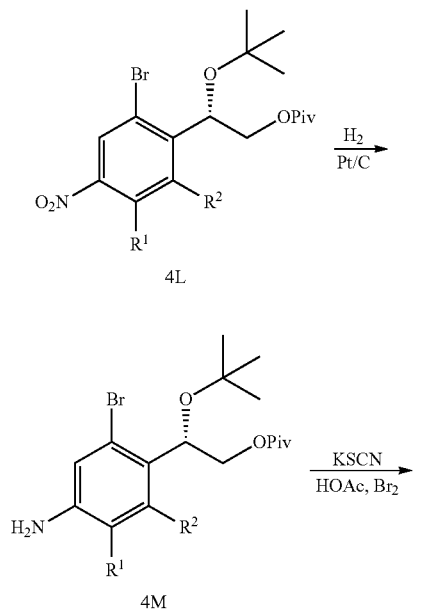
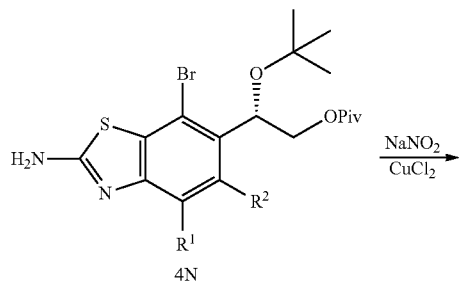

-continued

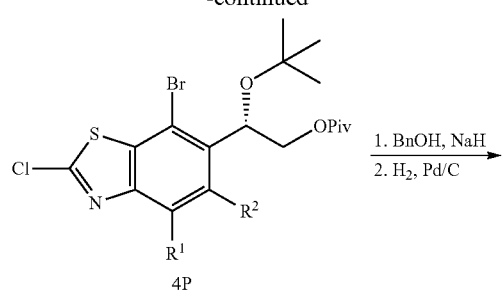

4P

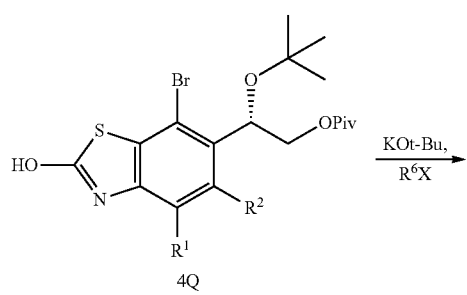

4Q

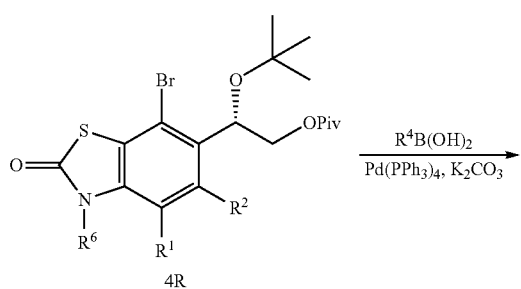

4R

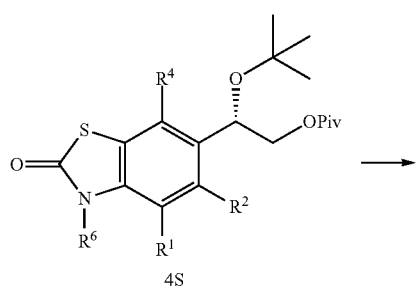

4S

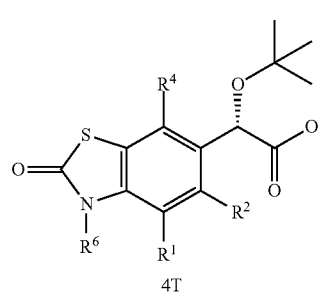

4T

The benzothiazoline intermediate 4S can be converted to the final compound 4T by the methods used to convert 1C to 1M as outlined in Scheme 1.

Scheme 7

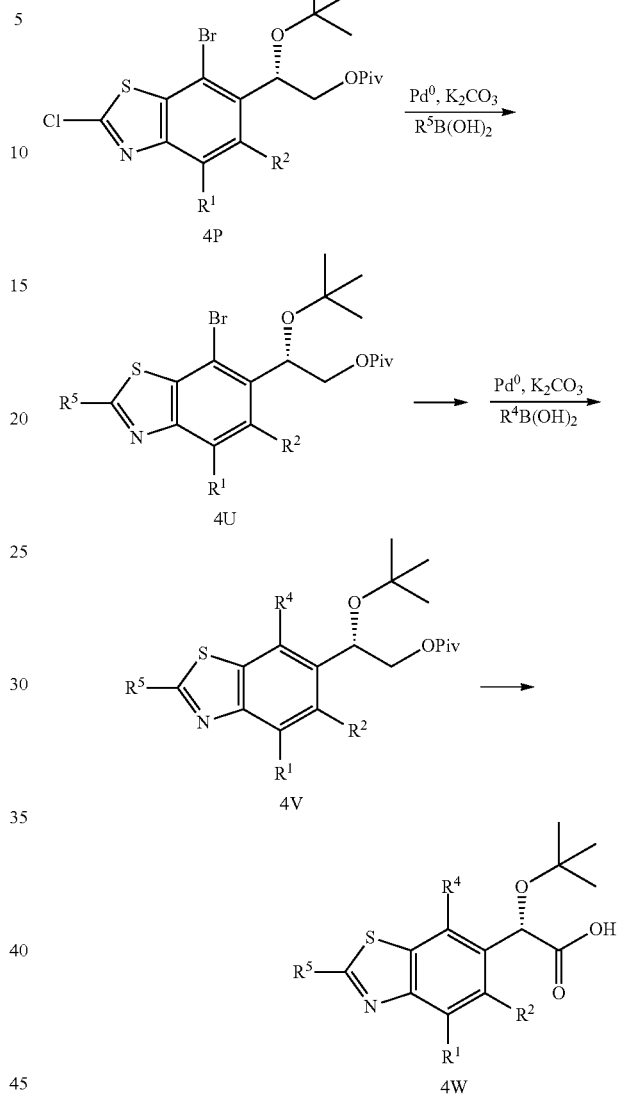

The benzothiazoline intermediate 4V can be converted to the final compound 4W by the methods used to convert 1C to 1M as outlined in Scheme 1.

A specific value for $R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups;

b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

A specific value for $R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

A specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

and $R^{3'}$ is H.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein:

$R^5$ is selected from:

a) aryl, heterocycle and heteroaryl, wherein aryl, heterocycle and heteroaryl are each optionally substituted with one or more (e.g. 1, 2 or 3) $Z^{11}$ groups; and b) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;

$R^2$ is H or $(C_1-C_6)$alkyl; and $R^3$ is —O$(C_1-C_6)$alkyl.

Another specific value for $R^5$ is aryl, heteroaryl, heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

Another specific group of compounds of formula I are compounds wherein:

$R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups; and $R^{3'}$ is H.

Another specific group of compounds of formula I are compounds wherein:

$R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H; and $R^2$ is H or $(C_1-C_6)$alkyl.

Another specific group of compounds of formula I are compounds wherein $R^5$ is selected from aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;
$R^2$ is H or $(C_1-C_6)$alkyl; and
$R^3$ is —O$(C_1-C_6)$alkyl.

Another specific value for $R^5$ is selected from:
a) aryl, wherein aryl is optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups.

Another specific group of compounds of formula I are compounds wherein:
$R^5$ is selected from:
a) aryl, wherein aryl is optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
and
$R^{3'}$ is H.

Another specific group of compounds of formula I are compounds wherein:
$R^5$ is selected from:
a) aryl, wherein aryl is optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H; $R^1$ is H; and
$R^2$ is H or $(C_1-C_6)$alkyl.

Another specific group of compounds of formula I are compounds wherein:
$R^5$ is selected from:
a) aryl, wherein aryl is optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H; $R^1$ is H;
$R^2$ is H or $(C_1-C_6)$alkyl; and
$R^3$ is —O$(C_1-C_6)$alkyl.

Another specific value for $R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl;
wherein each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific group of compounds of formula I are compounds wherein:
$R^5$ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;
$R^{3'}$ is H;
each $Z^{10}$ is independently selected from:
i) halo, oxo, thioxo, $(C_2-C_6)$alkenyl, $(C_1-C_6)$haloalkyl, $(C_3-C_7)$cycloalkyl, $(C_3-C_7)$cycloalkyl-$(C_1-C_6)$alkyl-, —OH, —O$(C_1-C_6)$alkyl, —O$(C_1-C_6)$haloalkyl, —SH, —S$(C_1-C_6)$alkyl, —SO$(C_1-C_6)$alkyl, —SO$_2(C_1-C_6)$alkyl, —NH$_2$, —NH$(C_1-C_6)$alkyl and —N$((C_1-C_6)$alkyl$)_2$;
ii) $(C_1-C_6)$alkyl substituted with —OH, —O—$(C_1-C_6)$haloalkyl, or —O—$(C_1-C_6)$alkyl; and
iii) aryl, heterocycle and heteroaryl, which aryl, heterocycle and heteroaryl is optionally substituted with halo, $(C_1-C_6)$alkyl or COOH; and
each $Z^{11}$ is independently selected from $Z^{10}$, —C(=O)—NH$_2$, —C(=O)—NH$(C_1-C_4)$alkyl, —C(=O)—N$((C_1-C_4)$alkyl$)_2$, —C(=O)-aryl, —C(=O)-heterocycle and —C(=O)-heteroaryl.

Another specific group of compounds of formula I are compounds wherein:

R⁵ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;
$R^2$ is H or $(C_1\text{-}C_6)$alkyl;
each $Z^{10}$ is independently selected from:
i) halo, oxo, thioxo, $(C_2\text{-}C_6)$alkenyl, $(C_1\text{-}C_6)$haloalkyl, $(C_3\text{-}C_7)$cycloalkyl, $(C_3\text{-}C_7)$cycloalkyl-$(C_1\text{-}C_6)$alkyl-, —OH, —O$(C_1\text{-}C_6)$alkyl, —O$(C_1\text{-}C_6)$haloalkyl, —SH, —S$(C_1\text{-}C_6)$alkyl, —SO$(C_1\text{-}C_6)$alkyl, —SO$_2$$(C_1\text{-}C_6)$alkyl, —NH$_2$, —NH$(C_1\text{-}C_6)$alkyl and —N$((C_1\text{-}C_6)$alkyl$)_2$;
ii) $(C_1\text{-}C_6)$alkyl substituted with —OH, —O—$(C_1\text{-}C_6)$haloalkyl, or —O—$(C_1\text{-}C_6)$alkyl; and
iii) aryl, heterocycle and heteroaryl, which aryl, heterocycle and heteroaryl is optionally substituted with halo, $(C_1\text{-}C_6)$alkyl or COOH; and each $Z^{11}$ is independently selected from $Z^{10}$, —C(=O)—NH$_2$, —C(=O)—NH$(C_1\text{-}C_4)$alkyl, —C(=O)—N$((C_1\text{-}C_4)$alkyl$)_2$, —C(=O)-aryl, —C(=O)-heterocycle and —C(=O)-heteroaryl.

Another specific group of compounds of formula I are compounds wherein:

R⁵ is selected from:
a) aryl, heterocycle and heteroaryl, wherein aryl, heterocycle and heteroaryl are each optionally substituted with one or more (e.g. 1, 2 or 3) $Z^{11}$ groups;
b) aryl, heteroaryl and heterocycle, wherein aryl, heteroaryl are heterocycle, are each independently substituted with one or more (e.g. 1, 2, 3, 4 or 5) $Z^5$ groups and optionally substituted with one or more (e.g. 1, 2, 3, 4 or 5) $Z^1$ groups; and
c) aryl, heteroaryl and heterocycle, wherein aryl, heteroaryl and heterocycle, are each independently substituted with one or more (e.g. 1, 2, 3, 4 or 5) $Z^{15}$ groups and optionally substituted with one or more (e.g. 1, 2, 3, 4 or 5) $Z^1$ groups;

$R^{3'}$ is H; $R^1$ is H;
$R^2$ is H or $(C_1\text{-}C_6)$alkyl;
$R^3$ is —O$(C_1\text{-}C_6)$alkyl;
each $Z^{10}$ is independently selected from:
i) halo, oxo, thioxo, $(C_2\text{-}C_6)$alkenyl, $(C_1\text{-}C_6)$haloalkyl, $(C_3\text{-}C_7)$cycloalkyl, $(C_3\text{-}C_7)$cycloalkyl-$(C_1\text{-}C_6)$alkyl-, —OH, —O$(C_1\text{-}C_6)$alkyl, —O$(C_1\text{-}C_6)$haloalkyl, —SH, —S$(C_1\text{-}C_6)$alkyl, —SO$(C_1\text{-}C_6)$alkyl, —SO$_2$$(C_1\text{-}C_6)$alkyl, —NH$_2$, —NH$(C_1\text{-}C_6)$alkyl and —N$((C_1\text{-}C_6)$alkyl$)_2$;
ii) $(C_1\text{-}C_6)$alkyl substituted with —OH, —O—$(C_1\text{-}C_6)$haloalkyl, or —O—$(C_1\text{-}C_6)$alkyl; and
iii) aryl, heterocycle and heteroaryl, which aryl, heterocycle and heteroaryl is optionally substituted with halo, $(C_1\text{-}C_6)$alkyl or COOH; and each $Z^{11}$ is independently selected from $Z^{10}$, —C(=O)—NH$_2$, —C(=O)—NH$(C_1\text{-}C_4)$alkyl, —C(=O)—N$((C_1\text{-}C_4)$alkyl$)_2$, —C(=O)-aryl, —C(=O)-heterocycle and —C(=O)-heteroaryl.

Another specific value for R⁵ is:

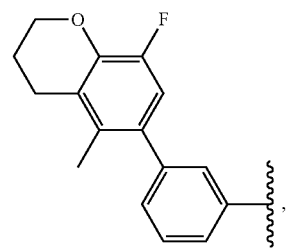

,

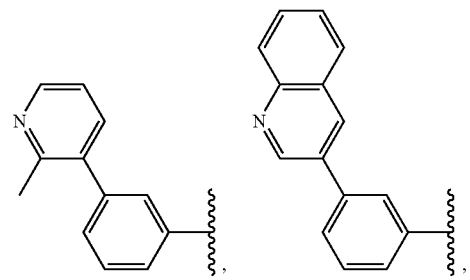

,

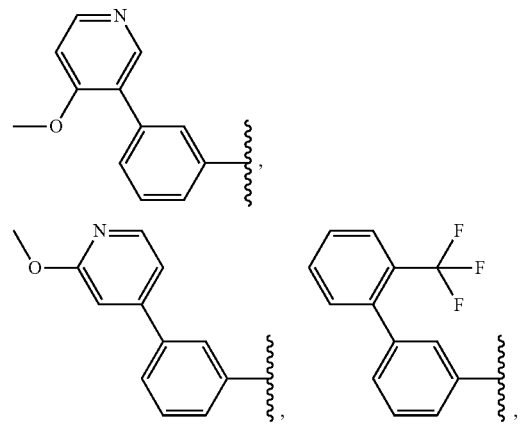

,

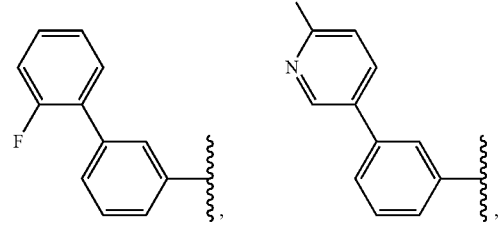

,

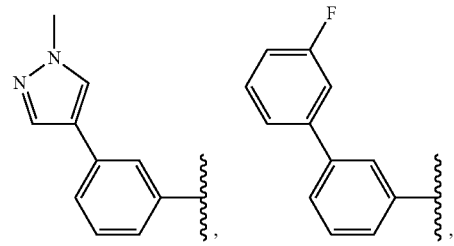

,

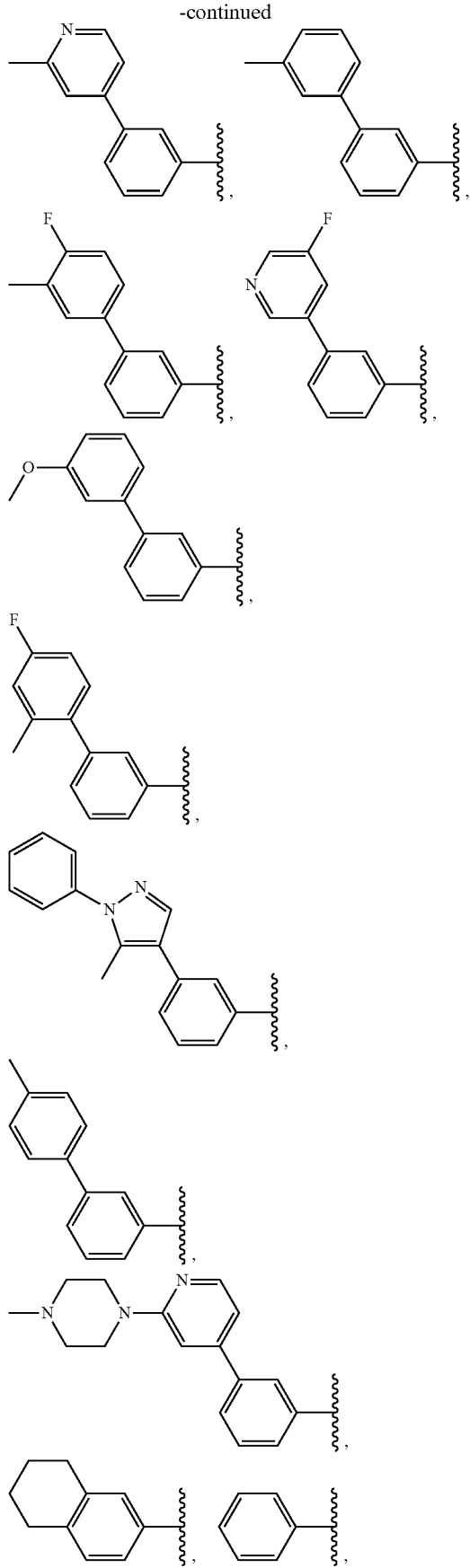
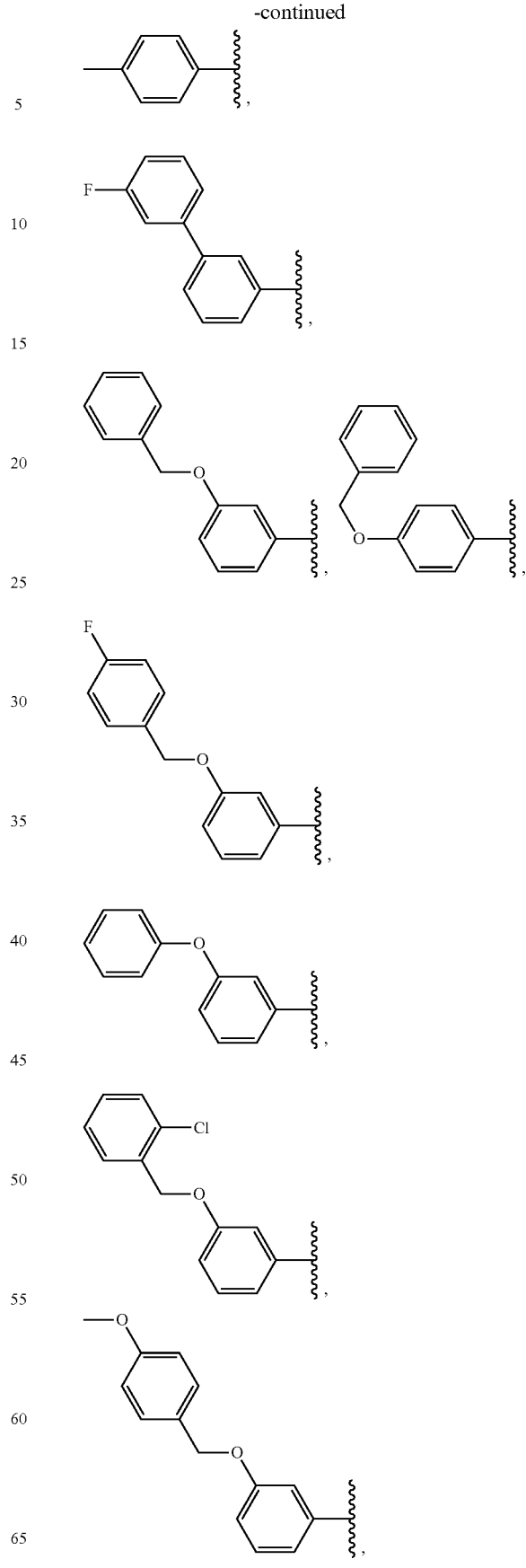

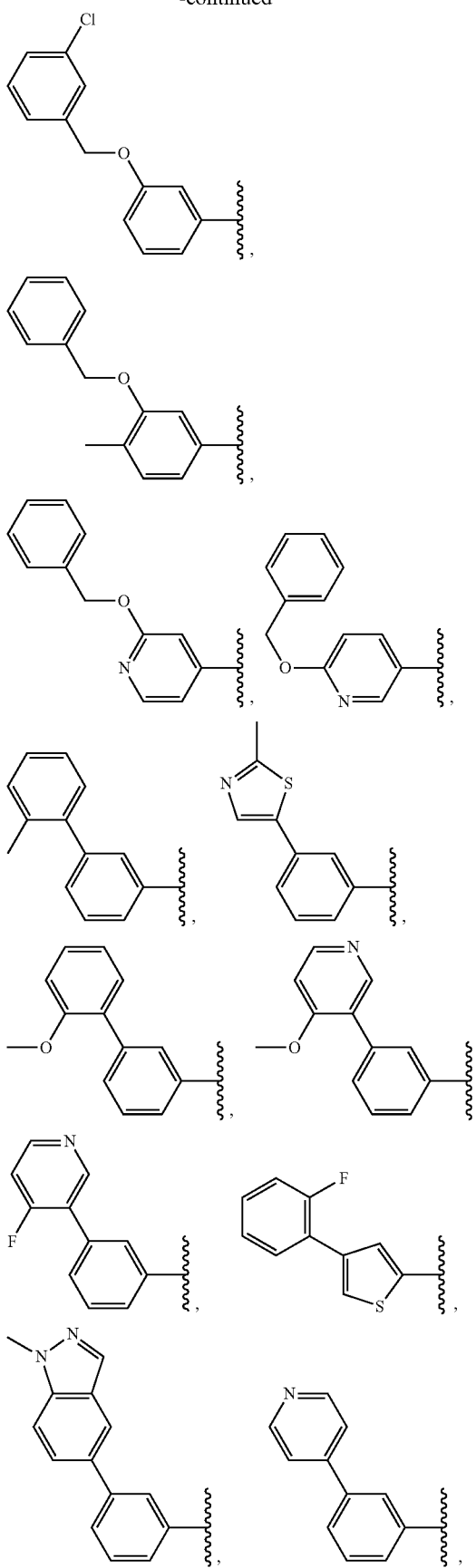
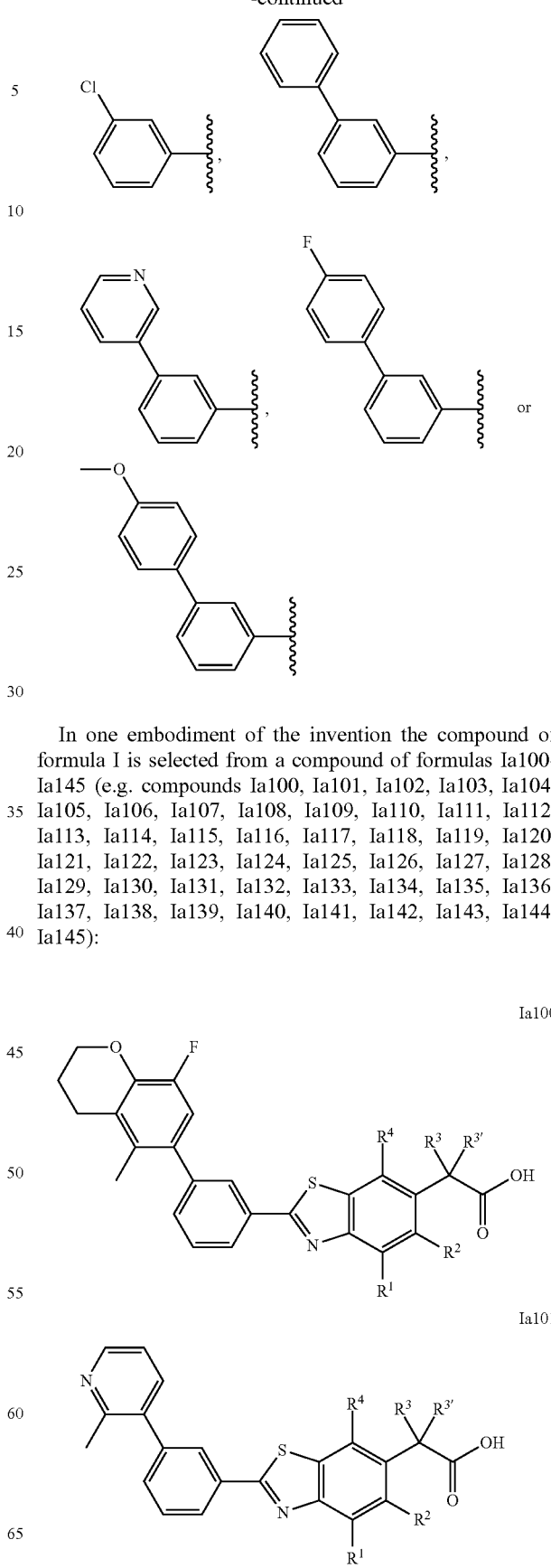
In one embodiment of the invention the compound of formula I is selected from a compound of formulas Ia100-Ia145 (e.g. compounds Ia100, Ia101, Ia102, Ia103, Ia104, Ia105, Ia106, Ia107, Ia108, Ia109, Ia110, Ia111, Ia112, Ia113, Ia114, Ia115, Ia116, Ia117, Ia118, Ia119, Ia120, Ia121, Ia122, Ia123, Ia124, Ia125, Ia126, Ia127, Ia128, Ia129, Ia130, Ia131, Ia132, Ia133, Ia134, Ia135, Ia136, Ia137, Ia138, Ia139, Ia140, Ia141, Ia142, Ia143, Ia144, Ia145):

-continued
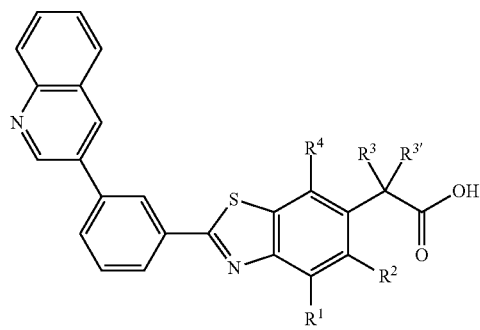
Ia102
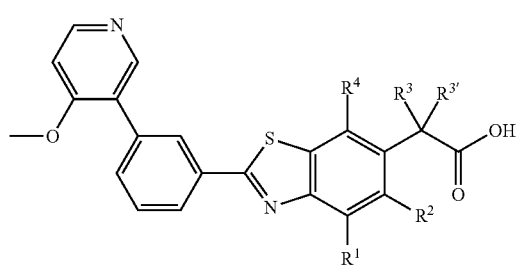
Ia103
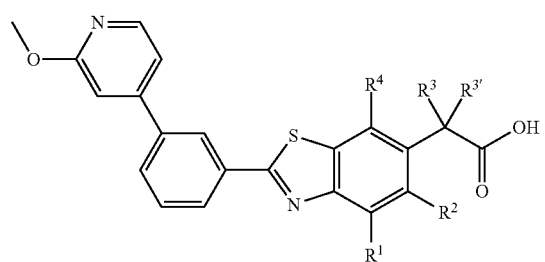
Ia104
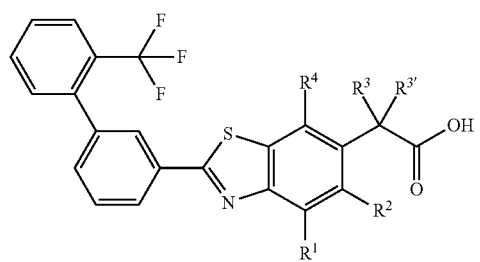
Ia105
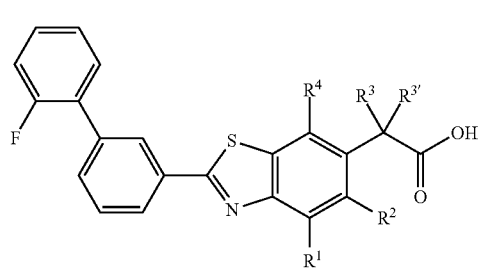
Ia106
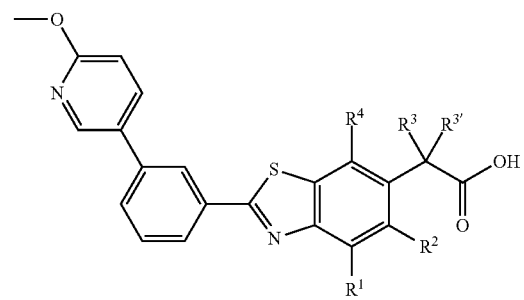
Ia107
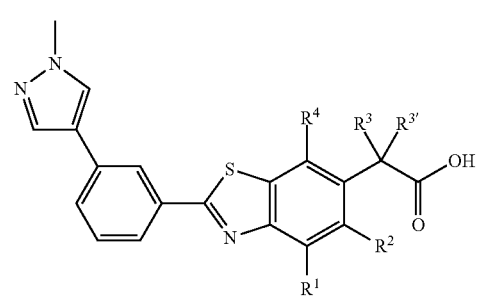
Ia108
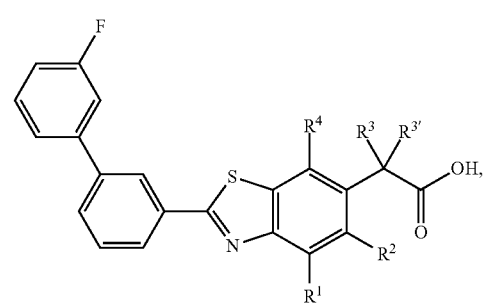
Ia109
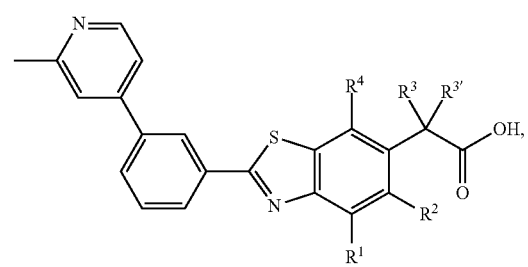
Ia110
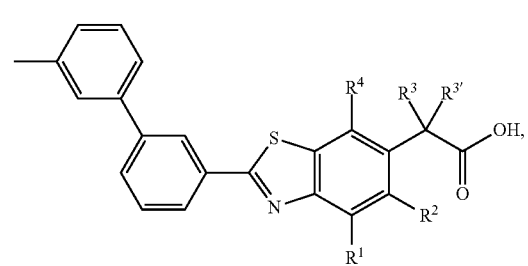
Ia111

Ia112
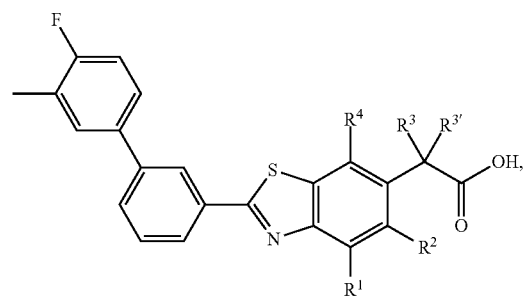
Ia113
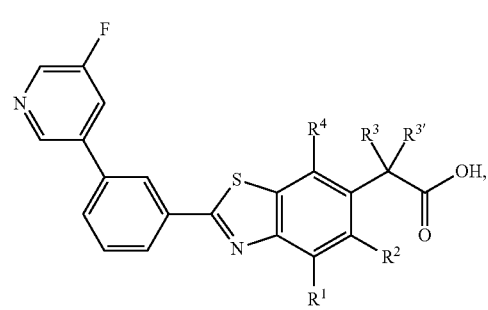
Ia114
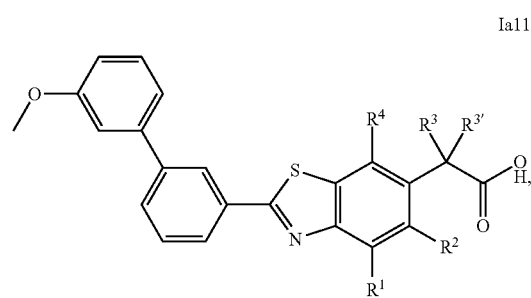
Ia115
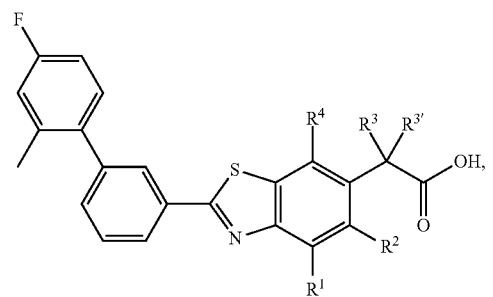
Ia116
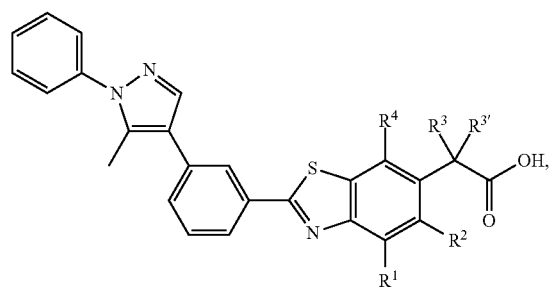
Ia117
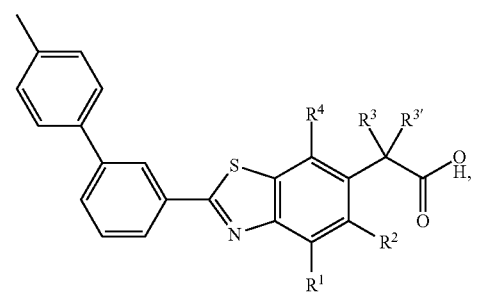
Ia118
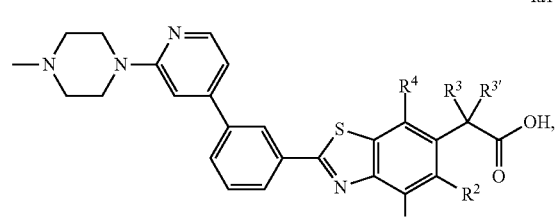
Ia119
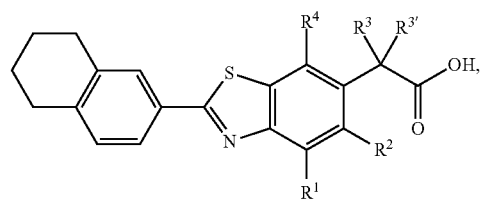
Ia120
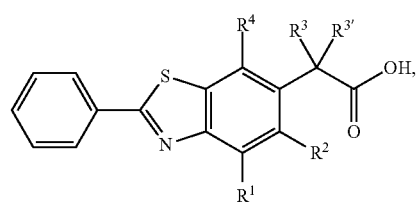
Ia121
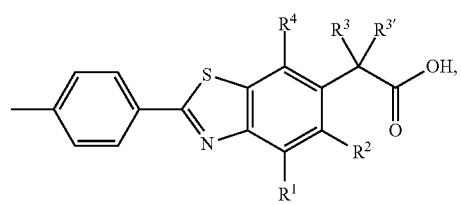
Ia122
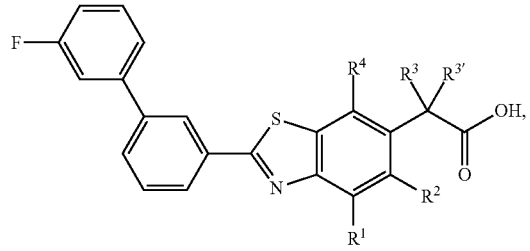

-continued
Ia123
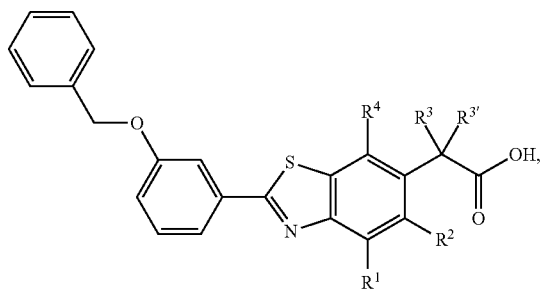
Ia124
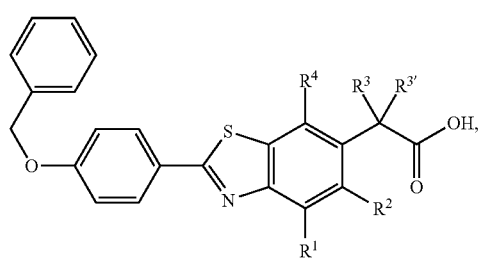
Ia125
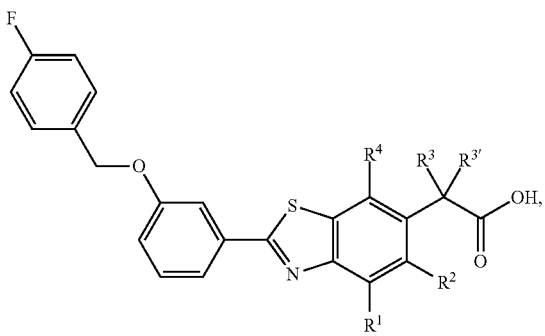
Ia126
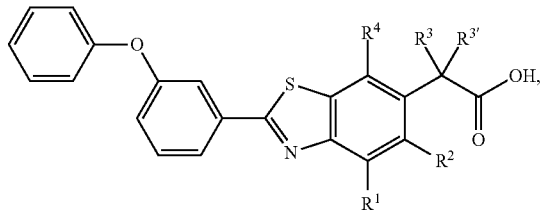
Ia127
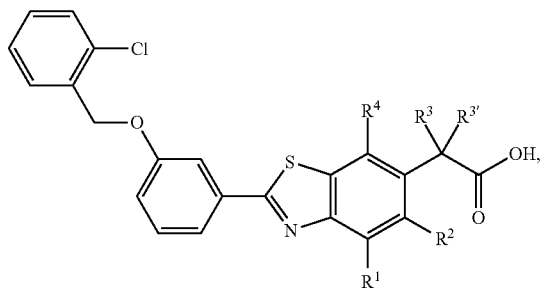
-continued
Ia128
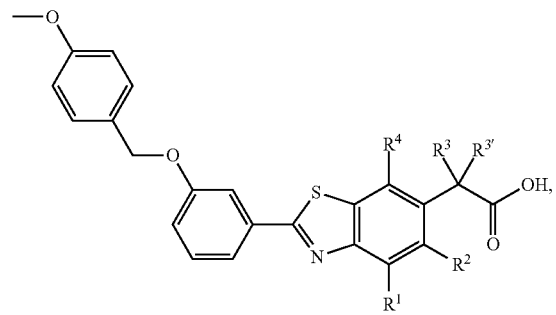
Ia129
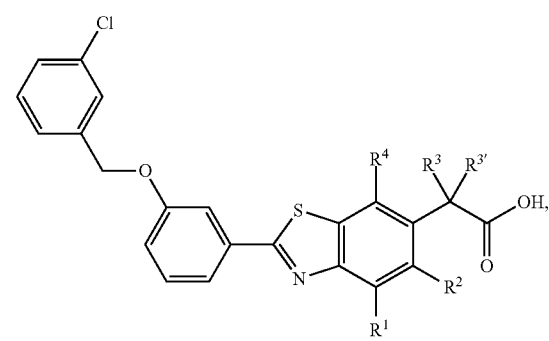
Ia130
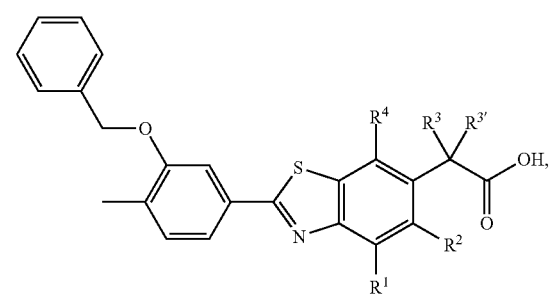
Ia131
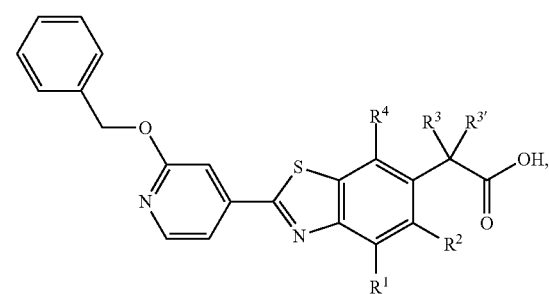
Ia132
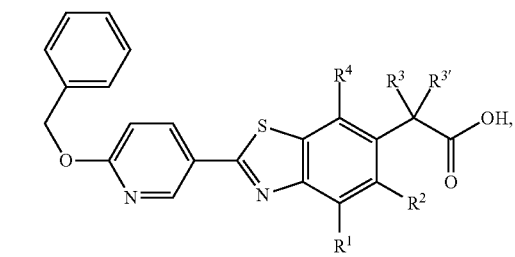

IA133
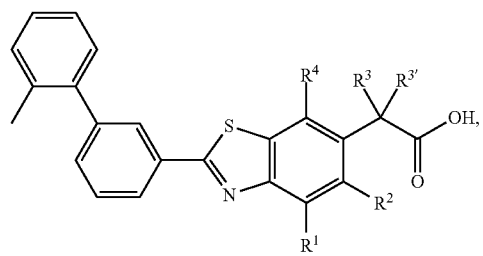
Ia134
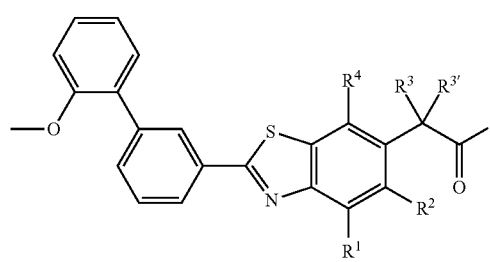
Ia135
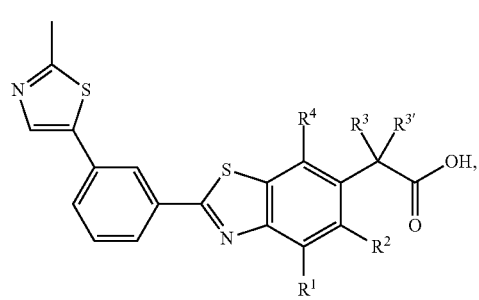
Ia136
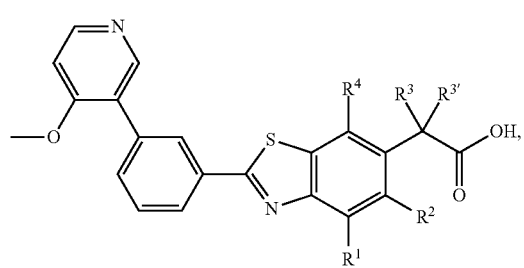
Ia137
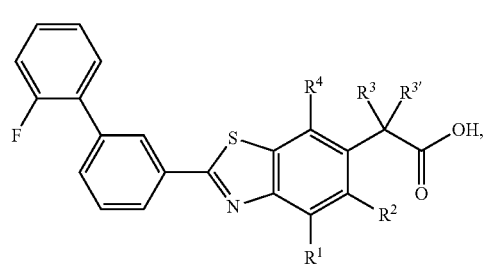
Ia138
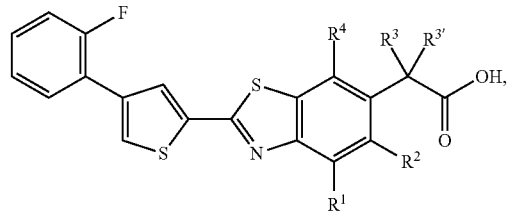
Ia139
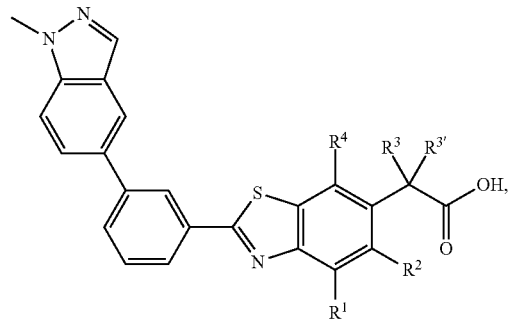
Ia140
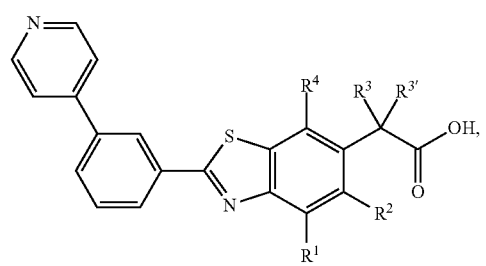
Ia141
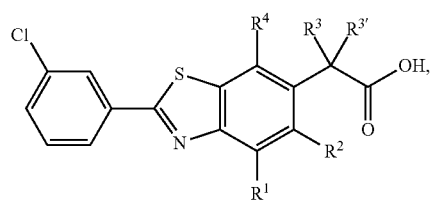
Ia142
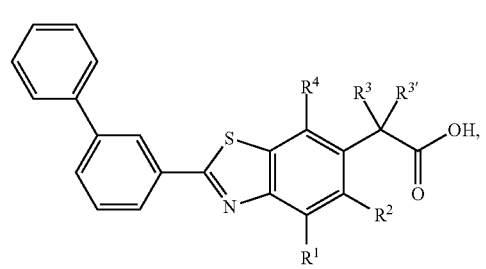
Ia143
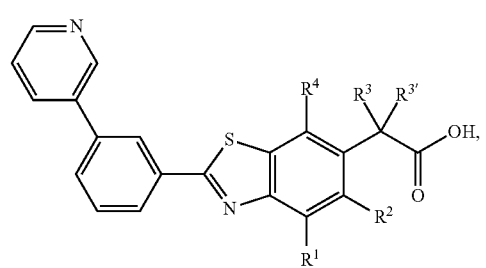

-continued

Ia144

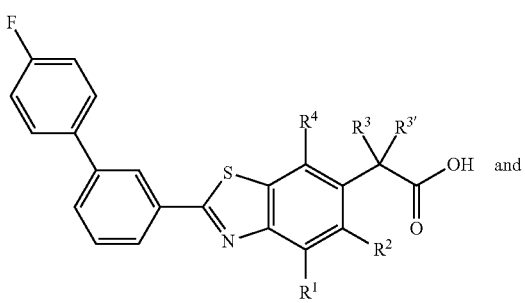

and

Ia145

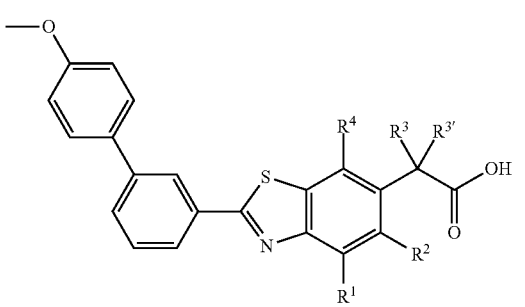

and salts thereof.

In one embodiment, the compounds of formula I are selected from the compounds of formulas Ia100-Ia145 wherein:
R$^1$ is H; R$^2$ is methyl, R$^{3'}$ is H; R$^3$ is -OtBu; and
R$^4$ is:

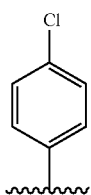

and salts thereof.

In another embodiment, the compounds of formula I are selected from the compounds of formulas Ia100-Ia145 wherein:
R$^1$ is H; R$^2$ is methyl, R$^{3'}$ is H; R$^3$ is -OtBu; and
R$^4$ is:

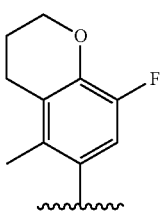 [SMILES: *c1cc(F)c2c(c1C)CCCO2]

and salts thereof.

In another embodiment, the compounds of formula I are selected from the compounds of formulas Ia100-Ia145 wherein:
R$^1$ is H; R$^2$ is methyl, R$^{3'}$ is H; R$^3$ is -OtBu; and
R$^4$ is:

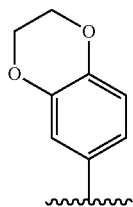 [SMILES: *c1ccc2c(c1)OCCO2]

and salts thereof.

In another embodiment of the invention, the compounds of formula I are selected from the compounds of formulas Ia100-Ia145 wherein:
R$^1$ is H; R$^2$ is methyl, R$^{3'}$ is H; R$^3$ is -OtBu; and
R$^4$ is:

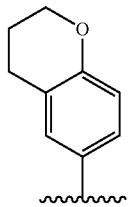 [SMILES: *c1ccc2c(c1)CCCO2]

and salts thereof.

In one embodiment of the invention the compounds of formula I are selected from the compounds of formulas Ia100-Ia145 wherein R$^{3'}$ is H; R$^3$ is —O(C$_1$-C$_6$)alkyl and the stereochemistry of the carbon bearing the R$^3$ (—O(C$_1$-C$_6$)alkyl) group is (S).

In another embodiment of the invention the compounds of formula I are selected from the compounds of formulas Ia100-Ia145 wherein R$^{3'}$ is H; R$^3$ is —O(C$_1$-C$_6$)alkyl and the stereochemistry of the carbon bearing the R$^3$ (—O(C$_1$-C$_6$)alkyl) group is (R).

In one embodiment of the invention, the compounds of formula I are selected from:

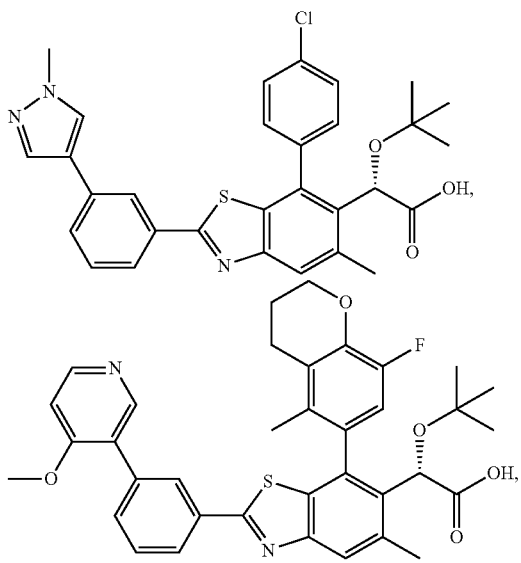

-continued

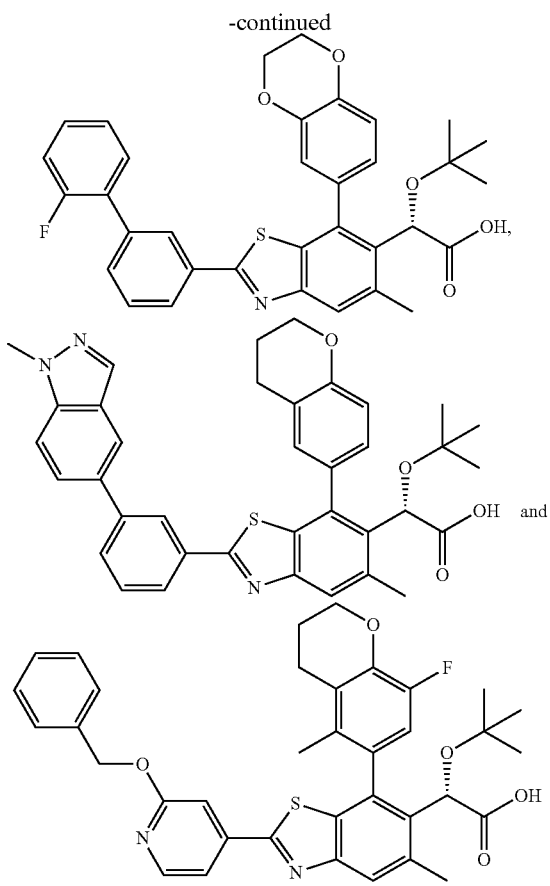

and salts thereof.

Prodrugs

In one embodiment, the invention provides for a prodrug of a compound of the invention. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 24; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Combination Therapy

In one embodiment, the invention provides for a method for treating an HIV infection, comprising administering to a patient in need thereof a therapeutically effective amount of a compound of the invention, or a pharmaceutically acceptable salt, thereof, in combination with a therapeutically effective amount of one or more additional therapeutic agents which are suitable for treating an HIV infection.

In one embodiment, the invention provides pharmaceutical compositions comprising a compound of the present invention, or a pharmaceutically acceptable salt thereof, in combination with at least one additional therapeutic agent, and a pharmaceutically acceptable carrier. For example, the therapeutic agent used in combination with the compound of the present invention can be any anti-HIV agent.

In one embodiment, the invention provides pharmaceutical compositions comprising a compound of the present invention, or a pharmaceutically acceptable salt thereof in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV, and combinations thereof, and a pharmaceutically acceptable carrier.

In another embodiment, the invention provides pharmaceutical compositions comprising a compound of the present invention, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunmavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In another embodiment, the invention provides pharmaceutical compositions comprising a compound of the present invention, or a pharmaceutically acceptable salt thereof, in combination with two, three, four or more additional therapeutic agents. For example, a compound of the present invention, or a pharmaceutically acceptable salt, thereof; is combined with two, three, four or more additional therapeutic agents selected from the classes of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drug for treating HIV. The two, three four or more additional therapeutic agents can be different therapeutic agents selected from the same class of therapeutic agents, or they can be selected from different classes of therapeutic agents.

In one embodiment, the invention provides for a combination pharmaceutical agent comprising:

a) a compound of the invention (e.g. a compound of Formula I), or a pharmaceutically acceptable salt, thereof; and b) at least one additional active agent which is suitable for treating an HIV infection.

In another embodiment, the invention provides a combination pharmaceutical agent comprising:

a) a compound of the invention (e.g. a compound of Formula I), or a pharmaceutically acceptable salt thereof; and b) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drug for treating HIV.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

It is also possible to co-administer a compound of the invention with one or more other active therapeutic agents. Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In yet another embodiment, the present application provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV.

In yet another embodiment, the present application provides a method for treating an HIV infection comprising administering to a patient in need thereof a therapeutically effective amount of a compound of the present invention, or a pharmaceutically acceptable salt, thereof, in combination with a therapeutically effective amount of one or more additional therapeutic agents selected from the group consisting of:

(1) HIV protease inhibiting compounds selected from the group consisting of amprenavir, atazanavir, fosamprenavir, indinavir, lopinavir, ritonavir, nelfmavir, saquinavir, tipranavir, brecanavir, danmavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound of the invention may be determined using Test A described below.

Test A: Antiviral Assays in MT4 Cells

For the antiviral assay utilizing MT-4 cells, 0.4 μL of 189× test concentration of 3-fold serially diluted compound in DMSO was added to 40 μL of cell growth medium (RPMI 1640, 10% FBS, 1% penicilline/Streptomycine, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @37° C. with 25 uL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 uL of 2000 (for MT4) cells is added to each well of the assay plates.

Assay plates were then incubated in a 37° C. incubator. After 5 days of incubation, 25 μl of 2× concentrated Cell-Titer-Glo™ Reagent (catalog #G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds of the present invention demonstrate antiviral activity in this assay (Test A) as depicted in the table below. Accordingly, the compounds of the invention may be useful for treating the proliferation of the HIV virus, treating AIDS or delaying the onset of AIDS or ARC symptoms

| Compound Number | EC50 (nM) |
|---|---|
| 5L | 2950 |
| 7 | 257 |
| 8K | 641 |
| 9 | 118 |
| 10 | 121 |
| 12 | 113 |
| 14 | 718 |
| 14b | 480 |
| 21 | 14.9 |
| 22 | 170 |
| 35 | 12.7 |
| 36 | 6211 |
| 40 | 722 |
| 41 | 923 |
| 42 | 10.3 |
| 43 | 5090 |
| 44 | 18.7 |
| 45 | 67.0 |
| 46 | 16.8 |
| 47 | 26500 |
| 48 | 67.0 |
| 49 | 13300 |
| 50 | 52.8 |
| 51 | 5250 |
| 52 | 53.4 |
| 53 | 37500 |
| 54 | 274 |
| 55 | 53000 |
| 56 | 62.4 |
| 57 | 147 |
| 58 | 3520 |
| 59 | 149 |
| 60 | 34510 |
| 61 | 987 |
| 62 | 4880 |

-continued

| Compound Number | EC50 (nM) |
|---|---|
| 63 | 351 |
| 64 | 53000 |
| 66 | 22.5 |
| 68 | 292 |
| 70 | 80.8 |
| 71 | 984 |
| 72 | 29.8 |
| 73 | 52.2 |
| 74 | 650 |
| 76 | 26 |
| 78 | 726 |
| 79 | 45900 |
| 80 | 136 |
| 81 | 27400 |
| 82 | 40.2 |
| 83 | 93.2 |
| 84 | 14900 |
| 85 | 66.4 |
| 86 | 61.7 |
| 87 | 1570 |
| 88 | 13.3 |
| 89 | 36.6 |
| 92 | 353 |
| 93 | 1420 |
| 95 | 655 |
| 97 | 1240 |
| 98 | 2510 |
| 99 | 560 |

In certain embodiments, the compounds demonstrate an EC50 of <50 μM. In certain embodiments, the compounds demonstrate an EC50 of <30 μM. In certain embodiments, the compounds demonstrate an EC50 of <10 μM. In certain embodiments, the compounds demonstrate an EC50 of <1 μM.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting Examples.

Example 1

Preparation of tert-butoxy-[7-chloro-5-(4-chlorophenyl)-2-methyl-quinolin-6-yl]-acetic acid (5L)

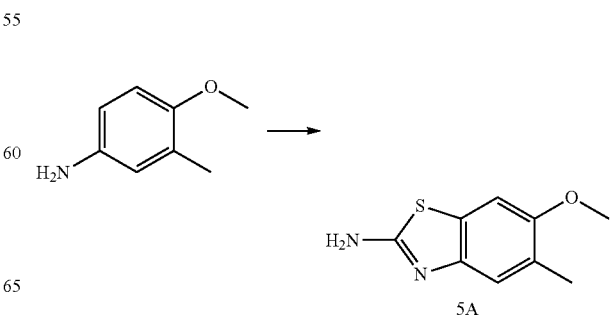

5A

-continued

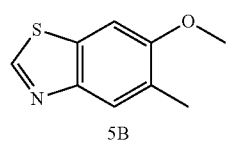
5B

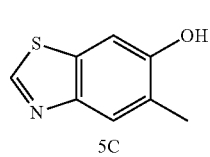
5C → 5D

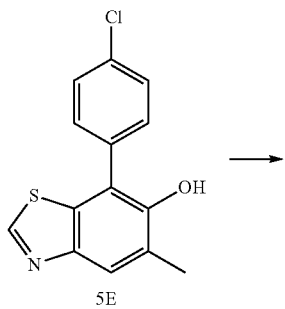
5E

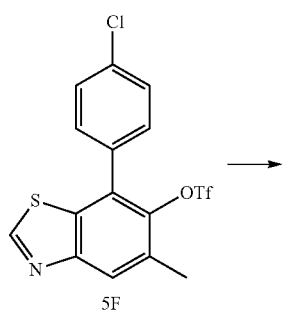
5F

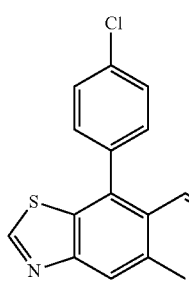
5G

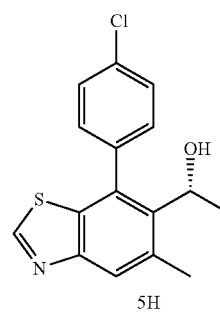
5H

-continued

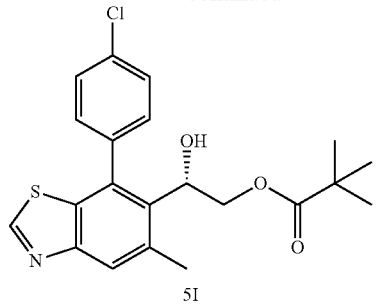
5I

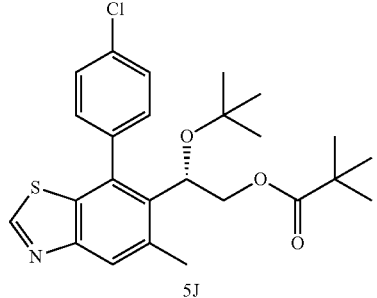
5J

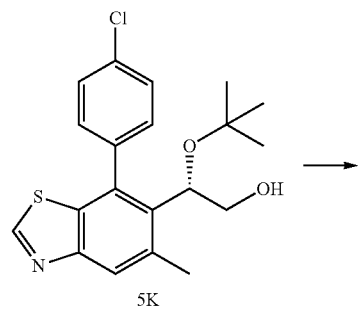
5K

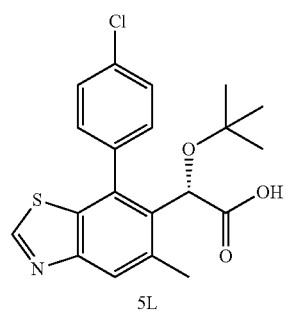
5L

(S)-2-tert-butoxy-2-(7-(4-chlorophenyl)-5-methyl-benzo[d]thiazol-6-yl)acetic acid (5L)

A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% $H_2O$) to a volume of 114 mL. This stock solution (0.090 mL) was added to a solution of (S)-2-tert-butoxy-2-(7-(4-chlorophenyl)-5-methylbenzo[d]thiazol-6-yl)ethanol (5K) (5 mg, 0.013 mmol) in wet acetonitrile (1.0 mL, 0.75% H2O) at 0° C. Reaction mixture was stirred for 0.5 hour at 0 OC. Then more stock solution (0.2 ml) was added and the reaction mixture was stirred for 1 h at 0° C. The reaction mixture was filtered and purified by reverse phase HPLC (Gemini, 10 to 95% ACN/H2O+ 0.1% TFA). Product lyophilized to give a white powder. $^1$H-NMR: 300 MHz, ($CD_3OD$) δ: 9.06 (s, 1H), 7.78 (s, 1H), 7.57-7.42 (m, 4H), 5.16 (s, 1H), 2.52 (s, 3H), 0.86 (s, 9H). LCMS-ESI$^+$: calc'd for $C_{20}H_{20}ClNO_3S$: 390.0 (M+H$^+$). Found: 390.1 (M+H$^+$).

Preparation of (S)-2-tert-butoxy-2-(7-(4-chlorophenyl)-5-methylbenzo[d]thiazol-6-yl)ethanol (5K)

Step 1

Preparation of 6-methoxy-5-methylbenzo[d]thiazol-2-amine (5A)

To a solution of 4-methoxy-3-methylbenzenamine (1.05 g, 7.66 mmol) in acetic acid (30 ml) at 0° C. as added KSCN with heavy stirring. The reaction mixture was then stirred at room temperature for 45 min. The reaction was cooled to 0 OC and bromine was added dropwise. The reaction was stirred at room temperature overnight. The precipitate was collected, washed by acetic acid, dichloromethane, minimal water and dried under high vacuum to give the product as brown yellow solid. LCMS-ESI$^+$: calc'd for $C_9H_{10}N_2OS$: 195.0 (M+H$^+$). Found: 195.1 (M+H$^+$).

Step 2

Preparation of 6-methoxy-5-methylbenzo[d]thiazole (5B)

To a solution of 6-methoxy-5-methylbenzo[d]thiazol-2-amine (5A) (1.24 g, 6.42 mmol) in $H_3PO_4$ (5 mL) at 0° C., was added $NaNO_2$ (2.2 g, 32 mmol) in minimal amount of water. The reaction mixture was stirred at 0° C. for 20 min. The reaction mixture was then transferred to ice-cold hypophosphorous acid (50%, 5 ml) and slowly warmed to room temperature and stirred at room temperature until gas evolution ceases. Solid $Na_2CO_3$ was added to neutralize the reaction and the mixture was extracted by ethyl acetate. The organic phase was dried over $MgSO_4$, filtered, concentrated and purified by silica gel column (0-100% ethyl acetate/hexanes). LCMS-ESI$^+$: calc'd for $C_9H_9NOS$: 180.0 (M+H$^+$). Found: 180.1 (M+H$^+$).

Step 3

Preparation of 5-methylbenzo[d]thiazol-6-ol (5C)

To a suspension of 6-methoxy-5-methylbenzo[d]thiazole (5B) (160 mg, 0.89 mmol) in dichloromethane (5 mL) was added boron tribromide (1 M in dichlormethane, 1.8 ml) at 0° C. The reaction mixture was stirred at 0° C. for 2 h. The reaction was quenched by adding a saturated $NaHCO_3$ solution, extracted with dichlormethane and trace MeOH. The organic layer was dried over $MgSO_4$, filtered, concentrated and purified by silica gel column (0-100% Ethyl acetate/hexanes). LCMS-ESI$^+$: calc'd for $C_8H_7NOS$: 166.0 (M+H$^+$). Found: 166.2 (M+H$^+$).

Step 4

Preparation of 7-bromo-5-methylbenzo[d]thiazol-6-ol (5D)

To a suspension of 5-methylbenzo[d]thiazol-6-ol (5C) (140 mg, 0.84 mmol) in acetic acid (5 ml), was added bromine (40 μL) slowly. The reaction mixture was stirred at room temperature for 1 h. The precipitate was collected, washed with acetic acid, water and dried under high vacuum. LCMS-ESI$^+$: calc'd for $C_8H_6BrNOS$: 244.0 (M+H$^+$). Found: 244.1 (M+H$^+$).

Step 5

Preparation of 7-(4-chlorophenyl)-5-methylbenzo[d]thiazol-6-ol (5E)

The reaction mixture of 7-bromo-5-methylbenzo[d]thiazol-6-ol (5D) (90 mg, 0.37 mmol), 4-chlorophenyl boronic acid (86 mg, 0.55 mmol), Pd(PPh$_3$)$_4$ (40 mg, 0.037 mmol), $K_2CO_3$ (153 mg, 1.11 mmol) in 1,2-dimethoxyethane (1 ml)/$H_2O$ (0.5 ml) was heated at 110° C. in the microwave for 10 min. Then the reaction mixture was diluted with water, extracted with ethyl acetate. The organic layer was dried over $MgSO_4$, filtered, concentrated and purified by silica gel column (0-100/% ethyl acetate/hexanes). LCMS-ESI$^+$: calc'd for $C_{14}H_{10}ClNOS$: 276.0 (M+H$^+$). Found: 276.2 (M+H$^+$).

Step 6

Preparation of 7-(4-chlorophenyl)-5-methyl-6-vinylbenzo[d]thiazole (5G)

To a solution of 7-(4-chlorophenyl)-5-methylbenzo[d]thiazol-6-ol (5E) (107 mg, 0.39 mmol) in dichloromethane (3 mL)/pyridine (1 mL) at 0 OC, was added trifluoromethanesulfonyl acid anhydride (130 μL, 0.80 mmol). The reaction mixture was stirred at 0° C. for 1 h. Then the reaction was quenched by adding saturated $NaHCO_3$ solution, extracted by ethyl ecetate. The organic layer was dried over $MgSO_4$, filtered, concentrated to give 7-(4-chlorophenyl)-5-methylbenzo[d]thiazol-6-yl trifluoromethanesulfonate (5F) which was used in next step without purification.

7-(4-chlorophenyl)-5-methylbenzo[d]thiazol-6-yl trifluoromethanesulfonate (5F) from above reaction was dissolved in DMF (3 ml). Tributylvinyltin (130 μL), PdCl$_2$(PPh$_3$)$_2$ (27 mg, 0.039 mmol) and LiCl (49 mg, 1.17 mmol) were added. The reaction mixture was stirred at 120° C. in microwave for 30 min. The reaction mixture was diluted by ethyl acetate, washed with saturated $NaHCO_3$ solution and extracted with ethyl acetate. The organic layer was dried over $MgSO_4$, filtered, concentrated and purified by silica gel column (0-50% ethyl acetate/hexanes). LCMS-ESI$^+$: calc'd for $C_{16}H_{20}ClNS$: 286.0 (M+H$^+$). Found: 286.1 (M+H$^+$).

Step 7

Preparation of (S)-1-(7-(4-chlorophenyl)-5-methylbenzo[d]thiazol-6-yl)ethane-1,2-diol (5H)

A biphasic mixture of AD mix-α (1.5 g) in tert-butanol (5 mL)/$H_2O$ (5 mL) was cooled to 0° C. and 7-(4-chlorophenyl)-5-methyl-6-vinylbenzo[d]thiazole (5G) (0.050 g, 0.175 mmol) was added. Reaction mixture was stirred overnight at 0° C. Sodium sulfite (1.5 g) was added at 0° C., then warmed to room temperature and stirred for 30 min to give a white mixture. Mixture was diluted with ethyl ecetate and $H_2O$. Extracted with ethyl ecetate (3×) and combined organic layer was dried (MgSO$_4$), concentrated and purified by flash column chromatography (silica gel, 0 to 100% ethyl acetate/hexanes) to give the product.

LCMS-ESI$^+$: calc'd for $C_{16}H_{14}ClNO_2S$: 320.0 (M+H$^+$). Found: 320.1 (M+H$^+$).

Step 8

Preparation of (S)-2-(7-(4-chlorophenyl)-5-methyl-benzo[d]thiazol-6-yl)-2-hydroxyethyl pivalate (5I)

To a solution of (S)-1-(7-(4-chlorophenyl)-5-methylbenzo[d]thiazol-6-yl)ethane-1,2-diol (5H) (0.018 g, 0.056 mmol) in pyridine (0.5 mL)/dichoromethane (1 mL) was added trimethylacetyl chloride (0.010 mL, 0.081 mmol). Reaction mixture was stirred for 1 h at room temperature and additional trimethylacetyl chloride (0.020 ml 0.081 mmol) was added and left it overnight at room temperature. More trimethylacetyl chloride (0.030 ml, 0.242 mmol) was added to the mixture and stirred at room temperature for 30 min. Reaction mixture was diluted with ethyl acetate. Organic layer was washed with saturated sodium bicarbonate solution, dried (MgSO$_4$), concentrated and purified by flash column chromatography (silica gel, 0 to 50% ethyl acetate/hexanes). LCMS-ESI$^+$: calc'd for $C_{21}H_{22}ClNO_3S$: 404.1 (M+H$^+$). Found: 404.1 (M+H$^+$).

Step 9

Preparation of (S)-2-tert-butoxy-2-(7-(4-chlorophenyl)-5-methylbenzo[d]thiazol-6-yl)ethyl pivalate (5J)

A solution of (S)-2-(7-(4-chlorophenyl)-S-methylbenzo[d]thiazol-6-yl)-2-hydroxyethyl pivalate (5I) (0.016 g, 0.040 mmol) and perchloric acid, 70% (6 µl, 0.1 mmol) in tert-butyl acetate (1 mL) was stirred at room temperature for 2 h. Reaction mixture was quenched with solid sodium bicarbonate (0.05 g) for 1 h. Saturated sodium bicarbonate solution was added and extracted with ethyl acetate (3×). The combined organic layer was dried (MgSO$_4$), concentrated and purified by flash column chromatography (silica gel, 0 to 50% ethyl acetate/hexanes). LCMS-ESI$^+$: calc'd for $C_{25}H_{30}ClNO_3S$: 460.2 (M+H$^+$). Found: 460.2 (M+H$^+$).

Step 10

Preparation of (S)-2-tert-butoxy-2-(7-(4-chlorophenyl)-5-methylbenzo[d]thiazol-6-yl)ethanol (5K)

To a solution of (S)-2-tert-butoxy-2-(7-(4-chlorophenyl)-5-methylbenzo[d]thiazol-6-yl)ethyl pivalate (5J) (8 mg, 0.0174 mmol) in MeOH (0.5 mL) and THF (1 mL) was added sodium hydroxide (2 M, 0.1 mL, 0.2 mmol) and the reaction mixture was stirred at room temperature overnight. Reaction mixture diluted with ethyl acetate and washed with saturated sodium bicarbonate solution. Aqueous layer back-extracted with ethyl acetate and combined organic layer was dried (MgSO$_4$), concentrated and purified by flash column chromatography (silica gel, 0 to 50% ethyl acetate/hexanes). LCMS-ESI$^+$: calc'd for $C_{20}H_{22}ClNO_2S$: 376.1 (M+H$^+$). Found: 376.1 (M+H$^+$).

Example 2

Preparation of 2-cyclopropyl-6-methoxy-5-methylbenzo[d]thiazole (6B)

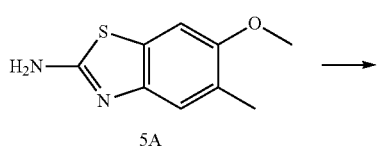

5A

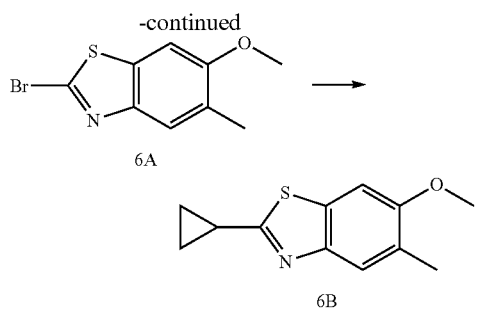

Step 1

To a solution of 2-bromo-6-methoxy-5-methylbenzo[d]thiazole (6A) (720 mg, 2.8 mmol) in dioxane (10 ml), was added cyclopropyl boronic acid (722 mg, 8.4 mmol), potassium phosphate (2.3 g, 10.9 mmol), PdCl$_2$dppf (294 mg, 0.40 mmol). The mixture was reacted at 100° C. overnight. The reaction mixture was cooled to room temperature, washed with water, extracted with EtOAc. The organic phase was combined, dried over MgSO$_4$, filtered, concentrated and purified by silica gel column, eluting by 0-50% EtOAc in hexanes. LCMS-ESI$^+$: calc'd for $C_{12}H_{13}NOS$: 220.1 (M+H$^+$). Found: 220.2 (M+H$^+$).

Step 2

Preparation of (2-bromo-6-methoxy-5-methylbenzo[d]thiazole (6A)

To a solution of t-butylnitrite (5.17 ml, 43.5 mmol) in acetonitrile (50 ml) was added copper (II) bromide (7.2 g, 32.2 mmol) slowly. The reaction mixture was stirred at room temperature for half hour. Then the reaction mixture was put to a 60° C. oil bath and 6-methoxy-5-methylbenzo[d]thiazol-2-amine (5A) (4.2 g, 21.76 mmol) was added slowly. The reaction mixture was stirred at 60° C. for 1 h. The reaction was cooled to room temperature, washed with water and extracted with EtOAc. The organic phase was combined, dried over MgSO$_4$, filtered, concentrated and purified by silica gel column, eluting by 0-50% EtOAc in hexanes. LCMS-ESI$^+$: calc'd for $C_9H_8BrNOS$: 257.9 (M+H$^+$). Found: 258.0 (M+H$^+$).

Example 3

Preparation of (S)-2-tert-butoxy-2-(7-(4-chlorophenyl)-2,5-dimethylbenzo[d]thiazol-6-yl)acetic acid (7)

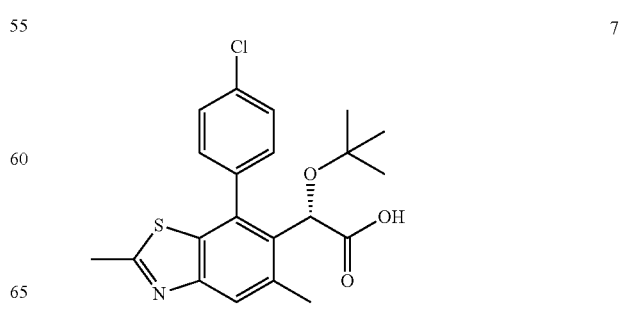

7

Compound 7 was synthesized from compound 6A according to the procedure used to prepare compound 6B (except that trimethylboxine was used instead of cyclopropyl boronic acid) followed by the procedures to convert compound 5B to compound 5L as outlined in Example 1. $^1$H-NMR 400 MHz, (CD$_3$OD) δ: 7.69 (s, 1H), 7.65-7.51 (m, 4H), 5.22 (s, 1H), 2.76 (s, 3H), 2.57 (s, 3H), 0.94 (s, 9H). LCMS-ESI$^+$: calc'd for C$_{21}$H$_{18}$ClNO$_3$; 404.1 (M+H$^+$). Found: 404.1 (M+H$^+$).

Example 4

Preparation of (S)-2-tert-butoxy-2-(7-(4-chlorophenyl)-2-isobutyl-5-methylbenzo[d]thiazol-6-yl)acetic acid (8J) and (S)-2-tert-butoxy-2-(2-isobutyl-5-methyl-7-phenylbenzo[d]thiazol-6-yl)acetic acid (8K)

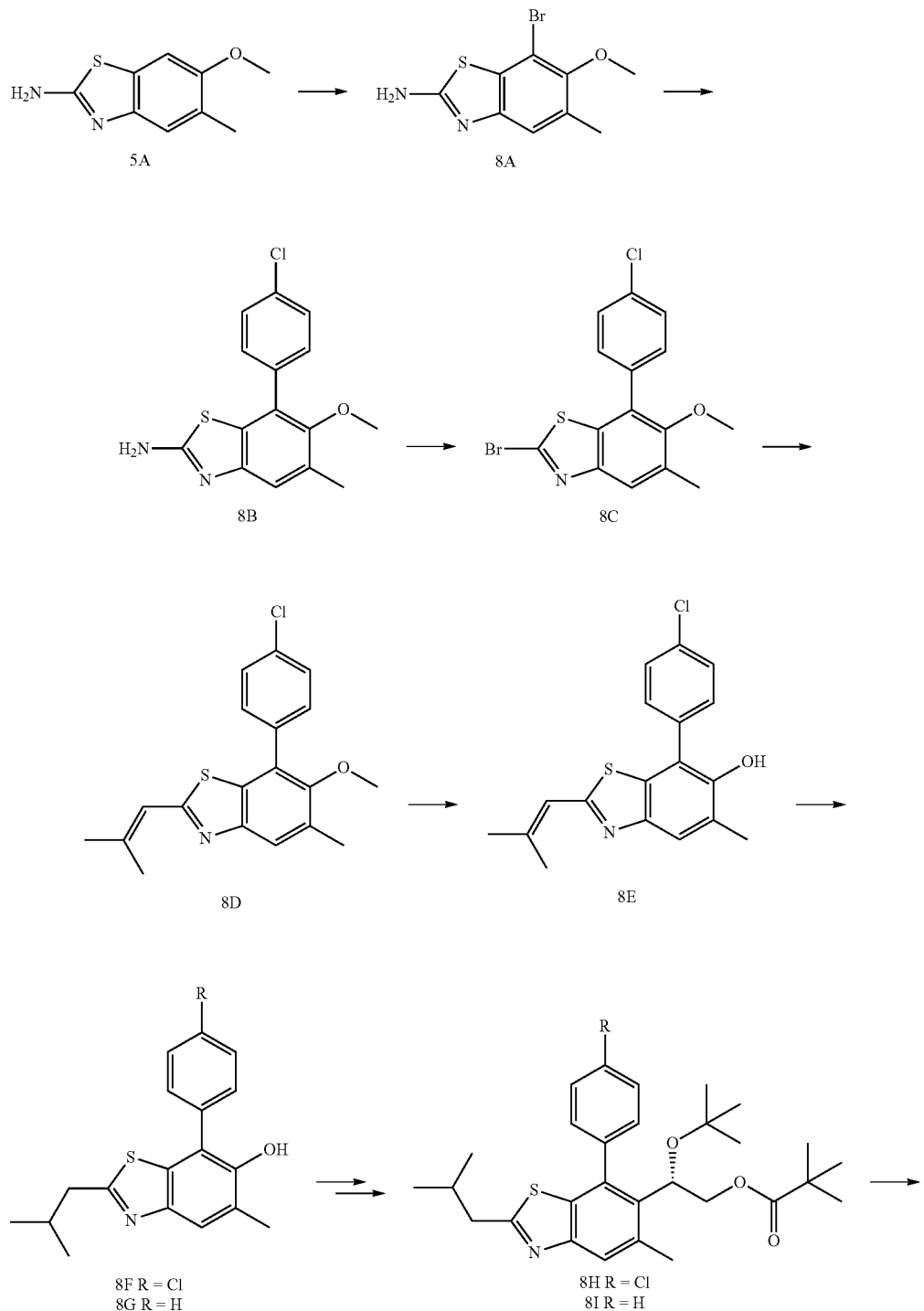

-continued

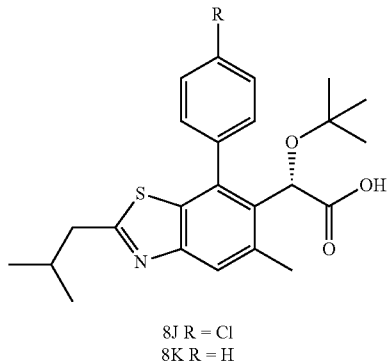

8J R = Cl
8K R = H

The mixture of 7-(4-chlorophenyl)-5-methyl-2-(2-methylprop-1-enyl)benzo[d]thiazol-6-ol (8E) (56 mg, 0.13 mmol), Pd/C (200 mg) in EtOH (5 ml) and EtOAc (5 ml) was stirred at room temperature under an atmosphere of $H_2$ for 30 mini, which gave a mixture of 7-(4-chlorphenyl)-2-isobutyl-5-methylbenzo[d]thiazol-6-ol (8F) and 2-isobutyl-5-methyl-7-phenylbenzo[d]thiazol-6-ol (8G). The reaction mixture was filtered over celite, concentrated and taken on to next step without purification.

The mixture was converted to a mixture of compound 8J and compound 8K by the same steps used to convert compound 5E to compound 5L as outlined in Example 1. The mixture of compounds 8J and 8K were separated by reverse phase HPLC to provide the pure compounds.

Compound 8J: $^1$H-NMR: 400 MHz, (CD$_3$OD) δ: 7.72 (s, 1H), 7.64-7.50 (m, 4H), 5.22 (s, 1H), 2.92 (d, J=3.6 Hz, 2H), 2.58 (s, 3H), 2.17-2.13 (m, 1H), 1.01-0.99 (m, 6H), 0.95 (s, 9H).

LCMS-ESI$^+$: calc'd for $C_{21}H_{18}ClNO_3$: 446.1 (M+H$^+$). Found: 446.2 (M+H$^+$).

Compound 8K: $^1$H-NMR: 400 MHz, (CD$_3$OD) δ: 7.70 (s, 1H), 7.64-7.50 (m, 5H), 5.29 (s, 1H), 2.92 (d, J=3.6 Hz, 2H), 2.57 (d, J=0.4 Hz, 3H), 2.17-2.13 (m, 1H), 1.01-0.99 (m, 6H), 0.92 (s, 9H). LCMS-ESI$^+$: calc'd for $C_{21}H_{18}ClNO_3$: 412.1 (M+H$^+$). Found: 412.2 (M+H$^+$).

Preparation of 7-(4-chlorophenyl)-5-methyl-2-(2-methylprop-1-enyl)benzo[d]thiazol-6-ol (8E)

Step 1

Preparation of 7-bromo-6-methoxy-5-methylbenzo[d]thiazol-2-amine (8A)

To a solution of 6-methoxy-5-methylbenzo[d]thiazol-2-amine (5A) (1.0 g, 5.15 mmol) in $H_2SO_4$ at 0° C., was added NBS (550 mg, 3.07 mmol). The reaction mixture was stirred at 0° C. for 2 h. Then the reaction mixture was poured to ice-water, neutralized by 50% KOH solution to pH about 3. The precipitation was collected, washed by water and dried over high vacuum. LCMS-ESI$^+$: calc'd for $C_9H_9BrN_2OS$: 273.0 (M+H$^+$). Found: 273.0 (M+H$^+$).

Step 2

Preparation of 7-(4-chlorophenyl)-6-methoxy-5-methylbenzo[d]thiazol-2-amine (8B)

The mixture of 7-bromo-6-methoxy-5-methylbenzo[d]thiazol-2-amine (8A) (1.72 g, 6.32 mmol), 4-chlorophenyl boronic acid (1.2 g, 7.67 mmol), $K_2CO_3$ (2.63 g, 18.9 mmol), Pd(PPh$_3$)$_4$ (364 mg, 0.315 mmol) in DME (8 ml) and $H_2O$ (4 ml) was reacted in microwave at 110° C. for 1 h. Then 4-chlorophenyl boronic acid (100 mg, 0.64 mmol), Pd(PPh$_3$)$_4$ (100 mg, 0.086 mmol) were added and reacted in microwave at 110° C. for 0.5 h and 120° C. for 20 min. The reaction mixture was washed by water, extracted by EtOAc. The organic phase was combined, dried over MgSO4, filtered, concentrated down and purified by silica gel column, eluting by 0-100% EtOAc in hexanes. LCMS-ESI$^+$: calc'd for $C_{15}H_{13}ClN_2OS$: 305.0 (M+H$^+$). Found: 305.1 (M+H$^+$).

Step 3

Preparation of 2-bromo-7-(4-chlorophenyl)-6-methoxy-5-methylbenzo[d]thiazole (8C)

Compound 8C was synthesized from 8B according to the procedure used to prepare compound 6A of Example 2. LCMS-ESI$^+$: calc'd for $C_{15}H_{11}BrClNOS$: 367.9 (M+H$^+$). Found: 368.0 (M+H$^+$).

Step 4

Preparation of 7-(4-chlorophenyl)-6-methoxy-5-methyl-2-(2-methylprop-1-enyl)benzo[d]thiazole (8D)

The mixture of 2-bromo-7-(4-chlorophenyl)-6-methoxy-5-methylbenzo[d]thiazole (8C) (0.153 g, 0.417 mmol), 4,4,5,5-tetramethyl-2-(2-methylprop-1-enyl)-1,3,2-dioxaborolane (0.256 ml, 1.24 mmol), $K_3PO_4$ (0.35 g, 1.66 mmol), PdCl$_2$(dppf) (45 mg, 0.062 mmol) in DME (1 mil) and $H_2O$ (0.5 ml) was reacted in microwave at 120° C. for 0.5 h. The reaction mixture was washed by water, extracted by EtOAc. The organic phase was combined, dried over MgSO4, filtered, concentrated down and purified by silica gel column, eluting by 0-100% EtOAc in hexanes. LCMS-ESI$^+$: calc'd for $C_{19}H_{18}ClNOS$: 344.1 (M+H$^+$). Found: 344.1 (M+H$^+$).

Step 5

Preparation of 7-(4-chlorophenyl)-5-methyl-2-(2-methylprop-1-enyl)benzo[d]thiazol-6-ol (8E)

Compound 8E was synthesized from compound 8D according to the procedure used to prepare compound 5C of Example 1.

LCMS-ESI$^+$: calc'd for C$_{19}$H$_{16}$ClNOS: 330.0 (M+H$^+$). Found: 330.2 (M+H$^+$).

Example 5

Preparation of Compound (9)

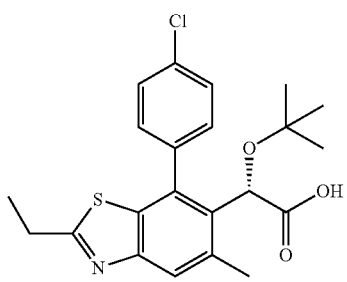

9

Compound 9 was synthesized from 8C by the method to used convert compound 8C to compound 8J as outlined in Example 4, except that tributylvinyltin was used in first the cross coupling reaction according to the procedure used to prepare compound 5G of Example 1. $^1$H-NMR: 400 MHz, (CD$_3$OD) δ: 7.71 (s, 1H), 7.65-7.51 (m, 4H), 5.22 (s, 1H), 3.11-3.07 (m, 2H), 2.58 (s, 3H), 1.40 (t, J=7.6 Hz, 3H), 0.94 (s, 9H). LCMS-ESI$^+$: calc'd for C$_{21}$H$_{18}$ClNO$_3$: 418.1 (M+H$^+$). Found: 418.1 (M+H$^+$).

Example 6

Preparation of Compound (10)

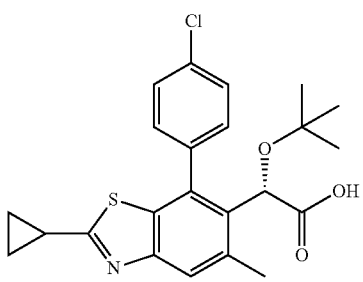

10

Compound 10 was synthesized from compound 8C by the method used to convert compound 8C to compound 8J as outlined in Example 4, except that cyclopropylboronic acid, was used in first the cross coupling reaction. $^1$H-NMR: 400 MHz, (CD$_3$OD) δ: 7.63 (s, 1H), 7.61-7.49 (m, 4H), 5.20 (s, 1H), 2.55 (s, 3H), 2.41-2.36 (m, 1H), 1.26-1.22 (m, 2H), 1.14-1.10 (m, 2H), 0.94 (s, 9H).

LCMS-ESI$^+$: calc'd for C$_{21}$H$_{18}$ClNO$_3$: 430.1 (M+H$^+$). Found: 430.1 (M+H$^+$).

Example 7

Preparation of Compound 12

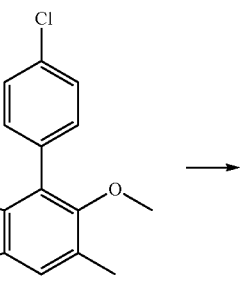

8C

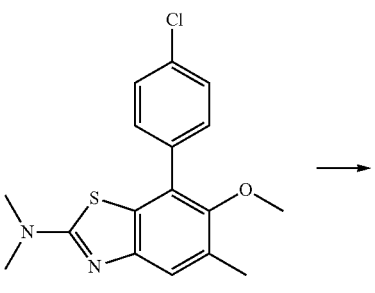

11

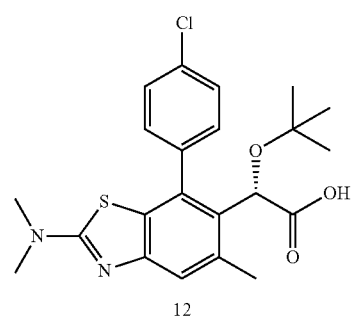

12

Compound 12 was synthesized from compound 11 according to the procedure used to prepare compound 8J from compound 8D as outlined in Example 4. $^1$H-NMR: 400 MHz, (CD$_3$OD) δ: 7.62-7.49 (m, 4H), 7.34 (s, 1H), 5.15 (s, 1H), 3.27 (s, 6H), 2.53 (s, 3H), 0.94 (s, 9H). LCMS-ESI$^+$: calc'd for C$_{21}$H$_{18}$ClNO$_3$: 433.1 (M+H$^+$). Found: 433.1 (M+H$^+$).

Preparation of 6-methoxy-N,N,5-trimethylbenzo[d]thiazol-2-amine (11)

To a solution of 2-bromo-7-(4-chlorophenyl)-6-methoxy-5-methylbenzo[d]thiazole (8C) (135 mg, 0.37 mmol) in DMF (2 ml), was added dimethylamine in THF (2M, 0.46 ml, 0.92 mmol). The reaction mixture was stirred at 80° C. After the reaction finished, the reaction was cooled and concentrated. The residue was purified by silica gel column, eluting by 0-100%/EtOAc in hexanes. LCMS-ESI$^+$: calc'd for C$_{17}$H$_{17}$ClN$_2$OS: 333.1 (M+H$^+$). Found: 333.1 (M+H$^+$).

Example 8

Preparation of Compound 14

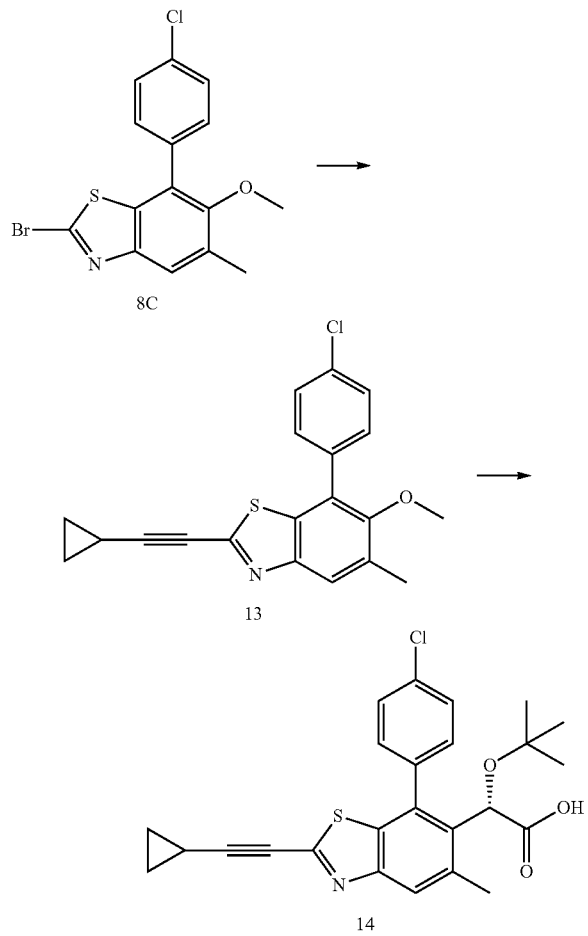

Compound 14 was synthesized from compound 13 according to the procedure used to prepare compound 8J from compound 8D as outlined in Example 4. $^1$H-NMR: 400 MHz, (CD$_3$OD) δ: 7.74 (s, 1H), 7.62-7.50 (m, 4H), 5.22 (s, 1H), 2.58 (s, 3H), 1.61-1.59 (m, 1H), 1.03-1.01 (m, 2H), 0.94 (s, 1H), 0.91-0.88 (m, 2H). LCMS-ESI$^+$: calc'd for C$_{21}$H$_{18}$ClNO$_3$: 454.1 (M+H$^+$). Found: 454.1 (M+H$^+$).

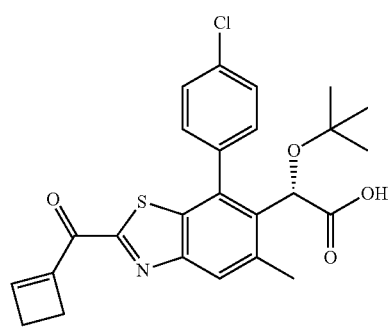

Compound 14b was obtained as a side-product of Compound 14.

$^1$H-NMR 400 MHz, (CD$_3$OD) δ: 7.99 (s, 1H), 7.64-7.55 (m, 5H), 5.26 (s, 1H), 2.91 (t, J=3 Hz, 2H), 2.70 (m, 2H), 2.62 (s, 3H), 0.95 (s, 9H).

LCMS-ESI$^+$: calc'd for C$_{25}$H$_{24}$ClNO$_4$S: 470.1 (M+H$^+$). Found: 470.1 (M+H$^+$).

Preparation of 2-(2-cyclopropylethynyl)-6-methoxy-5-methylbenzo[d]thiazole (13)

To a solution of 2-bromo-7-(4-chlorophenyl)-6-methoxy-5-methylbenzo[d]thiazole (5C) (188 mg, 0.512 mmol) in THF (3 ml), was added ethynylcyclopropane (0.09 ml, 1.2 mmol), CuI (10 mg, 0.052 mmol), Et$_3$N (0.36 ml, 2.58 mmol) and PdCl$_2$(dppf) (19 mg, 0.026 mmol). The reaction mixture was stirred at 60° C. for 2 hs. The reaction mixture was washed by water, extracted by EtOAc. The organic phase was combined, dried over MgSO$_4$, filtered, concentrated and purified by silica gel column, eluting by 0-50% EtOAc in hexanes.

LCMS-ESI$^+$: calc'd for C$_{20}$H$_{16}$ClNOS: 354.0 (M+H$^+$). Found: 354.1 (M+H$^+$).

Example 9

Preparation of (S)-2-tert-butoxy-2-((S)-2-cyclopropyl-7-(2,3-dihydropyrano[4,3,2-de]quinolin-7-yl)-5-methylbenzo[d]thiazol-6-yl)acetic acid (21) and (S)-2-tert-butoxy-2-((R)-2-cyclopropyl-7-(2,3-dihydropyrano[4,3,2-de]quinolin-7-yl)-5-methylbenzo[d]thiazol-6-yl)acetic acid (22)

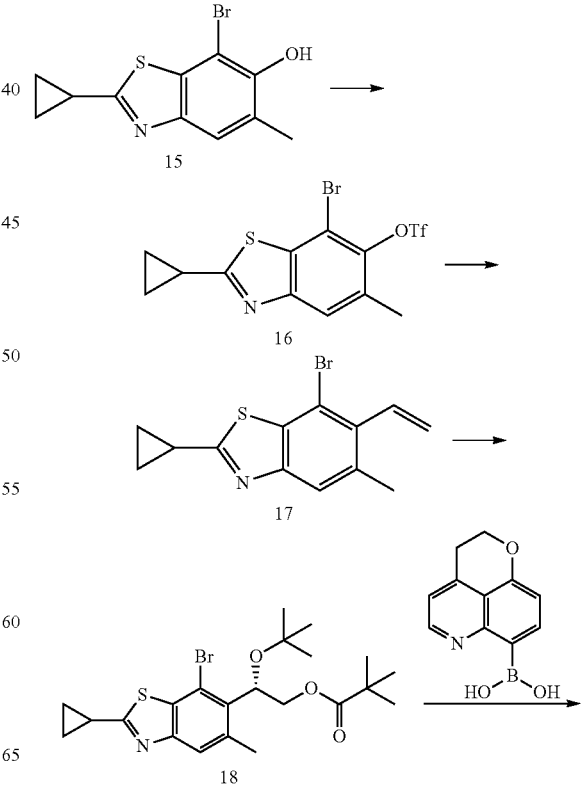

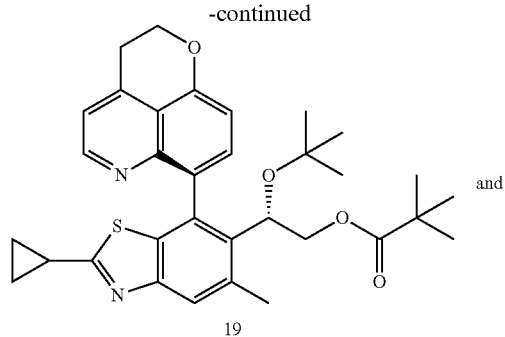

19

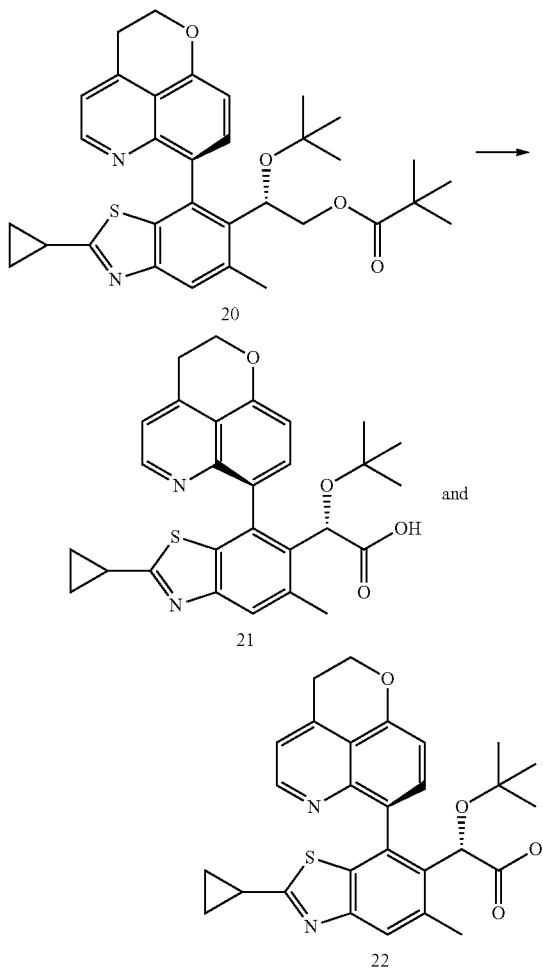

20

21

22

Compounds 21 and 22 were prepared from compounds 19 and 20 by the method to used convert compound 5J to compound 5L as outlined in Example 1.

Compound 21: $^1$H-NMR: 400 MHz, (CD$_3$OD) δ: 8.77 (d, J=3 Hz, 1H), 7.87-7.80 (m, 3H), 7.40 (d, J=4.2 Hz, 1H), 5.21 (s, 1H), 4.72-4.68 (m, 2H), 3.64 (t, J=6 Hz, 2H), 2.73 (s, 3H), 2.35-2.33 (m, 1H), 1.23-1.20 (min, 2H), 1.10-1.07 (m, 2H), 0.90 (s, 9H). LCMS-ESI$^+$: calc'd for C$_{21}$H$_{18}$ClNO$_3$: 489.1 (M+H$^+$). Found: 489.1 (M+H$^+$).

Compound 22: $^1$H-NMR: 400 MHz, (CD$_3$OD) δ: 8.66 (d, J=2.6 Hz 1H), 8.13 (d, J=4 Hz, 1H), 7.82 (s, 1H), 7.66 (d, J=2.8 Hz, 1H), 7.39 (d, J=4 Hz, 1H), 2.52 (s, 1H), 4.66 (t, J=6 Hz, 2H), 3.57 (t, J=5.8 Hz, 2H), 2.68 (s, 3H), 2.37-2.31 (m, 1H), 1.22-1.19 (m, 2H), 1.08-1.06 (m, 2H), 0.89 (s, 9H).

LCMS-ESI$^+$: calc'd for C$_{21}$H$_{18}$ClNO$_3$: 489.1 (M+H$^+$). Found: 489.1 (M+H$^+$).

Preparation of Compound 19 and Compound 20

Step 1

Preparation of 7-bromo-2-cyclopropyl-5-methylbenzo[d]thiazol-6-ol (15)

Compound 15 was prepared from compound 6B by the method used to prepare compound 5D from compound 5B as outlined in Example 1. LCMS-ESI$^+$: calc'd for C$_{141}$H$_{10}$BrNOS: 284.0 (M+H$^+$). Found: 284.2 (M+H$^+$).

Step 2

Preparation of 7-bromo-2-cyclopropyl-5-methylbenzo[d]thiazol-6-yl trifluoromethanesulfonate (16)

To a solution of 7-bromo-2-cyclopropyl-5-methylbenzo[d]thiazol-6-ol (15) (500 mg, 1.766 mmol) in DCM (8 ml) and 2,6-lutine (2 ml) at −78° C. was slowly added trifluoromethanesulfonic anhydride (0.59 ml, 3.51 mmol). The temperature was allowed to slowly warm to 0° C. over 2 h. The reaction mixture was washed by saturated NaHCO$_3$ solution, extracted with DCM. The organic phase was combined, dry over MgSO4, filtered, concentrated and purified by silica gel column, eluting by 0-50% EtOAc in hexanes. LCMS-ESI$^+$: calc'd for C$_{12}$H$_9$BrF$_3$NO$_3$S$_2$: 415.9 (M+H$^+$). Found: 415.9 (M+H$^+$).

Step 3

Preparation of 7-bromo-2-cyclopropyl-5-methyl-6-vinylbenzo[d]thiazole (17)

To a solution of 7-bromo-2-cyclopropyl-5-methylbenzo[d]thiazol-6-yl trifluoromethanesulfonate (16) (410 mg, 0.988 mmol) in DMF (4 ml), was added tributylvinyltin (0.43 ml, 1.47 mmol), LiCl (125 mg, 2.94 mmol) and PdCl$_2$(PPh$_3$)$_2$ (70 mg, 0.096 mmol). The reaction mixture was reacted at 80° C. overnight. The reaction was cooled down, washed by saturated NaHCO$_3$ solution, extracted by EtOAc. The organic phase was combined, dry over MgSO$_4$, filtered, concentrated and purified by silica gel column, eluting by 0-50% EtOAc in hexanes.

LCMS-ESI$^+$: calc'd for C$_{13}$H$_{12}$BrNS: 294.0 (M+H$^+$). Found: 294.1 (M+H$^+$).

Step 4

Preparation of (S)-2-(7-bromo-2-cyclopropyl-5-methylbenzo[d]thiazol-6-yl)-2-tert-butoxyethyl pivalate (18)

Compound 18 was prepared from compound 17 by the method used to convert compound 5G to compound 5J as outlined in Example 1. LCMS-ESI$^+$: calc'd for C$_{22}$H$_{30}$BrN$_2$O$_3$S: 468.1 (M+H$^+$). Found: 468.2 (M+H$^+$).

Step 5

Preparation of the (S)-2-tert-butoxy-2-(2-cyclopropyl-7-(2,3-dihydrpyrano[4,3,2-de]quinolin-7-yl)-5-methylbenzo[d]thiazol-6-yl)ethyl pivalate isomers (19 and 20)

To a solution of (S)-2-(7-bromo-2-cyclopropyl-5-methylbenzo[d]thiazol-6-yl)-2-tert-butoxyethyl pivalate (18) (23 mg, 0.047 mmol) in DMA (2 ml), was added 2,3-dihydro-pyrano[4,3,2-de]quinolin-7-ylboronic acid (25 mg, 0.099 mmol), 2N K$_2$CO$_3$ solution (0.11 ml, 0.22 mmol) and Pd(PPh$_3$)$_4$ (6 mg, 0.005 mmol). The reaction mixture was reacted at 85° C. for 2 hs. The reaction was cooled down, washed by saturated NaHCO$_3$ solution, extracted by EtOAc. The organic phase was combined, dry over MgSO$_4$, filtered, concentrated and purified by silica gel column, eluting by 0-50% EtOAc in hexanes. Two isomers were separated and went through the chemistry sequence as above. LCMS-ESI$^+$: calc'd for C$_{33}$H$_{38}$N$_2$O$_4$S: 559.2 (M+H$^+$). Found: 559.1 (M+H$^+$).

Example 10

Preparation of (S)-2-((S)-2-(azetidin-1-yl)-7-(2,3-dihydropyrano[4,3,2-de]quinolin-7-yl)-5-methyl-benzo[d]thiazol-6-yl)-2-tert-butoxyacetic acid (35) and (S)-2-((R)-2-(azetidin-1-yl)-7-(2,3-dihydropyrano[4,3,2-de]quinolin-7-yl)-5-methylbenzo[d]thiazol-6-yl)-2-tert-butoxyacetic acid (36)

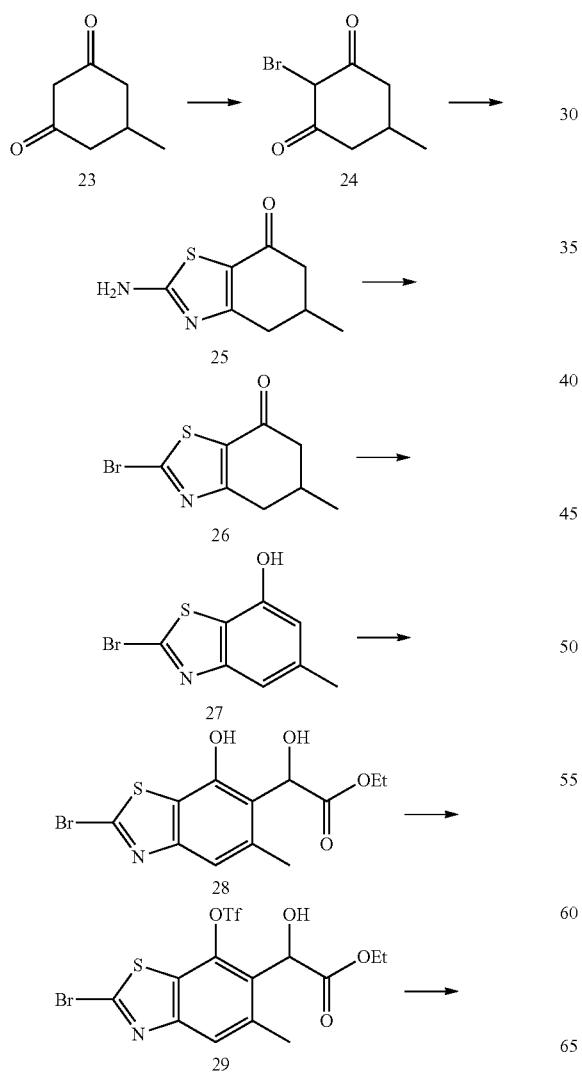

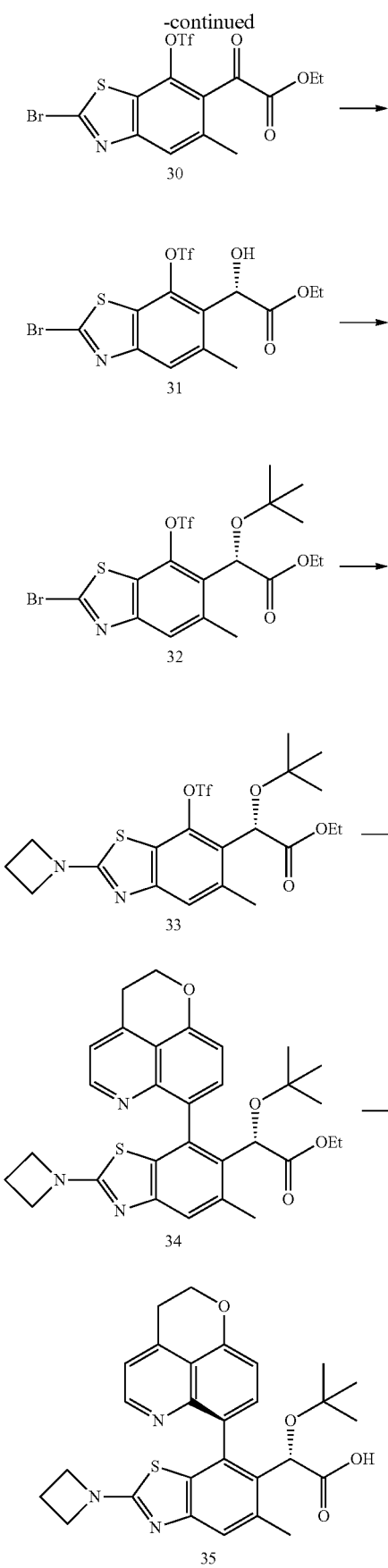

-continued

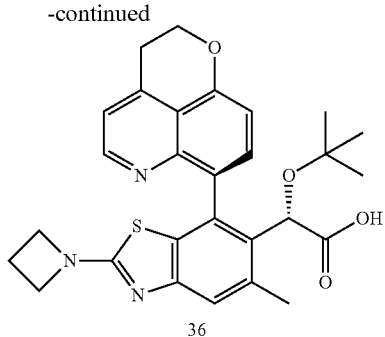

36

To a solution of 34 (23 mg, 0.043 mmol) in THF (1 mL) and MeOH (1 mL) was added a solution of NaOH (2 M, ~400 μL). The reaction mixture was heated at 70° C. for 4 h. The reaction was brought to ~pH 5 with TFA and was then purified by reverse phase HPLC (MeCN/H$_2$O containing 0.1% TFA) to give 6 mg of compound 35 and 10 mg of compound 36.

Compound 35: $^1$H-NMR: 400 MHz, (CD$_3$OD) δ: 8.75 (d, J=2.6 Hz, 1H), 7.80 (d, J=4.0 Hz, 1H), 7.72 (d, J=2.6 Hz, 1H), 7.47 (s, 1H), 7.34 (d, J=4.0 Hz, 1H), 5.13 (s, 1H), 4.67-4.65 (m, 2H), 4.17 (t, J=7.6 Hz, 4H), 3.59-3.58 (m, 2H), 2.66 (s, 3H), 2.52-2.50 (m, 2H), 0.88 (s, 9H). LCMS-ESI$^+$: calc'd for C$_{28}$H$_{29}$N$_3$O$_4$S: 504.2 (M+H$^+$). Found: 504.0 (M+H$^+$).

Compound 36: $^1$H-NMR 400 MHz, (CD$_3$OD) δ: 8.67 (d, J=2.2 Hz, 1H), 8.01 (d, J=4.0 Hz, 1H), 7.49 (d, J=2.6 Hz, 1H), 7.40 (s, 1H), 7.27 (d, J=4.2 Hz, 1H), 5.18 (s, 1), 4.60-4.57 (m, 2H), 4.27 (t, J=7.8 Hz, 4H), 3.48-3.45 (m, 2H), 2.61 (s, 3H), 2.58-2.54 (m, 2H), 0.80 (s, 9H). LCMS-ESI$^+$: calc'd for C$_{28}$H$_{29}$N$_3$O$_4$S: 504.2 (M+H$^+$). Found: 504.1 (M+H$^+$).

Preparation of (2S)-ethyl 2-(2-(azetidin-1-yl)-7-(2,3-dihydropyrano[4,3,2-de]quinolin-7-yl)-5-methyl-benzo[d]thiazol-6-yl)-2-tert-butoxyacetate (34)

Step 1

Preparation of 2-bromo-5-methylcyclohexane-1,3-dione (24)

To a solution of 5-methyl-1,3-cyclohexanedione (23) (45.4 g, 360 mmol) in acetic acid (540 mL) was added bromine (19.4 mL, 378 mmol) over 5 min. After 30 min of stirring (with mechanical stirrer), the reaction mixture was filtered. The solid was left under high vacuum overnight and used in the subsequent step without further purification.

Step 2

Preparation of 2-amino-5-methyl-5,6-dihydrobenzo[d]thiazol-7(4H)-one (25)

To a solution of 24 in acetic acid (540 mL) was added sodium acetate (44.3 g, 540 mmol) and thiourea (28.8 g, 378 mmol). The reaction mixture was stirred with a mechanical stirrer at 100 OC for 3 h. The reaction mixture was partially concentrated in vacuo. EtOAc was added (500 mL). The mixture was made basic with 1 M NaOH, and the layers were separated. The aqueous layer was extracted with EtOAc (2×300 mL). The combined organic layers were dried, filtered, and concentrated in vacuo to give 49.3 g of 25, which was taken on without further purification. LCMS-ESI$^+$: calc'd for C$_8$H$_{11}$N$_2$OS: 183.1 (M+H$^+$). Found: 183.1 (M+H$^+$).

Step 3

Preparation of 2-bromo-5-methyl-5,6-dihydrobenzo[d]thiazol-7(4H)-one (26)

To a solution of 25 (53.9 g, 296 mmol) in MeCN (600 mL) at 0° C., while mechanically stirred), was added copper (II) bromide (79.2 g, 355 mmol) then t-butyl nitrite (46.8 mL, 355 mmol). The reaction mixture was stirred from 0° C. to room temperature over 2 h and was then partially concentrated. EtOAc (400 mL) and a 0.5 M HCl solution were added. The layers were separated, and the organic layer was washed with a brine solution. The combined organic layers were dried, filtered, and concentrated in vacuo. The crude product was adsorbed on ~150 g of silica then run through a plug of silica with 40% EtOAc/hexanes to give 58.3 g of 26. $^1$H-NMR: 400 MHz, (CDCl$_3$) δ: 3.16 (dd, 1H. J=18, 4 Hz), 2.66 (m, 2H), 2.47 (m, 1H), 2.34 (dd, 1H, J=16, 12 Hz), 1.19 (d, 3H, J=7 Hz). LCMS-ESI$^+$: calc'd for C$_8$H$_9$BrNOS: 245.9 (M+H$^+$). Found: 246.1 (M+H$^+$).

Step 4

Preparation of 2-bromo-5-methylbenzo[d]thiazol-7-ol (27)

To a solution of 26 (7.38 g, 30.0 mmol) in CCl$_4$ (90 mL) was added NBS (5.61 g, 31.5 mmol) and dibenzoyl peroxide (727 mg, 3.0 mmol). The reaction was heated at 90° C. in a sealed reaction vessel for about 4 h. Then DBU (6.73 mL, 45.0 mmol) in CH$_2$Cl$_2$ (15 mL) was added. The mixture was heated a reflux for 30 min, then a 1 M HCl solution was added. The layers were separated, and the aqueous layer was extracted with CH$_2$Cl$_2$. The combined organic layers were washed with a brine solution. The organic layer was then dried, filtered, and concentrated in vacuo. The crude product was adsorbed on ~30 g of silica then run through a plug of silica with 40% EtOAc/hexanes to give 5.2 g of 27. $^1$H-NMR: 400 MHz, (CD$_3$OH) δ: 7.25 (s, 1H), 6.69 (s, 1H), 2.40 (s, 3H). LCMS-ESI$^+$: calc'd for C$_8$H$_7$BrNOS: 243.9 (M+H$^+$). Found: 244.1 (M+H$^+$).

Step 5

Preparation of ethyl 2-(2-bromo-7-hydroxy-5-methylbenzo[d]thiazol-6-yl)-2-hydroxyacetate (28)

To a solution of 27 (3.90 g, 16.0 mmol) in CH$_2$Cl$_2$ (80 mL) at 0° C. was added triethylamine (2.45 mL, 16.8 mmol) then a solution of titanium tetrachloride in CH$_2$C$_2$ (1.0 M, 16.8 mL, 16.8 mmol). After 15 min, ethyl glyoxalate (50% in toluene, 3.49 mL, 17.6 mmol) was added. The reaction mixture was stirred for 2 h while warming to room temperature. Water (50 mL) and a saturated solution of potassium sodium tartrate (50 mL) were added. The mixture was stirred vigorously for 2 h. The layers were separated, and the aqueous layer was extracted with CH$_2$Cl$_2$. The combined organic layers were dried, filtered, and concentrated in vacuo. The crude material was purified by column chromatography to give 2.48 g of 28 and recovered ~500 mg of 27. $^1$H-NMR: 400 MHz, (CD$_3$OH) δ: 7.33 (s, 1H), 5.69 (s, 1H), 4.17 (m, 2H), 2.50 (s, 3H), 1.18 (t, 3H, J=7 Hz). LCMS-ESI⁺: calc'd for $C_{12}H_{13}BrNO_4S$: 346.0 (M+H⁺). Found: 346.1 (M+H⁺).

Step 6

Preparation of ethyl 2-(2-bromo-5-methyl-7-(trifluoromethylsulfonyloxy)benzo[d]thiazol-6-yl)-2-hydroxyacetate (29)

To a solution of 28 (2.42 g, 7.00 mmol) in CH₂Cl₂ (30 mL) at ~78 OC was added triethylamine (1.02 mL, 7.70 mmol) followed by trifluoromethanesulfonic anhydride (1.24 mL, 7.35 mmol). After 15 min, saturated NH₄Cl was added. The layers were separated. The organic layer was dried, filtered, and concentrated in vacuo. The crude material was purified by column chromatography to give 2.17 g of 29. ¹H-NMR 400 MHz, (CDCl₃) δ: 7.84 (s, 1H), 5.67 (s, 1H), 4.27 (m, 2H), 2.50 (s, 3H), 1.23 (t, 3H, J=7 Hz). LCMS-ESI⁺: calc'd for $C_{13}H_{12}BrF_3NO_6S_2$: 477.9 (M+H⁺). Found: 478.2 (M+H⁺).

Step 7

Preparation of ethyl 2-(2-bromo-5-methyl-7-(trifluoromethylsulfonyloxy)benzo[d]thiazol-6-yl)-2-oxoacetate (30)

To a solution of 29 (9.85 g, 20.6 mmol) in CH₂Cl₂ (100 mL) was added Dess-Martin periodinane (9.61 g, 22.6 mmol). After 30 min, water (75 mL) and saturated Na₂S₂O₄ solution (75 mL) was added. The mixture was stirred vigorously for 30 min. The layers were separated, and the aqueous layer was extracted with CH₂Cl₂. The combined organic layers were dried, filtered, and concentrated in vacuo. The crude material was purified by column chromatography to give 8.32 g of 30. ¹H-NMR: 400 MHz, (CDCl₃) δ: 7.91 (s, 1H), 4.40 (q, 2H, J=7 Hz), 2.49 (s, 3H), 1.39 (t, 3H, J=7 Hz).
LCMS-ESI⁺: calc'd for $C_{13}H_{10}BrF_3NO_6S_2$: 475.9 (M+H⁺). Found: 476.1 (M+H⁺).

Step 8

Preparation of (S)-ethyl 2-(2-bromo-5-methyl-7-(trifluoromethylsulfonyloxy)benzo[d]thiazol-6-yl)-2-hydroxyacetate (31)

To a solution of 30 (8.30 g, 17.4 mmol) in toluene (70 mL) was added ((R)-2-methyl-CBS-oxazaborolidine (725 mg, 2.61 mmol). The reaction mixture was then cooled to −35 OC and a solution of catecholborane (freshly distilled) (1 M in toluene, 20.9 mL, 20.9 mmol) was added via addition funnel over 30 min. The reaction was stirred for 20 min while warming to −20° C. A 2 M solution of Na₂CO₃ was added (50 mL). The layers were separated, and the organic layer was washed with additional Na₂CO₃ solution (3×25 mL). The organic layer was dried, filtered, and concentrated in vacuo to give 31, which had analytical data to match 29. The compound was taken on to the next step without further purification.

Step 9

Preparation of (S)-ethyl 2-(2-bromo-5-methyl-7-(trifluoromethylaulfonyloxy)benzo[d]thiazol-6-yl)-2-tert-butoxyacetate (32)

To a solution of 31 (~17 mmol) in t-butylacetate (70 mL) was added perchloric acid (1.23 mL, 20.4 mmol). After 3 h, water was added (50 mL). The layers were separated. The organic layer was washed with a saturated solution of NaHCO₃. The organic layer was dried, filtered, and concentrated in vacuo. The crude material was purified by column chromatography (EtOAc/hexanes) to give 7.22 g of 32 and 1.58 g of 31. ¹H-NMR: 400 MHz, (CD₃OH) δ: 7.82 (s, 1H), 5.59 (s, 1H), 4.08-4.25 (m, 2H), 2.55 (s, 3H), 1.20 (s, 9H), 1.16 (t, 3H, J=7 Hz). LCMS-ESI⁺: calc'd for $C_{17}H_{20}BrF_3NO_6S_2$: 534.0 (M+H⁺). Found: 534.1 (M+H⁺).

Step 10

Preparation of (S)-ethyl 2-(2-(azetidin-1-yl)-5-methyl-7-(trifluoromethylsulfonyloxy)benzo[d]thiazol-6-yl)-2-tert-butoxyacetate (33)

To a solution of 32 (50 mg, 0.094 mmol) in THF (1 mL) was added azetidine (20 μL). The reaction mixture was heated at 70° C. for 30 min. A saturated solution of NH₄Cl (3 mL) was added, and the layers were separated. The aqueous layer was extracted with EtOAc. The combined organic layer were dried, filtered, and concentrated in vacuo. The crude material was purified by column chromatography (EtOAc/hexanes) to give 38 mg of 33. LCMS-ESI⁺: calc'd for $C_{20}H_{25}F_3N_2O_6S_2$: 511.1 (M+H⁺). Found. 511.0 (M+H⁺).

Step 11

Preparation of (2S)-ethyl 2-(2-(azetidin-1-yl)-7-(2,3-dihydropyrano[4,3,2-de]quinolin-7-yl)-5-methylbenzo[d]thiazol-6-yl)-2-tert-butoxyacetate (34)

To a solution of 33 (38 mg, 0.075 mmol) in freshly distilled DME (1 mL) was added 2,3-dihydropyrano[4,3,2-de]quinolin-7-ylboronic acid hydrochloride (24 mg, 0.097 mmol), chloro(2-dicyclohexylphosphino-2',6'-dimethoxy-1,1'-biphenyl)[2-(2-aminoethylphenyl)]palladium(II) methyl-t-butylether adduct, [SPhos Palladacycle](5 mg, 0.0075 mmol), and cesium fluoride (46 mg, 0.3 mmmol). The reaction mixture was heated in the microwave at 110° C. for 45 min. A saturated solution of NaHCO₃ (3 mL) was added, and the layers were separated. The aqueous layer was extracted with EtOAc. The combined organic layer were dried, filtered, and concentrated in vacuo. The crude material was purified by column chromatography (EtOAc/hexanes) to give 21 mg of 34.
LCMS-ESI⁺: calc'd for $C_{30}H_{33}NO_{34}S$: 532.2 (M+H⁺). Found: 532.0 (M+H⁺).

Example 11

Preparation (S)-2-tert-butoxy-2-((S)-2-carbamoyl-7-(2,3-dihydropyrano[4,3,2-de]quinolin-7-yl)-5-methylbenzo[d]thiazol-6-yl)acetic acid (40)

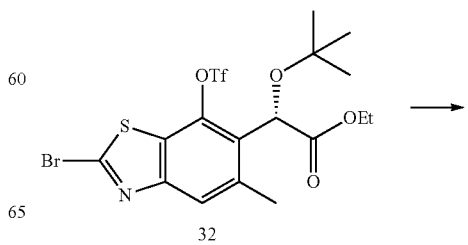

32

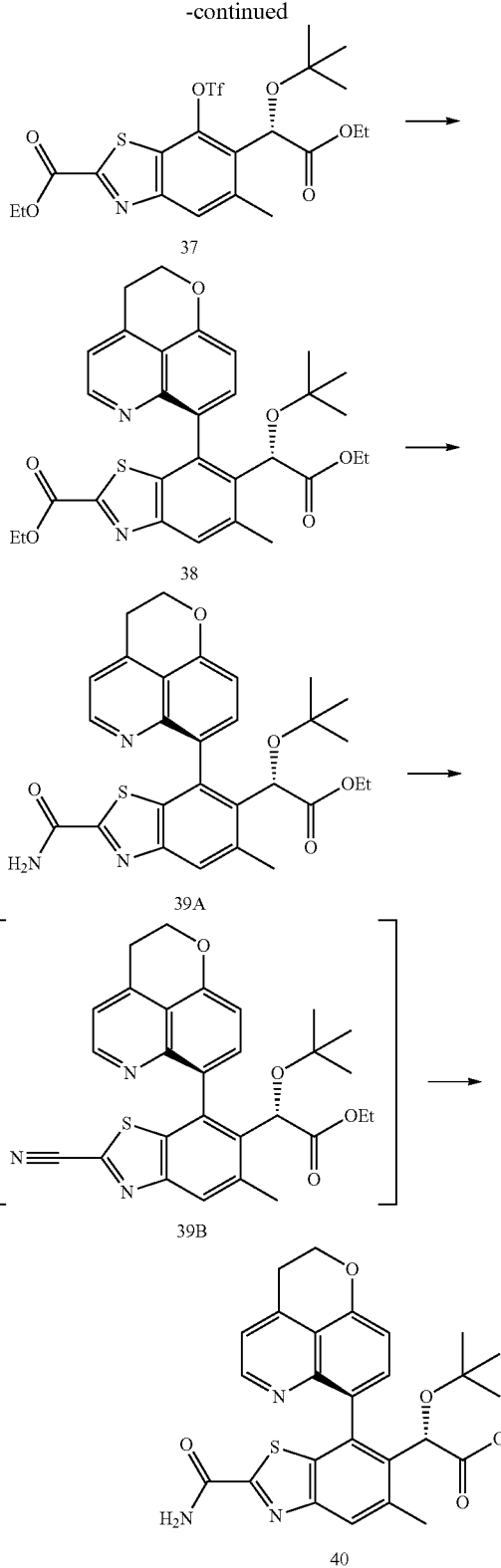

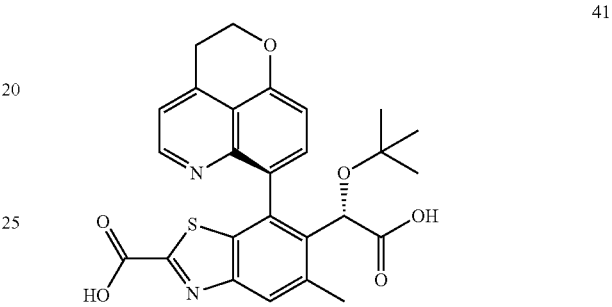

dried, filtered, and concentrated in vacuo. A solution of THF and MeOH was added (1:1, 5 mL) followed by NaOH solution (2 M, 200 μL). The reaction mixture was stirred at 45° C. for 6 h. The mixture was made acidic with 1 M HCl. The crude mixture was purified by reverse phase HPLC to give 10.8 mg of compound 40.

Compound 40. $^1$H-NMR: 400 MHz, (CD$_3$OD) δ: 8.79 (d, J=5.2 Hz, 1H); 8.21 (s, 1H); 7.92 (d, J=8.0 Hz, 1H); 7.87 (d, J=6.0 Hz, 1H); 7.46 (d, J=8.0 Hz, 1H); 5.27 (s, 1H); 4.74-4.72 (m, 2H); 3.68 (t, J=6.0 Hz, 2H); 2.80 (s, 3H); 0.93 (s, 9H).

LCMS-ESI$^+$: calc'd for C$_{26}$H$_{25}$N$_3$O$_5$S: 492.1 (M+H$^+$). Found: 492.1 (M+H$^+$).

Compound 41 was a by-product in the preparation of 40.

LCMS-ESI$^+$: calc'd for C$_{26}$H$_{24}$N$_2$O$_6$S: 493.1 (M+H$^+$). Found: 493.1 (M+H$^+$).

Preparation of (S)-ethyl 2-tert-butoxy-2-((S)-2-carbamoyl-7-(2,3-dihydropyrano[4,3,2-de]quinolin-7-yl)-5-methylbenzo[d]thiazol-6-yl)acetate (39)

Step 1

Preparation of (S)-ethyl 6-(1-tert-butoxy-2-ethoxy-2-oxoethyl)-5-methyl-7-(trifluoromethylsulfonyloxy)benzo[d]thiazole-2-carboxylate (37)

To a solution of (S)-ethyl 2-(2-bromo-5-methyl-7-(triluoromethysulfonyloxy)benzo[d]thiazol-6-yl)-2-tert-butoxyacetate (32) (1.07 g, 2.00 mmol) in DMF (10 mL) was added tributyl(1-ethoxyvinyl)stannane (867 mg, 2.40 mmol), copper iodide (38 mg, 0.20 mmol), and Pd(PPh$_3$)$_4$ (116 mg, 0.10 mmol). The reaction mixture was stirred at 45° C. for 2.5 h. A saturated solution of NH$_4$Cl was added and EtOAc. The layers were separated, and the aqueous layer was extracted with EtOAc. The combined organic layers were dried, filtered, and concentrated in vacuo. Methanol and CH$_2$Cl$_2$ (1:1, 20 mL) added. The mixture was cooled to −78° C. and ozone (O$_3$) was bubbled through the solution for about 15 min until the reaction mixture was blue-green. Dimethysulfide (1 mL) was added and the reaction was stirred at rt for 20 min. The mixture was concentrated in vacuo and purified by column chromatography (EtOAc/hexanes) to give 811 mg of 37.

$^1$H-NMR: 400 MHz, (CDCl$_3$): δ 8.06 (s, 1H), 5.65 (s, 1H), 4.56 (q, J=7 Hz, 2H), 4.14 (m, 2H), 2.59 (s, 3H), 1.49 (t, J=7 Hz, 3H), 1.21 (s, 9H), 1.16 (t, J=7 Hz, 3H).

Compound 40 was prepared from compound 39. To a solution of compound 39A (200 mg) in CH$_2$Cl$_2$ (5 mL) was added trietylamine (2 mL) and trifluoroacetic acid anhydride (100 μL). After 3 h, a saturated solution of NH$_4$Cl was added. The layers were separated, and the aqueous layer was extracted with CH$_2$Cl$_2$. The combined organic layers were

Step 2

Preparation of (S)-ethyl 6-((S)-1-tert-butoxy-2-ethoxy-2-oxoethyl)-7-(2,3-dihydropyrano[4,3,2-de]quinolin-7-yl)-5-methylbenzo[d]thiazole-2-carboxylate (38)

To a solution of 37 (807 mg, 1.53 mmol) and CsF (1.02 g, 6.73 mmol) in distilled dimethoxyethane (15 mL) was added 2,3-dihydropyrano[4,3,2-de]quinolin-7-ylboronic acid (HCl salt, 770 mg, 3.06 mmol) and chloro(2-dicyclohexylphosphino-2',6'-dimethoxy-1,1'-biphenyl)[2-(2-aminoethylphenyl)]palladium(II) methyl-t-butylether adduct, [SPhos Palladacycle](206 mg, 0.31 mmol). The reaction mixture was heated at 110° C. in a sealed tube for 2 h. The reaction was cooled to rt and saturated solution of NaHCO₃ was added. The layers were separated, and the aqueous layer was extracted with EtOAc. The combined organic layers were dried, filtered, and concentrated in vacuo. The crude material was purified by column chromagraphy (increasing EtOAc w/5% MeOH to hexanes) to give 224 mg of 38 and 348 mg of undesired atropisomer.

$^1$H-NMR 400 MHz, (CDCl₃): δ 8.54 (d, J=4 Hz, 1H), 8.04 (s, 1H), 7.55 (d, J=8 Hz, 1H), 7.29 (d, J=4 Hz, 1H), 7.10 (d, J=8 Hz, 1H), 5.18 (s, 1H), 4.55 (m, 2H), 4.41 (q, J=7 Hz, 2H), 4.01 (m, 1H), 3.88 (m, 1H), 3.37 (m, 2H), 2.77 (s, 3H), 1.36 (t, J=7 Hz, 3H), 1.00 (t, J=7 Hz, 3H), 0.90 (s, 9H).

Step 3

Preparation of (S)-ethyl 2-tert-butoxy-2-((S)-2-carbamoyl-7-(2,3-dihydropyrano[4,3,2-de]quinolin-7-yl)-5-methylbenzo[d]thiazol-6-yl)acetate (39)

To a solution of 38 (224 mg) in MeOH (5 mL) was added NH₄OH (500 μL). The reaction mixture was stirred at rt for 2 h and then concentrated in vacuo to give 220 mg of 39.

LCMS-ESI⁺ (m/z): [M+H]⁺ calcd for C₂₈H₂₉N₃O₅S: 520.2 (M+H⁺). Found: 520.1, 493.07 (M+H⁺).

Example 12

Preparation of (S)-2-tert-butoxy-2-((S)-7-(2,3-dihydropyrano[4,3,2-de]quinolin-7-yl)-2-(dimethylamino)-5-methylbenzo[d]thiazol-6-yl)acetic acid (42) and (S)-2-tert-butoxy-2-((R)-7-(2,3-dihydropyrano[4,3,2-de]quinolin-7-yl)-2-(dimethylamino)-5-methylbenzo[d]thiazol-6-yl)acetic acid (43)

Compounds 42 and 43 were prepared from compound 32 according to the procedure used to prepare compound 35 (except that dimethylamine was used instead of azetidine) in Example 10.

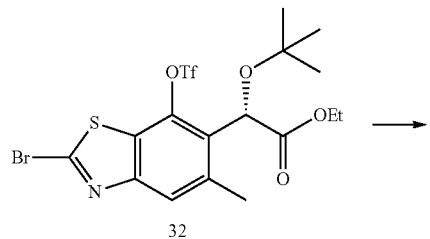

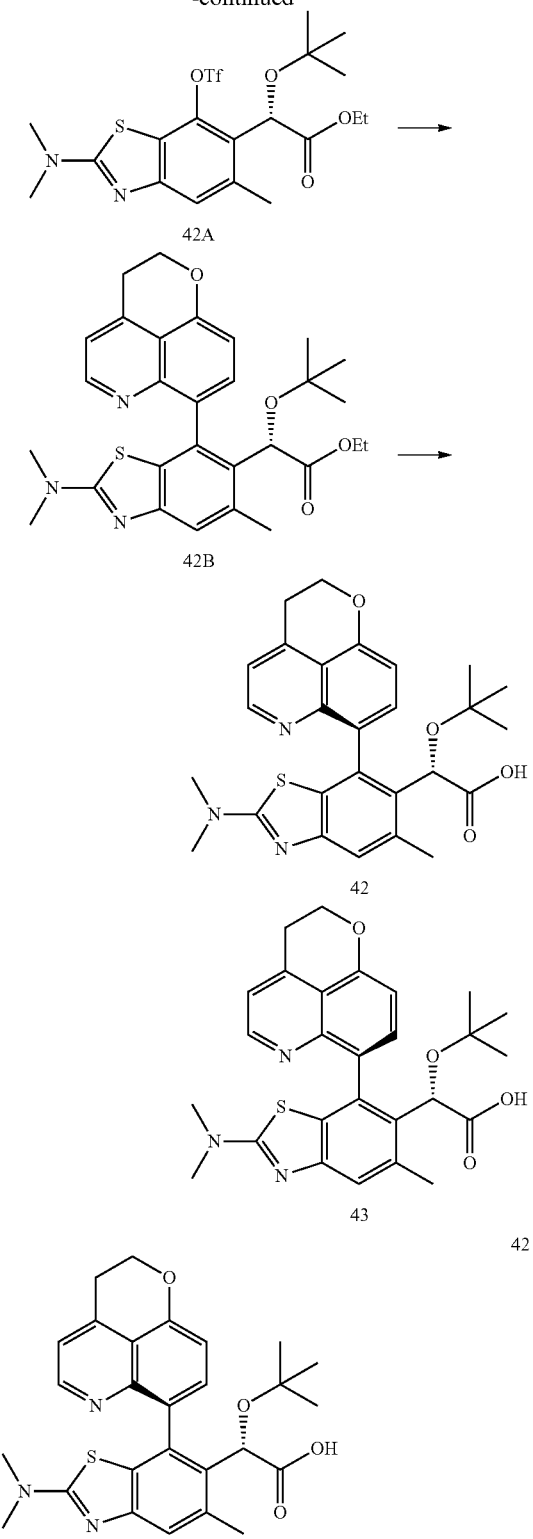

Compound 42: $^1$H-NMR 400 MHz, (CD₃OD) δ: 8.76 (d, J=4.8 Hz, 1H); 7.82 (d, J=8.0 Hz, 1H); 7.73 (d, J=5.2 Hz, 1H); 7.50 (s, 1H); 7.35 (d, J=7.6 Hz, 1H); 5.14 (s, 1H); 4.67 (m, 2H); 3.61 (t, J=5.8 Hz, 2H); 3.13 (s, 6H); 2.66 (s, 3H); 0.89 (s, 9H). LCMS-ESI⁺ (m/z): [M+H]⁺ calcd for C₂₇H₃₀N₃O₄S: 492.20 (M+H⁺). Found: 492.00, 493.07 (M+H⁺).

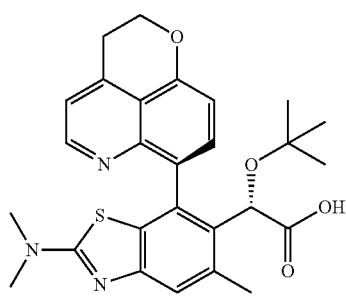

43

Compound 43: $^1$H-NMR: 400 MHz, (CD$_3$OD) δ 8.67 (d, J=4.9 Hz, 1H), 8.04 (d, J=8.1 Hz, 1H), 7.51 (d, J=4.9 Hz, 1H), 7.45 (s, 1H), 7.30 (d, J=8.1 Hz, 1H), 5.19 (s, 1H), 4.67-4.55 (m, 2H), 3.21 (s, 6H), 2.62 (s, 3H), 0.81 (s, 9H).
LCMS-ESI$^+$ (m/z): [M+H]$^+$ calcd for C$_{27}$H$_{29}$N$_3$O$_4$S: 492.20 (M+H$^+$). Found: 491.98, 492.96 (M+H$^+$).

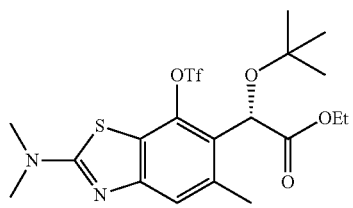

42A

Compound 42A: LCMS-ESI$^+$ (m/z): [M+H]$^+$ calcd for C$_{19}$H$_{25}$F$_3$N$_2$O$_6$S$_2$: 499.1 (M+H$^+$). Found: 499.0 (M+H$^+$).

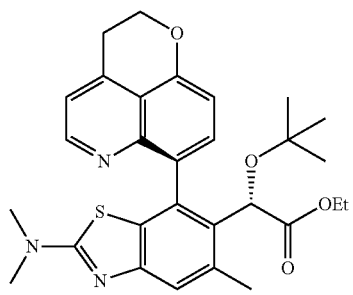

42B

Compound 42B: $^1$H-NMR 400 MHz, (CDCl$_3$) δ: 8.75 (d, J=1.8 Hz, 1H); 7.54 (d, J=4.0 Hz, 1H), 7.48 (s, 1H), 7.11 (d, J=2.2 Hz, 1H), 7.06 (d, J=3.8 Hz, 1H), 4.94 (s, 1H), 4.54 (t, J=5.6 Hz, 2H), 4.00-4.03 (m, 2H), 3.31-3.30 (m, 2H), 3.08 (s, 6H), 2.64 (s, 3H), 1.25-1.27 (m, 3H), 0.88 (s, 9H).
LCMS-ESI$^+$ (m/z): [M+H]$^+$ calcd for C$_{29}$H$_{33}$N$_3$O$_4$S: 520.2 (M+H$^+$). Found: 520.0 (M+H$^+$).

Example 13

Preparation of (S)-2-tert-butoxy-2-((S)-7-(2,3-dihydropyrano[4,3,2-de]quinolin-7-yl)-2-(ethyl(methyl) amino)-5-methylbenzo[d]thiazol-6-yl)acetic acid (44)

Compound 44 was prepared from compound 32 according to the procedure used to prepare compound 35 (except that methylethylamine was used instead of azetidine) in Example 10.

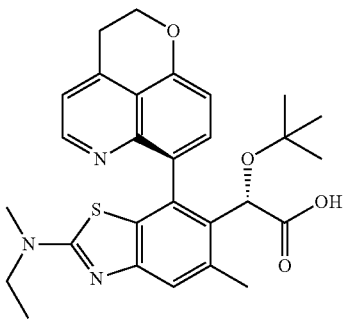

44

Compound 44: $^1$H NMR (400 MHz, CD$_3$OD) δ 8.77 (d, J=5.4 Hz, 1H), 7.82 (d, J=8.1 Hz, 1H), 7.72 (d, J 5.3 Hz, 1H), 7.49 (s, 1H), 7.35 (d, J=8.1 Hz, 1H), 5.14 (s, 1H), 4.67 (t, J=5.9 Hz, 2H), 3.59 (t, J=5.9 Hz, 2H), 3.52 (dd, J=14.3, 7.1 Hz, 2H), 3.12 (s, 3H), 2.66 (s, 3H), 1.20 (t, J=7.1 Hz, 3H), 0.90 (s, 9H). LCMS-ESI$^+$ (m/z): [M+H]$^+$ calcd for C$_{28}$H$_{31}$N$_3$O$_4$S: 506.21 (M+H$^+$). Found: 506.05, 507.00 (M+H$^+$).

Example 14

Preparation of (S)-2-tert-butoxy-2-((S)-2-(diethyl-amino)-7-(2,3-dihydropyrano[4,3,2-de]quinolin-7-yl)-5-methylbenzo[d]thiazol-6-yl)acetic acid (45)

Compound 45 was prepared from compound 32 according to the procedure used to prepare compound 35 (except that diethylamine was used instead of azetidine) in Example 10.

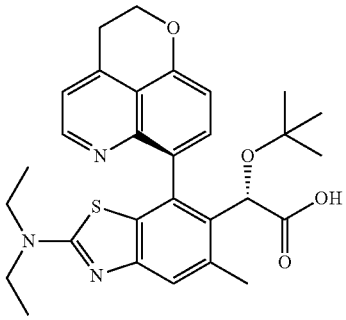

45

Compound 45: $^1$H NMR (400 MHz, CD$_3$OD) δ 8.90 (s, 1H), 7.90 (d, J=7.9 Hz, 2H), 7.61 (s, 1H), 7.44 (d, J=7.9 Hz, 1H), 5.17 (s, 1H), 4.71 (m, 2H), 3.66 (a, 6H), 2.73 (s, 3H), 1.95 (s, 4H), 1.29 (d, J=5.9 Hz, 6H), 0.90 (s, 8H).
LCMS-ESI$^+$ (m/z): [M+H]$^+$ calcd for C$_{29}$H$_{34}$N$_3$O$_4$S: 520.23 (M+H$^+$). Found: 520.05, 521.13 (M+H$^+$).

Example 15

Preparation of (S)-2-tert-butoxy-2-((S)-7-(2,3-dihydropyrano[4,3,2-de]quinolin-7-yl)-2-(isopropyl(methyl)amino)-5-methylbenzo[d]thiazol-6-yl)acetic acid (46) and (S)-2-tert-butoxy-2-((R)-7-(2,3-dihydropyrano[4,3,2-de]quinolin-7-yl)-2-(isopropyl(methyl)amino)-5-methylbenzo[d]thiazol-6-yl)acetic acid (47)

Compounds 46 and 47 were prepared from compound 32 according to the procedure used to prepare compound 35 (except that N-methyl-N-isopropylamine was used instead of azetidine) in Example 10.

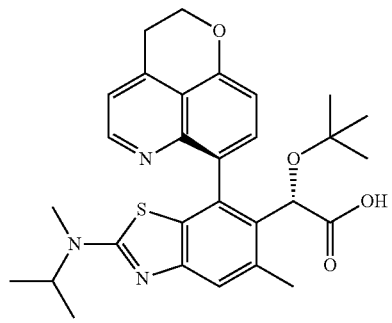

46

Compound 46: $^1$H-NMR: 400 MHz, (CD$_3$OD) δ 8.76 (d, J=5.4 Hz, 1H), 7.82 (d, J=8.2 Hz, 1H), 7.73 (d, J=5.2 Hz, 1H), 7.49 (a, 1H), 7.35 (d, J=8.1 Hz, 1H), 5.14 (a, 1H), 4.67 (t, J=5.7 Hz, 2H), 4.23-4.06 (m, 1H), 3.59 (t, J=5.8 Hz, 2H), 3.00 (s, 3H), 2.67 (s, 3H), 1.23 (t, J=6.5 Hz, 6H), 0.89 (s, 9H). LCMS-ESI$^+$ (m/z): [M+H]$^+$ calcd for C$_{29}$H$_{34}$N$_3$O$_4$S: 520.23 (M+H$^+$). Found: 519.95, 521.00 (M+H$^+$).

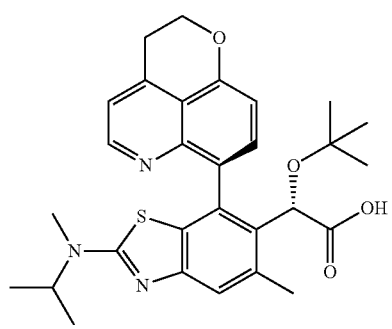

47

Compound 47: $^1$H-NMR 400 MHz, (CD$_3$OD) δ 8.67 (d, J=4.9 Hz, 1H), 8.02 (d, J=8.1 Hz, 1H), 7.48 (d, J=4.6 Hz, 1H), 7.44 (s, 1H), 7.28 (d, J=8.1 Hz, 1H), 5.19 (a, 1H), 4.67-4.52 (m, 2H), 4.11-4.00 (m, 1H), 3.50-3.43 (m, 1H), 3.08 (s, 5H), 2.62 (s, 4H), 1.26 (d, J=6.1 Hz, 6H), 0.80 (s, 9H).
LCMS-ESI$^+$ (m/z): [M+H]$^+$ calcd for C$_{27}$H$_{34}$N$_3$O$_4$S: 520.23 (M+H$^+$). Found: 520.05, 521.08 (M+H$^+$).

Example 16a

Preparation of (S)-2-tert-butoxy-2-((S)-7-(2,3-dihydropyrano[4,3,2-de]quinolin-7-yl)-2-(isobutyl(methyl)amino)-5-methylbenzo[d]thiazol-6-yl)acetic acid (48) and (S)-2-tert-butoxy-2-((R)-7-(2,3-dihydropyrano[4,3,2-de]quinolin-7-yl)-2-(isobutyl(methyl)amino)-5-methylbenzo[d]thiazol-6-yl)acetic acid (49)

Compounds 48 and 49 were prepared from compound 32 according to the procedure used to prepare compound 35 (except that N-methyl-N-isobuytlamine was used instead of azetidine) in Example 10.

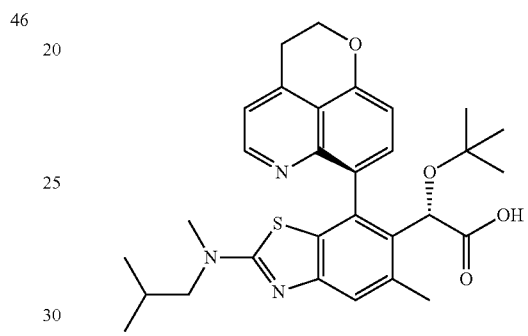

48

Compound 48: $^1$H-NMR: 400 MHz, (CD$_3$OD) δ 8.77 (d, J=5.4 Hz, 1H), 7.83 (d, J=8.3 Hz, 1H), 7.75 (d, J=5.1 Hz, 1H), 7.49 (s, 1H), 7.36 (d, J=8.0 Hz, 1H), 5.13 (s, 1H). 4.68 (dd, J=9.9, 6.0 Hz, 2H), 3.60 (t, J=6.0 Hz, 2H), 3.27 (m, 2H), 3.13 (s, 4H), 2.66 (s, 3H), 2.08 (m, 1H), 0.89-0.87 (m, 15H). LCMS-ESI$^+$ (m/z): [M+H]$^+$ calcd for C$_{30}$H$_{36}$N$_3$O$_4$S: 534.24 (M+H$^+$). Found: 533.9 (M+H$^+$).

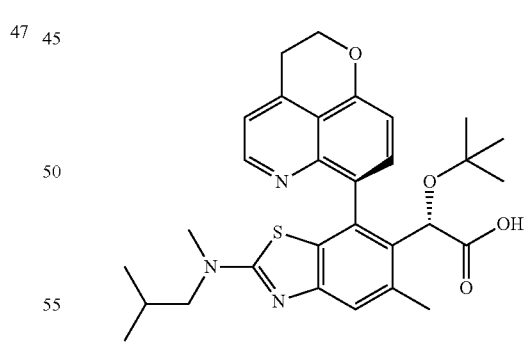

49

Compound 49: $^1$H-NMR: 400 MHz, (CD$_3$OD) δ 8.69 (d, J 5.0 Hz, 1H), 8.06 (d, J=8.1 Hz, 1H), 7.54 (d, J=4.9 Hz, 1H), 7.46 (s, 1H), 7.32 (d, J=8.1 Hz, 1H), 5.19 (s, 1H), 4.62 (m, Hz, 2H), 3.50 (t, J=5.8 Hz, 2H), 3.22 (s, 3H), 2.63 (s, 3H), 2.21-2.04 (m, 1H), 0.91 (d, J=6.6 Hz, 6H), 0.83 (s, 9H). LCMS-ESI$^+$ (m/z): [M+H]$^+$ calcd for C$_{30}$H$_{36}$N$_3$O$_4$S: 534.24 (M+H$^+$). Found: 534.04, 535.05 (M+H$^+$).

Example 16b

Preparation of (S)-2-tert-butoxy-2-((S)-7-(2,3-dihydrpyrano[4,3,2-de]quinolin-7-yl)-5-methyl-2-(pyrolidin-1-yl)benzo[d]thiazol-6-yl)acetic acid (50) and (S)-2-tert-butoxy-2-((R)-7-(2,3-dihydropyrano[4,3,2-de]quinolin-7-yl)-5-methyl-2-pyrrolidin-1-yl)benzo[d]thiazol-6-yl)acetic acid (51)

Compounds 50 and 51 were prepared from compound 32 according to the procedure used to prepare compound 35 (except that pyrrolidine was used instead of azetidine) in Example 10.

Example 17

Preparation of (S)-2-tert-butoxy-2-((S)-2-(3,3-difluoroazetidin-1-yl)-7-(2,3-dihydropyrano[4,3,2-de]quinolin-7-yl)-5-methylbenzo[d]thiazol-6-yl)acetic acid (52) and (S)-2-tert-butoxy-2-((R)-2-(3,3-difluoroazetidin-1-yl)-7-(2,3-dihydropyrano[4,3,2-de]quinolin-7-yl)-5-methylbenzo[d]thiazol-6-yl)acetic acid (53)

Compounds 52 and 53 were prepared from compound 32 according to the procedure used to prepare compound 35 (except that 2,2-difluoroazetidine was used instead of azetidine) in Example 10.

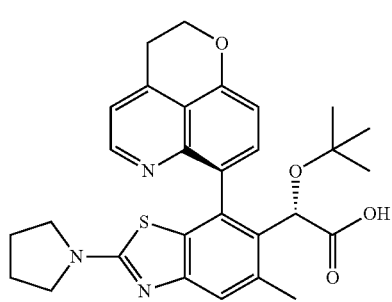

50

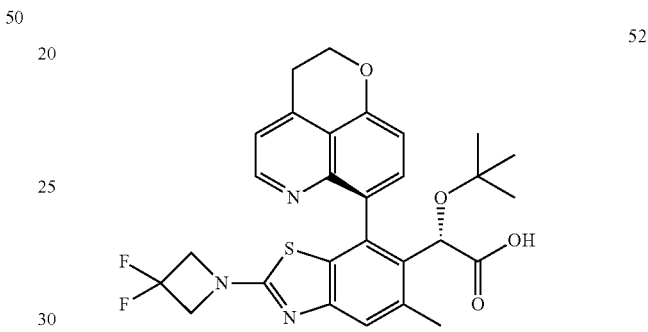

52

Compound 50: $^1$H-NMR: 400 MHz, (CD$_3$OD) δ 8.76 (d, J=5.3 Hz, 1H), 7.80 (d, J=8.1 Hz, 1H), 7.69 (d, J=5.1 Hz, 1H), 7.50 (s, 1H), 7.33 (d, J=8.0 Hz, 1H), 5.15 (s, 1H), 9.03-0.64 (m, 79H), 4.70-4.60 (m, 2H), 3.56 (dd, J=13.8, 7.7 Hz, 6H), 2.68 (s, 3H), 2.10 (t, J=6.7 Hz, 4H), 0.89 (s, 10H). LCMS-ESI$^+$ (m/z): [M+H]$^+$ calcd for C$_{29}$H$_{32}$N$_3$O$_4$S: 518.21 (M+H$^+$). Found: 517.99, 518.97 (M+H$^+$).

Compound 52: $^1$H-NMR: 400 MHz, (CD$_3$OD) δ 8.80 (d, J=5.6 Hz, 1H), 7.87 (d, J=8.2 Hz, 1H), 7.83 (d, J=5.6 Hz, 1H), 7.61 (s, 1H), 7.41 (d, J=8.2 Hz, 1H), 5.17 (s, 1H), 4.76-4.64 (m, 2H), 4.56-4.43 (m, 4H), 3.65 (t, J=5.9 Hz, 2H), 2.69 (s, 3H), 0.91 (s, 9H). $^{19}$F NMR (377 MHz, CD$_3$OD) δ-77.88 (s). LCMS-ESI$^+$ (m/z): [M+H]$^+$ calcd for C$_{28}$H$_{28}$F$_2$N$_3$O$_4$S: 540.18 (M+H$^+$). Found: 539.96, 540.96 (M+H$^+$).

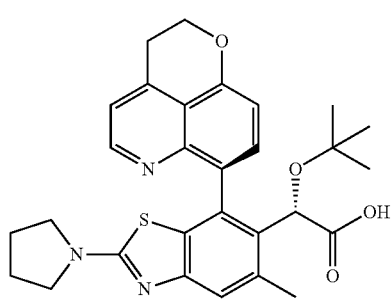

51

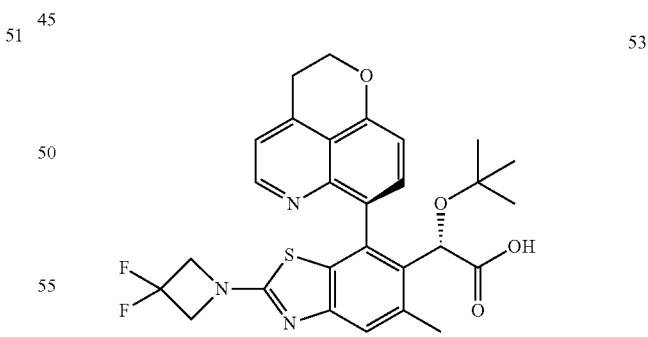

53

Compound 51: $^1$H-NMR: 400 MHz, (CD$_3$OD) δ 8.67 (d, J=4.7 Hz, 1H), 8.01 (d, J=8.1 Hz, 1H), 7.46 (d, J=4.8 Hz, 1H), 7.44 (s, 1H), 7.27 (d, J=8.1 Hz, 1H), 5.20 (s, 1H), 4.68-4.50 (m, 2H), 3.57 (s, 3H), 3.45 (t, J=5.8 Hz, 2H), 2.63 (s, 4H), 2.14 (t, J=6.3 Hz, 4H), 0.79 (s, 9H). LCMS-ESI$^+$ (m/z): [M+H]$^+$ calcd for C$_{29}$H$_{32}$N$_3$O$_4$S: 518.21 (M+H$^+$). Found: 518.07, 519.07 (M+H$^+$).

Compound 53: $^1$H-NMR: 400 MHz, (CD$_3$OD) δ 8.71 (d, J=5.4 Hz, 1H), 8.14 (d, J=8.2 Hz, 1H), 7.69 (d, J=5.4 Hz, 1H), 7.57 (s, 1H), 7.40 (d, J=8.2 Hz, 1H), 5.21 (s, 1H), 4.72-4.60 (m, 2H), 4.56-4.42 (m, 4H), 3.58 (t, J=6.0 Hz, 2H), 2.65 (s, 3H), 0.91 (s, 9H). LCMS-ESI$^+$ (m/z): [M+H]$^+$ calcd for C$_{28}$H$_{28}$F$_2$N$_3$O$_4$S: 540.18 (M+H$^+$). Found: 539.98, 541.02 (M+H$^+$).

Example 18

Preparation of (S)-2-tert-butoxy-2-((S)-7-(2,3-dihydropyrano[4,3,2-de]quinolin-7-yl)-2-(3-methoxyazetidin-1-yl)-5-methylbenzo[d]thiazol-6-yl)acetic acid (54) and (S)-2-tert-butoxy-2-((R)-7-(2,3-dihydropyrano[4,3,2-de]quinolin-7-yl)-2-(3-methoxyazetidin-1-yl)-5-methylbenzo[d]thiazol-6-yl)acetic acid (55)

Compounds 54 and 55 were prepared from compound 32 according to the procedure used to prepare compound 35 (except that 2-methoxyazetidine was used instead of azetidine) in Example 10.

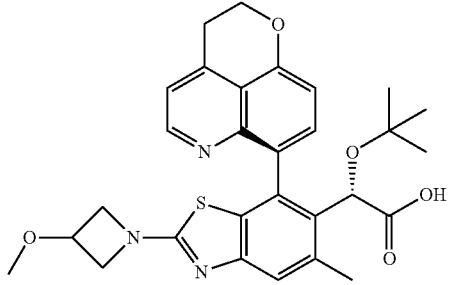

54

Compound 54: $^1$H-NMR 400 MHz, (CD$_3$OD) δ: 8.78 (d, J=5.5 Hz, 1H), 7.84 (d, J=8.5 Hz, 1H), 7.77 (d, J=6.1 Hz, 1H), 7.52 (s, 1H), 7.37 (d, J=7.8 Hz, 1H), 5.16 (s, 1H), 4.73-4.64 (m, 2H), 4.41 (ddd, J=9.9, 6.2, 3.4 Hz, 1H), 4.31 (td, J=7.7, 1.0 Hz, 2H), 4.02-3.90 (m, 2H), 3.62 (t, J=5.7 Hz, 2H), 2.68 (s, 4H), 0.91 (s, 11H). LCMS-ESI$^+$ (m/z): [M+H]$^+$ calcd for C$_{29}$H$_{32}$N$_3$O$_3$S: 534.21 (M+H$^+$). Found: 533.95, 534.97 (M+H$^+$).

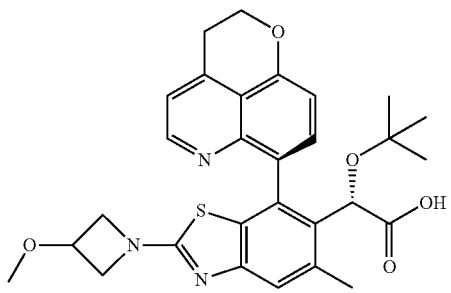

55

Compound 55: $^1$H-NMR: 400 MHz, (CD$_3$OD) δ: 8.67 (d, J=5.1 Hz, 1H), 8.04 (d, J=8.2 Hz, 1H), 7.52 (d, J=4.7 Hz, 1H), 7.43 (s, 1H), 7.30 (d, J=8.1 Hz, 1H), 5.19 (s, 1H), 4.66-4.56 (m, 2H), 4.42 (m, 1H), 4.38-4.32 (m, 2H), 4.08-4.01 (m, 2H), 3.49 (t, J=6.0 Hz, 3H), 2.61 (s, 3H), 0.82 (s, 10H). LCMS-ESI$^+$ (m/z): [M+H]$^+$ calcd for C$_{29}$H$_{32}$N$_3$O$_5$S: 534.21 (M+H$^+$). Found: 534.03, 535.08 (M+H$^+$).

Example 19

Preparation of (S)-2-tert-butoxy-2-((S)-7-(2,3-dihydropyrano[4,3,2-de]quinolin-7-yl)-2-(3-fluoroazetidin-1-yl)-5-methylbenzo[d]thiazol-6-yl)acetic acid (56)

Compound 56 was prepared from compound 32 according to the procedure used to prepare compound 35 (except that 2-fluoroazetidine was used instead of azetidine) in Example 10.

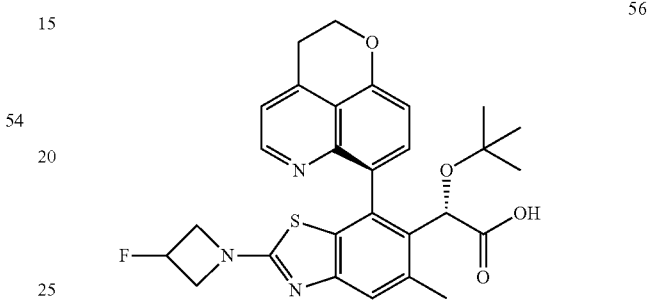

56

Compound 56: $^1$H-NMR: 400 MHz, (CD$_3$OD) δ 8.79 (d, J=5.5 Hz, 1H), 7.85 (d, J=8.1 Hz, 1H), 7.79 (d, J=5.1 Hz, 1H), 7.55 (s, 1H), 7.39 (d, J=7.9 Hz, 1H), 5.58-5.38 (m, 1H), 5.16 (s, 1H), 4.70 (td, J=5.9, 3.1 Hz, 2H), 4.49-4.35 (m, 2H), 4.28-4.12 (m, 2H), 3.63 (t, J=6.0 Hz, 2H), 2.68 (s, 3H), 0.91 (s, 9H).
LCMS-ESI$^+$ (m/z): [M+H]$^+$ calcd for C$_{28}$H$_{29}$FN$_3$O$_4$S: 522.19 (M+H$^+$). Found: 521.97, 523.02 (M+H$^+$).

Example 20a

Preparation of (S)-2-tert-butoxy-2-((S)-7-(2,3-dihydropyrano[4,3,2-de]quinolin-7-yl)-5-methyl-2-(3-methylazetidin-1-yl)benzo[d]thiazol-6-yl)acetic acid (57)

Compound 57 was prepared from compound 32 according to the procedure used to prepare compound 35 (except that 2-methylazetidine was used instead of azetidine) in Example 10.

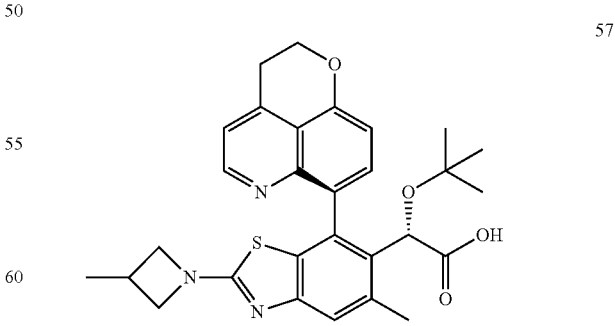

57

Compound 57: $^1$H-NMR: 400 MHz, (CD$_3$OD) δ: δ 8.92 (s, 1H), 7.90 (d, J=7.6 Hz, 2H), 7.56 (s, 1H), 7.44 (d, J=7.3 Hz, 1H), 5.18 (s, 1H), 4.73 (s, 2H), 4.48 (s, 2H), 3.99 (s, 2H), 3.68 (s, 2H), 3.12 (m, 1H), 2.73 (s, 3H), 1.35 (d, J=5.6 Hz, 3H), 0.91 (s, 9H). LCMS-ESI⁺ (m/z): [M+H]⁺ calcd for C₂₉H₃₂N₃O₄S: 518.21 (M+H⁺). Found: 518.09, 519.12 (M+H⁺).

Example 20b

Preparation of (S)-2-tert-butoxy-2-((S)-7-(2,3-dihydropyrano[4,3,2-de]quinolin-7-yl)-5-methyl-2-(3-(methylsulfonyl)azetidin-1-yl)benzo[d]thiazol-6-yl) acetic acid (58)

Compound 58 was prepared from compound 32 according to the procedure used to prepare compound 35 (except that 2-methylsulfonylazetidine was used instead of azetidine) in Example 10.

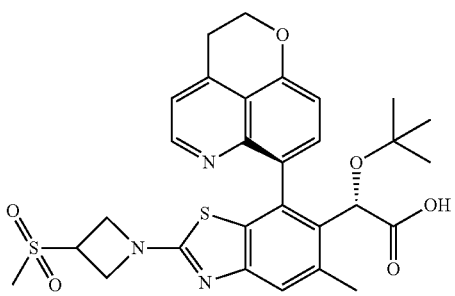

58

Compound 58: ¹H-NMR: 400 MHz, (CD₃OD) δ: ¹H NMR (400 MHz, cd₃od) δ 8.85 (d, J=5.3 Hz, 1H), 7.89 (t, J=6.7 Hz, 2H), 7.61 (s, 1H), 7.44 (d, J=8.1 Hz, 1H), 5.18 (s, 1H), 4.72 (dd, J=9.0, 6.2 Hz, 2H), 4.59-4.35 (m, 5H), 3.01 (s, 3H), 2.72 (s, 3H), 0.92 (s, 9H). LCMS-ESI⁺ (m/z): [M+H]⁺ calcd for C₂₉H₃₂N₃O₆S: 582.17 (M+H⁺). Found: 581.95, 583.02 (M+H⁺).

Example 21

Preparation of (S)-2-((S)-2-(((1,3-dioxolan-2-yl) methyl)(methyl)amino)-7-(2,3-dihydropyrano[4,3,2-de]quinolin-7-yl)-5-methylbenzo[d]thiazol-6-yl)-2-tertbutoxyacetic acid (59) and (S)-2-((R)-2-(((1,3-dioxolan-2-yl)methyl)(methyl)amino)-7-(2,3-dihydropyrano[4,3,2-de]quinolin-7-yl)-5-methylbenzo[d]thiazol-6-yl)-2-tert-butoxyacetic acid (60)

Compounds 59 and 60 were prepared from compound 32 according to the procedure used to prepare compound 35 (except that 1-(1,3-dioxolan-2-yl)-N-methylmethanamine was used instead of azetidine) in Example 10.

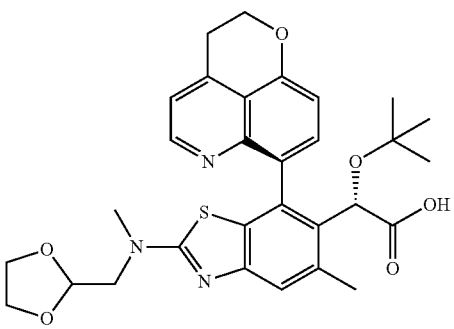

59

Compound 59: ¹H-NMR: 400 MHz, (CD₃OD) δ: 8.81 (d, J=6 Hz, 1H), 7.85 (d, J=8 Hz, 1H), 7.81 (d, J=6 Hz, 1H), 7.54 (s, 1H), 7.40 (d, J=8 Hz, 1H), 5.15 (s, 1H), 5.07 (m, 1H), 4.69 (m, 2H), 3.91 (m, 2H), 3.82 (m, 2H), 3.63 (m, 2H), 3.30 (s, 3H), 2.68 (s, 3H), 0.89 (s, 9H). LCMS-ESI⁺ (m/z): [M+H]⁺ calcd for C₃₀H₃₃N₃O₆S: 564.2 (M+H⁺). Found: 564.1 (M+H⁺).

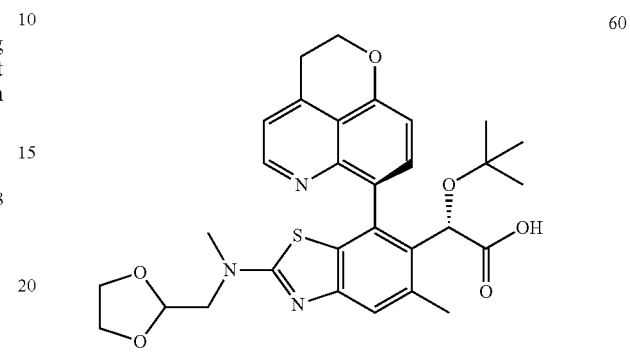

60

Compound 60: ¹H-NMR: 400 MHz, (CD₃OD) δ: 8.70 (d, J=6 Hz, 1H), 8.09 (d, J=8 Hz, 1H), 7.60 (d, J=6 Hz, 1H), 7.48 (s, 1H), 7.35 (d, J=8 Hz, 1H), 5.19 (s, 1H), 5.07 (m, 1H), 4.65 (m, 2H), 3.92 (m, 2H), 3.83 (m, 2H), 3.53 (m, 2H), 3.23 (s, 3H), 2.63 (s, 3H), 0.85 (s, 9H). LCMS-ESI⁺ (m/z): [M+H]⁺ calcd for C₃₀H₃₃N₃O₆S: 564.2 (M+H⁺). Found: 564.1 (M+H⁺).

Example 22

Preparation of (S)-2-tert-butoxy-2-((S)-7-(2,3-dihydropyrano[4,3,2-de]quinolin-7-yl)-2-((2-(dimethylamino)ethyl)(methyl)amino)-5-methylbenzo[d]thiazo-6-yl)acetic acid (61) and (S)-2-tert-butoxy-2-((R)-7-(2,3-dihydropyrano[4,3,2-de]quinolin-7-yl)-2-((2-(dimethylamino)ethyl)(methyl)amino)-5-methylbenzo[d]thiazol-6-yl)acetic acid (62)

Compounds 61 and 62 were prepared from compound 32 according to the procedure used to prepare compound 35 (except that N1,N1,N2-trimethylethane-1,2-diamine was used instead of azetidine) in Example 10.

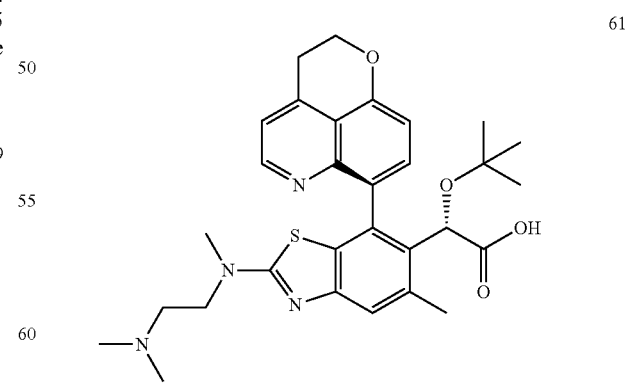

61

Compound 61: ¹H-NMR: 400 MHz, (CD₃OD) δ: 8.78 (d, J=6 Hz, 1H), 7.80 (m, 2H), 7.57 (s, 1H), 7.38 (d, J=8 Hz, 1H), 5.15 (s, 1H), 4.67 (m, 2H), 4.11 (m, 1H), 3.94 (s, 1H), 3.63 (t, J=6 Hz, 2H), 3.47 (m, 2H), 3.02 (s, 6H), 2.66 (s, 3H), 0.89 (s, 9H). LCMS-ESI⁺ (m/z): [M+H]⁺ calcd for C₃₀H₃₆N₄O₄S: 549.3 (M+H⁺). Found: 549.0 (M+H⁺).

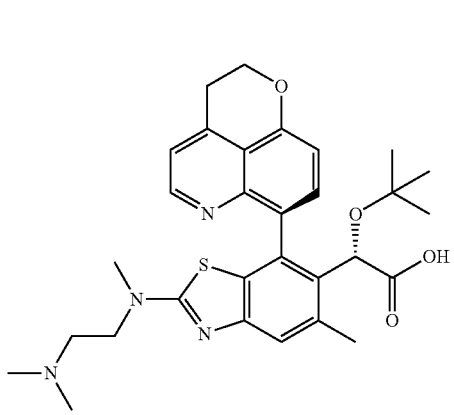

62

Compound 62: ¹H-NMR: 400 MHz, (CD₃OD) δ: 8.71 (d, J=6 Hz, 1H), 8.13 (d, J=8 Hz), 7.70 (d, J=6 Hz, 2H), 7.54 (s, 1H), 7.41 (d, J=8 Hz, 1H), 5.18 (s, 1H), 4.66 (m, 2H), 4.06 (m, 1H), 3.98 (s, 1H), 3.59 (t, J=6 Hz, 2H), 3.47 (m, 2H), 3.02 (s, 3H), 3.00 (s, 3H), 2.63 (s, 3H), 0.89 (s, 9H).
LCMS-ESI⁺ (m/z): [M+H]⁺ calcd for C₃₀H₃₆N₄O₄S: 549.3 (M+H⁺). Found: 549.0 (M+H⁺).

Example 23

Preparation of (2S)-2-(2-(benzyl(methyl)amino)-7-(2,3-dihydropyrano[4,3,2-de]quinolin-7-yl)-5-methylbenzo[d]thiazol-6-yl)-2-tert-butoxyacetic acid (63)

Compound 63 was prepared as a mixture of atropisomers from compound 32 according to the procedure used to prepare compound 35 (except that N-methyl-N-benzylamine was used instead of azetidine) in Example 10.

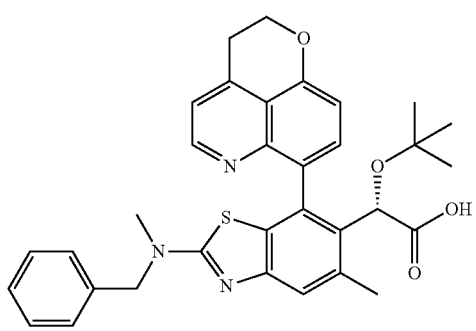

63

Compound 63: LCMS-ESI⁺ (m/z): [M+H]⁺ calcd for C₃₃H₃₃N₃O₄S: 568.2 (M+H⁺). Found: 568.1 (M+H⁺).

Example 24

Preparation of (S)-2-tert-butoxy-2-((R)-7-(2,3-dihydropyrano[4,3,2-de]quinolin-7-yl)-2-((2-(dimethylamino)-2-oxoethyl)(methyl)amino)-5-methylbenzo[d]thiazol-6-yl)acetic acid (64)

Compound 64 was prepared from compound 32 according to the procedure used to prepare compound 35 (except that N,N-dimethyl-2-(methylamino)acetamide was used instead of azetidine) in Example 10.

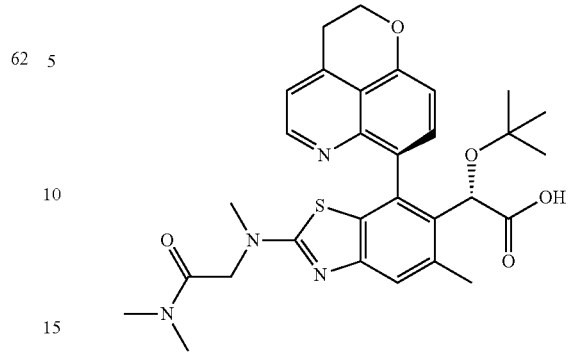

64

Compound 64: ¹H-NMR: 400 MHz, (CD₃OD) δ: 8.72 (d, J=6 Hz, 1H), 8.14 (d, J=8 Hz), 7.70 (d, J=6 Hz, 2H), 7.48 (s, 1H), 7.41 (d, J=8 Hz, 1H), 5.19 (s, 1H), 4.66 (m, 2H), 3.58 (t, J=6 Hz, 2H), 3.42 (s, 2H), 3.10 (s, 3H), 3.00 (s, 3H), 2.94 (s, 3H), 2.63 (a, 3H), 0.91 (s, 9H). LCMS-ESI⁺ (m/z): [M+H]⁺ calcd for C₃₀H₃₄N₄O₅S: 563.2 (M+H⁺). Found: 563.1 (M+H⁺).

Example 25

Preparation of (S)-2-tert-butoxy-2-((S)-7-(2,3-dihydropyrano[4,3,2-de]quinolin-7-yl)-2-methoxy-5-methylbenzo[d]thiazol-6-yl)acetic acid (66)

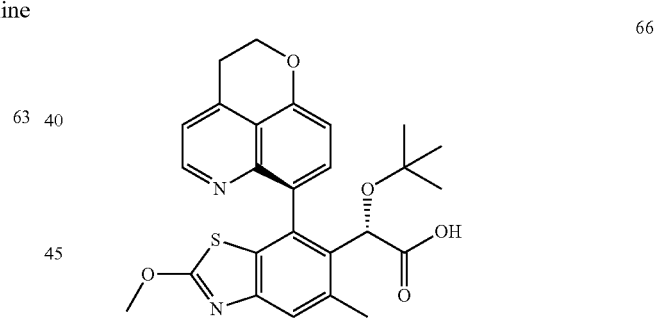

66

Compound 66: ¹H-NMR: 400 MHz, (CD₃OD) δ: 8.63 (d, J=4.4 Hz, 1H); 7.68 (d, J=8.0 Hz, 1H); 7.54 (s, 1H); 7.38 (d, J=4.8 Hz, 1H); 7.14 (d, J=7.6 Hz, 1H); 5.08 (s, 1H); 4.58-4.53 (m, 2H); 4.11 (s, 3H); 3.39 (t, J=6.0 Hz, 2H); 2.61 (s, 3H); 0.87 (s, 9H). LCMS-ESI⁺ (min): [M+H]⁺ calcd for C₂₆H₂₇N₂O₅S: 479.16 (M+H⁺). Found: 479.00, 480.02 (M+H⁺).

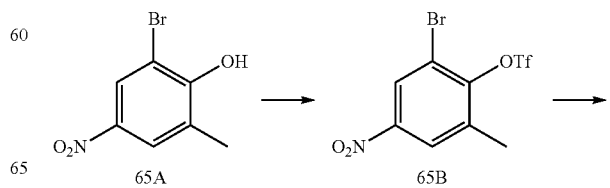

65A → 65B →

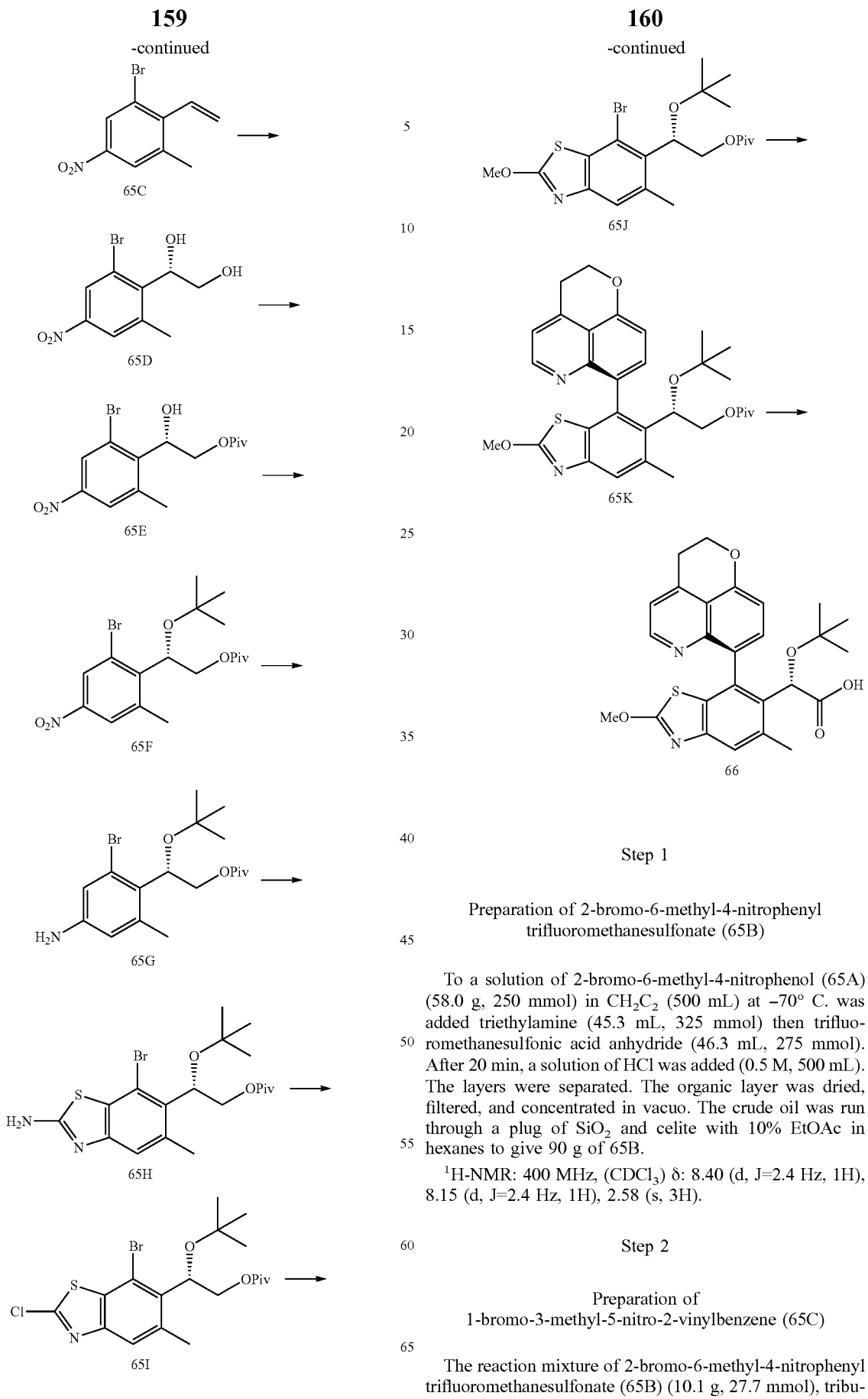

Step 1

Preparation of 2-bromo-6-methyl-4-nitrophenyl trifluoromethanesulfonate (65B)

To a solution of 2-bromo-6-methyl-4-nitrophenol (65A) (58.0 g, 250 mmol) in $CH_2C_2$ (500 mL) at −70° C. was added triethylamine (45.3 mL, 325 mmol) then trifluoromethanesulfonic acid anhydride (46.3 mL, 275 mmol). After 20 min, a solution of HCl was added (0.5 M, 500 mL). The layers were separated. The organic layer was dried, filtered, and concentrated in vacuo. The crude oil was run through a plug of $SiO_2$ and celite with 10% EtOAc in hexanes to give 90 g of 65B.

$^1$H-NMR: 400 MHz, ($CDCl_3$) δ: 8.40 (d, J=2.4 Hz, 1H), 8.15 (d, J=2.4 Hz, 1H), 2.58 (s, 3H).

Step 2

Preparation of 1-bromo-3-methyl-5-nitro-2-vinylbenzene (65C)

The reaction mixture of 2-bromo-6-methyl-4-nitrophenyl trifluoromethanesulfonate (65B) (10.1 g, 27.7 mmol), tributylvinyltin (8.18 ml, 27.7 mmol), LiCl (1.4 g, 33.2 mmol), PdCl$_2$dppf (607 mg, 0.83 mmol) in DMF (50 ml) was reacted at 70° C. for 3 h. Then 2N NaOH was added and stirred at 70° C. for 5 min. The reaction mixture was cooled down, washed by sat. NaHCO$_3$, extracted by EtOAc, dry over MgSO$_4$, filtered, concentrated down and purified by silica gel column, eluting by 0-100% EtOAc in Hexanes to give 65C (1.9 g, 30%). $^1$H-NMR: 400 MHz, (CDCl$_3$) δ: 8.30 (d, J=0.8 Hz, 1H), 8.03 (d, J=1 Hz, 1H), 6.71-6.64 (dd, J=18, 12 Hz, 1H), 5.77-5.74 (d, J=12 Hz, 1H), 5.51-5.46 (d, J=18 Hz, 1H), 2.48 (s, 3H).

Step 3

Preparation of (S)-1-(2-bromo-6-methyl-4-nitrophenyl)ethane-1,2-diol (65D)

The reaction mixture of 1-bromo-3-methyl-5-nitro-2-vinylbenzene (65C) (12.3 g, 50.83 mmol), AD-mix a (71 g), MeSO$_2$NH$_2$ (4.8 g, 50.8 mmol) in t-butyl alcohol/H2O (1:1) (200 ml) was stirred at 0° C. for 3 days. Na$_2$SO$_3$ (~6 g) was added to quench the reaction, stirred at rt for 40 min. The reaction mixture was washed by water, extracted by EtOAc, dry over MgSO$_4$, filtered, concentrated down and purified by silica gel column, eluting by 0-100% EtOAc in Hexanes to give 6.96 g of 65D and recovered 2.3 g of 65C.

$^1$H-NMR: 400 MHz, (CDCl$_3$) δ: 8.25 (d, J=2 Hz, 1H), 7.98 (d, J=2 Hz, 1H), 5.55 (m, 1H), 3.93 (dd, J=11, 9 Hz, 1H), 3.77 (dd, J=11, 4 Hz), 2.66 (s, 3H).

Step 4

Preparation of (S)-2-(2-bromo-6-methyl-4-nitrophenyl)-2-hydroxyethyl pivalate (65E)

To a suspension of (S)-1-(2-bromo-6-methyl-4-nitrophenyl)ethane-1,2-diol (65D) (6.96 g, 25.22 mmol) in DCM (100 ml), was added pyridine (5 mL) at 0° C. To the solution was added pivaloyl chloride (PivCl) slowly at 0 OC. The reaction mixture was stirred at 0 OC for 5 min, then raised to rt, stirred at rt for 5 h. The reaction mixture was washed by sat. NaHCO$_3$, extracted by DCM, dry over MgSO$_4$, filtered, purified by silica gel column, eluting by 0-40% EtOAc in Hexanes to give 9.13 g of 65E. The product taken on without full characterization.

Step 5

Preparation of (S)-2-(2-bromo-6-methyl-4-nitrophenyl)-2-tert-butoxyethyl pivalate (65F)

To a solution of (S)-2-(2-bromo-6-methyl-4-nitrophenyl)-2-hydroxyethyl pivalate (65E) in t-butyl acetate at 0 OC, was added HClO$_4$ (perchloric acid) (5.45 ml) slowly, stirred at 0° C. for 5 min, then the reaction mixture was warmed up to rt and stirred for 3 hs. The mixture was diluted by EtOAc, washed by sat. NaHCO$_3$, extracted by EtOAc, dry over MgSO$_4$, filtered, concentrated down and purified by silica gel column, eluting by 0-100% EtOAc in Hexanes to give 65F (9 g, 85%).

$^1$H-NMR: 400 MHz, (CDCl$_3$) δ: 8.23 (d, J=1 Hz, 1H), 7.96 (d, J=1.2 Hz, 1H), 5.58-5.54 (m, 1H), 4.30-4.25 (m, 1H), 4.16-4.12 (m, 1H), 2.71 (s, 3H), 1.154 (s, 9H), 1.151 (s, 9H).

Step 6

Preparation of (S)-2-(2-amino-7-bromo-5-methylbenzo[d]thiazol-6-yl)-2-tert-butoxyethyl pivalate (65H)

To a solution of S)-2-(2-bromo-6-methyl-4-nitrophenyl)-2-tert-butoxyethyl pivalate (9 g, 21.63 mmol) in EtOH (50 ml) and EtOAc (50 ml) was added Pt/C (1.5 g), attached with a balloon of H$_2$. More Pt/C (500 mg) Was added after 3 h. Then the reaction mixture was stirred at rt for another 21 h. The reaction mixture was filtered over celite, concentrated down to give product (S)-2-(4-amino-2-bromo-6-methylphenyl)-2-tert-butoxyethyl pivalate (65G) and went to next step without purification. To a solution of (S)-2-(4-amino-2-bromo-6-methylphenyl)-2-tert-butoxyethyl pivalate (65G) (21.63 mmol) in HOAc/THF (80 ml, 1:1) was added KSCN at 0° C. The reaction mixture was stirred at 0 OC for 0.5 h. Then Br$_2$ was added slowly, reacted at 0° C. The reaction was quenched by adding sat. NaHSO$_3$, extracted by EtOAc, dried over MgSO$_4$, purified by silica gel column, eluting by 0-40% EtOAc in Hexanes to give 65H (2.3 g, 24% over 2 steps).

$^1$H-NMR 400 MHz, (CD$_3$OD) δ: 7.15 (s, 1H), 5.51 (t, J=7 Hz, 1H), 4.28 (m, 1H), 4.14 (m, 1H), 2.62 (s, 3H), 1.15 (s, 9H), 1.10 (s, 9H).

LCMS-ESI$^+$: calc'd for C$_{19}$H$_{27}$BrN$_2$O$_4$S: 443.1 (M+H$^+$). Found: 443.1 (M+H$^+$).

Step 7

Preparation of (S)-2-(7-bromo-2-chloro-5-methylbenzo[d]thiazol-6-yl)-2-tert-butoxyethyl pivalate (65I)

The reaction mixture of (S)-2-(2-amino-7-bromo-5-methylbenzo[d]thiazol-6-yl)-2-tert-butoxyethyl pivalate (65H) (100 mg, 0.226 mmol), t-butyl nitrite (32 ul, 0.271 mmol), CuCl$_2$ (36 mg, 0.271 mmol) in acetonitrile (1.5 ml) was reacted at rt. The reaction mixture was diluted by EtOAc, washed by water, extracted by EtOAc, dried over MgSO$_4$, filtered, concentrated down and purified by silica gel column, eluting by 0-40% EtOAc in Hexanes to give 65I (90 mg, 86%).

LCMS-ESI$^+$: calc'd for C$_{19}$H$_{25}$ClBrNO$_3$S: 462.0 (M+H$^+$). Found: 462.1 (M+H$^+$).

Step 8

Preparation of (S)-2-(7-bromo-2-methoxy-5-methylbenzo[d]thiazol-6-yl)-2-tert-butoxyethyl pivalate (65J)

The reaction mixture of (S)-2-(7-bromo-2-chloro-5-methylbenzo[d]thiazol-6-yl)-2-tert-butoxyethyl pivalate (65I) (90 mg, 0.195 mmol), NaOMe in MeOH (25% wt, 66 ul) in MeOH (3 ml) was heated at 50° C. for 20 min in sealed microwave vial. The reaction mixture was washed by sat. NaHCO$_3$, extracted by EtOAc, dried over MgSO$_4$, filtered, concentrated down and purified by silica gel column, eluting by 0-100% EtOAc in Hexanes to give 65J (70 mg, 79%).

LCMS-ESI$^+$: calc'd for C$_{20}$H$_{28}$BrNO$_4$S: 458.1 (M+H$^+$). Found: 458.1 (M+H$^+$).

Step 9

Preparation of (S)-2-tert-butoxy-2-((S)-7-(2,3-dihydropyrano[4,3,2-de]quinolin-7-yl)-2-methoxy-5-methylbenzo[d]thiazol-6-yl)ethyl pivalate (65K)

The reaction mixture of (S)-2-(7-bromo-2-methoxy-5-methylbenzo[d]thiazol-6-yl)-2-tert-butoxyethyl pivalate (65K) (70 mg, 0.153 mmol), 2,3-dihydropyrano[4,3,2-de]quinolin-7-ylboronic acid hydrochloride (58 mg, 0.23 mmol), 2N K$_2$CO$_3$ (380 ul), Pd(PPh$_3$)$_4$ (17 mg, 0.015 mmol) in DME (3 ml) was heated at 90° C. overnight. The reaction mixture was washed by sat. NaHCO$_3$, extracted by EtOAc, dried over MgSO$_4$, filtered, concentrated down and purified by silica gel column, eluting by 0-100% EtOAc in Hexanes to give 65K.

LCMS-ESI$^+$: calc'd for C$_{31}$H$_{36}$N$_2$O$_5$S: 549.2 (M+H$^+$). Found: 549.0 (M+H$^+$).

Step 10

Preparation of (S)-2-tert-butoxy-2-((S)-7-(2,3-dihydropyrano[4,3,2-de]quinolin-7-yl)-2-methoxy-5-methylbenzo[d]thiazol-6-yl)ethanol The mixture of (S)-2-tert-butoxy-2-((S)-7-(2,3-dihydropyrano[4,3,2-de]quinolin-7-yl)-2-methoxy-5-methylbenzo[d]thiazol-6-yl)ethyl pivalate (65K) (20 mg, 0.036 mmol), 2N NaOH (360 ul) in THF/MeOH (1:1, 2 ml) was stirred at 40° C. overnight. The reaction mixture then was washed by sat. NaHCO$_3$, extracted by EtOAc, dried over MgSO$_4$, filtered, concentrated down and purified by silica gel column, eluting by 0-100% EtOAc in Hexanes to give the product (11 mg).

LCMS-ESI$^+$: calc'd for C$_{26}$H$_{28}$N$_2$O$_4$S: 465.2 (M+H$^+$). Found: 465.7 (M+H$^+$).

Step 11

Preparation of (S)-2-tert-butoxy-2-((S)-7-(2,3-dihydropyrano[4,3,2-de]quinolin-7-yl)-2-methoxy-5-methylbenzo[d]thiazol-6-yl)acetic acid (66)

To a solution of (S)-2-tert-butoxy-2-((S)-7-(2,3-dihydropyrano[4,3,2-de]quinolin-7 yl)-2-methoxy-5-methylbenzo[d]thiazol-6-yl)ethanol (11 mg, 0.024 mmol) in wet acetonitrile (0.75% v H2O), was added stock solution of H$_6$IO$_5$/CrO$_3$ (0.439 mmol, 500 ul) at 0° C. After the reaction was finished, the reaction was quenched by adding 1.5 M K$_2$HPO$_4$, extracted by EtOAc, the organic phase was washed by NaHSO$_3$/brine (1:1), dried over MgSO$_4$, filtered, concentrated down and purified by silica gel column, eluting by 20-80% EtOAc in hexanes to give 66 (3.1 mg).

$^1$H-NMR: 400 MHz, (CD$_3$OD) δ: 8.63 (d, J=4.4 Hz, 1H); 7.68 (d, J=8.0 Hz, 1H); 7.54 (s, 1H); 7.38 (d, J=4.8 Hz, 1H); 7.14 (d, J=7.6 Hz, 1H); 5.08 (s, 1H); 4.58-4.53 (m, 2H); 4.11 (s, 3H); 3.39 (t, J=6.0 Hz, 2H); 2.61 (s, 3H); 0.87 (s, 9H) ppm.

LCMS-ESI$^+$ (m/z): [M+H]$^+$ calcd for C$_{26}$H$_{27}$N$_2$O$_5$S: 479.16 (M+H$^+$). Found: 479.00, 480.02 (M+H$^+$).

Example 26

Preparation of (S)-2-tert-butoxy-2-((S)-7-(2,3-dihydropyrano[4,3,2-de]quinolin-7-yl)-3,5-dimethyl-2-oxo-2,3-dihydrobenzo[d]thiazol-6-yl)acetic acid (68)

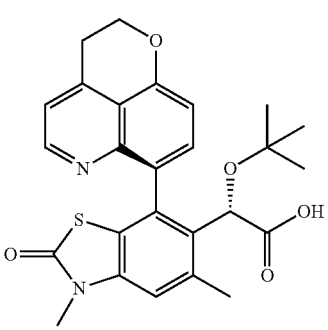

68

Compound 68: $^1$H-NMR: 400 MHz, (CDCl$_3$) δ: 8.66 (d, J=4.0 Hz, 1H); 7.69 (d, J=8.4 Hz, 1H); 7.29 (d, J=4.0 Hz, 1H); 7.16 (d, J=8.4 Hz, 1H); 6.97 (s, 1H); 4.94 (s, 1H); 4.59 (dd, J$_1$=5.2 Hz, J$_2$9.6 Hz, 2H); 3.44 (s, 3H); 3.39 (t, J=5.6 Hz, 2H); 2.64 (2, 3H); 0.90 (s, 9H). LCMS-ESI$^+$ (m/z): [M+H]$^+$ calcd for C$_{26}$H$_{27}$N$_2$O$_5$S: 479-0.16 (M+H$^+$). Found: 479.04, 480.06 (M+H$^+$).

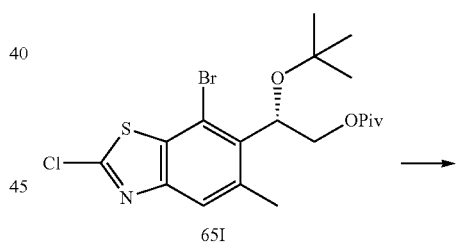

65I

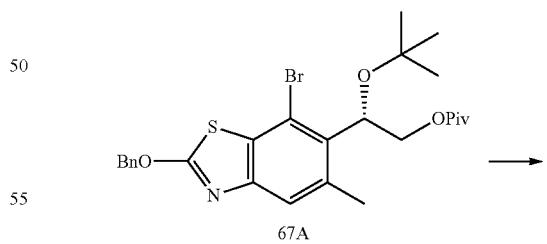

67A

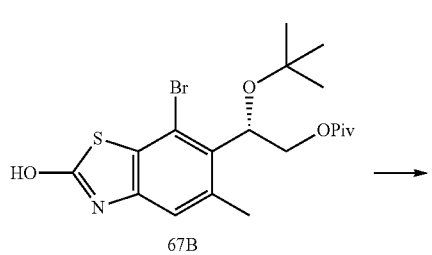

67B

-continued

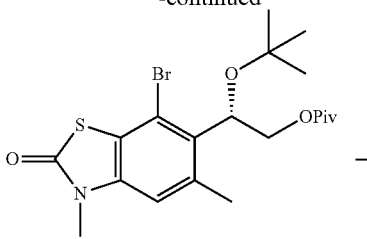

67C

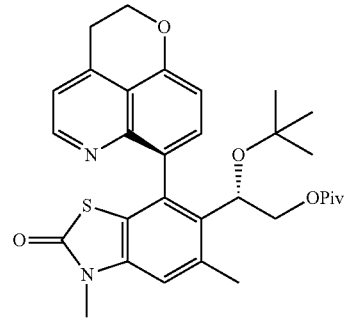

67D

Step 1

Preparation of (S)-2-(2-(benzyloxy)-7-bromo-5-methylbenzo[d]thiazol-6-yl)-2-tert-butoxyethyl pivalate (67A)

NaH (415 mg, 10.38 mmol) was added to BnOH, stirred at it for 0.5 h. The NaOBn solution was transferred to a flask charged with (S)-2-(7-bromo-2-chloro-5-methylbenzo[d]thiazol-6-yl)-2-tert-butoxyethyl pivalate (65I) (1.6 g, 3.46 mmol). The reaction mixture was heated at 60° C. for 45 min. The reaction mixture was washed by sat NaHCO₃, extracted by EtOAc, the organic phase was washed by brine, dry over MgSO₄, filtered, concentrated down, distilled most NaOH off. The residue was purified by silica gel column, eluting by 0-50% EtOAc in hexanes.

¹H-NMR: 400 MHz, (CDCl₃) δ: 7.52-7.24 (m, 6H), 5.58 (s, 2H), 5.57-5.45 (m, 1H), 4.35-4.27 (m, 1H), 4.18-4.12 (m, 1H), 2.68 (s, 3H), 1.07 (s, 18H).

Step 2

Preparation of (S)-2-(7-bromo-2-hydroxy-5-methyl-benzo[d]thiazol-6-yl)-2-tert-butoxyethyl pivalate (67B)

The mixture of (S)-2-(2-(benzyloxy)-7-bromo-5-methyl-benzo[d]thiazol-6-yl)-2-tert-butoxyethyl pivalate (67A), Pd/C (800 mg) in EtOAc/EtOH (10 ml, 1:1) was charged into a flask with a H₂ balloon, and stirred at rt for 1 h. The reaction mixture was filtered over celite, concentrated down, purified by silica gel column, eluting by 0-50% EtOAc in hexanes to give 67B (850 mg).

¹H-NMR: 400 MHz, (CDCl₃) δ: 8.99 (s, 1H), 6.88 (s, 1H), 5.45 (t, J=7 Hz, 4.26-4.22 (m, 1H), 4.14-4.09 (m, 1H), 2.62 (s, 3H), 1.13 (s, 18H).

Step 3

Preparation of (S)-2-(7-bromo-3,5-dimethyl-2-oxo-2,3-dihydrobenzo[d]thiazol-6-yl)-2-tert-butoxyethyl pivalate (67C)

To a solution of (S)-2-(7-bromo-2-hydroxy-5-methyl-benzo[d]thiazol-6-yl)-2-tert-butoxyethyl pivalate (67B) (40 mg, 0.090 mmol) in THF (1 ml) was added KOtBu (0.14 ml, 0.135 mmol, 1M in THF) slowly at −78 OC. After 15 min, MeI (8.5 ul, 0.135 mmol) was added at −78° C. and stirred at −78° C. for 15 min. Then the reaction was reacted at rt for 3 hs. The reaction mixture was washed by sat. NaHCO₃, extracted by EtOAc, dried over MgSO₄, filtered, concentrated down and purified by silica gel column, eluting by 0-40% EtOAc in hexanes to give 67C (30 mg, 73%).

¹H-NMR: 400 MHz, (CDCl₃) δ: 6.79 (s, 1H), 5.49-5.45 (m, 1H), 4.27-4.23 (m, 1H), 4.14-4.10 (m, 1H), 3.40 (s, 3H), 2.66 (s, 3H), 1.46 (s, 18H).

Step 4

Preparation of (S)-2-tert-butoxy-2-((S)-7-(2,3-dihydropyrano[4,3,2-de]quinolin-7-yl)-3,5=dimethyl-2-oxo-2,3-dihydrobenzo[d]thiazol-6-yl)ethyl pivalate (67D)

The reaction mixture of (S)-2-(7-bromo-3,5-dimethyl-2-oxo-2,3-dihydrobenzo[d]thiazol-6-yl)-2-tert-butoxyethyl pivalate (67C) (20 mg, 0.044 mmol), 2,3-dihydropyrano[4,3,2-de]quinolin-7-ylboronic acid hydrochloride (16.5 mg, 0.066 mmol), 2N K₂CO₃ (0.12 ml, 0.22 mmol), Pd(PPh₃)₄ (5.0 mg, 0.0044 mmol) in DME (1 ml) was heated at 120° C. in sealed microwave vial for 3 hs. The reaction mixture was washed by sat. NaHCO₃, extracted by EtOAc, the organic phase was dried over MgSO₄, filtered, concentrated down and purified by silica gel column, eluting by 0-60% EtOAc in hexanes to give the product (15 mg, 62%).

LCMS-ESI⁺: calc'd for $C_{31}H_{36}N_2O_5S$: 549.2 (M+H⁺). Found: 549.0 (M+H⁺).

The remainder of the synthesis of compound 68 is analogous to the preparation of compound 66 from compound 65K in example 25.

Example 27

Preparation of compound (S)-2-tert-butoxy-2-((S)-7-(2,3-dihydropyrano[4,3,2-de]quinolin-7-yl)-2-isopropoxy-5-methylbenzo[d]thiazol-6-yl)acetic acid (70)

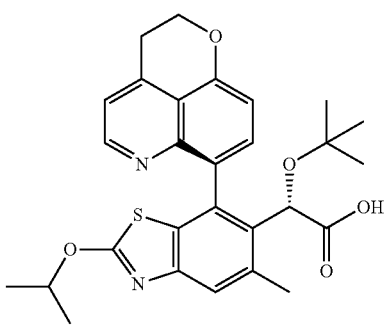

70

Compound 70: ¹H-NMR: 400 MHz, (CDCl₃) δ: 8.60 (d, J=4.8 Hz, 1H); 7.76 (d, J=7.6 Hz, 1H); 7.57 (s, 1H); 7.28-7.26 (m, 1H); 7.15 (d, J=8.0 Hz, 1H); 5.37-5.30 (m, 1H); 4.97 (s, 1H); 4.61-4.57 (m, 2H); 3.39 (t, J=6.2 Hz, 2H); 2.64 (s, 3H); 1.39 (dd, J₁=6.4 Hz, J₂=14 Hz, 6H); 0.91 (s, 9H).

LCMS-ESI⁺ (m/z): [M+H]⁺ calcd for $C_{28}H_{31}N_2O_5S$: 507.19 (M+H⁺). Found: 507.01, 508.07 (M+H⁺).

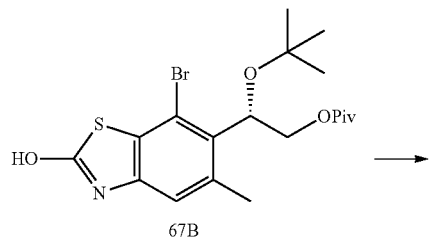

67B

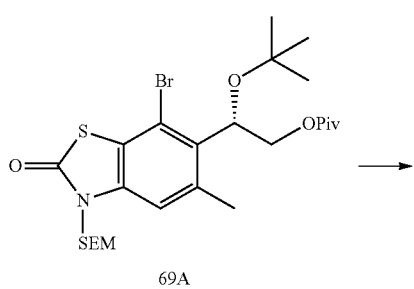

69A

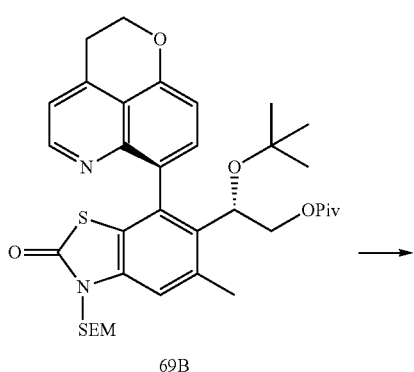

69B

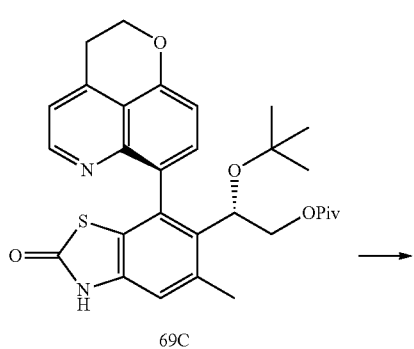

69C

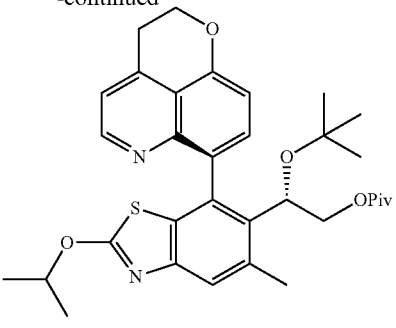

69D

Step 1

Preparation of (S)-2-(7-bromo-5-methyl-2-oxo-3-((2-(trimethylsilyl)ethoxy)methyl)-2,3-dihydrobenzo[d]thiazol-6-yl)-2-tert-butoxyethyl pivalate (69A)

Prepared by the similar method to make (S)-2-(7-bromo-3,5-dimethyl-2-oxo-2,3-dihydrobenzo[d]thiazol-6-yl)-2-tert-butoxyethyl pivalate (67C) in example 26 from 67B using 2-(trimethylsilyl)ethoxymethyl chloride (SEMCl) instead of methyl iodide.

¹H-NMR: 400 MHz, (CDCl₃) δ: 7.05 (s, 1H); 5.53-5.49 (s, 1H), 5.34 (s, 2H), 4.32-4.27 (m, 1H), 4.18-4.14 (m, 1H), 3.66 (t, J=8 Hz, 2H), 2.68 (s, 3H), 1.19 (s, 18H), 0.97-0.89 (m, 2H), 0.00 (s, 9H).

Step 2

Preparation of (S)-2-tert-butoxy-2-((S)-7-(2,3-dihydropyrano[4,3,2-de]quinolin-7-yl)-3,5-dimethyl-2-oxo-2,3-dihydrobenzo[d]thiazol-6-yl)ethyl pivalate (69B)

prepared by the similar method to make 67D from 67C in Example 26.

LCMS-ESI⁺: calc'd for $C_{36}H_{48}N_2O_6SSi$: 665.3 (M+H⁺). Found: 664.9 (M+H⁺).

Step 3

Preparation of (S)-2-tert-butoxy-2-((S)-7-(2,3-dihydropyrano[4,3,2-de]quinolin-7-yl)-5-methyl-2-oxo-2,3-dihydrobenzo[d]thiazol-6-yl)ethyl pivalate (69C)

The reaction mixture of (S)-2-tert-butoxy-2-((S)-7-(2,3-dihydropyrano[4,3,2-de]quinolin-7-yl)-3,5-dimethyl-2-oxo-2,3-dihydrobenzo[d]thiazol-6-yl)ethyl pivalate (69B) (250 mg, 0.376 mmol), TBAF (1M in THF, 1.1 ml, 1.1 mmol) in DME was heated at 120° C. in sealed microwave vial for 3 h. The reaction mixture was cooled down, washed by sat. NaHCO₃, extracted by EtOAc, the organic phase was dried over MgSO₄, filtered, concentrated down and purified by silica gel column, eluting by 0-100% EtOAc in hexanes to give 69C (30 mg, 15%).

LCMS-ESI⁺: calc'd for $C_{30}H_{34}N_2O_5S$: 535.2 (M+H⁺). Found: 535.0 (M+H⁺).

Step 4

Preparation of (S)-2-tert-butoxy-2-((S)-7-(2,3-dihydropyrano[4,3,2-de]quinolin-7-yl)-2-isopropoxy-5-methylbenzo[d]thiazol-6-yl)ethyl pivalate (69D)

The reaction mixture of (S)-2-tert-butoxy-2-((S)-7-(2,3-dihydropyrano[4,3,2-de]quinolin-7-yl)-5-methyl-2-oxo-2,3-dihydrobenzo[d]thiazol-6-yl)ethyl pivalate (69C) (30 mg, 0.056 mmol), Ag$_2$CO$_3$ (50% wt on celite, 310 mg, 0.56 mmol), isopropy bromide (160 ul, 1.68 mmol) in benzene/DME (1:1, 2 ml) was heated at 70° C. overnight. The reaction mixture was washed by water, extracted by EtOAc, the organic phase was dried over MgSO$_4$, filtered, concentrated down and purified by silica gel column, eluting by 0-60% EtOAc in hexanes to give the product (15 mg, 46%).

LCMS-ESI$^+$: calc'd for C$_{33}$H$_{40}$N$_2$O$_5$S: 577.3 (M+H$^+$). Found: 577.0 (M+H$^+$).

The remainder of the synthesis of compound 70 is analogous to the preparation of compound 66 from compound 65K in example 25.

Example 28

Preparation of (S)-2-tert-butoxy-2-((S)-7-(2,3-dihydropyrano[4,3,2-de]quinolin-7-yl)-5-methyl-2-oxo-3-(2-(trifluoromethyl)benzyl)-2,3-dihydrobenzo[d]thiazol-6-yl)acetic acid (71)

Compound 71 was prepared from compound 69C according to the procedure used to prepare compound 67C (except that 1-(bromomethyl)-2-(trifluoromethyl)benzene was used instead of methyl iodide) in Example 26, and the remainder of the synthesis of compound 71 is analogous to the preparation of compound 66 from compound 65K in example 25.

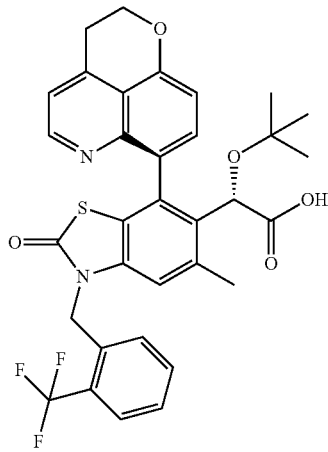

71

Compound 71: $^1$H-NMR 400 MHz, (CDCl$_3$) δ: 8.72 (s, 1H); 7.76-7.73 (m, 2H); 7.50 (t, J=7.6 Hz, 1H); 7.42 (t, J=7.4 Hz, 1H); 7.33 (t, J=4.0 Hz, 1H); 7.2 (d, J=8.0 Hz, 1H); 7.13 (d, J=6.8 Hz, 1H); 6.72 (s, 1H); 5.34 (s, 1H); 4.95 (s, 1H); 4.65-4.60 (m, 2H); 3.42 (t, J=5.4 Hz, 2H); 2.52 (2, 3H); 0.88 (s, 9H).

$^{19}$F NMR (377 MHz, CDCl$_3$) δ -60.73. LCMS-ESI$^+$ (m/z): [M+H]$^+$ calcd for C$_{33}$H$_{30}$F$_3$N$_2$O$_4$S: 623.18 (M+H$^+$). Found: 623.09, 624.09 (M+H$^+$).

Example 29

Preparation of (S)-2-((S)-3-benzyl-7-(2,3-dihydropyrano[4,3,2-de]quinolin-7-yl)-5-methyl-2-oxo-2,3-dihydrobenzo[d]thiazol-6-yl)-2-tert-butoxyacetic acid (72)

Compound 72 was prepared from compound 69C according to the procedure used to prepare compound 67C (except that benzyl bromide was used instead of methyl iodide) in Example 26, and the remainder of the synthesis of compound 72 is analogous to the preparation of compound 66 from compound 65K in example 25.

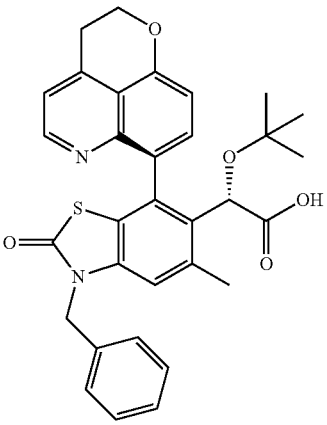

72

Compound 72: $^1$H-NMR: 400 MHz, (CDCl$_3$) δ: 8.67 (d, J=4.0 Hz, 1H); 7.70 (d, J=8.4 Hz, 1H); 7.37-7.36 (m, 4H); 7.34-7.29 (m, 2H); 7.16 (d, J=8.4 Hz, 1H); 6.92 (s, 1H); 5.21-5.01 (dd, J$_1$=15.6 Hz, J$_2$=79.6 Hz, 2H); 4.92 (s, 1H); 4.63-41.56 (m, 2H); 3.39 (t, J=5.8 Hz, 2H); 2.55 (s, 3H); 0.88 (s, 9H). LCMS-ESI$^+$ (m/z): [M+H]$^+$ calcd for C$_{32}$H$_{31}$N$_2$O$_5$S: 555.19 (M+H$^+$). Found: 555.08, 556.12 (M+H$^+$).

Example 30

Preparation of (S)-2-tert-butoxy-2-((S)-7-(2,3-dihydropyrano[4,3,2-de]quinolin-7-yl)-5-methyl-2-oxo-3-(3-(trifluoromethyl)benzyl)-2,3-dihydrobenzo[d]thiazol-6-yl)acetic acid (73)

Compound 73 was prepared from compound 69C according to the procedure used to prepare compound 67C (except that 1-(bromomethyl)-3-(trifluoromethyl)benzene was used instead of methyl iodide) in Example 26, and the remainder of the synthesis of compound 73 is analogous to the preparation of compound 66 from compound 65K in example 25.

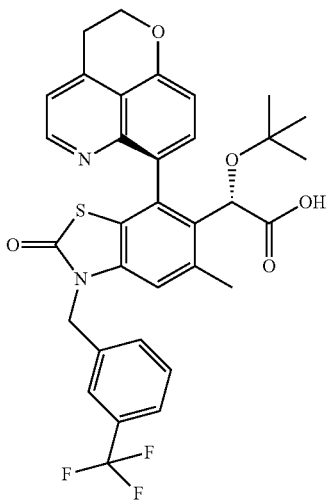

73

Compound 73: ¹H-NMR: 400 MHz, (CDCl₃) δ: 8.68 (s, 1H); 7.71 (d, J=7.6 Hz, 1H); 7.64 (s, 1H); 7.59 (d, J=6.4 Hz, 1H); 7.51-7.48 (m, 2H); 7.32 (d, J=3.2 Hz, 1H); 7.18 (d, J=7.6 Hz, 1H); 6.87 (s, 1H); 5.25-5.06 (dd, J₁=16 Hz, J₂=63.2 Hz, 2H); 4.94 (s, 1H); 4.65-4.59 (m, 2H); 3.43 (t, J=5.2 Hz, 2H); 2.56 (s, 3H); 0.88 (s, 9H). LCMS-ESI⁺ (m/z): [M+H]⁺ calcd for C₂₇H₂₉N₃O₄S: 623.18 (M+H⁺). Found: 623.04, 624.09 (M+H⁺).

Example 31

Preparation of (S)-2-tert-butoxy-2-((S)-7-(2,3-dihydropyrano[4,3,2-de]quinolin-7-yl)-5-methyl-2-oxo-3-(4-(trifluoromethyl)benzyl)-2,3-dihydrobenzo[d]thiazol-6-yl)acetic acid (74)

Compound 74 was prepared from compound 69C according to the procedure used to prepare compound 67C (except that 1-(bromomethyl)-4-(trifluoromethyl)benzene was used instead of methyl iodide) in Example 26, and the remainder of the synthesis of compound 74 is analogous to the preparation of compound 66 from compound 65K in example 25.

74

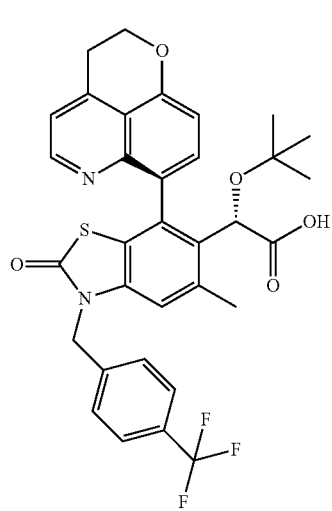

Compound 74: ¹H-NMR: 400 MHz, (CDCl₃) δ: 8.67 (d, J=4.4 Hz, 1H); 7.70 (d, J=8.0 Hz, 1H); 7.63 (d, J=8.0 Hz, 1H); 7.46 (d, J=7.6 Hz, 1H); 7.31 (d, J=4.0 Hz, 1H); 6.86 (s, 1H); 5.25-5.07 (dd, J₁=16, J₂=56.8 Hz, 2H); 4.93 (s, 1H); 4.63-4.58 (m, 2H); 3.40 (t, J=5.8 Hz, 2H); 2.56 (s, 3H); 0.88 (s, 9H). LCMS-ESI⁺ (m/z): [M+H]⁺ calcd for C₃₃H₃₀F₃N₂O₅S: 623.18 (M+H⁺). Found: 623.06, 624.14 (M+H⁺).

Example 32

Preparation of (S)-2-((S)-2-(azetidin-1-yl)-7-(2,3-dihydropyrano[4,3,2-de]quinolin-7-yl)-4-fluoro-5-methylbenzo[d]thiazol-6-yl)-2-tert-butoxyacetic acid (76)

76

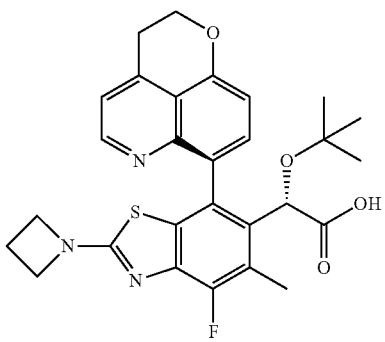

Compound 76: ¹H-NMR: 400 MHz, (CD₃OD) δ: 8.65 (d, J=4.4 Hz, 1H); 7.70 (d, J=7.6 Hz, 1H); 7.39 (d, J=4.4 Hz, 1H); 7.16 (d, J=7.6 Hz, 1H); 5.04 (s, 1H); 4.57 (t, J=6.0 Hz, 2H); 4.15-4.10 (m, 4H); 3.41 (t, J=6.0 Hz, 2H); 2.50-2.46 (m, 6H); 0.90 (s, 9H). LCMS-ESI⁺ (m/z): [M+H]⁺ calcd for C₂₈H₂₉FN₃O₄S: 522.19 (M+H⁺). Found: 521.99, 523.00 (M+H⁺).

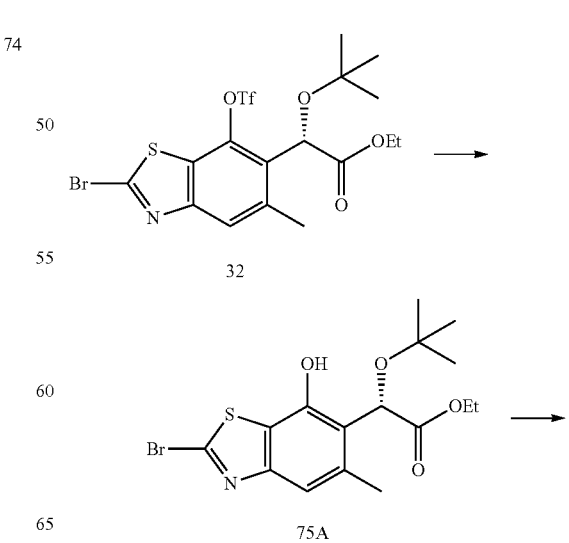

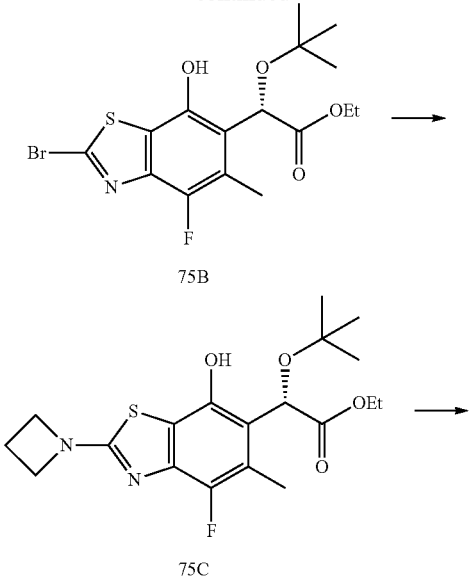

Step 1

Preparation of (S)-ethyl 2-(2-bromo-7-hydroxy-5-methylbenzo[d]thiazol-6-yl)-2-tert-butoxyacetate (75A)

To a solution of (S)-ethyl 2-(2-bromo-5-methyl-7-(trifluoromethylsulfonyloxy)benzo[d]thiazol-6-yl)-2-tert-butoxyacetate (32): (500 mg, 0.938 mmol) in THF (5 ml) was added TBAF (1.0 M in THF, 4 ml) slowly. The reaction mixture was stirred at rt for 1 h. The reaction mixture was washed by a mixture of $H_2O$ (20 ml) and HOAc (200 ul), extracted by EtOAc, the organic phase was washed by sat. NaHCO$_3$, dried over MgSO$_4$, filtered, concentrated down and purified by silica gel column, eluting by 0-40% EtOAc in hexanes to give 75A (380 mg). LCMS-ESI$^+$: calc'd for $C_{16}H_{20}BrNO_4S$: 402.0 (M+H$^+$). Found: 401.9 (M+H$^+$).

Step 2

Preparation of (S)-ethyl 2-(2-bromo-4-fluoro-7-hydroxy-5-methylbenzo[d]thiazol-6-yl)-2-tert-butoxyacetate (75B)

The reaction mixture of (S)-ethyl 2-(2-bromo-7-hydroxy-5-methylbenzo[d]thiazol-6-yl)-2-tert-butoxyacetate (75A) (380 mg, 0.948 mmol), Selectfluor (1.9 g, 4.74 mmol) in acetonitrile (7 ml) was reacted at 0° C. for 5 days. The reaction mixture was washed by 1.5 M KH$_2$PO$_4$, extracted by EtOAc, the organic phase was dried over MgSO$_4$, filtered, concentrated down and purified by silica gel column, eluting by 0-40% EtOAc in hexanes to give 75B (137 mg, 35%). LCMS-ESI$^+$: calc'd for $C_{16}H_{19}FNO_4S$: 420.0 (M+H$^+$). Found: 420.1 (M+H$^+$).

Step 3

Preparation of (S)-ethyl 2-(2-(azetidin-1-yl)-4-fluoro-7-hydroxy-5methylbenzo[d]thiazol-6-yl)-2-tert-butoxyacetate (75C)

Prepared by the similar method to make (S)-ethyl 2-(2-(azetidin-1-yl)-5-methyl-7-(trifluoromethylsulfonyloxy)benzo[d]thiazol-6-yl)-2-tert-butoxyacetate (33) in Example 10. LCMS-ESI$^+$: calc'd for $C_{19}H_{25}FN_2O_4S$: 397.2 (M+H$^+$). Found: 397.0 (M+H$^+$).

Step 4

Preparation of (S)-ethyl 2-(2-(azetidin-1-yl)-4-fluoro-5-methyl-7-(bifluoromethylsulfonyloxy)benzo[d]thiazol-6-yl)-2-tert-butoxyacetate (75D)

The reaction mixture of S)-ethyl 2-(2-(azetidin-1-yl)-4-fluoro-7-hydroxy-5methylbenzo[d]thiazol-6-yl)-2-tert-butoxyacetate (75C) (50 mg, 0.126 mmol), N-phenyl triflimite (90 mg, 0.252 mmol), Cs$_2$CO$_3$ (82 mg, 0.126 mmol) in THF (2 ml) was stirred at rt. After the reaction finished, the reaction was washed by sat NaHCO$_3$, extracted by EtOAc, the organic phase was dried over MgSO$_4$, filtered, concentrated down and purified by silica gel column, eluting by 0-40% EtOAc in hexanes to give 75D (50 mg, 75%). LCMS-ESI$^+$: calc'd for $C_{20}H_{24}F_4N_2O_6S_2$: 529.1 (M+H$^+$). Found: 529.0 (M+H$^+$).

The remainder of the synthesis of compound 76 is analogous to the preparation of compound 35 from compound 33 in example 10.

Example 33

Preparation of (S)-2-tert-butoxy-2-((S)-2-cyclopentenyl-7-(2,3-dihydropyrano[4,3,2-de]quinolin-7-yl)-5-methylbenzo[d]thiazol-6-yl)acetic acid (78) and (S)-2-tert-butoxy-2-((R)-2-cyclopentenyl-7-(2,3-dihydropyrano[4,3,2-de]quinolin-7-yl)-5-methylbenzo[d]thiazol-6-yl)acetic acid (79)

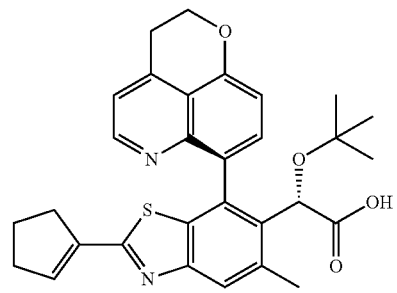

78

Compound 78: $^1$H-NMR: 400 MHz, (CD$_3$OD) δ:8.78 (d, J=5.6 Hz, 1H); 7.99 (s, 1H); 7.90 (d, J=8.0 Hz, 1H); 7.85 (d, J=5.6 Hz, 1H); 7.43 (d, J=7.6 Hz, 1H); 6.58 (s, 1H); 5.23 (s, 1H); 4.72-4.69 (m, 2H); 3.66 (t, J=5.8 Hz, 2H); 2.85-2.83 (m, 2H); 2.76 (s, 3H); 2.56 (m, 2H), 2.07-2.02 (m, 2H); 0.941 (s, 9H).

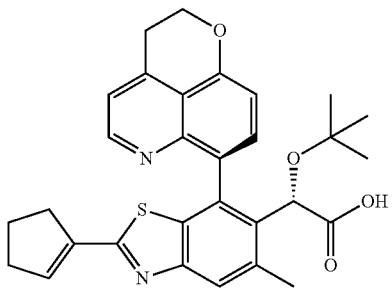

79

Compound 79: $^1$H-NMR: 400 MHz, (CD$_3$OD) δ: 8.71 (d, J=5.2 Hz, 1H); 8.22 (d, J=8.0 Hz, 1H); 7.97 (s, 1H); 7.77 (d, J=6.0 Hz, 1H); 7.47 (d, J=8.0 Hz, 1H); 6.56 (s, 1H); 5.27 (s, 1H); 4.70 (t, J=6.0 Hz, 2H); 3.63 (t, J=6.2 Hz, 2H); 2.84-2.83 (m, 2H); 2.72 (s, 3H); 2.55-2.54 (m, 2H); 2.07-2.03 (m, 2H); 0.94 (s, 9H).

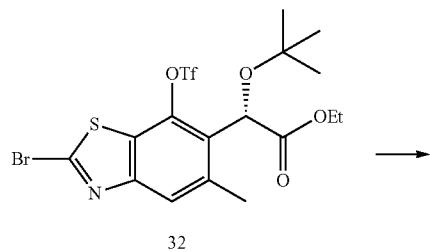

32

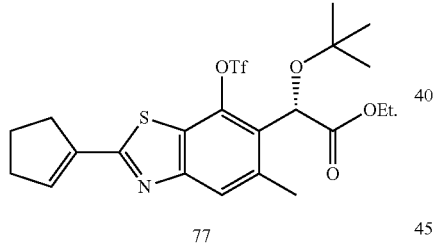

77

Preparation of (S)-ethyl 2-tert-butoxy-2-(2-cyclopentenyl-5-methyl-7-(trifluoromethylsulfonyloxy)benzo[d]thiazol-6-yl)acetate (77)

To a solution of 32 (100 mg, 0.19 mmol) in toluene (1 mL), ethanol (0.5 mL), water (0.5 mL) was added potassium carbonate (77 mg, 0.56 mmol), cyclopentenylboronic acid (25 mg, 0.22 mmol), and Pd(PPh$_3$). (11 mg, 0.0094 mmol). The reaction mixture was stirred at 90° C. for 2 h. The reaction was cooled to rt and diluted with water and EtOAc. The layers were separated, dried, filtered, and concentrated in vacuo. The crude material was purified by column chromatography (EtOAc/hexanes) to give 96 mg of 77. $^1$H-NMR 400 MHz, (CDCl$_3$) δ: 7.82 (s, 1H), 6.72 (m, 1H), 5.60 (s, 1H), 4.17 (m, 1H), 4.11 (m, 1H), 2.92 (m, 2H), 2.63 (m, 2H), 2.53 (s, 3H), 2.10 (m, 2H), 1.17 (s, 9H), 1.13 (t, J=7 Hz, 3H).

The remainder of the synthesis of 78 and 79 follows the same route as Example 10 from compound 33.

Example 34

Preparation of (S)-2-tert-butoxy-2-((S)-2-cyclopentyl-7-(2,3-dihydropyrano[4,3,2-de]quinolin-7-yl)-5-methylbenzo[d]thiazol-6-yl)acetic acid (80) and (S)-2-tert-butoxy-2-((R)-2-cyclopentyl-7-(2,3-dihydropyrano[4,3,2-de]quinolin-7-yl)-5-methylbenzo[d]thiazol-6-yl)acetic acid (81)

Compound 80 was prepared from compound 78 according to the procedure used to prepare compound 8F from 8E in Example 4.

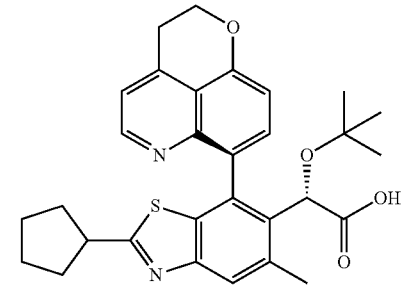

80

Compound 80: $^1$H-NMR: 400 MHz, (CD$_3$OD) δ: 8.77 (d, J=6.0 Hz, 1H); 7.96 (s, 1H); 7.88 (d, J=8.0 Hz, 1H); 7.83 (d, J=6.0 Hz, 1H); 7.42 (d, J=8.0 Hz, 1H); 5.23 (s, 1H); 4.73-4.69 (m, 2H); 3.67-3.64 (m, 2H); 3.53-3.44 (m, 1H); 2.75 (s, 1H); 2.17-2.14 (m, 2H); 1.81-1.71 (m, 6H); 0.90 (s, 9H).

Compound 81 was prepared from compound 79 according to the procedure used to prepare compound 8F from 8E in Example 4.

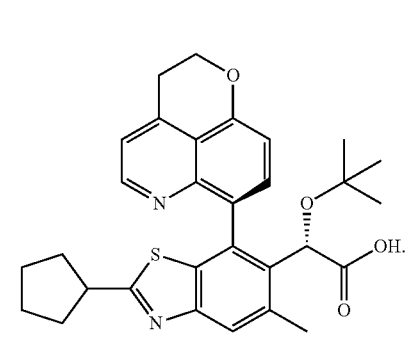

81

Compound 81: $^1$H-NMR: 400 MHz, (CD$_3$OD) δ: 8.67 (d, J=5.2 Hz, 1H); 8.15 (d, J=8.4 Hz, 1H); 7.90 (s, 1H); 7.68 (d, J=5.6 Hz, 1H); 7.41 (d, J=8.4 Hz, 1H); 5.27 (s, 1H); 4.69-4.65 (m, 2H); 4.67 (t, J=6.2 Hz, 2H); 3.59 (t, J=6.0 Hz, 2H); 3.50-3.42 (m, 1H); 2.71 (s, 3H); 2.16-2.13 (m, 2H); 1.78-1.70 (m, 6H); 0.90 (s, 9H).

Example 35

Preparation of (S)-2-tert-butoxy-2-((S)-2-cyclobutyl-7-(2,3-dihydropyrano[4,3,2-de]quinolin-7-yl)-S-methylbenzo[d]thiazol-6-yl)acetic acid (82)

Compound 82 was prepared from compound 32 according to the procedure used to prepare compound 77 in Example 33, except cyclobutyl zinc bromide was used instead of cyclopentenylboronic acid.

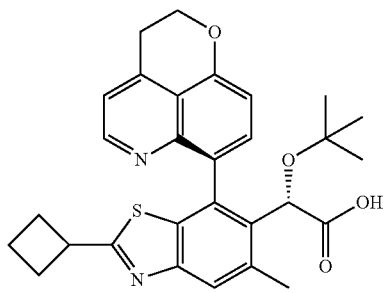

82

Compound 82: $^1$H-NMR 400 MHz, (CD$_3$OD) δ 8.79 (d, J=5.6 Hz, 1H), 7.98 (s, 1H), 7.87 (dd, J=13.1, 6.9 Hz, 2H), 7.44 (d, J=8.4 Hz, 1H), 5.23 (s, 1H), 4.71 (dt, J=11.5, 5.8 Hz, 2H), 3.91 (p, J=8.3 Hz, 1H), 3.67 (t, J=5.8 Hz, 3H), 2.76 (s, 3H), 2.50-2.40 (m, 2H), 2.39-2.27 (m, 2H), 2.19-2.05 (m, 1H), 0.91 (s, 9H). LCMS-ESI$^+$ (m/z): [M+H]$^+$ calcd for C$_{29}$H$_{31}$N$_2$O$_4$S: 503.20 (M+H$^+$). Found: 503.07, 504.10 (M+H$^+$).

Example 36

Preparation of (S)-2-tert-butoxy-2-((S)-7-(2,3-dihydropyrano[4,3,2-de]quinolin-7-yl)-2-isobutyl-5-methylbenzo[d]thiazol-6-yl)acetic acid (83) and (S)-2-tert-butoxy-2-((R)-7-(2,3-dihydropyrano[4,3,2-de]quinolin-7-yl)-2-isobutyl-5-methylbenzo[d]thiazol-6-yl)acetic acid (84)

Compounds 83 and 84 were prepared from compound 32 according to the procedure used to prepare compound 77 in Example 33, except tributyl(2-methylprop-1-enyl)stannane was used instead of cyclopentenylboronic acid. Also, hydrogenation was performed according to the procedure used to prepare 8F from 8E in Example 4.

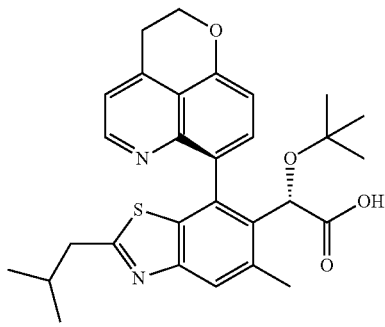

83

Compound 83: $^1$H-NMR: 400 MHz, (CD$_3$OD) δ: 8.74 (d, J=5.4 Hz, 1H), 7.95 (s, 1H), 7.85 (d, J=8.0 Hz, 1H), 7.74 (d, J=5.7 Hz, 1H), 7.37 (d, J=8.3 Hz, 1H), 5.22 (s, 1H), 4.69 (m, 2H), 3.61 (t, J=5.9 Hz, 2H), 2.90 (d, J=7.2 Hz, 2H), 2.75 (s, 3H), 0.97 (d, J=6.5 Hz, 6H), 0.91 (s, 9H). LCMS-ESI$^+$ (m/z): [M+H]$^+$ calcd for C$_{29}$H$_{33}$N$_2$O$_4$S: 505.22 (M+H$^+$). Found: 505.06, 506.06 (M+H$^+$).

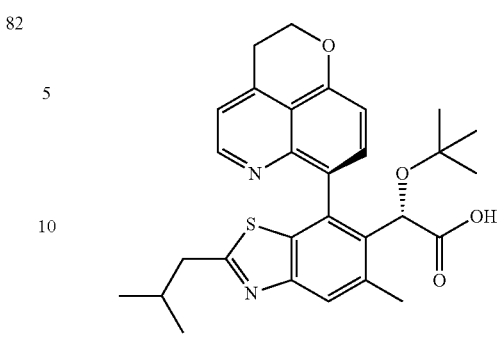

84

Compound 84: $^1$H-NMR: 400 MHz, (CD$_3$OD) δ 8.65 (d, J=5.2 Hz, 1H), 8.12 (d, J=8.1 Hz, 1H), 7.90 (s, 1H), 7.61 (d, J=5.1 Hz, 1H), 7.37 (d, J=8.2 Hz, 1H), 5.28 (s, 1H), 4.65 (t, J=6.1 Hz, 2H), 3.55 (t, J=5.9 Hz, 2H), 2.89 (d, J=7.2 Hz, 2H), 2.70 (s, 4H), 0.97 (dd, J=6.6, 3.2 Hz, 7H), 0.88 (s, 10H).
LCMS-ESI$^+$ (m/z): [M+H]$^+$ calcd for C$_{29}$H$_{33}$N$_2$O$_4$S: 505.22 (M+H$^+$). Found: 505.01, 506.07 (M+H$^+$).

Example 37

Preparation of (S)-2-tert-butoxy-2-((S)-2-cyclopropyl-7-(2,3-dihydrobenzo[de]chromen-7-yl)-5-methylbenzo[d]thiazol-6-yl)acetic acid (85)

Compound 85 was prepared from compound 18 according to the procedure used to prepare compounds 19 and 20 (except that 2,3-dihydrobenzo[de]chromen-7-ylboronic acid was used instead of 2,3-dihydropyrano[4,3,2-de]quinolin-7-ylboronic acid) in Example 9.

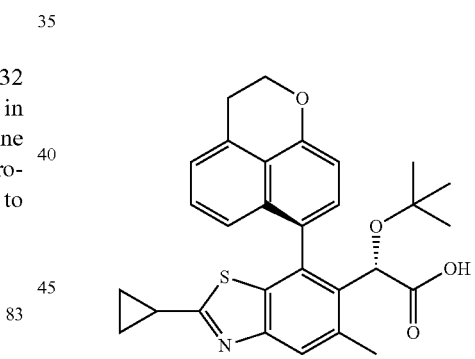

85

Compound 85: $^1$H-NMR: 400 MHz, (CD$_3$OD) δ: 7.70 (s, 1H); 7.29-7.19 (m, 4H), 6.95 (d, J=4 Hz, 1H), 5.07 (s, 1H), 4.48-4.45 (m, 2H), 3.29-3.27 (m, 2H), 2.64 (s, 3H), 2.32-2.28 (m, 1H), 1.20-1.18 (m, 2H), 1.056-1.03 (m, 2H), 0.96 (s, 9H).
LCMS-ESI$^+$ (m/z): [M+H]$^+$ calcd for C$_{29}$H$_{29}$NO$_4$S: 488.2 (M+H$^+$). Found: 488.1 (M+H$^+$).

Example 38

Preparation of (S)-2-tert-butoxy-2-((S)-7-(5-chloro-3,4-dihydro-2H-benzo[b][1,4]oxazin-6-yl)-2-cyclopropyl-5-methylbenzo[d]thiazol-6-yl)acetic acid (86) and (S)-2-tert-butoxy-2-((R)-7-(5-chloro-3,4-dihydro-2H-benzo[b][1,4]oxazin-6-yl)-2-cyclopropyl-5-methylbenzo[d]thiazol-6-yl)acetic acid (87)

Compounds 86 and 87 was prepared from compound 18 according to the procedure used to prepare compounds 19 and 20 (except that 5-chloro-3,4-dihydro-2H-benzo[b][1,4]oxazin-6-ylboronic acid was used instead of 2,3-dihydropyrano[4,3,2-de]quinolin-7-ylboronic acid) in Example 9.

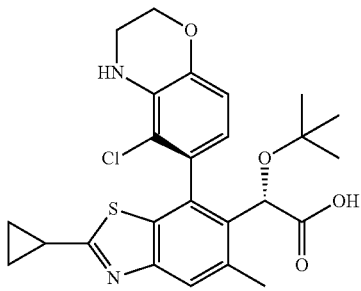

86

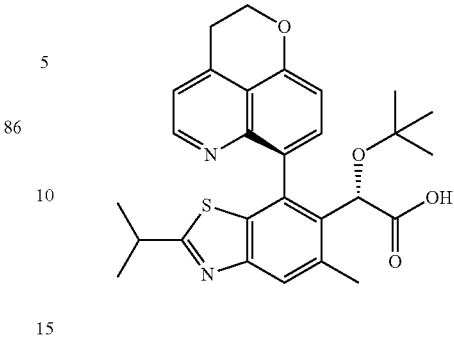

88

Compound 88: $^1$H NMR (400 MHz, CD$_3$OD) δ 8.70 (d, J=5.4 Hz, 1H), 7.90 (s, 1H), 7.80 (d, J=7.9 Hz, 1H), 7.66-7.60 (m, 1H), 7.31 (d, J=8.0 Hz, 1H), 5.20 (s, 1H), 4.70-4.61 (m, 2H), 3.59-3.51 (m, 2H), 3.15-3.09 (m, 1H), 2.72 (s, 3H), 1.36 (m, 6H), 0.90 (s, 9H). LCMS-ESI$^+$: calc'd for C$_{28}$H$_{30}$N$_2$O$_4$S: 491.2 (M+H$^+$). found: 491.4 (M+H$^+$).

Compound 86: $^1$H-NMR 400 MHz, (CD$_3$OD) δ: 7.63 (d, J=0.4 Hz, 1H); 6.74 (d, J=4.2 Hz, 1H), 6.44 (d, J=4.2 Hz, 1H), 5.21 (s, 1H), 4.26 (t, J=4.6 Hz, 2H), 3.51-3.49 (m, 2H), 2.65 (d, J=0.4 Hz, 3H), 2.40-2.36 (m, 1H), 1.26-1.23 (m, 2H), 1.13-1.11 (m, 2H), 1.09 (s, 9H). LCMS-ESI$^+$ (m/z): [M+H]$^+$ calcd for C$_{25}$H$_{27}$ClN$_2$O$_4$S: 487.1 (M+H$^+$). Found: 487.1 (M+H$^+$).

Example 40

Preparation of (S)-2-((S)-2-(azetidin-1-yl)-7-(2,3-dihydropyrano[4,3,2-de]quinolin-7-yl)-5-methyl-benzo[d]thiazol-6-yl)-2-(tert-pentyloxy)acetic acid (89)

87

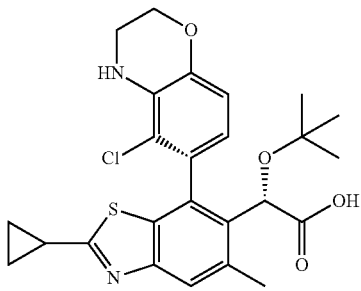

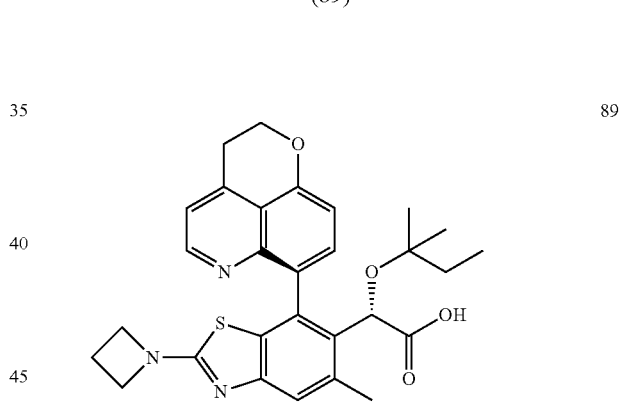

89

Compound 87: $^1$H-NMR: 400 MHz, (CD$_3$OD) δ: 7.60 (s, 1H); 6.83-6.78 (m, 2H), 5.27 (s, 1H), 4.27-4.24 (m, 2H), 3.51-3.48 (m, 2H), 2.55 (s, 3H), 2.40-2.36 (m, 1H), 1.28-1.23 (m, 2H), 1.13-1.12 (m, 2H), 1.01 (s, 9H).

LCMS-ESI$^+$ (m/z): [M+H]$^+$ calcd for C$_{25}$H$_{27}$ClN$_2$O$_4$S: 487.1 (M+H$^+$). Found: 487.1 (M+H$^+$).

Example 39

Preparation of (S)-2-tert-butoxy-2-((S)-7-(2,3-dihydropyrano[4,3,2-de]quinolin-7-yl)-2-isopropyl-5-methylbenzo[d]thiazol-6-yl)acetic acid (88)

Compound 88 was prepared from compound 32 according to the procedure used to prepare compound 77 in Example 33, except propen-2-yl-(tri-n-butyl)tin was used instead of cyclopentenylboronic acid. Also, hydrogenation was performed according to the procedure used to prepare 8F from 8E in Example 4.

Compound 89: $^1$H NMR (400 MHz, CD$_3$OD) δ 8.75 (d, J=5.1 Hz, 1H), 7.82 (d, J=8.3 Hz, 1H), 7.71 (d, J=5.6 Hz, 1H), 7.47 (s, 1H), 7.35 (d, J=8.1 Hz, 1H), 5.09 (d, J=0.6 Hz, 1H), 4.69-4.62 (m, 2H), 4.17 (t, J=7.7 Hz, 4H), 3.61-3.55 (m, 2H), 2.66 (s, 3H), 2.58-2.42 (m, 2H), 0.87 (d, J=2.9 Hz, 6H), 0.59 (t, J=7.0 Hz, 3H). $^{19}$F NMR (377 MHz, CD$_3$OD) δ −77.77. LCMS: calc'd=518.64, observed: 518.08

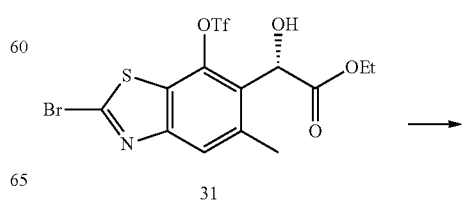

31

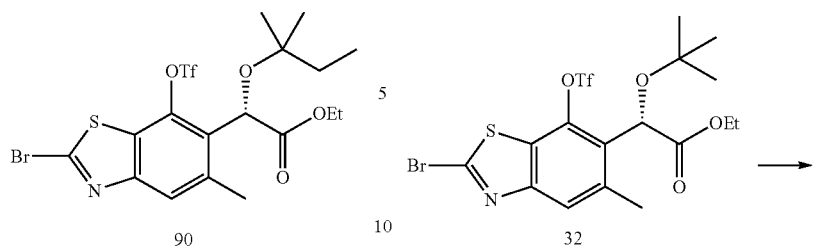

Preparation of 90: A slurry of 31 (740 mg, 1.55 mmol) in tert-amyl acetate (7.0 mL) was treated with 70% aq. HClO₄ (5 µL) was added at 23° C. Reaction became cloudy, but LCMS analysis indicated minimal conversion. More 70% aq. HClO₄ (50 µL) was introduced. After 2 h, the reaction was added dropwise over 5 min to sat. aq. NaHCO₃ (20 mL). H₂O (10 mL) was added, and the system was extracted with DCM (3×20 mL). Combined organic layers were dried (Na₂SO₄), filtered, concentrated, and treated with hexane (10 mL). The system was concentrated again to remove some residual t-amyl alcohol. The residue was treated with PhH and loaded onto a 12 gram "gold" ISCO silica gel column. Chromatography (eluent: Hexanes/Ethyl Acetate) gave 90 (134 mg, 16% yield) along with some recovered 31.

¹H-NMR: 400 MHz, (CDCl₃) δ: 7.80 (s, 1H), 5.49 (s, 1H), 4.24-4.06 (m, 2H), 2.57 (s, 3H), 1.60-1.40 (m, 2H), 1.17 (s, 3H), 1.16 (t, J=7.0 Hz, 3H), 1.05 (s, 3H), 0.80 (t, J=7.0 Hz, 3H). ¹⁹F-NMR: 376 MHz, (CDCl₃) δ: −73.8

The remainder of the synthesis of 89 follows the same route as Example 10 from compound 32.

Example 41

Preparation of (S)-2-tert-butoxy-2-((S)-2-(difluoromethyl)-7-(2,3-dihydropyrano[4,3,2-de]quinolin-7-yl)-5-methylbenzo[d]thiazol-6-yl)acetic acid (92)

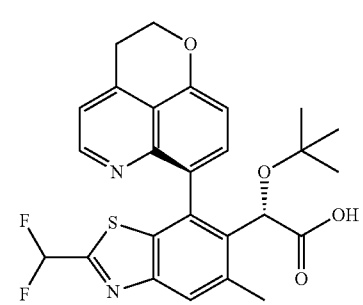

Compound 92: ¹H NMR (400 MHz, CD₃OD) δ 8.67 (d, J=5.6 Hz, 1H), 8.08 (d, J=5.9 Hz, 1H), 7.78-7.75 (m, 1H), 7.29-7.22 (m, 1H), 7.04 (s, 1H), 6.89 (s, 1H), 5.23 (s, 1H), 4.66-4.61 (m, 2H), 3.69 (s, 1H), 3.64 (s, 2H), 3.17-3.16 (m, 1H), 3.13 (dd, J=4.1, 2.4 Hz, 2H), 2.75 (a, 3H), 0.90 (s, 9H).

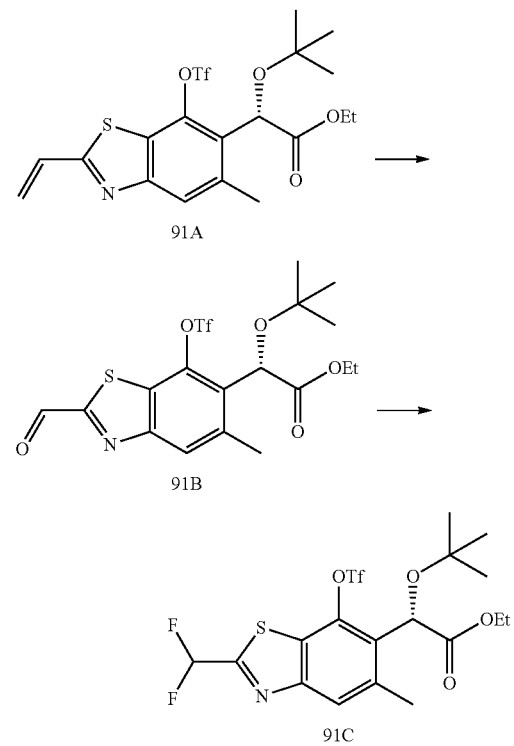

Step 1

Preparation of(S)-ethyl 2-tert-butoxy-2-(5-methyl-7-(trifluoromethylsulfonyloxy)-2-vinylbenzo[d]thiazol-6-yl)acetate (91A)

A microwave vial was charged with CuI (9.4 mg, 49 µmol), Pd(PPh₃)₄ (29 mg, 25 µmol), and 32 (250 mg, 0.494 mmol). The vial was sealed and placed under a vacuum. The vessel was backfilled with argon and charged with DMF (1.0 mL) followed by vinyl-(tri-n-butyl)tin (173 µL, 0593 mmol). Reaction was stirred at 65° C. for 1 h, then cooled to 23° C. Sat aq. NH₄Cl (40 mL) was added and the reaction was extracted with EtOAc (2×20 mL). Combined organic layers were dried (Na₂SO₄), filtered, and concentrated. Hexane was added, and the slurry was concentrated again. The residue was treated with PhH and purified by silica gel column chromatography (eluent: Hexanes/Ethyl Acetate) giving 91A (173 mg, 77% yield). ¹H-NMR 400 MHz, (CDCl₃) δ: 7.80 (s, 1H), 7.00 (dd, J=18.6, 10.9 Hz, 1H), 6.24 (d, J=18.6 Hz, 1H), 5.82 (d, J=10.9 Hz, 1H), 5.60 (s, 1H), 4.24-4.06 (m, 2H), 2.54 (s, 3H), 1.22 (a, 9H), 1.19 (t, J=6.8 Hz, 3H). ¹⁹F-NMR: 376 MHz, (CDCl₃) δ: −73.8.

Step 2

Preparation of (S)-ethyl 2-tert-butoxy-2-(2-formyl-5-methyl-7-(trifluoromethylsulfonyloxy)benzo[d]thiazol-6-yl)acetate (91B)

A solution of 91A (170 mg, 0.353 mmol), DCM (5.0 mL), and MeOH (5.0 mL) was cooled to −78° C. and perfused with oxygen gas for 3 min. Then using an ozonator, a stream of $O_3$ in oxygen gas was bubbled through the solution for 5 min. After this, the reaction was stirred for 10 min, then sparged with oxygen gas for 2 min to drive out unreacted ozone in solution. While the reaction was still at −78° C., dimethylsulfide (200 μL) was added and the reaction allowed to warm to 0° C. After 30 min, 10% w/v aq $Na_2S_2O_3$ (5 mL) was added and the reaction was warmed to 23° C. and stirred for 10 min. The reaction was diluted with $H_2O$ (20 mL) and extracted with DCM (3×15 mL). Combined organic layers were dried ($Na_2SO_4$), filtered, and concentrated. More DCM was added and the reaction was concentrated once more to remove residual methanol, giving 91B (165 mg, 97% yield). $^1$H-NMR: 400 MHz, (CDCl$_3$) δ: 10.04 (s, 1H). 8.00 (s, 1H), 5.60 (s, 1H), 4.22-4.00 (m, 2H), 2.51 (s, 3H), 1.16 (s, 9H), 1.14 (t, J=6.8 Hz, 3H). $^{19}$F-NMR 376 MHz, (CDCl$_3$) δ: −73.6.

Step 3

Preparation of (S)-ethyl 2-tert-butoxy-2-(2-(difluoromethyl)-5-methyl-7-(trifluoromethylsulfonyloxy)benzo[d]thiazol-6-yl)acetate (91C)

A solution of Fluolead® (318 mg, 1.27 mmol) in DCM (1.0 mL) was cooled to 0° C. and treated with a solution of 91B (123 mg, 0.254 mmol) in DCM (1.5 mL). The reaction was allowed to warm to 23° C. Absolute EtOH (5 μL) was added to initiate the reaction. After 1 h, additional Fluolead® (318 mg, 1.27 mmol) was added. Once 4 h had passed, 0.5 M aq. NaOH (5 mL) was added, and the reaction reached a pH of ~2. DCM (10 mL) was introduced. 1.0 M aq NaOH (~5 mL) was added dropwise until the pH reached 12. The system was extracted with DCM (3×10 mL). The combined organic layers were dried ($Na_2SO_4$), filtered, and carefully concentrated to a volume of ~3 mL. The system became a suspension, which was then filtered. The filtrate was directly loaded onto a 12 gram "gold" ISCO silica gel column. Purification by chromatography (eluent: Hexanes/Ethyl Acetate) gave 91C (67 mg, 52% yield).

$^1$H-NMR: 400 MHz, (CDCl$_3$) δ: 7.97 (s, 1H), 6.92 (t, $J_{HF}$=44.5 Hz, 1H), 5.62 (s, 1H), 4.24-4.08 (m, 2H), 2.59 (s, 3H), 1.27 (s, 9H), 1.19 (t, J=6.8 Hz, 3H). $^{19}$F-NMR: 376 MHz, (CDCl$_3$) δ: −73.7 (3F), −110.6 (app. dd, $J_{FF}$=4.0 Hz, $J_{HF}$=44.5 Hz, 2F).

The remainder of the synthesis of 92 follows the same route as Example 10 from compound 33.

Example 42

Preparation of (S)-2-((S)-2-acetamido-7-(2,3-dihydropyrano[4,3,2-de]quinolin-7-yl)-5-methylbenzo[d]thiazol-6-yl)-2-tert-butoxyacetic acid (93)

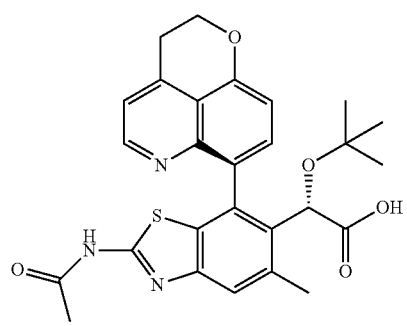

93

Compound 93: $^1$H-NMR: 400 MHz, (CD$_3$OD) δ: $^1$H NMR (400 MHz, cd$_3$od) δ 8.73 (d, J=5.4 Hz, 1H), 7.85 (d, J=8.2 Hz, 1H), 7.76-7.73 (m, 1H), 7.72 (d, J=5.6 Hz, 1H), 7.39 (t, J=10.0 Hz, 1H), 5.20 (s, 1H), 4.68 (m, 4H), 3.64-3.57 (m, 2H), 2.71 (s, 3H), 2.17 (s, 3H), 0.91 (s, 9H). LCMS-ESI$^+$ (m/z): [M+H]$^+$ calcd for $C_{27}H_{23}N_3O_5S$: 506.17 (M+H$^+$). Found: 506.02, 507.03 (M+H$^+$).

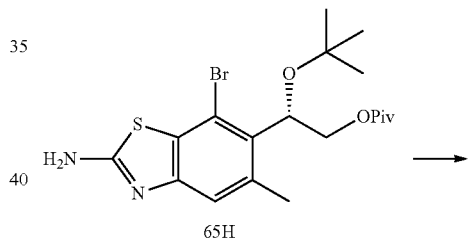

65H

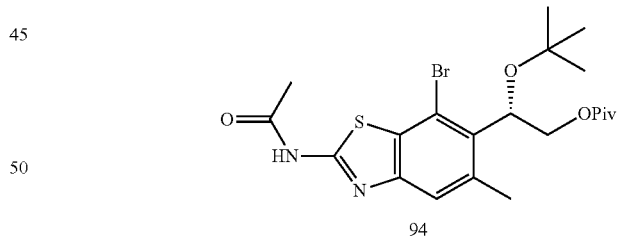

94

Preparation of compound (S)-2-(2-acetamido-7-bromo-5-methylbenzo[d]thiazol-6-yl)-2-tert-butoxyethyl pivalate (94). To a solution of 65H in $CH_2Cl_2$ was added pyridine, acetic anyhydride, and trace DMAP. Upon consumption of starting material by LC-MS, the mixture was concentrated in vacuo and purified by column chromatography to give 94.

LCMS-ESI$^+$ (m/z): [M+H]$^+$ calcd for $C_{21}H_{29}BrN_2O_4S$: 487.1 (M+H$^+$). Found: 486.9 (M+H$^+$).

The remainder of the synthesis of compound 93 is analogous to the preparation of compound 66 from compound 65J in example 25

Example 43

Preparation of (S)-2-tert-butoxy-2-((S)-7-(2,3-dihydropyrano[4,3,2-de]quinolin-7-yl)-5-methylbenzo[d]thiazol-6-yl)acetic acid (95)

Compound 95 was a by-product in the preparation of 40.

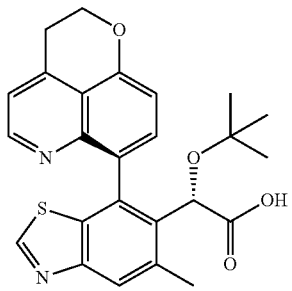

95

Compound 95: $^1$H-NMR: 400 MHz, (CD$_3$OD) δ: 9.40 (s, 1H); 8.82 (d, J=6.0 Hz, 1H); 8.17 (s, 1H); 7.93 (d, J=8.0 Hz, 1H); 7.89 (d, J=6.0 Hz, 1H); 7.46 (d, J=8.0 Hz, 1H); 5.27 (s, 1H); 4.76-4.71 (m, 2H); 3.69 (t, J=6.0 Hz, 2H); 2.81 (s, 3H); 0.92 (s, 9H). LCMS-ESI$^+$ (m/z): [M+H]$^+$ calcd for C$_{25}$H$_{24}$N$_2$O$_4$S: 449.2 (M+H$^+$). Found: 449.1 (M+H$^+$).

Example 44

Preparation of (S)-2-tert-butoxy-2-((S)-7-(2,3-dihydropyrano[4,3,2-de]quinolin-7-yl)-5-methyl-2-(methylcarbamoyl)benzo[d]thiazol-6-yl)acetic acid (97)

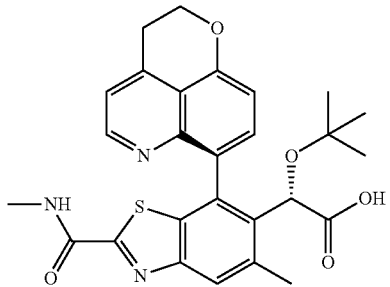

97

Compound 97: $^1$H-NMR: 400 MHz, (CD$_3$OD) δ: 8.77 (d, J=6.0 Hz, 1H); 8.18-8.15 (m, 1H); 7.91 (m, 1H); 7.84 (d, J=5.2 Hz, 1H); 7.45 (d, J=8.4 Hz, 1H); 5.26 (s, 1H); 4.75-4.71 (m, 2H); 3.67 (t, j=6.0 Hz, 2H); 2.93 (s, 3H); 2.79 (s, 3H); 0.92 (s, 9H). LCMS-ESI$^+$ (m/z): [M+H]$^+$ calcd for C$_{27}$H$_{27}$N$_3$O$_5$S: 506.2 (M+H$^+$). Found: 506.0 (M+H$^+$).

Step 1

Preparation of (S)-6-((S)-1-tert-butoxy-2-ethoxy-2-oxoethyl)-7-(2,3-dihydropyrano[4,3,2-de]quinolin-7-yl)-5-methylbenzo[d]thiazole-2-carboxylic acid (96A)

To a solution of compound 38 (40 mg) in THF/MeOH (1:1, 2 mL) was added a NaOH solution (2 M, 100 µL). The reaction mixture was stirred at rt for 1 h. A saturated solution of NH$_4$Cl was added, and the aqueous was extracted with EtOAc. The organic layer was dried, filtered, and concentrated in vacuo to give 95A. $^1$H-NMR: 400 MHz, (CD$_3$OD) δ: 8.63 (d, J=6 Hz, 1H), 8.05 (br s, 1H), 7.63 (d, J=8 Hz, 1H), 7.46 (d, J=6 Hz), 7.21 (d, J=8 Hz, 1H), 5.20 (s, 1H), 4.58 (m, 2H), 4.04 (m, 1H), 3.91 (m, 1H), 3.46 (m, 2H), 2.76 (s, 3H), 1.03 (t, J=7 Hz, 3H), 0.89 (s, 9H).

Step 2

To a solution of 96A (15 mg) in CH$_2$Cl$_2$ (1 mL) was added carbonyldiimidazole (10 mg) and then methylamine (solution in MeOH, 100 µL). Once conversion is complete by LC-MS, the solution was concentrated to give crude 96B. Then THF/MeOH added (1:1, 1 mL) followed by NaOH solution (2 M, 100 µL). The reaction mixture was stirred at 55-60° C. for 4 h. Purified by reverse phase HPLC to give 3.8 mg of 97.

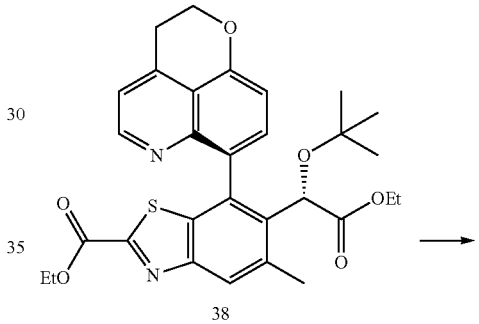

38

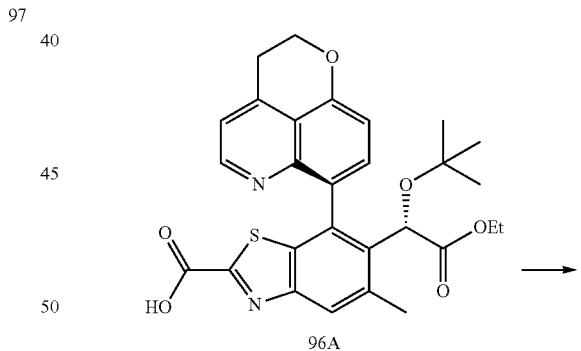

96A

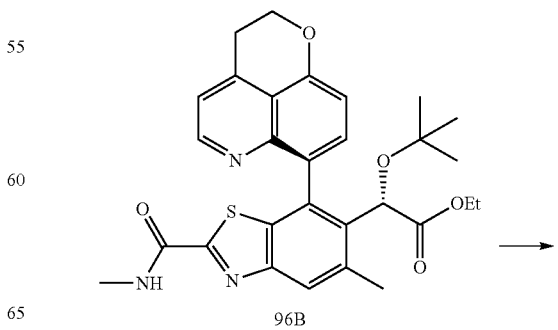

96B

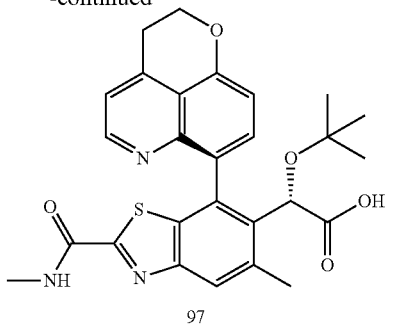

97

Example 45

Preparation of (S)-2-tert-butoxy-2-((S)-7-(2,3-dihydropyrano[4,3,2-de]quinolin-7-yl)-5-methyl-2-(phenethylcarbamoyl)benzo[d]thiazolyl)acetic acid (98)

Compound 98 was prepared from compound 96A according to the procedure used to prepare compound 97 (except that 2-phenylethanamine was used instead of methylamine) in Example 44.

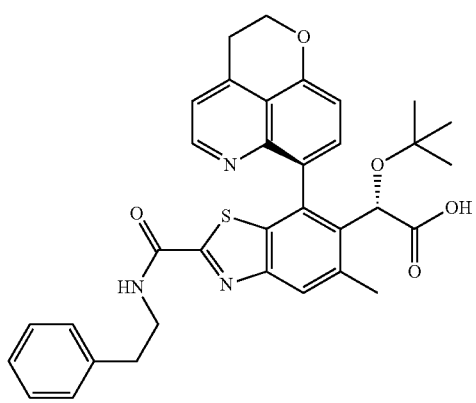

98

Compound 98: $^1$H-NMR: 400 MHz, (CD$_3$OD) δ: 8.76 (d, J=6.0 Hz, 1H); 8.17 (s, 1H); 7.90 (d, J=8 Hz, 1H); 7.82 (d, J=6 Hz, 1H); 7.43 (d, J=8 Hz, 1H); 7.20 (m, 5H); 5.26 (s, 1H); 4.71 (m, 2H); 3.64 (t, J=6 Hz, 2H); 2.91 (t, J=7 Hz, 2H), 2.77 (m, 2H), 2.72 (s, 3H), 0.92 (s, 9H). LCMS-ESI$^+$ (m/z): [M+H]$^+$ calcd for C$_{34}$H$_{33}$N$_3$O$_5$S: 596.2 (M+H$^+$). Found: 596.1 (M+H$^+$).

Example 46

Preparation of (S)-2-tert-butoxy-2-((S)-7-(2,3-dihydropyrano[4,3,2-de]quinolin-7-yl)-2-(4-methoxybenzylcarbamoyl)-5-methylbenzo[d]thiazol-6-yl)acetic acid (99)

Compound 99 was prepared from compound 96A according to the procedure used to prepare compound 97 (except that 4-methoxybenzylamine was used instead of methylamine) in Example 44.

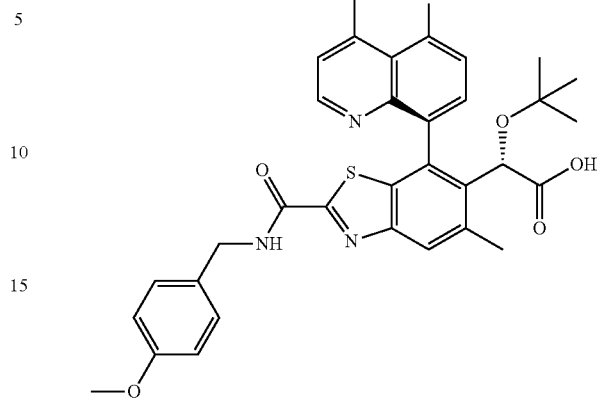

99

Compound 99: LCMS-ESI$^+$ (m/z): [M+H]$^+$ calcd for C$_{34}$H$_{33}$N$_3$O$_6$S: 612.2 (M+H$^+$). Found: 612.1 (M+H$^+$).

Example 47

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |

-continued

| (iv) Injection 1 (1 mg/ml) | mg/ml |
|---|---|
| Monobasic sodium phosphate | 0.7 |
| Sodium chloride | 4.5 |
| 1.0N Sodium hydroxide solution | q.s. |
| (pH adjustment to 7.0-7.5) | |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution | q.s. |
| (pH adjustment to 7.0-7.5) | |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound, or a pharmaceutically acceptable salt thereof, of formula Ie:

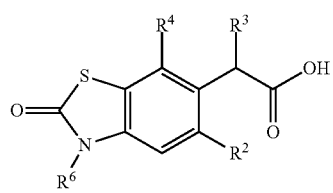

wherein:
$R^2$ is —CH$_3$;
$R^3$ is —OC(CH$_3$)$_3$;
$R^4$ is:

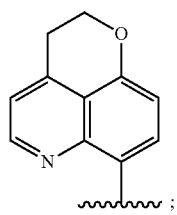

$R^6$ is:
selected from the group consisting of —CH$_3$, —CH$_2$C$_6$H$_5$, and —CH$_2$C$_6$H$_4$CF$_3$.

2. The compound of claim 1, or a pharmaceutically acceptable salt thereof, wherein $R^6$ is:

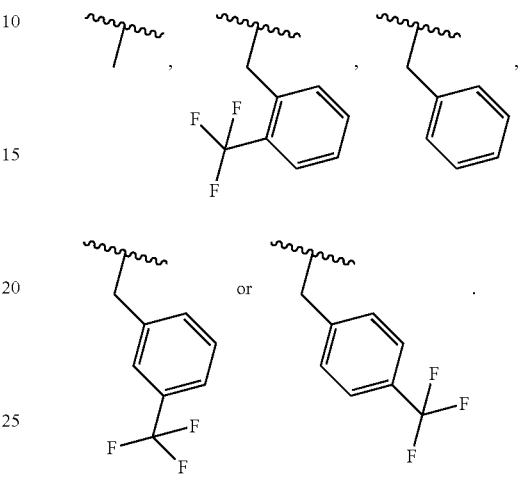

3. A pharmaceutical composition comprising a compound of claim 1 or claim 2, or a pharmaceutically acceptable salt thereof, and a pharmaceutically acceptable carrier.

4. A method of treating HIV infection in a patient in need thereof comprising administering a compound as described in claim 1, or a pharmaceutically acceptable salt thereof, to the patient.

5. A method for treating an HIV infection in a patient in need thereof comprising administering to the patient a compound as described in claim 1, or a pharmaceutically acceptable salt thereof, in combination with one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

6. A method for treating an HIV infection in a patient in need thereof comprising administering to the patient a compound as described in claim 1, or a pharmaceutically acceptable salt thereof, in combination with one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

* * * * *